(12) United States Patent
Cox et al.

(10) Patent No.: US 10,975,372 B2
(45) Date of Patent: Apr. 13, 2021

(54) DE NOVO SYNTHESIZED NUCLEIC ACID LIBRARIES

(71) Applicant: TWIST BIOSCIENCE CORPORATION, San Francisco, CA (US)

(72) Inventors: Anthony Cox, Mountain View, CA (US); Siyuan Chen, San Mateo, CA (US)

(73) Assignee: TWIST BIOSCIENCE CORPORATION, San Francisco, CA (US)

(*) Notice: Subject to any disclaimer, the term of this patent is extended or adjusted under 35 U.S.C. 154(b) by 184 days.

(21) Appl. No.: 16/031,784

(22) Filed: Jul. 10, 2018

(65) Prior Publication Data

US 2018/0312834 A1    Nov. 1, 2018

Related U.S. Application Data

(62) Division of application No. 15/682,100, filed on Aug. 21, 2017, now Pat. No. 10,053,688.

(60) Provisional application No. 62/419,881, filed on Nov. 9, 2016, provisional application No. 62/411,388, filed on Oct. 21, 2016, provisional application No. 62/393,948, filed on Sep. 13, 2016, provisional application No. 62/382,191, filed on Aug. 31, 2016, provisional application No. 62/378,134, filed on Aug. 22, 2016.

(51) Int. Cl.
| | | |
|---|---|---|
| *C12N 15/10* | (2006.01) |
| *C12Q 1/6806* | (2018.01) |
| *C40B 50/14* | (2006.01) |
| *C12Q 1/6816* | (2018.01) |
| *C40B 40/06* | (2006.01) |
| *C12N 15/11* | (2006.01) |

(52) U.S. Cl.
CPC ..... *C12N 15/1068* (2013.01); *C12N 15/1093* (2013.01); *C12Q 1/6806* (2013.01); *C12Q 1/6816* (2013.01); *C12N 15/111* (2013.01); *C12N 2310/10* (2013.01); *C12N 2310/20* (2017.05); *C12N 2330/31* (2013.01); *C40B 40/06* (2013.01); *C40B 50/14* (2013.01)

(58) Field of Classification Search
None
See application file for complete search history.

(56) References Cited

U.S. PATENT DOCUMENTS

| | | |
|---|---|---|
| 3,549,368 A | 12/1970 | Robert et al. |
| 3,920,714 A | 11/1975 | Streck |
| 4,123,661 A | 10/1978 | Wolf et al. |
| 4,415,732 A | 11/1983 | Caruthers et al. |
| 4,613,398 A | 9/1986 | Chiong et al. |
| 4,726,877 A | 2/1988 | Fryd et al. |
| 4,808,511 A | 2/1989 | Holmes |
| 4,837,401 A | 6/1989 | Hirose et al. |
| 4,863,557 A | 9/1989 | Kokaku et al. |
| 4,981,797 A | 1/1991 | Jessee et al. |
| 4,988,617 A | 1/1991 | Landegren et al. |
| 5,102,797 A | 4/1992 | Tucker et al. |
| 5,118,605 A | 6/1992 | Urdea |
| 5,137,814 A | 8/1992 | Rashtchian et al. |
| 5,143,854 A | 9/1992 | Pirrung et al. |
| 5,242,794 A | 9/1993 | Whiteley et al. |
| 5,242,974 A | 9/1993 | Holmes |
| 5,288,514 A | 2/1994 | Ellman |
| 5,291,897 A | 3/1994 | Gastrin et al. |
| 5,299,491 A | 4/1994 | Kawada |
| 5,384,261 A | 1/1995 | Winkler et al. |
| 5,387,541 A | 2/1995 | Hodge et al. |
| 5,395,753 A | 3/1995 | Prakash |
| 5,431,720 A | 7/1995 | Nagai et al. |
| 5,445,934 A | 8/1995 | Fodor et al. |
| 5,449,754 A | 9/1995 | Nishioka |
| 5,459,039 A | 10/1995 | Modrich et al. |
| 5,474,796 A | 12/1995 | Brennan |
| 5,476,930 A | 12/1995 | Letsinger et al. |
| 5,487,993 A | 1/1996 | Herrnstadt et al. |
| 5,494,810 A | 2/1996 | Barany et al. |
| 5,501,893 A | 3/1996 | Laermer et al. |
| 5,508,169 A | 4/1996 | Deugau et al. |
| 5,510,270 A | 4/1996 | Fodor et al. |
| 5,514,789 A | 5/1996 | Kempe |
| 5,527,681 A | 6/1996 | Holmes |
| 5,530,516 A | 6/1996 | Sheets |
| 5,556,750 A | 9/1996 | Modrich et al. |
| 5,586,211 A | 12/1996 | Dumitrou et al. |
| 5,641,658 A | 6/1997 | Adams et al. |
| 5,677,195 A | 10/1997 | Winkler et al. |
| 5,679,522 A | 10/1997 | Modrich et al. |
| 5,683,879 A | 11/1997 | Laney et al. |
| 5,688,642 A | 11/1997 | Chrisey et al. |

(Continued)

FOREIGN PATENT DOCUMENTS

| | | |
|---|---|---|
| AU | 3157000 A | 9/2000 |
| CA | 2362939 A1 | 8/2000 |

(Continued)

OTHER PUBLICATIONS

Assembly manual for the POSaM: THE ISB Piezoelelctric Oligonucleotide Synthesizer and Microarrayer, The Institute for Systems Biology, May 28, 2004 (50 pages).

(Continued)

*Primary Examiner* — Kaijiang Zhang
(74) *Attorney, Agent, or Firm* — Wilson Sonsini Goodrich & Rosati

(57) ABSTRACT

Disclosed herein are methods for the generation of nucleic acid libraries encoding for gRNA sequences. The gRNAs encoded by methods described herein may be single or double gRNA sequences. Methods described provide for the generation of gRNA libraries, as a DNA precursor or as a RNA transcription product, with improved accuracy and uniformity.

16 Claims, 32 Drawing Sheets

Specification includes a Sequence Listing.

(56) References Cited

U.S. PATENT DOCUMENTS

| | | |
|---|---|---|
| 5,700,637 A | 12/1997 | Southern |
| 5,700,642 A | 12/1997 | Monforte et al. |
| 5,702,894 A | 12/1997 | Modrich et al. |
| 5,707,806 A | 1/1998 | Shuber |
| 5,712,124 A | 1/1998 | Walker |
| 5,739,386 A | 4/1998 | Holmes |
| 5,750,672 A | 5/1998 | Kempe |
| 5,780,613 A | 7/1998 | Letsinger et al. |
| 5,830,643 A | 11/1998 | Yamamoto et al. |
| 5,830,655 A | 11/1998 | Monforte et al. |
| 5,830,662 A | 11/1998 | Soares et al. |
| 5,834,252 A | 11/1998 | Stemmer et al. |
| 5,843,669 A | 12/1998 | Kaiser et al. |
| 5,843,767 A | 12/1998 | Beattie |
| 5,846,717 A | 12/1998 | Brow et al. |
| 5,854,033 A | 12/1998 | Lizardi |
| 5,858,754 A | 1/1999 | Modrich et al. |
| 5,861,482 A | 1/1999 | Modrich et al. |
| 5,863,801 A | 1/1999 | Southgate et al. |
| 5,869,245 A | 2/1999 | Yeung |
| 5,877,280 A | 3/1999 | Wetmur |
| 5,882,496 A | 3/1999 | Northrup et al. |
| 5,922,539 A | 7/1999 | Modrich et al. |
| 5,922,593 A | 7/1999 | Livingston |
| 5,928,907 A | 7/1999 | Woudenberg et al. |
| 5,962,272 A | 10/1999 | Chenchik et al. |
| 5,976,842 A | 11/1999 | Wurst |
| 5,976,846 A | 11/1999 | Passmore et al. |
| 5,989,872 A | 11/1999 | Luo et al. |
| 5,994,069 A | 11/1999 | Hall et al. |
| 6,001,567 A | 12/1999 | Brow et al. |
| 6,008,031 A | 12/1999 | Modrich et al. |
| 6,013,440 A | 1/2000 | Lipshutz et al. |
| 6,015,674 A | 1/2000 | Woudenberg et al. |
| 6,017,434 A | 1/2000 | Simpson et al. |
| 6,020,481 A | 2/2000 | Benson et al. |
| 6,027,898 A | 2/2000 | Gjerde et al. |
| 6,028,189 A | 2/2000 | Blanchard |
| 6,028,198 A | 2/2000 | Liu et al. |
| 6,040,138 A | 3/2000 | Lockhart et al. |
| 6,077,674 A | 6/2000 | Schleifer et al. |
| 6,087,482 A | 7/2000 | Teng et al. |
| 6,090,543 A | 7/2000 | Prudent et al. |
| 6,090,606 A | 7/2000 | Kaiser et al. |
| 6,103,474 A | 8/2000 | Dellinger et al. |
| 6,107,038 A | 8/2000 | Choudhary et al. |
| 6,110,682 A | 8/2000 | Dellinger et al. |
| 6,114,115 A | 9/2000 | Wagner, Jr. |
| 6,130,045 A | 10/2000 | Wurst et al. |
| 6,132,997 A | 10/2000 | Shannon |
| 6,136,568 A | 10/2000 | Hiatt et al. |
| 6,171,797 B1 | 1/2001 | Perbost |
| 6,180,351 B1 | 1/2001 | Cattell |
| 6,201,112 B1 | 3/2001 | Ach |
| 6,218,118 B1 | 4/2001 | Sampson et al. |
| 6,221,653 B1 | 4/2001 | Caren et al. |
| 6,222,030 B1 | 4/2001 | Dellinger et al. |
| 6,232,072 B1 | 5/2001 | Fisher |
| 6,235,483 B1 | 5/2001 | Wolber et al. |
| 6,242,266 B1 | 6/2001 | Schleifer et al. |
| 6,251,588 B1 | 6/2001 | Shannon et al. |
| 6,251,595 B1 | 6/2001 | Gordon et al. |
| 6,251,685 B1 | 6/2001 | Dorsel et al. |
| 6,258,454 B1 | 7/2001 | Lefkowitz et al. |
| 6,262,490 B1 | 7/2001 | Hsu et al. |
| 6,274,725 B1 | 8/2001 | Sanghvi et al. |
| 6,284,465 B1 | 9/2001 | Wolber |
| 6,287,776 B1 | 9/2001 | Hefti |
| 6,287,824 B1 | 9/2001 | Lizardi |
| 6,297,017 B1 | 10/2001 | Schmidt et al. |
| 6,300,137 B1 | 10/2001 | Earhart et al. |
| 6,306,599 B1 | 10/2001 | Perbost |
| 6,309,822 B1 | 10/2001 | Fodor et al. |
| 6,309,828 B1 | 10/2001 | Schleifer et al. |
| 6,312,911 B1 | 11/2001 | Bancroft et al. |
| 6,319,674 B1 | 11/2001 | Fulcrand et al. |
| 6,323,043 B1 | 11/2001 | Caren et al. |
| 6,329,210 B1 | 12/2001 | Schleifer |
| 6,346,423 B1 | 2/2002 | Schembri |
| 6,365,355 B1 | 4/2002 | McCutchen-Maloney |
| 6,372,483 B2 | 4/2002 | Schleifer et al. |
| 6,375,903 B1 | 4/2002 | Cerrina et al. |
| 6,376,285 B1 | 4/2002 | Joyner et al. |
| 6,384,210 B1 | 5/2002 | Blanchard |
| 6,387,636 B1 | 5/2002 | Perbost et al. |
| 6,399,394 B1 | 6/2002 | Dahm et al. |
| 6,399,516 B1 | 6/2002 | Ayon |
| 6,403,314 B1 | 6/2002 | Lange et al. |
| 6,406,849 B1 | 6/2002 | Dorsel et al. |
| 6,406,851 B1 | 6/2002 | Bass |
| 6,408,308 B1 | 6/2002 | Maslyn et al. |
| 6,419,883 B1 | 7/2002 | Blanchard |
| 6,428,957 B1 | 8/2002 | Delenstarr |
| 6,440,669 B1 | 8/2002 | Bass et al. |
| 6,444,268 B2 | 9/2002 | Lefkowitz et al. |
| 6,446,642 B1 | 9/2002 | Caren et al. |
| 6,446,682 B1 | 9/2002 | Viken |
| 6,451,998 B1 | 9/2002 | Perbost |
| 6,458,526 B1 | 10/2002 | Schembri et al. |
| 6,458,535 B1 | 10/2002 | Hall et al. |
| 6,458,583 B1 | 10/2002 | Bruhn et al. |
| 6,461,812 B2 | 10/2002 | Barth et al. |
| 6,461,816 B1 | 10/2002 | Wolber et al. |
| 6,469,156 B1 | 10/2002 | Schafer et al. |
| 6,472,147 B1 | 10/2002 | Janda et al. |
| 6,492,107 B1 | 12/2002 | Kauffman et al. |
| 6,518,056 B2 | 2/2003 | Schembri et al. |
| 6,521,427 B1 | 2/2003 | Evans |
| 6,521,453 B1 | 2/2003 | Crameri et al. |
| 6,555,357 B1 | 4/2003 | Kaiser et al. |
| 6,558,908 B2 | 5/2003 | Wolber et al. |
| 6,562,611 B1 | 5/2003 | Kaiser et al. |
| 6,566,495 B1 | 5/2003 | Fodor et al. |
| 6,582,908 B2 | 6/2003 | Fodor et al. |
| 6,582,938 B1 | 6/2003 | Su et al. |
| 6,586,211 B1 | 7/2003 | Staehler et al. |
| 6,587,579 B1 | 7/2003 | Bass |
| 6,589,739 B2 | 7/2003 | Fisher |
| 6,599,693 B1 | 7/2003 | Webb |
| 6,602,472 B1 | 8/2003 | Zimmermann et al. |
| 6,610,978 B2 | 8/2003 | Yin et al. |
| 6,613,513 B1 | 9/2003 | Parce et al. |
| 6,613,523 B2 | 9/2003 | Fischer |
| 6,613,560 B1 | 9/2003 | Tso et al. |
| 6,613,893 B1 | 9/2003 | Webb |
| 6,621,076 B1 | 9/2003 | Van et al. |
| 6,630,581 B2 | 10/2003 | Dellinger et al. |
| 6,632,641 B1 | 10/2003 | Brennan et al. |
| 6,635,226 B1 | 10/2003 | Tso et al. |
| 6,642,373 B2 | 11/2003 | Manoharan et al. |
| 6,649,348 B2 | 11/2003 | Bass et al. |
| 6,660,338 B1 | 12/2003 | Hargreaves |
| 6,664,112 B2 | 12/2003 | Mulligan et al. |
| 6,670,127 B2 | 12/2003 | Evans |
| 6,670,461 B1 | 12/2003 | Wengel et al. |
| 6,673,552 B2 | 1/2004 | Frey |
| 6,682,702 B2 | 1/2004 | Barth et al. |
| 6,689,319 B1 | 2/2004 | Fisher et al. |
| 6,692,917 B2 | 2/2004 | Neri et al. |
| 6,702,256 B2 | 3/2004 | Killeen et al. |
| 6,706,471 B1 | 3/2004 | Brow et al. |
| 6,706,875 B1 | 3/2004 | Goldberg et al. |
| 6,709,852 B1 | 3/2004 | Bloom et al. |
| 6,709,854 B2 | 3/2004 | Donahue et al. |
| 6,713,262 B2 | 3/2004 | Gillibolian et al. |
| 6,716,629 B2 | 4/2004 | Hess et al. |
| 6,716,634 B1 | 4/2004 | Myerson |
| 6,723,509 B2 | 4/2004 | Ach |
| 6,728,129 B2 | 4/2004 | Lindsey et al. |
| 6,743,585 B2 | 6/2004 | Dellinger et al. |
| 6,753,145 B2 | 6/2004 | Holcomb et al. |
| 6,768,005 B2 | 7/2004 | Mellor et al. |
| 6,770,748 B2 | 8/2004 | Imanishi et al. |
| 6,770,892 B2 | 8/2004 | Corson et al. |

(56) References Cited

U.S. PATENT DOCUMENTS

| | | |
|---|---|---|
| 6,773,676 B2 | 8/2004 | Schembri |
| 6,773,888 B2 | 8/2004 | Li et al. |
| 6,780,982 B2 | 8/2004 | Lyamichev et al. |
| 6,787,308 B2 | 9/2004 | Balasubramanian et al. |
| 6,789,965 B2 | 9/2004 | Barth et al. |
| 6,790,620 B2 | 9/2004 | Bass et al. |
| 6,794,499 B2 | 9/2004 | Wengel et al. |
| 6,796,634 B2 | 9/2004 | Caren et al. |
| 6,800,439 B1 | 10/2004 | McGall et al. |
| 6,814,846 B1 | 11/2004 | Berndt |
| 6,815,218 B1 | 11/2004 | Jacobson et al. |
| 6,824,866 B1 | 11/2004 | Glazer et al. |
| 6,830,890 B2 | 12/2004 | Lockhart et al. |
| 6,833,246 B2 | 12/2004 | Balasubramanian |
| 6,833,450 B1 | 12/2004 | McGall et al. |
| 6,835,938 B2 | 12/2004 | Ghosh et al. |
| 6,838,888 B2 | 1/2005 | Peck |
| 6,841,131 B2 | 1/2005 | Zimmermann et al. |
| 6,845,968 B2 | 1/2005 | Killeen et al. |
| 6,846,454 B2 | 1/2005 | Peck |
| 6,846,922 B1 | 1/2005 | Manoharan et al. |
| 6,852,850 B2 | 2/2005 | Myerson et al. |
| 6,858,720 B2 | 2/2005 | Myerson et al. |
| 6,879,915 B2 | 4/2005 | Cattell |
| 6,880,576 B2 | 4/2005 | Karp et al. |
| 6,884,580 B2 | 4/2005 | Caren et al. |
| 6,887,715 B2 | 5/2005 | Schembri |
| 6,890,723 B2 | 5/2005 | Perbost et al. |
| 6,890,760 B1 | 5/2005 | Webb |
| 6,893,816 B1 | 5/2005 | Beattie |
| 6,897,023 B2 | 5/2005 | Fu et al. |
| 6,900,047 B2 | 5/2005 | Bass |
| 6,900,048 B2 | 5/2005 | Perbost |
| 6,911,611 B2 | 6/2005 | Wong et al. |
| 6,914,229 B2 | 7/2005 | Corson et al. |
| 6,916,113 B2 | 7/2005 | De et al. |
| 6,916,633 B1 | 7/2005 | Shannon |
| 6,919,181 B2 | 7/2005 | Hargreaves |
| 6,927,029 B2 | 8/2005 | Lefkowitz et al. |
| 6,929,951 B2 | 8/2005 | Corson et al. |
| 6,936,472 B2 | 8/2005 | Earhart et al. |
| 6,938,476 B2 | 9/2005 | Chesk |
| 6,939,673 B2 | 9/2005 | Bass et al. |
| 6,943,036 B2 | 9/2005 | Bass |
| 6,946,285 B2 | 9/2005 | Bass |
| 6,950,756 B2 | 9/2005 | Kincaid |
| 6,951,719 B1 | 10/2005 | Dupret et al. |
| 6,958,119 B2 | 10/2005 | Yin et al. |
| 6,960,464 B2 | 11/2005 | Jessee et al. |
| 6,969,449 B2 | 11/2005 | Maher et al. |
| 6,969,488 B2 | 11/2005 | Bridgham et al. |
| 6,976,384 B2 | 12/2005 | Hobbs et al. |
| 6,977,223 B2 | 12/2005 | George et al. |
| 6,987,263 B2 | 1/2006 | Hobbs et al. |
| 6,989,267 B2 | 1/2006 | Kim et al. |
| 6,991,922 B2 | 1/2006 | Dupret et al. |
| 7,008,037 B2 | 3/2006 | Caren et al. |
| 7,025,324 B1 | 4/2006 | Slocum et al. |
| 7,026,124 B2 | 4/2006 | Barth et al. |
| 7,027,930 B2 | 4/2006 | Cattell |
| 7,028,536 B2 | 4/2006 | Karp et al. |
| 7,029,854 B2 | 4/2006 | Collins et al. |
| 7,034,290 B2 | 4/2006 | Lu et al. |
| 7,041,445 B2 | 5/2006 | Chenchik et al. |
| 7,045,289 B2 | 5/2006 | Allawi et al. |
| 7,051,574 B2 | 5/2006 | Peck |
| 7,052,841 B2 | 5/2006 | Delenstarr |
| 7,062,385 B2 | 6/2006 | White et al. |
| 7,064,197 B1 | 6/2006 | Rabbani et al. |
| 7,070,932 B2 | 7/2006 | Leproust et al. |
| 7,075,161 B2 | 7/2006 | Barth |
| 7,078,167 B2 | 7/2006 | Delenstarr et al. |
| 7,078,505 B2 | 7/2006 | Bass et al. |
| 7,094,537 B2 | 8/2006 | Leproust et al. |
| 7,097,974 B1 | 8/2006 | Staehler et al. |
| 7,101,508 B2 | 9/2006 | Thompson et al. |
| 7,101,986 B2 | 9/2006 | Dellinger et al. |
| 7,105,295 B2 | 9/2006 | Bass et al. |
| 7,115,423 B1 | 10/2006 | Mitchell |
| 7,122,303 B2 | 10/2006 | Delenstarr et al. |
| 7,122,364 B1 | 10/2006 | Lyamichev et al. |
| 7,125,488 B2 | 10/2006 | Li |
| 7,125,523 B2 | 10/2006 | Sillman |
| 7,128,876 B2 | 10/2006 | Yin et al. |
| 7,129,075 B2 | 10/2006 | Gerard et al. |
| 7,135,565 B2 | 11/2006 | Dellinger et al. |
| 7,138,062 B2 | 11/2006 | Yin et al. |
| 7,141,368 B2 | 11/2006 | Fisher et al. |
| 7,141,807 B2 | 11/2006 | Joyce et al. |
| 7,147,362 B2 | 12/2006 | Caren et al. |
| 7,150,982 B2 | 12/2006 | Allawi et al. |
| 7,153,689 B2 | 12/2006 | Tolosko et al. |
| 7,163,660 B2 | 1/2007 | Lehmann |
| 7,166,258 B2 | 1/2007 | Bass et al. |
| 7,179,659 B2 | 2/2007 | Stolowitz et al. |
| 7,183,406 B2 | 2/2007 | Belshaw et al. |
| 7,192,710 B2 | 3/2007 | Gellibolian et al. |
| 7,193,077 B2 | 3/2007 | Dellinger et al. |
| 7,198,939 B2 | 4/2007 | Dorsel et al. |
| 7,202,264 B2 | 4/2007 | Ravikumar et al. |
| 7,202,358 B2 | 4/2007 | Hargreaves |
| 7,205,128 B2 | 4/2007 | Ilsley et al. |
| 7,205,400 B2 | 4/2007 | Webb |
| 7,206,439 B2 | 4/2007 | Zhou et al. |
| 7,208,322 B2 | 4/2007 | Stolowitz et al. |
| 7,217,522 B2 | 5/2007 | Brenner |
| 7,220,573 B2 | 5/2007 | Shea et al. |
| 7,221,785 B2 | 5/2007 | Curry et al. |
| 7,226,862 B2 | 6/2007 | Staehler et al. |
| 7,227,017 B2 | 6/2007 | Mellor et al. |
| 7,229,497 B2 | 6/2007 | Stott et al. |
| 7,247,337 B1 | 7/2007 | Leproust et al. |
| 7,247,497 B2 | 7/2007 | Dahm et al. |
| 7,252,938 B2 | 8/2007 | Leproust et al. |
| 7,269,518 B2 | 9/2007 | Corson |
| 7,271,258 B2 | 9/2007 | Dellinger et al. |
| 7,276,336 B1 | 10/2007 | Webb et al. |
| 7,276,378 B2 | 10/2007 | Myerson |
| 7,276,599 B2 | 10/2007 | Moore et al. |
| 7,282,183 B2 | 10/2007 | Peck |
| 7,282,332 B2 | 10/2007 | Caren et al. |
| 7,282,705 B2 | 10/2007 | Brennen |
| 7,291,471 B2 | 11/2007 | Sampson et al. |
| 7,302,348 B2 | 11/2007 | Ghosh et al. |
| 7,306,917 B2 | 12/2007 | Prudent et al. |
| 7,314,599 B2 | 1/2008 | Roitman et al. |
| 7,323,320 B2 | 1/2008 | Oleinikov |
| 7,344,831 B2 | 3/2008 | Wolber et al. |
| 7,348,144 B2 | 3/2008 | Minor |
| 7,351,379 B2 | 4/2008 | Schleifer |
| 7,353,116 B2 | 4/2008 | Webb et al. |
| 7,361,906 B2 | 4/2008 | Ghosh et al. |
| 7,364,896 B2 | 4/2008 | Schembri |
| 7,368,550 B2 | 5/2008 | Dellinger et al. |
| 7,371,348 B2 | 5/2008 | Schleifer et al. |
| 7,371,519 B2 | 5/2008 | Wolber et al. |
| 7,371,580 B2 | 5/2008 | Yakhini et al. |
| 7,372,982 B2 | 5/2008 | Le |
| 7,384,746 B2 | 6/2008 | Lyamichev et al. |
| 7,385,050 B2 | 6/2008 | Dellinger et al. |
| 7,390,457 B2 | 6/2008 | Schembri |
| 7,393,665 B2 | 7/2008 | Brenner |
| 7,396,676 B2 | 7/2008 | Robotti et al. |
| 7,399,844 B2 | 7/2008 | Sampson et al. |
| 7,402,279 B2 | 7/2008 | Schembri |
| 7,411,061 B2 | 8/2008 | Myerson et al. |
| 7,413,709 B2 | 8/2008 | Roitman et al. |
| 7,417,139 B2 | 8/2008 | Dellinger et al. |
| 7,422,911 B2 | 9/2008 | Schembri |
| 7,427,679 B2 | 9/2008 | Dellinger et al. |
| 7,432,048 B2 | 10/2008 | Neri et al. |
| 7,435,810 B2 | 10/2008 | Myerson et al. |
| 7,439,272 B2 | 10/2008 | Xu |
| 7,476,709 B2 | 1/2009 | Moody et al. |

(56) References Cited

U.S. PATENT DOCUMENTS

| | | |
|---|---|---|
| 7,482,118 B2 | 1/2009 | Allawi et al. |
| 7,488,607 B2 | 2/2009 | Tom-Moy et al. |
| 7,504,213 B2 | 3/2009 | Sana et al. |
| 7,514,369 B2 | 4/2009 | Li et al. |
| 7,517,979 B2 | 4/2009 | Wolber |
| 7,524,942 B2 | 4/2009 | Wang et al. |
| 7,524,950 B2 | 4/2009 | Dellinger et al. |
| 7,527,928 B2 | 5/2009 | Neri et al. |
| 7,531,303 B2 | 5/2009 | Dorsel et al. |
| 7,534,561 B2 | 5/2009 | Sana et al. |
| 7,534,563 B2 | 5/2009 | Hargreaves |
| 7,537,936 B2 | 5/2009 | Dahm et al. |
| 7,541,145 B2 | 6/2009 | Prudent et al. |
| 7,544,473 B2 | 6/2009 | Brenner |
| 7,556,919 B2 | 7/2009 | Chenchik et al. |
| 7,563,600 B2 | 7/2009 | Oleinikov |
| 7,572,585 B2 | 8/2009 | Wang |
| 7,572,907 B2 | 8/2009 | Dellinger et al. |
| 7,572,908 B2 | 8/2009 | Dellinger et al. |
| 7,585,970 B2 | 9/2009 | Dellinger et al. |
| 7,588,889 B2 | 9/2009 | Wolber et al. |
| 7,595,350 B2 | 9/2009 | Xu |
| 7,604,941 B2 | 10/2009 | Jacobson |
| 7,604,996 B1 | 10/2009 | Stuelpnagel et al. |
| 7,608,396 B2 | 10/2009 | Delenstarr |
| 7,618,777 B2 | 11/2009 | Myerson et al. |
| 7,629,120 B2 | 12/2009 | Bennett et al. |
| 7,635,772 B2 | 12/2009 | McCormac |
| 7,648,832 B2 | 1/2010 | Jessee et al. |
| 7,651,762 B2 | 1/2010 | Xu et al. |
| 7,659,069 B2 | 2/2010 | Belyaev et al. |
| 7,678,542 B2 | 3/2010 | Lyamichev et al. |
| 7,682,809 B2 | 3/2010 | Sampson |
| 7,709,197 B2 | 5/2010 | Drmanac |
| 7,718,365 B2 | 5/2010 | Wang |
| 7,718,786 B2 | 5/2010 | Dupret et al. |
| 7,723,077 B2 | 5/2010 | Young et al. |
| 7,737,088 B1 | 6/2010 | Staehler et al. |
| 7,737,089 B2 | 6/2010 | Guimil et al. |
| 7,741,463 B2 | 6/2010 | Gormley et al. |
| 7,749,701 B2 | 7/2010 | Leproust et al. |
| 7,759,471 B2 | 7/2010 | Dellinger et al. |
| 7,776,021 B2 | 8/2010 | Borenstein et al. |
| 7,776,532 B2 | 8/2010 | Gibson et al. |
| 7,790,369 B2 | 9/2010 | Stahler et al. |
| 7,790,387 B2 | 9/2010 | Dellinger et al. |
| 7,807,356 B2 | 10/2010 | Sampson et al. |
| 7,807,806 B2 | 10/2010 | Allawi et al. |
| 7,811,753 B2 | 10/2010 | Eshoo |
| 7,816,079 B2 | 10/2010 | Fischer |
| 7,820,387 B2 | 10/2010 | Neri et al. |
| 7,829,314 B2 | 11/2010 | Prudent et al. |
| 7,855,281 B2 | 12/2010 | Dellinger et al. |
| 7,862,999 B2 | 1/2011 | Zheng et al. |
| 7,867,782 B2 | 1/2011 | Barth |
| 7,875,463 B2 | 1/2011 | Adaskin et al. |
| 7,879,541 B2 | 2/2011 | Kincaid |
| 7,879,580 B2 | 2/2011 | Carr et al. |
| 7,894,998 B2 | 2/2011 | Kincaid |
| 7,919,239 B2 | 4/2011 | Wang |
| 7,919,308 B2 | 4/2011 | Schleifer |
| 7,927,797 B2 | 4/2011 | Nobile et al. |
| 7,927,838 B2 | 4/2011 | Shannon |
| 7,932,025 B2 | 4/2011 | Carr et al. |
| 7,932,070 B2 | 4/2011 | Hogrefe et al. |
| 7,935,800 B2 | 5/2011 | Allawi et al. |
| 7,939,645 B2 | 5/2011 | Borns |
| 7,943,046 B2 | 5/2011 | Martosella et al. |
| 7,943,358 B2 | 5/2011 | Hogrefe et al. |
| 7,960,157 B2 | 6/2011 | Borns |
| 7,977,119 B2 | 7/2011 | Kronick et al. |
| 7,979,215 B2 | 7/2011 | Sampas |
| 7,998,437 B2 | 8/2011 | Berndt et al. |
| 7,999,087 B2 | 8/2011 | Dellinger et al. |
| 8,021,842 B2 | 9/2011 | Brenner |
| 8,021,844 B2 | 9/2011 | Wang |
| 8,034,917 B2 | 10/2011 | Yamada |
| 8,036,835 B2 | 10/2011 | Sampas et al. |
| 8,048,664 B2 | 11/2011 | Guan et al. |
| 8,053,191 B2 | 11/2011 | Blake |
| 8,058,001 B2 | 11/2011 | Crameri et al. |
| 8,058,004 B2 | 11/2011 | Oleinikov |
| 8,058,055 B2 | 11/2011 | Barrett et al. |
| 8,063,184 B2 | 11/2011 | Allawi et al. |
| 8,067,556 B2 | 11/2011 | Hogrefe et al. |
| 8,073,626 B2 | 12/2011 | Troup et al. |
| 8,076,064 B2 | 12/2011 | Wang |
| 8,076,152 B2 | 12/2011 | Robotti |
| 8,097,711 B2 | 1/2012 | Timar et al. |
| 8,137,936 B2 | 3/2012 | Macevicz |
| 8,148,068 B2 | 4/2012 | Brenner |
| 8,154,729 B2 | 4/2012 | Baldo et al. |
| 8,168,385 B2 | 5/2012 | Brenner |
| 8,168,388 B2 | 5/2012 | Gormley et al. |
| 8,173,368 B2 | 5/2012 | Staehler et al. |
| 8,182,991 B1 | 5/2012 | Kaiser et al. |
| 8,194,244 B2 | 6/2012 | Wang et al. |
| 8,198,071 B2 | 6/2012 | Goshoo et al. |
| 8,202,983 B2 | 6/2012 | Dellinger et al. |
| 8,202,985 B2 | 6/2012 | Dellinger et al. |
| 8,206,952 B2 | 6/2012 | Carr et al. |
| 8,213,015 B2 | 7/2012 | Kraiczek et al. |
| 8,242,258 B2 | 8/2012 | Dellinger et al. |
| 8,247,221 B2 | 8/2012 | Fawcett |
| 8,263,335 B2 | 9/2012 | Carr et al. |
| 8,268,605 B2 | 9/2012 | Sorge et al. |
| 8,283,148 B2 | 10/2012 | Sorge et al. |
| 8,288,093 B2 | 10/2012 | Hall et al. |
| 8,298,767 B2 | 10/2012 | Brenner et al. |
| 8,304,273 B2 | 11/2012 | Stellacci et al. |
| 8,309,307 B2 | 11/2012 | Barrett et al. |
| 8,309,706 B2 | 11/2012 | Dellinger et al. |
| 8,309,710 B2 | 11/2012 | Sierzchala et al. |
| 8,314,220 B2 | 11/2012 | Mullinax et al. |
| 8,318,433 B2 | 11/2012 | Brenner |
| 8,318,479 B2 | 11/2012 | Domansky et al. |
| 8,357,489 B2 | 1/2013 | Chua et al. |
| 8,357,490 B2 | 1/2013 | Froehlich et al. |
| 8,367,016 B2 | 2/2013 | Quan et al. |
| 8,367,335 B2 | 2/2013 | Staehler et al. |
| 8,380,441 B2 | 2/2013 | Webb et al. |
| 8,383,338 B2 | 2/2013 | Kitzman et al. |
| 8,415,138 B2 | 4/2013 | Leproust |
| 8,435,736 B2 | 5/2013 | Gibson et al. |
| 8,445,205 B2 | 5/2013 | Brenner |
| 8,445,206 B2 | 5/2013 | Bergmann et al. |
| 8,470,996 B2 | 6/2013 | Brenner |
| 8,476,018 B2 | 7/2013 | Brenner |
| 8,476,598 B1 | 7/2013 | Pralle et al. |
| 8,481,292 B2 | 7/2013 | Casbon et al. |
| 8,481,309 B2 | 7/2013 | Zhang et al. |
| 8,491,561 B2 | 7/2013 | Borenstein et al. |
| 8,497,069 B2 | 7/2013 | Hutchison, III et al. |
| 8,500,979 B2 | 8/2013 | Elibol et al. |
| 8,501,454 B2 | 8/2013 | Liu et al. |
| 8,507,226 B2 | 8/2013 | Carr et al. |
| 8,507,239 B2 | 8/2013 | Lubys et al. |
| 8,507,272 B2 | 8/2013 | Zhang et al. |
| 8,530,197 B2 | 9/2013 | Li et al. |
| 8,552,174 B2 | 10/2013 | Dellinger et al. |
| 8,563,478 B2 | 10/2013 | Gormley et al. |
| 8,569,046 B2 | 10/2013 | Love et al. |
| 8,577,621 B2 | 11/2013 | Troup et al. |
| 8,586,310 B2 | 11/2013 | Mitra et al. |
| 8,614,092 B2 | 12/2013 | Zhang et al. |
| 8,642,755 B2 | 2/2014 | Sierzchala et al. |
| 8,664,164 B2 | 3/2014 | Ericsson et al. |
| 8,669,053 B2 | 3/2014 | Stuelpnagel et al. |
| 8,679,756 B1 | 3/2014 | Brenner et al. |
| 8,685,642 B2 | 4/2014 | Sampas |
| 8,685,676 B2 | 4/2014 | Hogrefe et al. |
| 8,685,678 B2 | 4/2014 | Casbon et al. |
| 8,715,933 B2 | 5/2014 | Oliver |
| 8,715,967 B2 | 5/2014 | Casbon et al. |

(56) References Cited

U.S. PATENT DOCUMENTS

| | | |
|---|---|---|
| 8,716,467 B2 | 5/2014 | Jacobson |
| 8,722,368 B2 | 5/2014 | Casbon et al. |
| 8,722,585 B2 | 5/2014 | Wang |
| 8,728,766 B2 | 5/2014 | Casbon et al. |
| 8,741,606 B2 | 6/2014 | Casbon et al. |
| 8,808,896 B2 | 8/2014 | Choo et al. |
| 8,808,986 B2 | 8/2014 | Jacobson et al. |
| 8,815,600 B2 | 8/2014 | Liu et al. |
| 8,889,851 B2 | 11/2014 | Leproust et al. |
| 8,932,994 B2 | 1/2015 | Gormley et al. |
| 8,962,532 B2 | 2/2015 | Shapiro et al. |
| 8,968,999 B2 | 3/2015 | Gibson et al. |
| 8,980,563 B2 | 3/2015 | Zheng et al. |
| 9,018,365 B2 | 4/2015 | Brenner |
| 9,023,601 B2 | 5/2015 | Oleinikov |
| 9,051,666 B2 | 6/2015 | Oleinikov |
| 9,073,962 B2 | 7/2015 | Fracchia et al. |
| 9,074,204 B2 | 7/2015 | Anderson et al. |
| 9,085,797 B2 | 7/2015 | Gebeyehu et al. |
| 9,133,510 B2 | 9/2015 | Andersen et al. |
| 9,139,874 B2 | 9/2015 | Myers et al. |
| 9,150,853 B2 | 10/2015 | Hudson et al. |
| 9,187,777 B2 | 11/2015 | Jacobson et al. |
| 9,194,001 B2 | 11/2015 | Brenner |
| 9,216,414 B2 | 12/2015 | Chu |
| 9,217,144 B2 | 12/2015 | Jacobson et al. |
| 9,279,149 B2 | 3/2016 | Efcavitch et al. |
| 9,286,439 B2 | 3/2016 | Shapiro et al. |
| 9,295,965 B2 | 3/2016 | Jacobson et al. |
| 9,315,861 B2 | 4/2016 | Hendricks et al. |
| 9,328,378 B2 | 5/2016 | Earnshaw et al. |
| 9,347,091 B2 | 5/2016 | Bergmann et al. |
| 9,375,748 B2 | 6/2016 | Harumoto et al. |
| 9,376,677 B2 | 6/2016 | Mir |
| 9,376,678 B2 | 6/2016 | Gormley et al. |
| 9,384,320 B2 | 7/2016 | Church |
| 9,384,920 B1 | 7/2016 | Bakulich |
| 9,388,407 B2 | 7/2016 | Jacobson |
| 9,394,333 B2 | 7/2016 | Wada et al. |
| 9,403,141 B2 | 8/2016 | William |
| 9,409,139 B2 | 8/2016 | Banyai et al. |
| 9,410,149 B2 | 8/2016 | Brenner et al. |
| 9,410,173 B2 | 8/2016 | Betts et al. |
| 9,416,411 B2 | 8/2016 | Stuelpnagel et al. |
| 9,422,600 B2 | 8/2016 | Ramu et al. |
| 9,487,824 B2 | 11/2016 | Kutyavin et al. |
| 9,499,848 B2 | 11/2016 | Carr et al. |
| 9,523,122 B2 | 12/2016 | Zheng et al. |
| 9,528,148 B2 | 12/2016 | Zheng et al. |
| 9,534,251 B2 | 1/2017 | Young et al. |
| 9,555,388 B2 | 1/2017 | Banyai et al. |
| 9,568,839 B2 | 2/2017 | Stahler et al. |
| 9,580,746 B2 | 2/2017 | Leproust et al. |
| 9,670,529 B2 | 6/2017 | Osborne et al. |
| 9,670,536 B2 | 6/2017 | Casbon et al. |
| 9,677,067 B2 | 6/2017 | Toro |
| 9,695,211 B2 | 7/2017 | Wada et al. |
| 9,718,060 B2 | 8/2017 | Venter et al. |
| 9,745,573 B2 | 8/2017 | Stuelpnagel et al. |
| 9,745,619 B2 | 8/2017 | Rabbani et al. |
| 9,765,387 B2 | 9/2017 | Rabbani et al. |
| 9,771,576 B2 | 9/2017 | Gibson et al. |
| 9,833,761 B2 | 12/2017 | Banyai |
| 9,834,774 B2 | 12/2017 | Carstens |
| 9,839,894 B2 | 12/2017 | Banyai |
| 9,879,283 B2 | 1/2018 | Ravinder et al. |
| 9,889,423 B2 | 2/2018 | Banyai |
| 9,895,673 B2 | 2/2018 | Peck |
| 9,925,510 B2 | 3/2018 | Jacobson et al. |
| 9,932,576 B2 | 4/2018 | Raymond et al. |
| 9,981,239 B2 | 5/2018 | Banyai |
| 10,053,688 B2 | 8/2018 | Cox |
| 10,583,415 B2 | 3/2020 | Banyai et al. |
| 10,754,994 B2 | 8/2020 | Peck |
| 10,773,232 B2 | 9/2020 | Banyai et al. |
| 2001/0018512 A1 | 8/2001 | Blanchard |
| 2001/0039014 A1 | 11/2001 | Bass et al. |
| 2001/0055761 A1 | 12/2001 | Kanemoto et al. |
| 2002/0012930 A1 | 1/2002 | Rothberg et al. |
| 2002/0025561 A1 | 2/2002 | Hodgson |
| 2002/0076716 A1 | 6/2002 | Sabanayagam et al. |
| 2002/0081582 A1 | 6/2002 | Gao et al. |
| 2002/0094533 A1 | 7/2002 | Hess et al. |
| 2002/0095073 A1 | 7/2002 | Jacobs et al. |
| 2002/0119459 A1 | 8/2002 | Griffiths et al. |
| 2002/0132308 A1 | 9/2002 | Liu et al. |
| 2002/0155439 A1 | 10/2002 | Rodriguez et al. |
| 2002/0160536 A1 | 10/2002 | Regnier et al. |
| 2002/0164824 A1 | 11/2002 | Xiao et al. |
| 2003/0008411 A1 | 1/2003 | Van et al. |
| 2003/0022207 A1 | 1/2003 | Balasubramanian et al. |
| 2003/0022240 A1 | 1/2003 | Luo et al. |
| 2003/0022317 A1 | 1/2003 | Jack et al. |
| 2003/0044781 A1 | 3/2003 | Korlach et al. |
| 2003/0058629 A1 | 3/2003 | Hirai et al. |
| 2003/0064398 A1 | 4/2003 | Barnes |
| 2003/0068633 A1 | 4/2003 | Belshaw et al. |
| 2003/0082719 A1 | 5/2003 | Schumacher et al. |
| 2003/0100102 A1 | 5/2003 | Rothberg et al. |
| 2003/0108903 A1 | 6/2003 | Wang et al. |
| 2003/0120035 A1 | 6/2003 | Gao et al. |
| 2003/0138782 A1 | 7/2003 | Evans |
| 2003/0143605 A1 | 7/2003 | Lok et al. |
| 2003/0148291 A1 | 8/2003 | Robotti |
| 2003/0148344 A1 | 8/2003 | Rothberg et al. |
| 2003/0171325 A1 | 9/2003 | Gascoyne et al. |
| 2003/0186226 A1 | 10/2003 | Brennan et al. |
| 2003/0228602 A1 | 12/2003 | Parker et al. |
| 2003/0228620 A1 | 12/2003 | Du |
| 2004/0009498 A1 | 1/2004 | Short |
| 2004/0043509 A1 | 3/2004 | Stahler et al. |
| 2004/0053362 A1 | 3/2004 | De et al. |
| 2004/0086892 A1 | 5/2004 | Crothers et al. |
| 2004/0087008 A1 | 5/2004 | Schembri |
| 2004/0106130 A1 | 6/2004 | Besemer et al. |
| 2004/0106728 A1 | 6/2004 | McGall et al. |
| 2004/0110133 A1 | 6/2004 | Xu et al. |
| 2004/0175710 A1 | 9/2004 | Haushalter |
| 2004/0175734 A1 | 9/2004 | Stahler et al. |
| 2004/0191810 A1 | 9/2004 | Yamamoto |
| 2004/0213795 A1 | 10/2004 | Collins et al. |
| 2004/0219663 A1 | 11/2004 | Page et al. |
| 2004/0236027 A1 | 11/2004 | Maeji et al. |
| 2004/0248161 A1 | 12/2004 | Rothberg et al. |
| 2004/0259146 A1 | 12/2004 | Friend et al. |
| 2005/0022895 A1 | 2/2005 | Barth et al. |
| 2005/0049796 A1 | 3/2005 | Webb et al. |
| 2005/0053968 A1 | 3/2005 | Bharadwaj et al. |
| 2005/0079510 A1 | 4/2005 | Berka et al. |
| 2005/0100932 A1 | 5/2005 | Lapidus et al. |
| 2005/0112608 A1 | 5/2005 | Grossman et al. |
| 2005/0112636 A1 | 5/2005 | Hurt et al. |
| 2005/0112679 A1 | 5/2005 | Myerson et al. |
| 2005/0124022 A1 | 6/2005 | Srinivasan et al. |
| 2005/0137805 A1 | 6/2005 | Lewin et al. |
| 2005/0208513 A1 | 9/2005 | Agbo et al. |
| 2005/0227235 A1 | 10/2005 | Carr et al. |
| 2005/0255477 A1 | 11/2005 | Carr et al. |
| 2005/0266045 A1 | 12/2005 | Canham et al. |
| 2005/0277125 A1 | 12/2005 | Benn et al. |
| 2005/0282158 A1 | 12/2005 | Landegren |
| 2006/0003381 A1 | 1/2006 | Gilmore et al. |
| 2006/0003958 A1 | 1/2006 | Melville et al. |
| 2006/0012784 A1 | 1/2006 | Ulmer |
| 2006/0012793 A1 | 1/2006 | Harris |
| 2006/0019084 A1 | 1/2006 | Pearson |
| 2006/0024678 A1 | 2/2006 | Buzby |
| 2006/0024711 A1 | 2/2006 | Lapidus et al. |
| 2006/0024721 A1 | 2/2006 | Pedersen |
| 2006/0076482 A1 | 4/2006 | Hobbs et al. |
| 2006/0078909 A1 | 4/2006 | Srinivasan et al. |
| 2006/0078927 A1 | 4/2006 | Peck et al. |
| 2006/0078937 A1 | 4/2006 | Korlach et al. |
| 2006/0127920 A1 | 6/2006 | Church et al. |

(56) References Cited

U.S. PATENT DOCUMENTS

| | | |
|---|---|---|
| 2006/0134638 A1 | 6/2006 | Mulligan et al. |
| 2006/0160138 A1 | 7/2006 | Church |
| 2006/0171855 A1 | 8/2006 | Yin et al. |
| 2006/0202330 A1 | 9/2006 | Reinhardt et al. |
| 2006/0203236 A1 | 9/2006 | Ji et al. |
| 2006/0203237 A1 | 9/2006 | Ji et al. |
| 2006/0207923 A1 | 9/2006 | Li |
| 2006/0219637 A1 | 10/2006 | Killeen et al. |
| 2007/0031857 A1 | 2/2007 | Makarov et al. |
| 2007/0031877 A1 | 2/2007 | Stahler et al. |
| 2007/0043516 A1 | 2/2007 | Gustafsson et al. |
| 2007/0054127 A1 | 3/2007 | Hergenrother et al. |
| 2007/0059692 A1 | 3/2007 | Gao et al. |
| 2007/0087349 A1 | 4/2007 | Staehler et al. |
| 2007/0099208 A1 | 5/2007 | Drmanac et al. |
| 2007/0122817 A1 | 5/2007 | Church et al. |
| 2007/0141557 A1 | 6/2007 | Raab et al. |
| 2007/0196854 A1 | 8/2007 | Stahler et al. |
| 2007/0207482 A1 | 9/2007 | Church et al. |
| 2007/0207487 A1 | 9/2007 | Emig et al. |
| 2007/0231800 A1 | 10/2007 | Roberts et al. |
| 2007/0238104 A1 | 10/2007 | Barrett et al. |
| 2007/0238106 A1 | 10/2007 | Barrett et al. |
| 2007/0238108 A1 | 10/2007 | Barrett et al. |
| 2007/0259344 A1 | 11/2007 | Leproust et al. |
| 2007/0259345 A1 | 11/2007 | Sampas |
| 2007/0259346 A1 | 11/2007 | Gordon et al. |
| 2007/0259347 A1 | 11/2007 | Gordon et al. |
| 2007/0269870 A1 | 11/2007 | Church et al. |
| 2008/0085511 A1 | 4/2008 | Peck et al. |
| 2008/0085514 A1 | 4/2008 | Peck et al. |
| 2008/0087545 A1 | 4/2008 | Jensen et al. |
| 2008/0161200 A1 | 7/2008 | Yu et al. |
| 2008/0182296 A1 | 7/2008 | Chanda et al. |
| 2008/0214412 A1 | 9/2008 | Stahler et al. |
| 2008/0227160 A1 | 9/2008 | Kool |
| 2008/0233616 A1 | 9/2008 | Liss |
| 2008/0287320 A1 | 11/2008 | Baynes et al. |
| 2008/0300842 A1 | 12/2008 | Govindarajan et al. |
| 2008/0308884 A1 | 12/2008 | Kalvesten |
| 2008/0311628 A1 | 12/2008 | Shoemaker |
| 2009/0036664 A1 | 2/2009 | Peter |
| 2009/0053704 A1 | 2/2009 | Novoradovskaya et al. |
| 2009/0062129 A1 | 3/2009 | McKernan et al. |
| 2009/0087840 A1 | 4/2009 | Baynes et al. |
| 2009/0088679 A1 | 4/2009 | Wood et al. |
| 2009/0105094 A1 | 4/2009 | Heiner et al. |
| 2009/0170802 A1 | 7/2009 | Stahler et al. |
| 2009/0176280 A1 | 7/2009 | Hutchison, III et al. |
| 2009/0181861 A1 | 7/2009 | Li et al. |
| 2009/0194483 A1 | 8/2009 | Robotti et al. |
| 2009/0230044 A1 | 9/2009 | Bek |
| 2009/0238722 A1 | 9/2009 | Mora-Fillat et al. |
| 2009/0239759 A1 | 9/2009 | Balch |
| 2009/0246788 A1 | 10/2009 | Albert et al. |
| 2009/0263802 A1 | 10/2009 | Drmanac |
| 2009/0285825 A1 | 11/2009 | Kini et al. |
| 2009/0324546 A1 | 12/2009 | Notka et al. |
| 2010/0004143 A1 | 1/2010 | Shibahara |
| 2010/0009872 A1 | 1/2010 | Eid et al. |
| 2010/0047805 A1 | 2/2010 | Wang |
| 2010/0051967 A1 | 3/2010 | Bradley et al. |
| 2010/0069250 A1 | 3/2010 | White, III et al. |
| 2010/0090341 A1 | 4/2010 | Wan et al. |
| 2010/0099103 A1 | 4/2010 | Hsieh et al. |
| 2010/0160463 A1 | 6/2010 | Wang et al. |
| 2010/0167950 A1 | 7/2010 | Juang et al. |
| 2010/0173364 A1 | 7/2010 | Evans, Jr. et al. |
| 2010/0216648 A1 | 8/2010 | Staehler et al. |
| 2010/0256017 A1 | 10/2010 | Larman et al. |
| 2010/0258487 A1 | 10/2010 | Zelechonok et al. |
| 2010/0286290 A1 | 11/2010 | Lohmann et al. |
| 2010/0292102 A1 | 11/2010 | Nouri |
| 2010/0300882 A1 | 12/2010 | Zhang et al. |
| 2011/0009607 A1 | 1/2011 | Komiyama et al. |
| 2011/0082055 A1 | 4/2011 | Fox et al. |
| 2011/0114244 A1 | 5/2011 | Yoo et al. |
| 2011/0114549 A1 | 5/2011 | Yin et al. |
| 2011/0124049 A1 | 5/2011 | Li et al. |
| 2011/0124055 A1 | 5/2011 | Carr et al. |
| 2011/0126929 A1 | 6/2011 | Velasquez-Garcia et al. |
| 2011/0171651 A1 | 7/2011 | Richmond |
| 2011/0172127 A1 | 7/2011 | Jacobson et al. |
| 2011/0201057 A1 | 8/2011 | Carr et al. |
| 2011/0217738 A1 | 9/2011 | Jacobson |
| 2011/0230653 A1 | 9/2011 | Novoradovskaya et al. |
| 2011/0254107 A1 | 10/2011 | Bulovic et al. |
| 2011/0287435 A1 | 11/2011 | Grunenwald et al. |
| 2012/0003713 A1 | 1/2012 | Hansen et al. |
| 2012/0021932 A1 | 1/2012 | Mershin et al. |
| 2012/0027786 A1 | 2/2012 | Gupta et al. |
| 2012/0028843 A1 | 2/2012 | Ramu et al. |
| 2012/0032366 A1 | 2/2012 | Ivniski et al. |
| 2012/0046175 A1 | 2/2012 | Rodesch et al. |
| 2012/0050411 A1 | 3/2012 | Mabritto et al. |
| 2012/0094847 A1 | 4/2012 | Warthmann et al. |
| 2012/0128548 A1 | 5/2012 | West et al. |
| 2012/0129704 A1 | 5/2012 | Gunderson et al. |
| 2012/0149602 A1 | 6/2012 | Friend et al. |
| 2012/0164127 A1 | 6/2012 | Short et al. |
| 2012/0164633 A1 | 6/2012 | Laffler |
| 2012/0164691 A1 | 6/2012 | Eshoo et al. |
| 2012/0184724 A1 | 7/2012 | Sierzchala et al. |
| 2012/0220497 A1 | 8/2012 | Jacobson et al. |
| 2012/0231968 A1 | 9/2012 | Bruhn et al. |
| 2012/0238737 A1 | 9/2012 | Dellinger et al. |
| 2012/0258487 A1 | 10/2012 | Chang et al. |
| 2012/0264653 A1 | 10/2012 | Carr et al. |
| 2012/0270750 A1 | 10/2012 | Oleinikov |
| 2012/0270754 A1 | 10/2012 | Blake |
| 2012/0283140 A1 | 11/2012 | Chu |
| 2012/0288476 A1 | 11/2012 | Hartmann et al. |
| 2012/0289691 A1 | 11/2012 | Dellinger et al. |
| 2012/0315670 A1 | 12/2012 | Jacobson et al. |
| 2012/0322681 A1 | 12/2012 | Kung et al. |
| 2013/0005585 A1 | 1/2013 | Anderson et al. |
| 2013/0005612 A1 | 1/2013 | Carr et al. |
| 2013/0017642 A1 | 1/2013 | Milgrew et al. |
| 2013/0017977 A1 | 1/2013 | Oleinikov |
| 2013/0017978 A1 | 1/2013 | Kavanagh et al. |
| 2013/0035261 A1 | 2/2013 | Sierzchala et al. |
| 2013/0040836 A1 | 2/2013 | Himmler et al. |
| 2013/0045483 A1 | 2/2013 | Treusch et al. |
| 2013/0053252 A1 | 2/2013 | Xie et al. |
| 2013/0059296 A1 | 3/2013 | Jacobson et al. |
| 2013/0059761 A1 | 3/2013 | Jacobson et al. |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0123129 A1 | 5/2013 | Zeiner et al. |
| 2013/0130321 A1 | 5/2013 | Staehler et al. |
| 2013/0137161 A1 | 5/2013 | Zhang et al. |
| 2013/0137173 A1 | 5/2013 | Zhang et al. |
| 2013/0137174 A1 | 5/2013 | Zhang et al. |
| 2013/0137861 A1 | 5/2013 | Leproust et al. |
| 2013/0164308 A1 | 6/2013 | Foletti et al. |
| 2013/0196864 A1 | 8/2013 | Govindarajan et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0261027 A1 | 10/2013 | Li et al. |
| 2013/0281308 A1 | 10/2013 | Kung et al. |
| 2013/0296192 A1 | 11/2013 | Jacobson et al. |
| 2013/0296194 A1 | 11/2013 | Jacobson et al. |
| 2013/0298265 A1 | 11/2013 | Cunnac et al. |
| 2013/0309725 A1 | 11/2013 | Jacobson et al. |
| 2013/0323725 A1 | 12/2013 | Peter et al. |
| 2013/0330778 A1 | 12/2013 | Zeiner et al. |
| 2014/0011226 A1 | 1/2014 | Bernick et al. |
| 2014/0018441 A1 | 1/2014 | Fracchia et al. |
| 2014/0031240 A1 | 1/2014 | Behlke et al. |
| 2014/0038240 A1 | 2/2014 | Temme et al. |
| 2014/0106394 A1 | 4/2014 | Ko et al. |
| 2014/0141982 A1 | 5/2014 | Jacobson et al. |

(56) References Cited

U.S. PATENT DOCUMENTS

| | | |
|---|---|---|
| 2014/0170665 A1 | 6/2014 | Hiddessen et al. |
| 2014/0178992 A1 | 6/2014 | Nakashima et al. |
| 2014/0221250 A1 | 8/2014 | Vasquez et al. |
| 2014/0274729 A1 | 9/2014 | Kurn et al. |
| 2014/0274741 A1 | 9/2014 | Hunter et al. |
| 2014/0303000 A1 | 10/2014 | Armour et al. |
| 2014/0309119 A1 | 10/2014 | Jacobson et al. |
| 2014/0309142 A1 | 10/2014 | Tian |
| 2015/0010953 A1 | 1/2015 | Lindstrom et al. |
| 2015/0012723 A1 | 1/2015 | Park et al. |
| 2015/0031089 A1 | 1/2015 | Lindstrom |
| 2015/0038373 A1 | 2/2015 | Banyai et al. |
| 2015/0056609 A1 | 2/2015 | Daum et al. |
| 2015/0057625 A1 | 2/2015 | Coulthard |
| 2015/0065357 A1 | 3/2015 | Fox |
| 2015/0065393 A1 | 3/2015 | Jacobson |
| 2015/0099870 A1 | 4/2015 | Bennett et al. |
| 2015/0120265 A1 | 4/2015 | Amirav-Drory |
| 2015/0159152 A1 | 6/2015 | Allen et al. |
| 2015/0183853 A1 | 7/2015 | Sharma et al. |
| 2015/0191524 A1 | 7/2015 | Smith et al. |
| 2015/0191719 A1 | 7/2015 | Hudson et al. |
| 2015/0196917 A1 | 7/2015 | Kay et al. |
| 2015/0203839 A1 | 7/2015 | Jacobson et al. |
| 2015/0211047 A1 | 7/2015 | Borns |
| 2015/0225782 A1 | 8/2015 | Walder et al. |
| 2015/0240232 A1 | 8/2015 | Zamore et al. |
| 2015/0240280 A1 | 8/2015 | Gibson et al. |
| 2015/0261664 A1 | 9/2015 | Goldman et al. |
| 2015/0269313 A1 | 9/2015 | Church |
| 2015/0293102 A1 | 10/2015 | Shim |
| 2015/0307875 A1 | 10/2015 | Happe et al. |
| 2015/0321191 A1 | 11/2015 | Kendall et al. |
| 2015/0322504 A1 | 11/2015 | Lao et al. |
| 2015/0344927 A1 | 12/2015 | Sampson et al. |
| 2015/0353921 A9 | 12/2015 | Tian |
| 2015/0353994 A1 | 12/2015 | Myers et al. |
| 2015/0361420 A1 | 12/2015 | Hudson et al. |
| 2015/0361422 A1 | 12/2015 | Sampson et al. |
| 2015/0361423 A1 | 12/2015 | Sampson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0002621 A1 | 1/2016 | Nelson et al. |
| 2016/0002622 A1 | 1/2016 | Nelson et al. |
| 2016/0010045 A1 | 1/2016 | Cohen et al. |
| 2016/0017394 A1 | 1/2016 | Liang et al. |
| 2016/0017425 A1 | 1/2016 | Ruvolo et al. |
| 2016/0019341 A1 | 1/2016 | Harris et al. |
| 2016/0024138 A1 | 1/2016 | Gebeyehu et al. |
| 2016/0024576 A1 | 1/2016 | Chee et al. |
| 2016/0026753 A1 | 1/2016 | Krishnaswami et al. |
| 2016/0026758 A1 | 1/2016 | Jabara et al. |
| 2016/0032396 A1 | 2/2016 | Diehn et al. |
| 2016/0046973 A1 | 2/2016 | Efcavitch et al. |
| 2016/0046974 A1 | 2/2016 | Efcavitch et al. |
| 2016/0082472 A1 | 3/2016 | Perego et al. |
| 2016/0089651 A1 | 3/2016 | Banyai |
| 2016/0090592 A1 | 3/2016 | Banyai et al. |
| 2016/0096160 A1 | 4/2016 | Banyai et al. |
| 2016/0097051 A1 | 4/2016 | Jacobson et al. |
| 2016/0102322 A1 | 4/2016 | Ravinder et al. |
| 2016/0108466 A1 | 4/2016 | Nazarenko et al. |
| 2016/0122755 A1 | 5/2016 | Hall et al. |
| 2016/0122800 A1 | 5/2016 | Bernick et al. |
| 2016/0152972 A1 | 6/2016 | Stapleton et al. |
| 2016/0168611 A1 | 6/2016 | Efcavitch et al. |
| 2016/0184788 A1 | 6/2016 | Hall et al. |
| 2016/0200759 A1 | 7/2016 | Srivastava et al. |
| 2016/0215283 A1 | 7/2016 | Braman et al. |
| 2016/0229884 A1 | 8/2016 | Indermuhle |
| 2016/0230175 A1 | 8/2016 | Carstens |
| 2016/0230221 A1 | 8/2016 | Bergmann et al. |
| 2016/0251651 A1 | 9/2016 | Banyai et al. |
| 2016/0256846 A1 | 9/2016 | Smith et al. |
| 2016/0264958 A1 | 9/2016 | Toro et al. |
| 2016/0289758 A1 | 10/2016 | Akeson et al. |
| 2016/0289839 A1 | 10/2016 | Harumoto et al. |
| 2016/0303535 A1 | 10/2016 | Banyai et al. |
| 2016/0304862 A1 | 10/2016 | Igawa et al. |
| 2016/0304946 A1 | 10/2016 | Betts et al. |
| 2016/0310426 A1 | 10/2016 | Wu |
| 2016/0310927 A1 | 10/2016 | Banyai et al. |
| 2016/0318016 A1 | 11/2016 | Hou et al. |
| 2016/0333340 A1 | 11/2016 | Wu |
| 2016/0339409 A1 | 11/2016 | Banyai |
| 2016/0340672 A1 | 11/2016 | Banyai et al. |
| 2016/0348098 A1 | 12/2016 | Stuelpnagel et al. |
| 2016/0354752 A1 | 12/2016 | Banyai et al. |
| 2016/0355880 A1 | 12/2016 | Gormley et al. |
| 2017/0017436 A1 | 1/2017 | Church |
| 2017/0066844 A1 | 3/2017 | Glanville |
| 2017/0067099 A1 | 3/2017 | Zheng et al. |
| 2017/0073664 A1 | 3/2017 | McCafferty et al. |
| 2017/0073731 A1 | 3/2017 | Zheng et al. |
| 2017/0081660 A1 | 3/2017 | Cox |
| 2017/0081716 A1 | 3/2017 | Peck |
| 2017/0088887 A1 | 3/2017 | Makarov et al. |
| 2017/0095785 A1 | 4/2017 | Banyai |
| 2017/0096706 A1 | 4/2017 | Behlke et al. |
| 2017/0114404 A1 | 4/2017 | Behlke et al. |
| 2017/0141793 A1 | 5/2017 | Strauss et al. |
| 2017/0147748 A1 | 5/2017 | Staehler et al. |
| 2017/0151546 A1 | 6/2017 | Peck et al. |
| 2017/0159044 A1 | 6/2017 | Toro et al. |
| 2017/0175110 A1 | 6/2017 | Jacobson et al. |
| 2017/0218537 A1 | 8/2017 | Olivares |
| 2017/0233764 A1 | 8/2017 | Young et al. |
| 2017/0247473 A1 | 8/2017 | Short |
| 2017/0249345 A1 | 8/2017 | Malik et al. |
| 2017/0253644 A1 | 9/2017 | Steyaert et al. |
| 2017/0320061 A1 | 11/2017 | Venter et al. |
| 2017/0327819 A1 | 11/2017 | Banyai |
| 2017/0355984 A1 | 12/2017 | Evans et al. |
| 2017/0357752 A1 | 12/2017 | Diggans |
| 2017/0362589 A1 | 12/2017 | Banyai |
| 2018/0029001 A1 | 2/2018 | Banyai |
| 2018/0051278 A1 | 2/2018 | Cox et al. |
| 2018/0051280 A1 | 2/2018 | Gibson et al. |
| 2018/0068060 A1 | 3/2018 | Ceze et al. |
| 2018/0101487 A1 | 4/2018 | Peck |
| 2018/0104664 A1 | 4/2018 | Fernandez |
| 2018/0126355 A1 | 5/2018 | Peck |
| 2018/0142289 A1 | 5/2018 | Zeitoun |
| 2018/0171509 A1 | 6/2018 | Cox |
| 2018/0236425 A1 | 8/2018 | Banyai et al. |
| 2018/0253563 A1 | 9/2018 | Peck |
| 2018/0264428 A1 | 9/2018 | Banyai et al. |
| 2018/0326388 A1 | 11/2018 | Banyai et al. |
| 2018/0346585 A1 | 12/2018 | Zhang et al. |
| 2018/0355351 A1 | 12/2018 | Nugent et al. |
| 2019/0060345 A1 | 2/2019 | Harrison et al. |
| 2019/0118154 A1 | 4/2019 | Marsh et al. |
| 2019/0135926 A1 | 5/2019 | Glanville |
| 2019/0240636 A1 | 8/2019 | Peck et al. |
| 2019/0244109 A1 | 8/2019 | Bramlett et al. |
| 2019/0352635 A1 | 11/2019 | Toro et al. |
| 2019/0366293 A1 | 12/2019 | Banyai et al. |
| 2020/0017907 A1 | 1/2020 | Zeitoun et al. |
| 2020/0102611 A1 | 4/2020 | Zeitoun et al. |
| 2020/0156037 A1 | 5/2020 | Banyai et al. |
| 2020/0181667 A1 | 6/2020 | Wu et al. |
| 2020/0222875 A1 | 7/2020 | Peck et al. |
| 2020/0283760 A1 | 9/2020 | Nugent et al. |
| 2020/0299322 A1 | 9/2020 | Indermuhle et al. |
| 2020/0299684 A1 | 9/2020 | Toro et al. |
| 2020/0308575 A1 | 10/2020 | Sato |

FOREIGN PATENT DOCUMENTS

| | | |
|---|---|---|
| CA | 2792676 A1 | 9/2011 |
| CN | 1771336 A | 5/2006 |
| CN | 102159726 A | 8/2011 |
| CN | 103907117 A | 7/2014 |

(56) References Cited

FOREIGN PATENT DOCUMENTS

| | | | |
|---|---|---|---|
| CN | 104520864 A | 4/2015 |
| CN | 104562213 A | 4/2015 |
| CN | 104734848 A | 6/2015 |
| DE | 10260805 A1 | 7/2004 |
| EP | 0090789 A1 | 10/1983 |
| EP | 0126621 B1 | 8/1990 |
| EP | 0753057 A1 | 1/1997 |
| EP | 1314783 A1 | 5/2003 |
| EP | 1363125 A2 | 11/2003 |
| EP | 1546387 A2 | 6/2005 |
| EP | 1153127 B1 | 7/2006 |
| EP | 1728860 A1 | 12/2006 |
| EP | 1072010 B1 | 4/2010 |
| EP | 2175021 A2 | 4/2010 |
| EP | 2330216 A1 | 6/2011 |
| EP | 1343802 B1 | 5/2012 |
| EP | 2504449 A1 | 10/2012 |
| EP | 2751729 A1 | 7/2014 |
| EP | 2872629 A1 | 5/2015 |
| EP | 2928500 A1 | 10/2015 |
| EP | 2971034 A1 | 1/2016 |
| EP | 3030682 A2 | 6/2016 |
| EP | 3044228 A4 | 4/2017 |
| EP | 2994509 B1 | 6/2017 |
| EP | 3204518 A1 | 8/2017 |
| JP | 2002536977 A | 11/2002 |
| JP | 2002538790 A | 11/2002 |
| JP | 2006503586 A | 2/2006 |
| JP | 2008523786 A | 7/2008 |
| JP | 2008218579 A | 9/2008 |
| JP | 2009294195 A | 12/2009 |
| JP | 2016527313 A | 9/2016 |
| WO | WO-9015070 A1 | 12/1990 |
| WO | WO-9210092 A1 | 6/1992 |
| WO | WO-9210588 A1 | 6/1992 |
| WO | WO-9309668 A1 | 5/1993 |
| WO | WO-9525116 A1 | 9/1995 |
| WO | WO-9526397 A1 | 10/1995 |
| WO | WO-9615861 A1 | 5/1996 |
| WO | WO-9710365 A1 | 3/1997 |
| WO | WO-9822541 A2 | 5/1998 |
| WO | WO-9841531 A2 | 9/1998 |
| WO | WO-9942813 A1 | 8/1999 |
| WO | WO-0013017 A2 | 3/2000 |
| WO | WO-0018957 A1 | 4/2000 |
| WO | WO-0042559 A1 | 7/2000 |
| WO | WO-0042560 A2 | 7/2000 |
| WO | WO-0042561 A2 | 7/2000 |
| WO | WO-0049142 A1 | 8/2000 |
| WO | WO-0053617 A1 | 9/2000 |
| WO | WO-0156216 A2 | 8/2001 |
| WO | WO-0210443 A1 | 2/2002 |
| WO | WO-0156216 A3 | 3/2002 |
| WO | WO-0220537 A2 | 3/2002 |
| WO | WO-0224597 A2 | 3/2002 |
| WO | WO-0227638 A1 | 4/2002 |
| WO | WO-0233669 A1 | 4/2002 |
| WO | WO-02072791 A2 | 9/2002 |
| WO | WO-03040410 A1 | 5/2003 |
| WO | WO-03046223 A1 | 6/2003 |
| WO | WO-03054232 A2 | 7/2003 |
| WO | WO-03064026 A1 | 8/2003 |
| WO | WO-03064027 A2 | 8/2003 |
| WO | WO-03064699 A2 | 8/2003 |
| WO | WO-03065038 A2 | 8/2003 |
| WO | WO-03066212 A2 | 8/2003 |
| WO | WO-03089605 A2 | 10/2003 |
| WO | WO-03093504 A1 | 11/2003 |
| WO | WO-03100012 A2 | 12/2003 |
| WO | WO-2004024886 A2 | 3/2004 |
| WO | WO-2004029220 A2 | 4/2004 |
| WO | WO-2004029586 A1 | 4/2004 |
| WO | WO-2004031351 A2 | 4/2004 |
| WO | WO-2004031399 A2 | 4/2004 |
| WO | WO-2004059556 A2 | 7/2004 |
| WO | WO-2005014850 A2 | 2/2005 |
| WO | WO-2005051970 A2 | 6/2005 |
| WO | WO-2005059096 A2 | 6/2005 |
| WO | WO-2005059097 A2 | 6/2005 |
| WO | WO-2006023144 | 3/2006 |
| WO | WO-2006044956 A1 | 4/2006 |
| WO | WO-2006076679 A1 | 7/2006 |
| WO | WO-2006116476 A1 | 11/2006 |
| WO | WO-2007109221 A2 | 9/2007 |
| WO | WO-2007120627 A2 | 10/2007 |
| WO | WO-2007137242 A2 | 11/2007 |
| WO | WO-2008003116 A2 | 1/2008 |
| WO | WO-2008006078 A2 | 1/2008 |
| WO | WO-2008027558 A2 | 3/2008 |
| WO | WO-2008045380 | 4/2008 |
| WO | WO-2008054543 A2 | 5/2008 |
| WO | WO-2008063134 A1 | 5/2008 |
| WO | WO-2008063135 A1 | 5/2008 |
| WO | WO-2008109176 A2 | 9/2008 |
| WO | WO-2010025310 A2 | 3/2010 |
| WO | WO-2010025566 A1 | 3/2010 |
| WO | WO-2010027512 A2 | 3/2010 |
| WO | WO-2010089412 A1 | 8/2010 |
| WO | WO-2010141433 A2 | 12/2010 |
| WO | WO-2010141433 A3 | 4/2011 |
| WO | WO-2011053957 A2 | 5/2011 |
| WO | WO-2011056644 A2 | 5/2011 |
| WO | WO-2011056872 A2 | 5/2011 |
| WO | WO-2011066185 A1 | 6/2011 |
| WO | WO-2011066186 A1 | 6/2011 |
| WO | WO-2011085075 A2 | 7/2011 |
| WO | WO-2011103468 A2 | 8/2011 |
| WO | WO-2011109031 A1 | 9/2011 |
| WO | WO-2011143556 A1 | 11/2011 |
| WO | WO-2011150168 A1 | 12/2011 |
| WO | WO-2011161413 A2 | 12/2011 |
| WO | WO-2012013913 A1 | 2/2012 |
| WO | WO-2012061832 A1 | 5/2012 |
| WO | WO-2012078312 A2 | 6/2012 |
| WO | WO-2012149171 A1 | 11/2012 |
| WO | WO-2012154201 A1 | 11/2012 |
| WO | WO-2013030827 A1 | 3/2013 |
| WO | WO-2013032850 A2 | 3/2013 |
| WO | WO-2013036668 A1 | 3/2013 |
| WO | WO-2013101896 A1 | 7/2013 |
| WO | WO-2013154770 A1 | 10/2013 |
| WO | WO-2013177220 A1 | 11/2013 |
| WO | WO-2014004393 A1 | 1/2014 |
| WO | WO-2014008447 A1 | 1/2014 |
| WO | WO-2014035693 A2 | 3/2014 |
| WO | WO-2014088693 A1 | 6/2014 |
| WO | WO-2014089160 A1 | 6/2014 |
| WO | WO-2014093330 A1 | 6/2014 |
| WO | WO-2014093694 A1 | 6/2014 |
| WO | WO-2014151117 A1 | 9/2014 |
| WO | WO-2014151696 A1 | 9/2014 |
| WO | WO-2014160004 A1 | 10/2014 |
| WO | WO-2014160059 A1 | 10/2014 |
| WO | WO-2014206304 A1 | 12/2014 |
| WO | WO-2015017527 A2 | 2/2015 |
| WO | WO-2015021080 A2 * | 2/2015 ............ C12N 15/66 |
| WO | WO-2015021280 A2 | 2/2015 |
| WO | WO-2015031689 A1 | 3/2015 |
| WO | WO-2015040075 A1 | 3/2015 |
| WO | WO-2015054292 A1 | 4/2015 |
| WO | WO-2015066174 A1 | 5/2015 |
| WO | WO-2015081114 A2 | 6/2015 |
| WO | WO-2015081142 A1 | 6/2015 |
| WO | WO-2015090879 A1 | 6/2015 |
| WO | WO-2015095404 A2 | 6/2015 |
| WO | WO-2015120403 A1 | 8/2015 |
| WO | WO-2015136072 A1 | 9/2015 |
| WO | WO-2015160004 A1 | 10/2015 |
| WO | WO-2015175832 A1 | 11/2015 |
| WO | WO-2016007604 A1 | 1/2016 |
| WO | WO-2016011080 A2 * | 1/2016 ............ C12N 15/63 |
| WO | WO-2016022557 A1 | 2/2016 |
| WO | WO-2016053883 A1 | 4/2016 |
| WO | WO-2016055956 A1 | 4/2016 |

(56) References Cited

FOREIGN PATENT DOCUMENTS

| | | |
|---|---|---|
| WO | WO-2016065056 A1 | 4/2016 |
| WO | WO-2016126882 A1 | 8/2016 |
| WO | WO-2016126987 A1 | 8/2016 |
| WO | WO-2016130868 A2 | 8/2016 |
| WO | WO-2016161244 A2 | 10/2016 |
| WO | WO-2016162127 A1 | 10/2016 |
| WO | WO-2016172377 A1 | 10/2016 |
| WO | WO-2016173719 A1 | 11/2016 |
| WO | WO-2016183100 A1 | 11/2016 |
| WO | WO-2017017423 A1 | 2/2017 |
| WO | WO-2017049231 A1 | 3/2017 |
| WO | WO-2017053450 A1 | 3/2017 |
| WO | WO-2017059399 A1 | 4/2017 |
| WO | WO-2017095958 A1 | 6/2017 |
| WO | WO-2017100441 A1 | 6/2017 |
| WO | WO-2017118761 A1 | 7/2017 |
| WO | WO-2017158103 A1 | 9/2017 |
| WO | WO-2017214574 A1 | 12/2017 |
| WO | WO-2018026920 A1 | 2/2018 |
| WO | WO-2018038772 A1 | 3/2018 |
| WO | WO-2018057526 A2 | 3/2018 |
| WO | WO-2018094263 A1 | 5/2018 |
| WO | WO-2018112426 A1 | 6/2018 |
| WO | WO-2018156792 A1 | 8/2018 |
| WO | WO-2018170164 A1 | 9/2018 |
| WO | WO-2018170169 A1 | 9/2018 |
| WO | WO-2018200380 A1 | 11/2018 |
| WO | WO-2018231872 A1 | 12/2018 |
| WO | WO-2019051501 A1 | 3/2019 |
| WO | WO-2019079769 A1 | 4/2019 |
| WO | WO-2019084500 A1 | 5/2019 |
| WO | WO-2019136175 A1 | 7/2019 |
| WO | WO-2019222706 A1 | 11/2019 |
| WO | WO-2020139871 A1 | 7/2020 |
| WO | WO-2020176362 A1 | 9/2020 |
| WO | WO-2020176678 A1 | 9/2020 |
| WO | WO-2020176680 A1 | 9/2020 |

OTHER PUBLICATIONS

European Patent Application No. 14834665.3 Further Examination Report dated Nov. 28, 2018.
European Patent Application No. 16847497.1 Extended European Search Report dated Jan. 9, 2019.
European Patent Application No. 16871446.7 European Search Report dated Apr. 10, 2019.
International Application No. PCT/US2017/026232 International Preliminary Report on Patentability dated Feb. 26, 2019.
International Application No. PCT/US2017/045105 International Preliminary Report on Patentability dated Feb. 5, 2019.
International Application No. PCT/US2017/052305 International Preliminary Report on Patentability dated Apr. 30, 2019.
International Application No. PCT/US2017/062391 International Preliminary Report on Patentability dated May 21, 2019.
International Application No. PCT/US2018/050511 International Search Report and Written Opinion dated Jan. 11, 2019.
International Application No. PCT/US2018/057857 International Search Report and Written Opinion dated Mar. 18, 2019.
International Application No. PCT/US2019/012218 International Search Report and Written Opinion dated Mar. 21, 2019.
Light source unit for printable patterning VUV-Aligner / USHIO Inc., Link here: https://www.ushio.co.jp/en/products/1005.html, published Apr. 25, 2016, printed from the internet on Aug. 2, 2016, 3 pages.
Mazor et al.: Isolation of Full-Length IgG Antibodies from Combinatorial Libraries Expressed in *Escherichia coli;* Antony S. Dimitrov (ed.), Therapeutic Antibodies: Methods and Protocols, vol. 525, Chapter 11, pp. 217-239 (2009).
Jo et al.: Engineering therapeutic antibodies targeting G-protein-coupled receptors; Experimental & Molecular Medicine; 48; 9 pages (2016).
Lausted et al.: POSaM: a fast, flexible, open-source, inkjet oligonucleotide synthesizer and microarrayer; Genome Biology 2004, 5:R58.
Douthwaite et al.: Affinity maturation of a novel antagonistic human monoclonal antibody with a long VH CDR3 targeting the Class A GPCR formyl-peptide receptor 1; mAbs, vol. 7, Iss. 1, pp. 152-166 (Jan. 1, 2015).
PCT/US2018/037161 International Search Report and Written Opinion dated Oct. 22, 2018.
PCT/US2018/056783 International Search Report and Written Opinion of the International Searching Authority dated Dec. 20, 2018.
Martinez-Torrecuadrada et al.: Targeting the Extracellular Domain of Fibroblast Growth Factor Receptor 3 with Human Single-Chain Fv Antibodies Inhibits Bladder Carcinoma Cell Line Proliferation; Clinical Cancer Research; vol. 11; pp. 6282-6290 (2005).
U.S. Appl. No. 15/187,714 Office Action dated Apr. 4, 2019.
U.S. Appl. No. 15/603,013 Office Action dated Jun. 26, 2019.
U.S. Appl. No. 14/885,963 Office Action dated Feb. 5, 2016.
U.S. Appl. No. 15/015,059 Office Action dated Feb. 7, 2019.
U.S. Appl. No. 15/156,134 Office Action dated Apr. 4, 2019.
U.S. Appl. No. 15/187,714 Restriction Requirement dated Sep. 17, 2018.
U.S. Appl. No. 15/268,422 Office Action dated Mar. 1, 2019.
U.S. Appl. No. 15/268,422 Restriction Requirement dated Oct. 4, 2018.
U.S. Appl. No. 15/377,547 Final Office Action dated Feb. 8, 2019.
U.S. Appl. No. 15/433,909 Non-Final Office Action dated Feb. 8, 2019.
U.S. Appl. No. 15/433,909 Restriction Requirement dated Sep. 17, 2018.
U.S. Appl. No. 15/602,991 Final Office Action dated Dec. 13, 2018.
U.S. Appl. No. 15/602,991 Office Action dated May 31, 2019.
U.S. Appl. No. 15/709,274 Notice of Allowance dated Apr. 3, 2019.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated May 30, 2019.
U.S. Appl. No. 15/816,995 Restriction Requirement dated Apr. 4, 2019.
U.S. Appl. No. 15/844,395 Restriction Requirement dated May 17, 2019.
U.S. Appl. No. 15/860,445 Final Office Action dated Dec. 13, 2018.
U.S. Appl. No. 15/921,479 Restriction Requirement dated May 24, 2019.
U.S. Appl. No. 15/151,316 Final Office Action dated Feb. 21, 2019.
Wu, et al. "Sequence-Specific Capture of Protein-DNA Complexes for Mass Spectrometric Protein Identification" PLoS ONE. Oct. 20, 2011, vol. 6, No. 10.
Zhou, et al. "Establishment and application of a loop-mediated isothermal amplification (LAMP) system for detection of cry1Ac transgenic sugarcane" Scientific Reports May 9, 2014, vol. 4, No. 4912.
Abudayyeh et al., C2c2 is a single-component programmable RNA-guided RNA-targeting CRISPR effector. Science, available on line, Jun. 13, 2016, at: http://zlab.mit.edu/assets/reprints/Abudayyeh_OO_Science_2016.pdf , 17 pages.
Acevedo-Rocha et al. Directed evolution of stereoselective enzymes based on genetic selection as opposed to screening systems. J. Biotechnol. 191:3-10 (2014).
Adessi, et al. Solid phase DNA amplification: characterisation of primer attachment and amplification mechanisms. Nucleic Acids Res. 28(20):E87, 2000.
Alexeyev, Mikhail F. et al., Gene synthesis, bacterial expression and purification of the Rickettsia prowazekii ATP/ADP translocase, Biochimica et Biophysics Acta, 1419:299-306, 1999.
Al-Housseiny et al., Control of interfacial instabilities using flow geometry Nature Physics, 8:747-750, 2012.
Amblard, Francois et al., A magnetic manipulator for studying local rheology and micromechanical properties of biological systems, Rev. Sci. Instrum., 67(3):18-827, 1996.
Andoni and Indyk, Near-Optimal Hashing Algorithms for Approximate Nearest Neighbor in High Dimensions, Communications of the ACM, 51(1):117-122, 2008.

(56) References Cited

OTHER PUBLICATIONS

Arand et al. Structure of Rhodococcus erythropolis limonene-1,2-epoxide hydrolase reveals a novel active site. EMBO J. 22:2583-2592 (2003).
Arkles, et al. The Role of Polarity in the Structure of Silanes Employed in Surface Modification. Silanes and Other Coupling Agents. 5:51-64, 2009.
Arkles, Hydrophobicity, Hydrophilicity Reprinted with permission from the Oct. 2006 issue of Paint & Coatings Industry magazine, Retrieved on Mar. 19, 2016, 10 pages.
Assi, Fabiano et al., Massive-parallel adhesion and reactivity—measurements using simple and inexpensive magnetic tweezers, J. Appl. Phys., 92(9):5584-5586, 2002.
ATDBio, Nucleic Acid Structure, Nucleic Acids Book, 9 pages, published on Jan. 22, 2005. from: http://www.atdbio.com/content/5/Nucleic-acid-structure.
ATDBio, Solid-Phase Oligonucleotide Synthesis, Nucleic Acids Book, 20 pages, Published on Jul. 31, 2011. from: http://www.atdbio.com/content/17/Solid-phase-oligonucleotide-synthesis.
Au, Lo-Chun et al. Gene synthesis by a LCR-based approach: high level production of Leptin-L54 using synthetic gene in *Escherichia coli*, Biochemical and Biophysical Research Communications, 248:200-203, 1998.
Baedeker, Mathias et al., Overexpression of a designed 2.2kb gene of eukaryotic phenylalanine ammonialyase in *Escherichia coli*. FEBS Letters, 457:57-60, 1999.
Barbee, et al. Magnetic Assembly of High-Density DNA Arrays for Genomic Analyses. Anal Chem. 80(6):2149-2154, 2008.
Barton et al., A desk electrohydrodynamic jet printing system. Mechatronics, 20:611-616, 2010.
Beaucage, et al. Advances in the synthesis of oligonucleotides by the phosphoramidite approach. Tetrahedron. 48:2223-2311, 1992.
Beaucage, et al. Deoxynucleoside phosphoramidites—A new class of key intermediates for deoxypolynucleotide synthesis. Tetrahedron Lett. 22(20):1859-1862, 1981.
Beaucage, Serge L. et al., The Chemical synthesis of DNA/RNA Chapter 2 in: Encyclopedia of Cell Biology, 1:36-53, 2016.
Beaulieu, Martin et al., PCR candidate region mismatch scanning adaptation to quantitative, high-throughput genotyping, Nucleic Acids Research, 29(5):1114-1124, 2001.
Beigelman, et al. Base-modified phosphoramidite analogs of pyrimidine ribonucleosides for RNA structure-activity studies. Methods Enzymol. 317:39-65, 2000.
Bethge et al., Reverse synthesis and 3'-modification of RNA. Jan. 1, 2011, pp. 64-64, XP055353420. Retrieved from the Internet: URL:http://www.is3na.org/assets/events/Category%202-Medicinal %20Chemistry%20of%20Oligonucleotides%20%2864-108%29.pdf.
Binkowski et al., Correcting errors in synthetic DNA through consensus shuffling. Nucleic Acids Research, 33(6):e55, 8 pages, 2005.
Biswas, Indranil et al., Identification and characterization of a thermostable MutS homolog from Thermus aquaticus, The Journal of Biological Chemistry, 271(9):5040-5048, 1996.
Biswas, Indranil et al., Interaction of MutS protein with the major and minor grooves of a heteroduplex DNA, The Journal of Biological Chemistry, 272(20):13355-13364, 1997.
Bjornson, Keith P. et al., Differential and simultaneous adenosine Di- and Triphosphate binding by MutS, The Journal of Biological Chemistry, 278(20):18557-18562, 2003.
Blanchard, et al. High-Density Oligonucleotide Arrays. Biosens. & Bioelectronics. 1996; 11:687-690.
Blanchard, in: Genetic Engineering, Principles and Methods, vol. 20, Ed. J. Sedlow, New York: Plenum Press, p. 111-124, 1979.
Blawat et al., Forward error correction for DNA data storage. Procedia Computer Science, 80:1011-1022, 2016.
Bonini and Mondino, Adoptive T-cell therapy for cancer: The era of engineered T cells. European Journal of Immunology, 45:2457-2469, 2015.
Bornholt et al., A DNA-Based Archival Storage System, in International Conference on Architectural Support for Programming Languages and Operating Systems (ASPLOS), Apr. 2-6, 2016, Atlanta, GA, 2016, 637-649.
Borovkov et al., High-quality gene assembly directly from unpurified mixtures of microassay-synthesized oligonucleotides. Nucleic Acid Research, 38(19):e180, 10 pages, 2010.
Brunet, Aims and methods of biosteganography. Journal of Biotechnology, 226:56-64, 2016.
Buermans et al., Next Generation sequencing technology: Advances and applications, Biochimica et Biophysica Acta (BBA)—Molecular Basis of Disease, 1842:1931-1941, 2014.
Butler, et al. In situ synthesis of oligonucleotide arrays by using surface tension. J Am Chem Soc. 123(37):8887-94, 2001.
Calvert. Lithographically patterned self-assembled films. In: Organic Thin Films and Surfaces: Directions for the Nineties, vol. 20, p. 109, ed. By Abraham Ulman, San Diego: Academic Press, 1995.
Cardelli, Two-Domain DNA Strand Displacement, Electron. Proc. Theor. Comput. Sci., 26:47-61, 2010.
Carlson, Time for New DNA Synthesis and Sequencing Cost Curves, 2014. [Online]. Available: http://www.synthesis.cc/synthesis/2014/02/time_for_new_cost_curves_2014. 10 pages.
Carr, et al. Protein-mediated error correction for de novo DNA synthesis. Nucleic Acids Res. 32(20):e162, 9 pages, 2004.
Carter and Friedman, DNA synthesis and Biosecurity: Lessons learned and options for the future. J. Craig Venter Institute, La Jolla, CA, 28 pages, Oct. 2015.
Caruthers, Chemical synthesis of deoxyoligonucleotides by the phosphoramidite method. In Methods in Enzymology, Chapter 15, 154:287-313, 1987.
Caruthers. Gene synthesis machines: DNA chemistry and its uses. Science 230(4723):281-285 (1985).
Caruthers, The Chemical Synthesis of DNA/RNA: Our Gift to Science. J. Biol. Chem., 288(2):1420-1427, 2013.
Casmiro, Danilo R. et al., PCR-based gene synthesis and protein NMR spectroscopy, Structure, 5(11):1407-1412, 1997.
CeGaT. Tech Note available at https://www.cegat.de/web/wp-content/uploads/2018/06/Twist-Exome-Tech-Note.pdf (4 pgs.) (2018).
Cello, et al. Chemical synthesis of poliovirus cDNA: generation of infectious virus in the absence of natural template. Science. 297(5583):1016-8, 2000.
Chalmers, et al. Scaling up the ligase chain reaction-based approach to gene synthesis. Biotechniques. 30(2):249-52, 2001.
Chan, et al. Natural and engineered nicking endonucleases—from cleavage mechanism to engineering of strand-specificity. Nucleic Acids Res. 39(1):1-18, 2011.
Chen, et al. Chemical modification of gene silencing oligonucleotides for drug discovery and development. Drug Discov Today. 10(8):587-93 2005.
Chen et al., Programmable chemical controllers made from DNA, Nat. Nanotechnol., 8(10):755-762, 2013.
Cheng, et al. High throughput parallel synthesis of oligonucleotides with 1536 channel synthesizer. Nucleic Acids Res. 30(18):e93, 2002.
Chilamakuri et al. Performance comparison of four exome capture systems for deep sequencing. BMC Genomics 15(1):449 (2014).
Cho, et al. Capillary passive valve in microfluidic systems. NSTI-Nanotech. 2004; 1:263-266.
Chrisey et al., Fabrication of patterned DNA surfaces Nucleic Acids Research, 24(15):3040-3047 (1996).
Chung et al., One-step preparation of competent *Escherichia coli*: Transformation and storage of bacterial cells in the same solution. Proc Natl Acad Sci U S A. Apr. 1989;86(7):2172-2175.
Church et al., Next-generation digital information storage in DNA. Science, 337:6102, 1628-1629, 2012.
Cleary et al. Production of complex nucleic acid libraries using highly parallel in situ oligonucleotide synthesis. Nat Methods 1(3):241-248 (2004).
Cohen et al., Human population: The next half century. Science, 302:1172-1175, 2003.
Co-pending U.S. Appl. No. 15/921,479, filed Mar. 14, 2018.
Co-pending U.S. Appl. No. 15/921,537, filed Mar. 14, 2018.
Co-pending U.S. Appl. No. 16/006,581, filed Jun. 12, 2018.

(56) References Cited

OTHER PUBLICATIONS

Crick. On protein synthesis. Symp Soc Exp Biol12:138-163,1958.
Cruse et al. Atlas of Immunology, Third Edition. Boca Raton:CRC Press (pp. 282-283) (2010).
Cutler, David J. et al., High-throughput variation detection and genotyping using microarrays, Genome Research, vol. 11, 1913-19 (2001).
Dahl, et al. Circle-to-circle amplification for precise and sensitive DNA analysis. Proc Natl Acad Sci U S A. Mar. 30, 2004;101(13):4548-53. Epub Mar. 15, 2004.
De Mesmaeker, et al. Backbone modifications in oligonucleotides and peptide nucleic acid systems. Curr Opin Struct Biol. Jun. 1995;5(3):343-55.
De Silva et al. New Trends of Digital Data Storage in DNA. BioMed Res Int. 2016:8072463 (2016).
Deamer, David W. et al., Characterization of nucleic acids by nanopore analysis, Ace. Cham. Res., vol. 35, No. 10, 817-825 (2002).
Deaven, The Human Genome Project: Recombinant clones for mapping and sequencing DNA. Los Alamos Science, 20:218-249, 1992.
Deng et al., Targeted bisulfite sequencing reveals changes in DNA methylation associated with nuclear reprogramming Nature Biotechnology, 27:352-360 (2009).
Dietrich, Rudiger.et al., Gene assembly based on blunt-ended double-stranded DNA-modules, Biotechnology Techniques, vol. 12, No. 1, 49-54 (Jan. 1998).
Dillon et al. Exome sequencing has higher diagnostic yield compared to simulated disease-specific panels in children with suspected monogenic disorders. Eur J Hum Genet 26(5):644-651 (2018).
Dormitzer et al., Synthetic generation of influenza vaccine viruses for rapid response to pandemics. Sci Translational Medicine, 5(185):185ra68, 14 pages, 2013.
Doudna et al. Genome editing. The new frontier of genome engineering with CRISPR-Cas9. Science 346(6213):1258096-1-1258096-9, 2014.
Dower et al., High efficiency transformation of E.coli by high voltage electroporation. Nucleic Acids Res. 16(13):6127-45 (1988).
Dressman, et al. Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Drmanac, et al. Human genome sequencing using unchained base reads on self-assembling DNA nanoarrays. Science. Jan. 1, 2010;327(5961):78-81. doi: 10.1126/science.1181498. Epub Nov. 5, 2009.
Droege and Hill, The Genome Sequencer FLXTM System-Longer reads, more applications, straight forward bioinformatics and more complete data sets Journal of Biotechnology, 136:3-10, 2008.
Duffy, et al. Rapid Prototyping of Microfluidic Systems in Poly(dimethylsiloxane). Anal Chem. Dec. 1, 1998;70(23):4974-84. doi: 10.1021/ac980656z.
Duggan, et al. Expression profiling using cDNA microarrays. Nat Genet. Jan. 1999;21(1 Suppl):10-4.
Dvorsky. Living Bacteria Can Now Store Data. GIZMODO internet publication. Retrieved from https://gizmodo.com/living-bacteria-can-now-store-data-1781773517 (4 pgs) (Jun. 10, 2016).
Eadie, et al. Guanine modification during chemical DNA synthesis. Nucleic Acids Res. Oct. 26, 1987;15(20):8333-49.
Eisen, Jonathan A., A phylogenomic study of the MutS family of proteins, Nucleic Acids Research, vol. 26, No. 18, 4291-4300 (1998).
Ellis, et al. DNA assembly for synthetic biology: from parts to pathways and beyond. Integr Biol (Camb). Feb. 2011;3(2):109-18. doi: 10.1039/c0ib00070a. Epub Jan. 19, 2011.
El-Sagheer, et al. Biocompatible artificial DNA linker that is read through by DNA polymerases and is functional in *Escherichia coli*. Proc Natl Acad Sci U S A. Jul. 12, 2011;108(28):11338-43. doi: 10.1073/pnas.1101519108. Epub Jun. 27, 2011.
Elsik et al., The Genome sequence of taurine cattle: A window of ruminant biology and evolution. Science, 324:522-528, 2009.
Elsner et al., 172 nm excimer VUV-triggered photodegradation and micropatterning of aminosilane films, Thin Solid Films, 517:6772-6776 (2009).
Engler, et al. A one pot, one step, precision cloning method with high throughput capability. PLoS One. 2008;3(11):e3647. doi: 10.1371/journal.pone.0003647. Epub Nov. 5, 2008.
Engler, et al. Golden gate shuffling: a one-pot DNA shuffling method based on type IIs restriction enzymes. PLoS One. 2009;4(5):e5553. doi: 10.1371/journal.pone.0005553. Epub May 14, 2009.
Erlich and Zielinski, DNA fountain enables a robust and efficient storage architecture. Science, 355(6328):950-054, 2017.
European Patent Application No. 12827479.2 Extended European Search Report dated May 18, 2015.
European Patent Application No. 12827479.2 Partial European Search Report dated Jan. 29, 2015.
European Patent Application No. 14834665.3 Communication dated Jan. 16, 2018.
European Patent Application No. 14834665.3 extended European Search Report dated Apr. 28, 2017.
European Patent Application No. 14834665.3 Office Action dated May 2, 2018.
Evans et al., DNA Repair Enzymes. Current Protocols in Molecular Biology 84:III:3.9:3.9.1-3.9.12 http://www.ncbi.nlm.nih.gov/pubmed/18972391 (Published online Oct. 1, 2008 Abstract only provided).
Fahy, et al. Self-sustained sequence replication (3SR): an isothermal transcription-based amplification system alternative to PCR. PCR Methods Appl. Aug. 1991;1(1):25-33.
Fedoryak, Olesya D. et al., Brominated hydroxyquinoline as a photolabile protecting group with sensitivity to multiphoton excitation, Org. Lett., vol. 4, No. 2, 3419-3422 (2002).
Ferretti et al., Total synthesis of a gene for bovine rhodopsin. PNAS, 83:599-603 (1986).
Finger et al., The wonders of Flap Endonucleases: Structure, function, mechanism and regulation. Subcell Biochem., 62:301-326, 2012.
Fodor et al. Light-Directed, Spatially Addressable Parallel Chemical Synthesis. Science 251(4995):767-773 (1991).
Fogg et al., Structural basis for uracil recognition by archaeal family B DNA polymerases. Nature Structural Biology, 9(12):922-927, 2002.
Foldesi, et al. The synthesis of deuterionucleosides. Nucleosides Nucleotides Nucleic Acids. Oct.-Dec. 2000;19(10-12):1615-56.
Frandsen, et al. Efficient four fragment cloning for the construction of vectors for targeted gene replacement in filamentous fungi. BMC Molecular Biology 2008, 9:70.
Frandsen. Experimental setup. Dec. 7, 2010, 3 pages. http://www.rasmusfrandsen.dk/experimental_setup.htm.
Frandsen. The User Friendly technology. User cloning. Oct. 7, 2010, 2 pages. http://www.rasmusfrandsen.dk/user_cloning.htm.
Fullwood et al., Next-generation DNA sequencing of paired-end tags [PET] for transcriptome and genome analysis Genome Research, 19:521-532, 2009.
Galneder. et al., Microelectrophoresis of a bilayer-coated silica bead in an optical trap: application to enzymology. Biophysical Journal, vol. 80, No. 5, 2298-2309 (May 2001).
Gao, et al. A flexible light-directed DNA chip synthesis gated by deprotection using solution photogenerated acids. Nucleic Acids Res. Nov. 15, 2001;29(22):4744-50.
Gao et al. A method for the generation of combinatorial antibody libraries using pIX phage display. PNAS 99(20):12612-12616 (2002).
Gao, et al. Thermodynamically balanced inside-out (TBIO) PCR-based gene synthesis: a novel method of primer design for high-fidelity assembly of longer gene sequences. Nucleic Acids Res. Nov. 15, 2003;31(22):e143.
Garaj, et al. Graphene as a subnanometre trans-electrode membrane. Nature. Sep. 9, 2010;467(7312):190-3. doi: 10.1038/nature09379.
Garbow, Norbert et al., Optical tweezing electrophoresis of isolated, highly charged colloidal spheres, Colloids and Surfaces A: Physiochem. Eng. Aspects, vol. 195, 227-241 (2001).

(56) References Cited

OTHER PUBLICATIONS

GeneArt Seamless Cloning and Assembly Kits. Life Technologies Synthetic Biology. 8 pages, available online Jun. 15, 2012.
Genomics 101. An Introduction to the Genomic Workflow. 2016 edition, 64 pages. Available at: http://www.frontlinegenomics.com/magazine/6757/genomics-101/.
Geu-Flores, et al. USER fusion: a rapid and efficient method for simultaneous fusion and cloning of multiple PCR products. Nucleic Acids Res. 2007;35(7):e55. Epub Mar. 27, 2007.
Gibson Assembly. Product Listing. Application Overview. 2 pages, available online Dec. 16, 2014.
Gibson, et al. Complete chemical synthesis, assembly, and cloning of a Mycoplasma genitalium genome. Science. Feb. 29, 2008;319(5867):1215-20. doi: 10.1126/science.1151721. Epub Jan. 24, 2008.
Gibson et al. Creation of a Bacterial Cell Controlled by a Chemically Synthesized Genome. Science 329(5989):52-56 (2010).
Goldfeder et al. Medical implications of technical accuracy in genome sequencing. Genome Med 8(1):24 (2016).
Goldman et al., Towards practical, high-capacity, low-maintenance information storage in synthesized DNA, Nature, 494(7435):77-80, 2013.
Gosse, Charlie et al. Magnetic tweezers: micromanipulation and force measurement at the molecular level, Biophysical Journal, vol. 8, 3314-3329 (Jun. 2002).
Grass, et al., Robust chemical preservation of digital information on DNA in silica with error-correcting codes, Angew. Chemie—Int. Ed., 54(8):2552-2555, 2015.
Greagg et al., A read-ahead function in archaeal DNA polymerases detects promutagenic template-strand uracil. Proc. Nat. Acad. Sci. USA, 96:9045-9050, 1999.
Grovenor. Microelectronic materials. Graduate Student Series in Materials Science and Engineering. Bristol, England: Adam Hilger, 1989; p. 113-123.
Gu et al., Depletion of abundant sequences by hybridization (DASH): using Cas9 to remove unwanted high-abundance species in sequencing libraries and molecular counting applications. Genome Biology, 17:41, 13 pages, 2016.
Haber, Charbel et al., Magnetic tweezers for DNA micromanipulation, Rev. Sci. Instrum., vol. 71, No. 12, 4561-4570 (Dec. 2000).
Han et al. Linking T-cell receptor sequence to functional phenotype at the single-cell level. Nat Biotechnol 32(7):684-692 (2014).
Hanahan and Cold Spring Harbor Laboratory, Studies on transformation of *Escherichia coli* with plasmids J. Mol. Biol. 166:557-580 (1983).
Hanahan et al., Plasmid transformation of *Escherichia coli* and other bacteria. Methods Enzymol, vol. 204, p. 63-113 (1991).
Harada, et al. Unexpected substrate specificity of T4 DNA ligase revealed by in vitro selection. Nucleic Acids Res. May 25, 1993;21(10):2287-91.
Heckers Karl H. et al., Error analysis of chemically synthesized polynucleotides, BioTechniques, vol. 24, No. 2, 256-260 (1998).
Herzer et al.: Fabrication of patterned silane based self-assembled monolayers by photolithography and surface reactions on silicon-oxide substrates Chem. Commun., 46:5634-5652 (2010).
Hoover et al., DNAWorks: an automated method for designing oligonucleotides for PCR-based gene synthesis, Nucleic Acids Research, vol. 30, No. 10, e43, 7 pages (2002).
Hosu, Basarab G. et al., Magnetic tweezers for intracellular applications., Rev. Sci. Instrum., vol. 74, No. 9, 4158-4163 (Sep. 2003).
Huang, Hayden et al., Three-dimensional cellular deformation analysis with a two-photon magnetic manipulator workstation, Biophysical Journal, vol. 82, No. 4, 2211-2223 (Apr. 2002).
Hughes, et al. Expression profiling using microarrays fabricated by an ink-jet oligonucleotide synthesizer. Nat Biotechnol. Apr. 2001;19(4):342-7.
Hughes et al. Principles of early drug discovery. Br J Pharmacol 162(2):1239-1249, 2011.
Hutchison, et al. Cell-free cloning using phi29 DNA polymerase. Proc Natl Acad Sci U S A. Nov. 29, 2005;102(48):17332-6. Epub Nov. 14, 2005.
Imgur: The magic of the internet. Uploaded May 10, 2012, 2 pages, retrieved from: https://imgur.com/mEWuW.
In-Fusion Cloning: Accuracy, Not Background. Cloning & Competent Cells, ClonTech Laboratories, 3 pages, available online Jul. 6, 2014.
Jackson, Brian A. et al., Recognition of DNA base mismatches by a rhodium intercalator, J. Am. Chem. Soc., vol. 19, 12986-12987 (1997).
Jacobs et al. DNA glycosylases: In DNA repair and beyond. Chromosoma 121:1-20 (2012)—http://www.ncbi.nlm.nih.gov/pmc/articles/PMC3260424/.
Jacobus et al. Optimal cloning of PCR fragments by homologous recombination in *Escherichia soli*. PLoS One 10(3):e0119221 (2015).
Jager et al. Simultaneous Humoral and Cellular: Immune Response against Cancer—Testis Antigen NY-ES0-1: Definition of Human Histocompatibility LeukocyteAntigen (HLA)-binding Peptide Epitopes. J. Exp. Med. 187(2):265-270 (1998).
Jinek et al., A Programmable dual-RNA-guided DNA endonuclease in adaptive bacterial immunity. Science, 337:816-821, 2012.
Karagiannis and Ei-Osta, RNA interference and potential therapeutic applications of short interfering RNAs Cancer Gene Therapy, 12:787-795, 2005.
Ke, Song-Hua et al., Influence of neighboring base pairs on the stability of single base bulges and base pairs in a DNA fragment, Biochemistry, Vo. 34, 4593-4600 (1995).
Kelley, Shana, et al. Single-base mismatch detection based on charge transduction through DNA, Nucleic Acids Research, vol. 27, No. 24, 4830-4837 (1999).
Kim et al., High-resolution patterns of quantum dots formed by electrohydrodynamic jet printing for light-emitting diodes. Nano Letters, 15:969-973, 2015.
Kim, Yang-Gyun et al., Chimeric restriction endonuclease, Proc. Natl. Acad. Sci. USA, vol. 91, 883-887 (Feb. 1994).
Kim, Yang-Gyun, the interaction between Z-ONA and the Zab domain of double-stranded RNA adenosine deaminase characterized using fusion nucleases, The Journal of Biological Chemistry, vol. 274, No. 27, 19081-19086 (1999).
Kim, Yan-Gyun et al., Site specific cleavage of DNA-RNA hybrids by zinc finger/Fok I cleavage domain fusions Gene, vol. 203, 43-49 (1997).
Kinde, et al. Detection and quantification of rare mutations with massively parallel sequencing. Proc Natl Acad Sci U S A. Jun. 7, 2011;108(23):9530-5. doi: 10.1073/pnas.1105422108. Epub May 17, 2011.
Kodumal, et al. Total synthesis of long DNA sequences: synthesis of a contiguous 32-kb polyketide synthase gene cluster. Proc Natl Acad Sci U S A. Nov. 2, 2004;101(44):15573-8. Epub Oct. 20, 2004.
Koike-Yusa et al., Genome-wide recessive genetic screening in mammalian cells with a lentiviral CRISPR-guide RNA library. Nature Biotechnology, 32:267-273, 2014 (with three pages of supplemental Online Methods).
Kong et al., Parallel gene synthesis in a microfluidic device. Nucleic Acids Res., 35(8):e61 (2007).
Kong. Microfluidic Gene Synthesis. MIT Thesis. Submitted to the program in Media Arts and Sciences, School of Architecture and Planning, in partial fulfillment of the requirements for the degree of Doctor of Philosophy in Media Arts and Sciences at the Massachusetts Institute of Technology. 143 pages Jun. 2008.
Kopp, Martin U. et al., Chemical amplification: continuous-flow PCR on a chip, Science, vol. 280, 1046-1048 (May 15, 1998).
Kosuri and Church, Large-scale de novo DNA synthesis: technologies and applications, Nature Methods, 11:499-507, 2014. Available at: http://www.nature.com/nmeth/journal/v11/n5/full/nmeth.2918.html.
Kosuri, et al. A scalable gene synthesis by selective amplification of DNA pools from high-fidelity microchips. Nature Biotechnology. 2010; 28:1295-1299.

(56) References Cited

OTHER PUBLICATIONS

Krayden, Inc., A Guide to Silane Solutions. Silane coupling agents. 7 pages. Published on May 31, 2005 at: http://krayden.com/pdf/xia_silane_chemistry.pdf.
Lagally, et al. Single-Molecule DNA Amplification and Analysis in an Integrated Microfluidic Device. Analytical Chemistry. 2001;73(3): 565-570.
Lahue, R.S. et al., DNA mismatch correction in a defined system, Science, vol. 425; No. 4914, 160-164 (Jul. 14, 1989).
Lambrinakos, A. et al., Reactivity of potassium permanganate and tetraethylammonium chloride with mismatched bases and a simple mutation detection protocol, Nucleic Acids Research, vol. 27, No. 8, 1866- 1874 (1999).
Landegren, et al. A ligase-mediated gene detection technique. Science. Aug. 26, 1988;241(4869):1077-80.
Lang, Matthew J. et al., An automated two-dimensional optical force clamp for single molecule studies, Biophysical Journal, vol. 83, 491-501 (Jul. 2002).
Lashkari, et al. An automated multiplex oligonucleotide synthesizer: development of high-throughput, low-cost DNA synthesis. Proc Natl Acad Sci U S A. Aug. 15, 1995;92(17):7912-5.
Lausted et al., POSaM: a fast, flexible, open-source, inkjet oligonucleotide synthesizer and microarrayer, Genome Biology, 5:R58, 17 pages, 2004. available at https://www.ncbi.nlm.nih.gov/pmc/articles/PMC507883/.
Leamon, et al. A massively parallel PicoTiterPlate based platform for discrete picoliter-scale polymerase chain reactions. Electrophoresis. Nov. 2003;24(21):3769-77.
Lee, Covalent end-immobilization of oligonucleotides onto solid surfaces. Thesis submitted to the Department of Chemical Engineering in Partial Fulfillment of the Requirements for the Degree of Doctor of Philosophy in Chemical Engineering at the Massachusetts Institute of Technology. Aug. 2001, 315 pages.
Lee, C.S. et al., Microelectromagnets for the control of magnetic nanoparticles, Appl. Phys. Lett., vol. 79, No. 20, 3308-3310 (Nov. 12, 2001).
Lee, et al. A microfluidic oligonucleotide synthesizer. Nucleic Acids Research 2010 vol. 38(8):2514-2521. DOI: 10.1093/nar/gkq092.
Leproust, et al. Agilent's Microarray Platform: How High-Fidelity DNA Synthesis Maximizes the Dynamic Range of Gene Expression Measurements. 2008; 1-12. http://www.miltenyibiotec.com/~/media/Files/Navigation/Genomie/020Services/Agilent_DNA_Microarray_Platform.ashx.
Leproust et al., Synthesis of high-quality libraries of long (150mer) oligonucleotides by a novel depurination controlled process, Nucleic Acids Research, 35(8):2522-2540, 2010.
Lesnikowski, et al. Nucleic acids and nucleosides containing carboranes. J. Organometallic Chem. 1999; 581:156-169.
Leumann. DNA analogues: from supramolecular principles to biological properties. Bioorg Med Chem. Apr. 2002;10(4):841-54.
Levene, et al. Zero-mode waveguides for single-molecule analysis at high concentrations. Science. Jan. 31, 2003;299(5607):682-6.
Lewontin and Harti, Population genetics in forensic DNA typing. Science, 254:1745-1750, 1991.
Li et al., Beating bias in the directed evolution of proteins: Combining high-fidelity on-chip solid-phase gene synthesis with efficient gene assembly for combinatorial library construction. First published Nov. 24, 2017, 2 pages. retrieved from: https://doi.org/10.1002/cbic.201700540.
Li et al. Beating Bias in the Directed Evolution of Proteins: Combining High-Fidelity on-Chip Solid-Phase Gene Synthesis with Efficient Gene Assembly for Combinatorial Library Construction. ChemBioChem 19:221-228 (2018).
Limbachiya et al., Natural data storage: A review on sending information from now to then via Nature. ACM Journal on Emerging Technologies in Computing Systems, V(N):Article A, May 19, 2015, 17 pages.
Link Technologies. Product Guide 2010. Nov. 27, 2009, 136 pages. XP055353191. Retrieved from the Internet: URL:http://www.linktech.co.uk/documents/517/517.pdf.
Lipshutz, Robert J. et al., High density synthetic oligonucleotide arrays, Nature Genetics Supplement, vol. 21, 20-24 (Jan. 1999).
Lishanski, Alia et al., Mutation detection by mismatch binding protein, MutS, in amplified DNA: application to the cystic fibrosis gene, Proc. Natl. Acad. Sci. USA, vol. 91, 2674-2678 (Mar. 1994).
Liu et al., Comparison of Next-Generation Sequencing Systems. Journal of Biomedicine and Biotechnology, 11 pages, 2012.
Liu, et al. Enhanced Signals and Fast Nucleic Acid Hybridization by Microfluidic Chaotic Mixing. Angew. Chem. Int. Ed. 2006; 45:3618-3623.
Liu et al., Rational design of CXCR4 specific antibodies with elongated CDRs. JACS, 136:10557-10560, 2014.
Lizard!, et al. Mutation detection and single-molecule counting using isothermal rolling-circle amplification. Nat Genet. Jul. 1998;19(3):225-32.
Li, Lin et al., Functional domains in Fok I restriction endonuclease, Proc. Natl. Acad. Sci. USA, 89:4275-4279, 1992.
Lu, A.-Lien et al., Methyl-directed repair of DNA base-pair mismatches in vitro, Proc. Natl. Acad. Sci. USA, 80:4639-4643, 1983.
Lund, et al. A validated system for ligation-free uracilexcision based assembly of expression vectors for mammalian cell engineering. DTU Systems of Biology. 2011. 1 page. http://www.lepublicsystempco.com/files/modules/gestion_rubriques/REF-B036-Lund_Anne%20Mathilde.pdf.
Ma, et al. DNA synthesis, assembly and application in synthetic biology. Current Opinion in Chemical Biology. 16:260-267, 2012.
Ma et al., Versatile surface functionalization of cyclic olefin copolymer (COC) with sputtered SiO2 thin film for potential BioMEMS applications. Journal of Materials Chemistry, 11 pages, 2009.
Mahato et al., Modulation of gene expression by antisense and antigene oligodeoxynucleotides and small interfering RNA Expert Opin. Drug Delivery, 2(1):3-28, 2005.
Margulies, et al. Genome sequencing in open microfabricated high-density picolitre reactors. Nature. 437(7057):376-80, 2005.
Matteucci, et al. Synthesis of deoxyoligonucleotides on a polymer support. J. Am. Chem. Soc. 103(11):3185-3191, 1981.
Matzas et al., Next generation gene synthesis by targeted retrieval of bead-immobilized, sequence verified DNA clones from a high throughput pyrosequencing device. Nat. Biotechnol., 28(12):1291-1294, 2010.
McBride & Caruthers, An investigation of several deoxynucleoside phosphoramidites useful for synthesizing deoxyoligonucleotides. Tetrahedron Lett. 24: 245-248, 1983.
McGall, et al. Light-directed synthesis of high-density oligonucleotide arrays using semiconductor photoresists. Proc Natl Acad Sci U S A. 93(24):13555-60, 1996.
McGall, et al. The Efficiency of Light-Directed Synthesis of DNA Arrays on Glass Substrates. J. Am. Chem. Soc. 119(22):5081-5090, 1997.
Mei et al., Cell-free protein synthesis in microfluidic array devices Biotechnol. Prog., 23(6):1305-1311, 2007.
Mendel-Hartvig. Padlock probes and rolling circle amplification. New possibilities for sensitive gene detection. Comprehensive Summaries of Uppsala Dissertations from the Faculty of Medicine 1175. Uppsala University. 2002, 39 pages. http://www.diva-portal.org/smash/get/diva2:161926/FULLTEXT01.pdf.
Meyers and Friedland, Knowledge-based simulation of genetic regulation in bacteriophage lambda. Nucl. Acids Research, 12(1):1-16, 1984.
Meynert et al. Quantifying single nucleotide variant detection sensitivity in exome sequencing. BMC Bioinformatics 14:195 (2013).
Meynert et al. Variant detection sensitivity and biases in whole genome and exome sequencing. BMC Bioinformatics 15:247 (2014).
Milo and Phillips, Numbers here reflect the number of protein coding genes and excludes tRNA and non-coding RNA. Cell Biology by the Numbers, p. 286, 2015.
Mitra, et al. In situ localized amplification and contact replication of many individual DNA molecules. Nucleic Acids Res. 27(24):e34, 1999.
Morin et al., Profiling the HeLa S3 transcriptome using randomly primed cDNA and massively parallel short-read sequencing. Biotechniques, 45:81-94, 2008.

(56) References Cited

OTHER PUBLICATIONS

Morris and Stauss, Optimizing T-cell receptor gene therapy for hematologic malignancies. Blood, 127(26):3305-3311, 2016.
Muller, Caroline et al. Protection and labelling of thymidine by a fluorescent photolabile group, Helvetica Chimica Acta, vol. 84, 3735-3741 (2001).
Mulligan. Commercial Gene Synthesis Technology PowerPoint presentation. BlueHeron® Biotechnology. Apr. 5, 2006 (48 pgs).
Nakatani, Kazuhiko et al., Recognition of a single guanine bulge by 2-Acylamino-1,8-naphthyridine, J. Am. Chem. Soc., vol. 122, 2172-2177 (2000).
Neiman M.S,. Negentropy principle in information processing systems. Radiotekhnika, 1966, N211, p. 2-9.
Neiman M.S., On the bases of the theory of information retrieval. Radiotekhnika, 1967, No. 5, p. 2-10.
Neiman M.S., On the molecular memory systems and the directed mutations. Radiotekhnika, 1965, No. 6, pp. 1-8.
Neiman M.S., On the relationships between the reliability, performance and degree of microminiaturization at the molecular-atomic level. Radiotekhnika, 1965, No. 1, pp. 1-9.
Neiman M.S., Some fundamental issues of microminiaturization. Radiotekhnika, 1964, No. 1, pp. 3-12.
Nishikura, A short primer on RNAi: Rna-directed Rna polymerase acts as a key catalyst Cell, 107:415-418, 2001.
Nour-Eldin, et al. USER Cloning and USER Fusion: The Ideal Cloning Techniques for Small and Big Laboratories. Plant Secondary Metabolism Engineering. Methods in Molecular Biology vol. 643, 2010, pp. 185-200.
Ochman, et al. Genetic applications of an inverse polymerase chain reaction. Genetics. Nov. 1988;120(3):621-3.
Organick et al., Random access in large-scale DNA data storage. Nature Biotechnology, Advance Online Publication, 8 pages, 2018.
Organick et al., Scaling up DNA data storage and random access retrieval, bioRxiv, preprint first posted online Mar. 7, 2017, 14 pages.
Pan, et al. An approach for global scanning of single nucleotide variations. Proc Natl Acad Sci U S A. Jul. 9, 2002;99(14):9346-51.
Pankiewicz. Fluorinated nucleosides. Carbohydr Res. Jul. 10, 2000;327(1-2):87-105.
PCT/IL2012/000326 International Preliminary Report on Patentability dated Dec. 5, 2013.
PCT/IL2012/000326 International Search Report dated Jan. 29, 2013.
PCT/US14/049834 International Preliminary Report on Patentability dated Feb. 18, 2016.
PCT/US2014/049834 International Search Report and Written Opinion dated Mar. 19, 2015.
PCT/US2014/049834, Invitation to Pay Additional Fees and, where applicable, protest fee, dated Jan. 5, 2015.
PCT/US2015/043605 International Preliminary Report on Patentability dated Feb. 16, 2017.
PCT/US2015/043605 International Search Report and Written Opinion dated Jan. 6, 2016.
PCT/US2015/043605 Invitation to Pay Additional Fees dated Oct. 28, 2015.
PCT/US2016/016459 International Preliminary Report on Patentability dated Aug. 17, 2017.
PCT/US2016/016459 International Search Report and Written Opinion dated Apr. 13, 2016.
PCT/US2016/016636 International Preliminary Report on Patentability dated Aug. 17, 2017.
PCT/US2016/016636 International Search Report and Written Opinion dated May 2, 2016.
PCT/US2016/028699 International Preliminary Report on Patentability dated Nov. 2, 2017.
PCT/US2016/028699 International Search Report and Written Opinion dated Jul. 29, 2016.
PCT/US2016/031674 International Preliminary Report on Patentability dated Nov. 23, 2017.
PCT/US2016/031674 International Search Report and Written Opinion dated Aug. 11, 2016.
PCT/US2016/052336 International Preliminary Report on Patentability dated Mar. 29, 2018.
PCT/US2016/052336 International Search Report and Written Opinion dated Dec. 7, 2016.
PCT/US2016/052916 International Preliminary Report on Patentability dated Apr. 5, 2018.
PCT/US2016/052916 International Search Report and Written Opinion dated Dec. 30, 2016.
PCT/US2016/064270 International Preliminary Report on Patentability dated Jun. 14, 2018.
PCT/US2016/064270 International Search Report and Written Opinion dated Apr. 28, 2017.
PCT/US2017/026232 International Search Report and Written Opinion dated Aug. 28, 2017.
PCT/US2017/036868 International Search Report and Written Opinion dated Aug. 11, 2017.
PCT/US2017/045105 International Search Report and Written Opinion dated Oct. 20, 2017.
PCT/US2017/052305 International Search Report and Written Opinion dated Feb. 2, 2018.
PCT/US2017/062391 International Search Report and Written Opinion dated Mar. 28, 2018.
PCT/US2017/066847 International Search Report and Written Opinion dated May 4, 2018.
PCT/US2018/022487 International Search Report and Written Opinion dated Aug. 1, 2018.
PCT/US2018/022493 International Search Report and Written Opinion dated Aug. 1, 2018.
PCT/US2018/037152 International Search Report and Written Opinion dated Aug. 28, 2018.
PCT/US2018/037161 Invitation to Pay Additional Fees dated Aug. 27, 2018.
PCT/US2018/19268 International Search Report and Written Opinion dated Jun. 26, 2018.
PCT/US2018/19268 Invitation to Pay Additional Fees and, where applicable, protest fee dated May 2, 2018.
PCT/US2018/22487 Invitation to Pay Additional Fees and, where applicable, protest fee dated May 31, 2018.
PCT/US2018/22493 Invitation to Pay Additional Fees and, where applicable, protest fee dated May 31, 2018.
Pease, et al. Light-generated oligonucleotide arrays for rapid DNA sequence analysis. Proc Natl Acad Sci U S A. May 24, 1994;91(11):5022-6.
Peisajovich, et al. BBF RFC 28: A method for combinatorial multi-part assembly based on the type-IIs restriction enzyme aarI. Sep. 16, 2009, 7 pages.
Pellois, et al. Individually addressable parallel peptide synthesis on microchips, Nature Biotechnology, vol. 20:922-926 (Sep. 2002).
Petersen, et al. LNA: a versatile tool for therapeutics and genomics. Trends Biotechnol. Feb. 2003;21(2):74-81.
Pierce, et al. Linear-after-the-exponential polymerase chain reaction and allied technologies. Real-time detection strategies for rapid, reliable diagnosis from single cells. Methods Mol Med. 2007;132:65-85.
Pirrung. How to make a DNA chip. Angew. Chem. Int. Ed., 41:1276-1289, 2002.
Plesa et al., Multiplexed gene synthesis in emulsions for exploring protein functional landscapes. Science, 10.1126/science.aao5167, 10 pages, 2018.
Pon. Solid-phase supports for oligonucleotide synthesis. Methods Mol Biol. 1993;20:465-96.
Poster. Reimagine Genome Scale Research. 2016, 1 page. Available at http://www2.twistbioscience.com/Oligo_Pools_CRISPR_poster.
Powers et al. Optimal strategies for the chemical and enzymatic synthesis of bihelical deoxyribonucleic acids. J Am Chem Soc., 97(4):875-884, 1975.
Pray. Discovery of DNA Structure and Function: Watson and Crick, Nature Education, 2008, 6 pages. available at: http://www.nature.com/scitable/topicpage/discovery-of-dna-structure-and-function-watson-397.

(56) References Cited

OTHER PUBLICATIONS

Prodromou, et al. Recursive PCR: a novel technique for total gene synthesis. Protein Eng. Dec. 1992;5(8):827-9.
Puigbo. Optimizer: a web server for optimizing the codon usage of DNA sequences. Nucleic Acid Research, 35(14):126-131, 2007.
Qian and Winfree, Scaling up digital circuit computation with DNA strand displacement cascades. Science, 332(6034):196-1201, 2011.
Qian, et al., Neural network computation with DNA strand displacement cascades, Nature, 475(7356):368-372, 2011.
Quan, et al. Parallel on-chip gene synthesis and application to optimization of protein expression. Nature Biotechnology. 2011; 29:449-452.
Rafalski and Morgante, Corn and humans: recombination and linkage disequilibrium in two genomes of similar size. Trends in Genetics, 20(2):103-111, 2004.
Raje and Murma, A Review of electrohydrodynamic-inkjet printing technology. International Journal of Emerging Technology and Advanced Engineering, 4(5):174-183, 2014.
Rastegari, et al., XNOR-Net: ImageNet Classification Using Binary Convolutional Neural Networks, in ECCV 2016, Part IV, LNCS 9908, p. 525-542, 2016.
Reimagine SequenceSpace, Reimagine Research, Twist Bioscience, Product Brochure, Published Apr. 6, 2016 online at: www2.twistbioscience.com/TB_Product_Brochure_04.2016, 8 pages.
RF Electric discharge type excimer lamp. Products Catalog. Excimer lamp light source flat excimer, 16 pages dated Jan. 2016. From: http://www.hamamatsu.com/jp/en/product/category/1001/3026/index.html.
Richmond, et al. Amplification and assembly of chip-eluted DNA (AACED): a method for high-throughput gene synthesis. Nucleic Acids Res. Sep. 24, 2004;32(17):5011-8. Print 2004.
Roche. Restriction Enzymes from Roche Applied Science—A Tradition of Premium Quality and Scientific Support. FAQS and Ordering Guide. Roche Applied Science. Accessed Jan. 12, 2015, 37 pages.
Rogozin et al., Origin and evolution of spliceosomal introns. Biology Direct, 7:11, 2012.
Ruminy, et al., Long-range identification of hepatocyte nuclear factor-3 (FoxA) high and low-affinity binding Sites with a chimeric nuclease, J. Mol. Bioi., vol. 310, 523-535 (2001).
Saaem et al., In situ synthesis of DNA microarray on functionalized cyclic olefin copolymer substrate ACS Applied Materials & Interfaces, 2(2):491-497, 2010.
Saboulard, et al. High-throughput site-directed mutagenesis using oligonucleotides synthesized on DNA chips. Biotechniques. Sep. 2005;39(3):363-8.
Sacconi, L. et al., Three-dimensional magneto-optic trap for micro-object manipulation, Optics Letters, vol. 26, No. 17, 1359-1361 (Sep. 1, 2001).
Saiki et al. Analysis of enzymatically amplified beta-globin and HLA-DQ alpha DNA with allele-specific oligonucleotide probes. Nature 324:163-166 (1986).
Sandhu, et al. Dual asymmetric PCR: one-step construction of synthetic genes. Biotechniques. Jan. 1992;12(1):14-6.
Sargolzaei et al., Extent of linkage disequilibrium in Holstein cattle in North America. J.Dairy Science, 91:2106-2117, 2007.
Schaller, et al. Studies on Polynucleotides. XXV.1 The Stepwise Synthesis of Specific Deoxyribopolynucleotides (5). Further Studies on the Synthesis of Internucleotide Bond by the Carbodiimide Method. The Synthesis of Suitably Protected Dinucleotides as Intermediates in the Synthesis of Higher Oligonucleotides. J. Am. Chem. Soc. 1963; 85(23):3828-3835.
Schmalzing et al. Microchip electrophoresis: a method for high-speed SNP detection. Nucleic Acids Res 28(9):E43 (2000).
Schmitt et al., New strategies in engineering T-cell receptor gene-modified T cells to more effectively target malignancies. Clinical Cancer Research, 21(23):5191-5197, 2015.
Seelig, et al., Enzyme-Free Nucleic Acid Logic Circuits, Science 314(5805):1585-1588, 2006.

Sharan et al. Recombineering: a homologous recombination-based method of genetic engineering. Nat Profile 4(2):1-37 (originally pp. 206-223) (2009).
Sharpe and Mount, Genetically modified T cells in cancer therapy: opportunities and challenges. Disease Models and Mechanisms, 8:337-350, 2015.
Sierzchala, Agnieszka B. et al., Solid-phase oligodeoxynucleotide synthesis : a two-step cycle using peroxy anion deprotection, J. Am. Chem. Soc., vol. 125, No. 44, 13427-13441 (2003).
Simonyan and Zisserman, Very Deep Convolutional Networks for Large-Scale Image Recognition, Published as a conference paper at Int. Conf. Learn. Represent., pp. 1-14, 2015.
Singh-Gasson, Sangeet et al., Maskless fabrication of light-directed oligonucleotide microarrays using a digital micromirror array, Nature Biotechnology, vol. 17, 974-978 (Oct. 1999).
Skerra. Phosphorothioate primers improve the amplification of DNA sequences by DNA polymerases with proofreading activity. Nucleic Acids Res. Jul. 25, 1992; 20(14):3551-4.
Smith, et al. Generating a synthetic genome by whole genome assembly: phiX174 bacteriophage from synthetic oligonucleotides. Proc Natl Acad Sci U S A. Dec. 23, 2003;100(26):15440-5. Epub Dec. 2, 2003.
Smith, et al. Generation of cohesive ends on PCR products by UDG-mediated excision of dU, and application for cloning into restriction digest-linearized vectors. PCR Methods Appl. May 1993;2(4):328-32.
Smith, Jane et al., Mutation detection with MutH, MutL, and MutS mismatch repair proteins, Proc. Natl. Acad. Sci. USA, vol. 93, 4374-4379 (Apr. 1996).
Smith Jane et al., Removal of Polymerase-Produced mutant sequences from PCR products, Proc. Natl. Acad. Sci. USA, vol. 94, 6847-6850 (Jun. 1997).
Smith, Steven B. et al., Direct mechanical measurements of the elasticity of single DNA molecules using magnetic beads, Science, vol. 258, 1122-1126 (Nov. 13, 1992).
Soni, et al. Progress toward ultrafast DNA sequencing using solid-state nanopores. Clin Chem. Nov. 2007;53(11):1996-2001. Epub Sep. 21, 2007.
Southern, et al. Analyzing and comparing nucleic acid sequences by hybridization to arrays of oligonucleotides: evaluation using experimental models. Genomics. Aug. 1992;13(4):1008-17.
Sproat, et al. An efficient method for the isolation and purification of oligoribonucleotides. Nucleosides & Nucleotides. 1995; 14(1 &2):255-273.
Srivannavit et al., Design and fabrication of microwell array chips for a solution-based, photogenerated acid-catalyzed parallel oligonucleotide DNA synthesis. Sensors and Actuators A, 116:150-160, 2004.
Srivastava et al., RNA synthesis: phosphoramidites for RNA synthesis in the reverse direction. Highly efficient synthesis and application to convenient introduction of ligands, chromphores and modifications of synthetic RNA at the 3'-end, Nucleic Acids Symposium Series, 52(1):103-104, 2008.
Steel, The Flow-Thru Chip a Three-dimensional biochip platform. In: Schena, Microarray Biochip Technology, Chapter 5, Natick, MA: Eaton Publishing, 2000, 33 pages.
Stemmer, et al. Single-step assembly of a gene and entire plasmid from large numbers of oligodeoxyribonucleotides. Gene. Oct. 16, 1995;164(1):49-53.
Stryer. DNA Probes and genes can be synthesized by automated solid-phase methods. Biochemistry, 3rd edition, New York: W.H. Freeman and Company, 1988; 123-125.
Stutz, et al. Novel fluoride-labile nucleobase-protecting groups for the synthesis of 3'(2')-O-amino-acylated RNA sequences. Helv. Chim. Acta. 2000; 83(9):2477-2503.
Sullivan et al. Library construction and evaluation for site saturation mutagenesis. Enzyme Microb. Technol. 53:70-77 (2013).
Sun et al. Structure-Guided Triple-Code Saturation Mutagenesis: Efficient Tuning of the Stereoselectivity of an Epoxide Hydrolase. ACS Catal. 6:1590-1597 (2016).
Takahashi, Cell-free cloning using multiply-primed rolling circle amplification with modified RNA primers. Biotechniques. Jul. 2009;47(1):609-15. doi: 10.2144/000113155.

(56) References Cited

OTHER PUBLICATIONS

Tanase, M. et al., Magnetic trapping of multicomponent nanowires, The Johns Hopkins University, Baltimore, Maryland, p. 1-3 (Jun. 25, 2001).
Taylor et al., Impact of surface chemistry and blocking strategies on DNA microarrays. Nucleic Acids Research, 31(16):e87, 19 pages, 2003.
The Hood Laboratory, Beta Group. Assembly Manual for the POSaM: The ISB Piezoelectric Oligonucleotide Synthesizer and Microarrayer, Inkjet Microarrayer Manual Version 1.2, 50 pages, May 28, 2004.
The SLIC, Gibson, CPEC and SLiCE assembly methods (and GeneArt Seamless, In-Fusion Cloning). 5 pages, available online Sep. 2, 2010.
Tian, et al. Accurate multiplex gene synthesis from programmable DNA microchips. Nature. Dec. 23, 2004;432(7020):1050-4.
Tsai et al., Dimeric CRISPR RNA-guided FokI nucleases for highly specific genome editing Nat. Biotechnol., 32(6):569-576, 2014.
Twist Bioscience | White Paper. DNA-Based Digital Storage. Retrieved from the internet, Twistbioscience.com, Mar. 27, 2018, 5 pages.
Unger, et al. Monolithic microfabricated valves and pumps by multilayer soft lithography. Science. Apr. 7, 2000;288(5463):113-6.
U.S. Appl. No. 14/241,874 Office Action dated Feb. 27, 2017.
U.S. Appl. No. 14/241,874 Office Action dated Jul. 14, 2016.
U.S. Appl. No. 14/241,874 Office Action dated May 4, 2018.
U.S. Appl. No. 14/452,429 Notice of Allowance dated Jun. 7, 2016.
U.S. Appl. No. 14/452,429 Office Action dated Oct. 21, 2015.
U.S. Appl. No. 14/452,429 Restriction Requirement dated Dec. 12, 2014.
U.S. Appl. No. 14/885,962 Notice of Allowance dated Nov. 8, 2017 and dated Sep. 29, 2017.
U.S. Appl. No. 14/885,962 Office Action dated Dec. 16, 2016.
U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,965 Office Action dated Aug. 28, 2018.
U.S. Appl. No. 14/885,965 Office Action dated Aug. 30, 2017.
U.S. Appl. No. 14/885,965 Office Action dated Feb. 10, 2017.
U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/135,434 Notice of Allowance dated Feb. 9, 2018.
U.S. Appl. No. 15/135,434 Office Action dated Nov. 30, 2017.
U.S. Appl. No. 15/135,434 Restriction Requirement dated Jul. 12, 2017.
U.S. Appl. No. 15/151,316 Office Action dated Jun. 7, 2018.
U.S. Appl. No. 15/154,879 Notice of Allowance dated Feb. 1, 2017.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Office Action dated Mar. 21, 2017.
U.S. Appl. No. 15/245,054 Office Action dated Oct. 19, 2016.
U.S. Appl. No. 15/377,547 Office Action dated Jul. 27, 2018.
U.S. Appl. No. 15/377,547 Office Action dated Mar. 24, 2017.
U.S. Appl. No. 15/377,547 Office Action dated Nov. 30, 2017.
U.S. Appl. No. 15/602,991 Notice of Allowance dated Oct. 25, 2017.
U.S. Appl. No. 15/602,991 Office Action dated May 31, 2018.
U.S. Appl. No. 15/602,991 Office Action dated Sep. 21, 2017.
U.S. Appl. No. 15/603,013 Office Action dated Jan. 30, 2018.
U.S. Appl. No. 15/603,013 Office Action dated Jul. 10, 2018.
U.S. Appl. No. 15/603,013 Office Action dated Oct. 20, 2017.
U.S. Appl. No. 15/682,100 Office Action dated Jan. 2, 2018.
U.S. Appl. No. 15/682,100 Restriction Requirement dated Nov. 8, 2017.
U.S. Appl. No. 15/729,564 Office Action dated Jun. 6, 2018.
U.S. Appl. No. 15/860,445 Office Action dated May 30, 2018.
U.S. Appl. No. 14/452,429 Office Action dated Apr. 9, 2015.
Vaijayanthi, et al. Recent advances in oligonucleotide synthesis and their applications. Indian J Biochem Biophys. Dec. 2003;40(6):377-91.
Van Den Brulle, et al. A novel solid phase technology for high-throughput gene synthesis. Biotechniques. 2008; 45(3):340-343.
Van Der Werf et al. Limonene-1,2-epoxide hydrolase from Rhodococcus erythropolis DCL14 belongs to a novel class of epoxide hydrolases. J. Bacteriol. 180:5052-5057 (1998).
Van Tassell et al., SNP discovery and allele frequency estimation by deep sequencing of reduced representation libraries. Nature Methods, 5:247-252, 2008.
Vargeese, et al. Efficient activation of nucleoside phosphoramidites with 4,5-dicyanoimidazole during oligonucleotide synthesis. Nucleic Acids Res. Feb. 15, 1998;26(4):1046-50.
Verma et al. Modified oligonucleotides: synthesis and strategy for users. Annu Rev Biochem 67:99-134 (1998).
Vincent, et al. Helicase-dependent isothermal DNA amplification. EMBO Rep. 2004 Aug;5(8):795-800.
Visscher et al., Construction of multiple-beam optical traps with nanometer-resolution position sensing, IEEE Journal of Selected Topics in Quantum Electronics, vol. 2, No. 4, 1066-1076 (Dec. 1996).
Voldmans Joel et al., Holding forces of single-particle dielectrophoretic traps. Biophysical Journal, vol. 80, No. 1, 531-541 (Jan. 2001).
Vos, et al. AFLP:A new technique for DNA fingerprinting. Nucleic Acids Res. Nov. 11, 1995;23(21):4407-14.
Wagner et al., Nucleotides, Part LXV, Synthesis of 2'-Deoxyribonucleoside 5'-Phosphoramidites: New Building Blocks for the Inverse (5'-3')-Oiigonucleotide Approach. Helvetica Chimica Acta, 83(8):2023-2035, 2000.
Wah, David A. et al., Structure of Fok I has implications for DNA cleavage, Proc. Natl. Acad. Sci. USA, vol. 95, 10564-10569 (Sep. 1998).
Wah, David A. et al., Structure of the multimodular endonuclease Fok I bound to DNA, Nature, vol. 388, 97-100 ( Jul. 1997).
Walker, et al. Strand displacement amplification--an isothermal, in vitro DNA amplification technique. Nucleic Acids Res. Apr. 11, 1992;20(7):1691-6.
Wan et al., Deep Learning for Content-Based Image Retrieval: A comprehensive study. in Proceedings of the 22nd ACM International Conference on Multimedia—Nov. 3-7, 2014, Orlando, FL, p. 157-166, 2014.
Warr et al. Exome Sequencing: current and future perspectives. G3: (Bethesda) 5(8):1543-1550 (2015).
Weber, et al. A modular cloning system for standardized assembly of multigene constructs. PLoS One. Feb. 18, 2011;6(2):e16765. doi: 10.1371/journal.pone.0016765.
Welz, et al. 5-(Benzylmercapto)-1H-tetrazole as activator for 2'-O-TBDMS phosphoramidite building blocks in RNA synthesis. Tetrahedron Lett. 2002; 43(5):795-797.
Westin et al., Anchored multiplex amplification on a microelectronic chip array Nature Biotechnology, 18:199-202 (2000) (abstract only).
Whitehouse, Adrian et al. Analysis of the mismatch and insertion/deletion binding properties of Thermus thermophilus, HB8, MutS, Biochemical and Biophysical Research Communications, vol. 233, 834-837 (1997).
Wiedenheft et al., RNA-guided genetic silencing systems in bacteria and archaea. Nature, 482:331-338, 2012.
Wijshoff, Herman. Structure and fluid-dynamics in Piezo inkjet printheads. Thesis. Venio, The Netherlands, published 2008, p. 1-185.
Wirtz, Denis, Direct measurement of the transport properties of a single DNA molecule, Physical Review Letters, vol. 75, No. 12, 2436-2439 (Sep. 18, 1995).
Withers-Martinez, Chrislaine et al., PCR-based gene synthesis as an efficient approach for expression of the A+ T-rich malaria genome, Protein Engineering, vol. 12, No. 12, 1113-1120 (1999).

(56) References Cited

OTHER PUBLICATIONS

Wood, Richard D. et al., Human DNA repair genes, Science, vol. 291, 1284-1289 (Feb. 16, 2001).
Wosnick, et al. Rapid construction of large synthetic genes: total chemical synthesis of two different versions of the bovine prochymosin gene. Gene. 1987;60(1):115-27.
Wright and Church, An open-source oligomicroarray standard for human and mouse. Nature Biotechnology, 20:1082-1083, 2002.
Wu, et al. RNA-mediated gene assembly from DNA arrays. Angew Chem Int Ed Engl. May 7, 2012;51(19):4628-32. doi: 10.1002/anie.201109058.
Wu, et al. Specificity of the nick-closing activity of bacteriophage T4 DNA ligase. Gene. 1989;76(2):245-54.
Wu, Xing-Zheng et al., An improvement of the on-line electrophoretic concentration method for capillary electrophoresis of proteins an experimental factors affecting he concentration effect, Analytical Sciences, vol. 16, 329-331 (Mar. 2000).
Xiong, et al. A simple, rapid, high-fidelity and cost-effective PCR-based two-step DNA synthesis method for long gene sequences. Nucleic Acids Res. 2004, 32(12):e98.
Xiong et al., Chemical gene synthesis: Strategies, softwares, error corrections, and applications. FEMS Microbiol. Rev., 32:522-540, 2008.
Xiong, et al. Non-polymerase-cycling-assembly-based chemical gene synthesis: Strategies, methods, and progress. Biotechnology Advances. 26(2):121-134, 2008.
Xu et al., Design of 240,000 orthogonal 25mer DNA barcode probes. PNAS, 106(7):2289-2294, 2009.
Yang, et al Purification, cloning, and characterization of the CEL I nuclease, Biochemistry, 39(13):3533-35, 2000.
Yazdi, et al., A Rewritable, Random-Access DNA-Based Storage System, Scientific Reports, 5, Article No. 14138, 27 pages, 2015.
Yehezkel et al., De novo DNA synthesis using single molecule PCR Nucleic Acids Research, 36(17):e107, 2008.
Yes HMDS vapor prime process application note Prepared by UC Berkeley and University of Texas at Dallas and re-printed by Yield Engineering Systems, Inc., 6 pages (http://www.yieldengineering.com/Portals/0/HMDS%20Application%20Note.pdf (Published online Aug. 23, 2013).
Youil, Rima et al., Detection of 81 of 81 known mouse beta-globin promoter mutations with T4 Endonuclease VII. The EMC Method, Genomics, 32:431-435, 1996.
Young, et al. Two-step total gene synthesis method. Nucleic Acids Res. 32(7):e59, 2004.
Zhang and Seelig, Dynamic DNA nanotechnology using strand-displacement reactions, Nat. Chem., 3(2):103-113, 2011.
Zheleznaya, et al. Nicking endonucleases. Biochemistry (Mosc). 74(13):1457-66, 2009.
Zheng et al. Manipulating the Stereoselectivity of Limonene Epoxide Hydrolase by Directed Evolution Based on Iterative Saturation Mutagenesis. J. Am. Chem. Soc. 132:15744-15751 (2010).
Zhirnov et al., Nucleic acid memory. Nature Materials, 15:366, 2016.
Zhou et al., Microfluidic PicoArray synthesis of oligodeoxynucleotides and simultaneous assembling of multiple DNA sequences Nucleic Acids Research, 32(18):5409-5417, 2004.
Eroshenko et al.: Gene Assembly from Chip-Synthesized Oligonucleotides; Current Protocols in Chemical biology 4: 1-17 (2012).
European Patent Application No. 16871446.7 First Official Action dated Nov. 13, 2019.
Galka et al.: QuickLib, a method for building fully synthetic plasmid libraries by seamless cloning of degenerate oligonucleotides. PLOS ONE, 12, e0175146:1-9 (2017).
Galka et al.: QuickLib, a method for building fully synthetic plasmid libraries by seamless cloning of degenerate oligonucleotides. PLOS ONE, 12, e0175146:S1 figure (2017).
Galka et al.: QuickLib, a method for building fully synthetic plasmid libraries by seamless cloning of degenerate oligonucleotides. PLOS ONE, 12, e0175146:S1 Table (2017).
Galka et al.: QuickLib, a method for building fully synthetic plasmid libraries by seamless cloning of degenerate oligonucleotides. PLOS ONE, 12, e0175146:52 figure (2017).
International Application No. PCT/US2018/019268 International Preliminary Report on Patentability dated Sep. 6, 2019.
International Application No. PCT/US2019/032992 International Search Report and Written Opinion dated Oct. 28, 2019.
International Application No. PCT/US2019/032992 Invitation to Pay Additional Fees dated Sep. 6, 2019.
U.S. Appl. No. 14/241,874 Final Office Action dated Jan. 28, 2019.
U.S. Appl. No. 15/015,059 Final Office Action dated Jul. 17, 2019.
U.S. Appl. No. 15/015,059 Office Action dated Aug. 19, 2019.
U.S. Appl. No. 15/151,316 Office Action dated Oct. 4, 2019.
U.S. Appl. No. 15/156,134 Final Office Action dated Jan. 3, 2020.
U.S. Appl. No. 15/187,714 Final Office Action dated Sep. 17, 2019.
U.S. Appl. No. 15/268,422 Final Office Action dated Oct. 3, 2019.
U.S. Appl. No. 15/603,013 Final Office Action dated Nov. 6, 2019.
U.S. Appl. No. 15/619,322 Office Action dated Aug. 14, 2019.
U.S. Appl. No. 15/816,995 Office Action dated Sep. 20, 2019.
U.S. Appl. No. 15/835,342 Office Action dated Dec. 2, 2019.
U.S. Appl. No. 15/835,342 Restriction Requirement dated Sep. 10, 2019.
U.S. Appl. No. 15/921,479 Office Action dated Nov. 12, 2019.
U.S. Appl. No. 15/960,319 Office Action dated Aug. 16, 2019.
U.S. Appl. No. 16/006,581 Office Action dated Sep. 25, 2019.
U.S. Appl. No. 16/239,453 Office Action dated Nov. 7, 2019.
U.S. Appl. No. 16/409,608 Office Action dated Sep. 9, 2019.
U.S. Appl. No. 16/530,717 Office Action dated Sep. 6, 2019.
Alberts et al.: Molecular Biology of the Cell. 4th edition. New York: Garland Science; 2002. The Generation of Antibody Diversity. https://www.ncbi.nlm.nih.gov/books/NBK26860/.
Almagro et al.: Progress and Challenges in the Design and Clinical Development of Antibodies for Cancer Therapy. Frontiers in immunology; 8, 1751 (2018) doi:10.3389/fimmu.2017.01751 https://www.frontiersin.org/articles/10.3389/fimmu.2017.01751/full.
Chervin et al.: Design of T-cell receptor libraries with diverse binding properties to examine adoptive T-cell responses. Gene Therapy. 20(6):634-644 (2012).
Cui et al.: Information Security Technology Based on DNA Computing. International Workshop on Anti-Counterfeiting, Security and Identification (ASID); IEEE Xplore 4 page (2007).
European Patent Application No. 17844060.8 Extended Search Report dated Apr. 20, 2020.
European Patent Application No. 17872347.4 Extended European Search Report dated Jun. 30, 2020.
European Patent Application No. 17881617.9 European Search Report and Written Opinion dated Jul. 2, 2020.
Goodwin et al.: immunoglobulin heavy chain variable region, partial [*Homo sapiens*]. Genbank entry (online). National Institute of Biotechnology Information. (2018) https://www.ncbi.nim.nih.gov/protein/AXA12486.1.
Hauser et al.: Trends in GPCR drug discovery: new agents, targets and indications. Nature Reviews Drug Discovery, 16, 829-842 (2017). doi:10.1038/nrd.2017.178 https://www.nature.com/articles/nrd.2017.178.
Hopcroft et al.: What is the Young's Modulus of Silicon?. Journal of Microelectromechanical Systems. 19(2):229-238 (2010).
Hötzel et al.: A strategy for risk mitigation of antibodies with fast clearance. mAbs, 4(6), 753-760 (2012). doi:10.4161/mabs.22189 https://www.ncbi.nlm.nih.gov/pubmed/23778268.
Jaiswal et al.: An architecture for creating collaborative semantically capable scientific data sharing infrastructures. Proceeding WIDM '06 Proceedings of the 8th annual ACM international workshop on Web information and data management. ACM Digital Library pp. 75-82 (2006).
Kosuri et al.: A scalable gene synthesis platform using high-fidelity DNA microchips Nat.Biotechnol., 28(12):1295-1299, 2010.
Malecek et al.: Engineering improved T cell receptors using an alanine-scan guided T cell display selection system. Journal of Immunological Methods. Elsevier Science Publishers. 392(1):1-11 (2013).
(Novartis Institutes for Biomedical Research) Immunoglobulin Heavy Chain [*Homo sapiens*]. National Center for Biotechnology Infor-

(56) References Cited

OTHER PUBLICATIONS mation. Genbank Entry. pp. 1-2 (2018) https://www.ncbi.nlm.nih.gov/nuccore/MH975524.1ttps://https://www.ncbi.nlm.nih.gov/nuccore/MH975524.1.

(Novartis Institutes for Biomedical Research) Immunoglobulin Lambda Chain [*Homo sapiens*]. National Center for Biotechnology Information. Genbank Entry. pp. 1-2 (2018) https://www.ncbi.nlm.nih.gov/nuccore/MH975524.1.

Paul et al.: Acid binding and detritylation during oligonucleotide synthesis. Nucleic Acids Research. 15. pp. 3048-3052 (1996).

PCT/US2018/037152 International Preliminary Report on Patentability dated Dec. 17, 2019.

PCT/US2018/037161 International Preliminary Report on Patentability dated Dec. 17, 2019.

PCT/US2018/050511 International Preliminary Report on Patentability dated Mar. 17, 2020.

PCT/US2018/056783 International Preliminary Report on Patentability dated Apr. 30, 2020.

PCT/US2018/057857 International Preliminary Report on Patentability dated Apr. 28, 2020.

PCT/US2019/012218 International Preliminary Report on Patentability dated Jul. 16, 2020.

PCT/US2019/068435 International Search Report and Written Opinion dated Apr. 23, 2020.

PCT/US2020/019371 International Search Report and Written Opinion dated Jun. 25, 2020.

PCT/US2020/019986 International Search Report and Written Opinion dated Jul. 29, 2020.

PCT/US2020/019986 Invitation to Pay Additional Fees dated Jun. 5, 2020.

PCT/US2020/019988 International Search Report and Written Opinion dated Jul. 29, 2020.

PCT/US2020/019988 Invitation to Pay Additional Fees dated Jun. 8, 2020.

PubChem Data Sheet Acetonitrile. Printed from website https://pubchem.ncbi.nlm.nig.gov/ pp. 1-124 (2020).

PubChem Data Sheet Methylene Chloride. Printed from website https://pubchem.ncbi.nlm.nih.gov/ pp. 1-140 (2020).

Rajpal et al.: A general method for greatly improving the affinity of antibodies by using combinatorial libraries. Proc. Natl. Acad. Sci. 102(24):8466-8471 (2005).

Solomon et al.: Genomics at Agilent: Driving Value in DNA Sequencing.https://www.agilent.com/labs/features/2010_genomics.html, 8 pages (Aug. 5, 2010).

U.S. Appl. No. 15/151,316 Final Office Action dated Jul. 9, 2020.

U.S. Appl. No. 15/272,004 Office Action dated Jun. 12, 2020.

U.S. Appl. No. 15/619,322 Final Office Action dated Mar. 30, 2020.

U.S. Appl. No. 15/816,995 Office Action dated May 19, 2020.

U.S. Appl. No. 15/835,342 Final Office Action dated Sep. 8, 2020.

U.S. Appl. No. 15/844,395 Office Action dated Jan. 24, 2020.

U.S. Appl. No. 15/921,479 Final Office Action dated Jun. 15, 2020.

U.S. Appl. No. 15/991,992 Office Action dated May 21, 2020.

U.S. Appl. No. 15/991,992 Restriction Requirement dated Mar. 10, 2020.

U.S. Appl. No. 16/039,256 Office Action dated Aug. 20, 2020.

U.S. Appl. No. 16/039,256 Restriction Requirement dated May 18, 2020.

U.S. Appl. No. 16/128,372 Office Action dated Oct. 8, 2020.

U.S. Appl. No. 16/128,372 Restriction Requirement dated May 18, 2020.

U.S. Appl. No. 16/165,952 Office Action dated Mar. 12, 2020.

U.S. Appl. No. 16/239,453 Office Action dated May 11, 2020.

U.S. Appl. No. 16/384,678 Office Action dated Jan. 21, 2020.

U.S. Appl. No. 16/530,717 Final Office Action dated Apr. 15, 2020.

U.S. Appl. No. 16/535,777 Office Action dated Jan. 23, 2020.

U.S. Appl. No. 16/535,779 First Action Interview dated Feb. 10, 2020.

U.S. Appl. No. 15/921,537 Office Action dated Apr. 1, 2020.

Van der Velde: Thesis. Finding the Strength of Glass. Delft University of Technology. 1-16 (2015).

\* cited by examiner

Design 1

5'TAATACGACTCACTATAGGGGATGCGCGCAGTGTCCGTTTTAGAGCTAGAAATAGCA3'
    1201    1233                        1211  1213    1215

5'GTTTTAGAGCTAGAAATAGCAAGTTAAAA[...]TGGCACCGAGTCGGTGCTTTT3' → 1220
                                                           1217              1219        1221

Design 2

5'GAAATTAATACGACTCACTATAGGGGATGCGCGCAGTTGTCCGTTTTAGAGCTAGAAATAGCAAG3'
            1201    1233                      1211  1213   1215

5'GTTTTAGAGCTAGAAATAGCAAGTTAAAA[...]TGGCACCGAGTCGGTGCTTTT3' → 1222
                                                           1217              1219        1221

Design 3

5'GAGCTAATATACGACTCACTATAGGGGATGCGCGCAGTTGTCCGTTTTAGAGCTAGAAATAGCAAGTT3'
       1201   1233                       1211  1213    1215  1223

5'GTTTTAGAGCTAGAAATAGCAAGTTAAAA[...]TGGCACCGAGTCGGTGCTTTT3' → 1224
                                                           1217              1219        1221

Design 4

5'CGAGCTAATACGACTCACTATAGGGGATGCGCGCAGTTGTCCGTTTTAGAGCTAGAAATAGCAAGTTAAAATAAGG3'
        1201    1233                       1211  1213    1215    1225

5'GTTTTAGAGCTAGAAATAGCAAGTTAAAATAAGG[...]GCACCGAGTCGGTGCTTTT3' → 1226
                                                          1217              1219        1221

Design 1, 2, 3: [...] = TAAGGCTAGTCCGTTATCAACTTGAAAAAG
Design 4: [...] = CTAGTCCGTTATCAACTTGAAAAAGTG

FIG. 12 sgRNA Template Assembly

Post-Transcription sgRNA

■ Control cluster

■ Control cluster

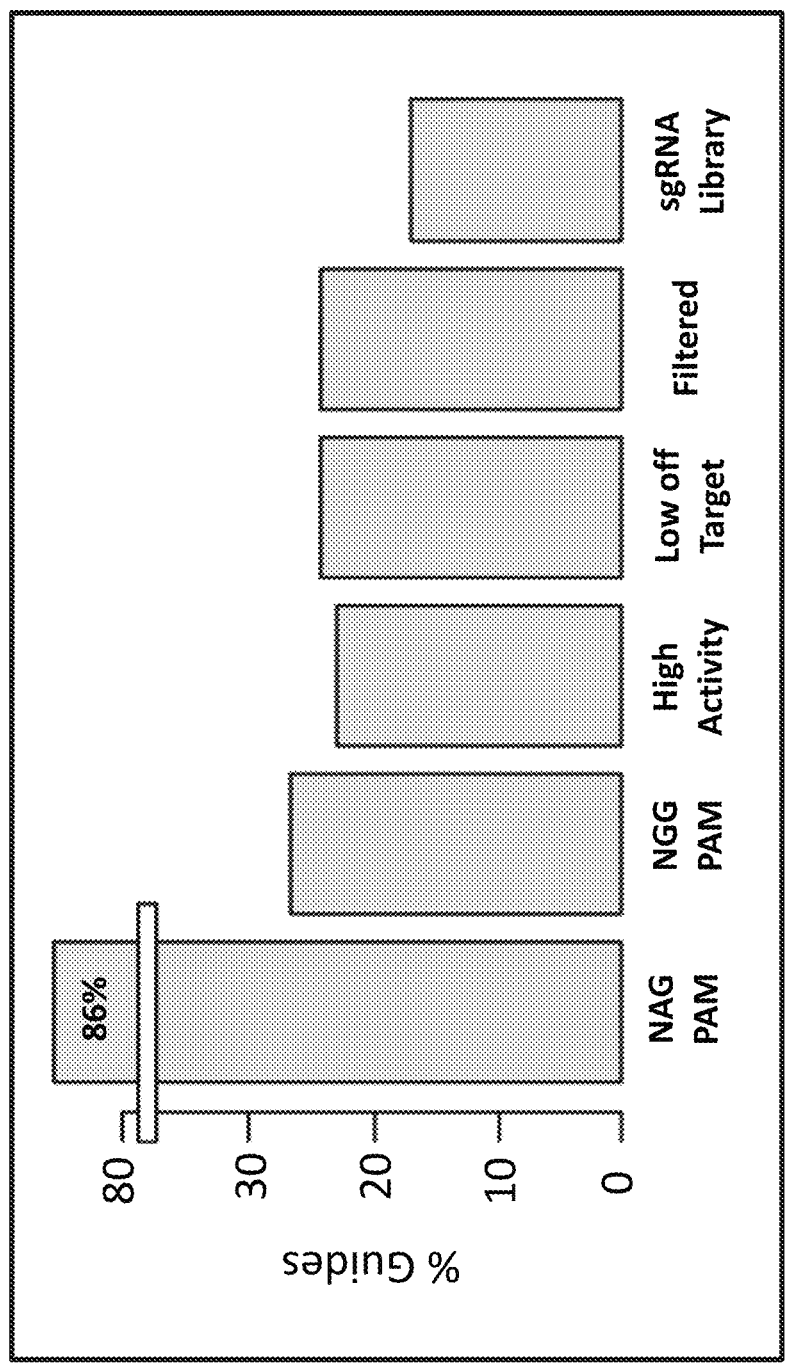

```
SEQUENCE LISTING

<160> NUMBER OF SEQ ID NOS: 44

<210> SEQ ID NO 1
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (51)..(52)
<223> OTHER INFORMATION: Thymidine-succinyl hexamide CED phosphoramidite

<400> SEQUENCE: 1
agacaatcaa ccatttgggg tggacagcct tgacctctag acttcggcat tttttttttt      60
tt                                                                     62

<210> SEQ ID NO 2
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (101)..(102)
<223> OTHER INFORMATION: Thymidine-succinyl hexamide CED phosphoramidite

<400> SEQUENCE: 2
cgggatcctt atcgtcatcg tcgtacagat cccgacccat ttgctgtcca ccagtcatgc      60
tagccatacc atgatgatga tgatgatgag aaccccgcat tttttttttt tt             112

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atgcggggtt ctcatcatc                                                   19

<210> SEQ ID NO 4
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 4
cgggatcctt atcgtcatcg                                                   20

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ataactcaat ttgtaaaaaa gttttagagc tatgctgttt tg                          42

<210> SEQ ID NO 6
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggaaccattc aaaacagcat agcaagttaa ataaggcta gtccgttatc aacttgaaaa        60
agtggcaccg agtcggtgct tttttt                                            86

<210> SEQ ID NO 7
<211> LENGTH: 38
<212> TYPE: DNA
<213> ORGANISM: Streptococcus thermophilus

<400> SEQUENCE: 7
tactcaactt gaaaaggtgg caccgattcg gtgttttt                               38

<210> SEQ ID NO 8
<211> LENGTH: 39
<212> TYPE: DNA
<213> ORGANISM: Streptococcus mutans

<400> SEQUENCE: 8
tacacaactt gaaaaagtgc gcaccgattc ggtgctttt                              39

<210> SEQ ID NO 9
<211> LENGTH: 40
<212> TYPE: DNA
<213> ORGANISM: Listeria innocua

<400> SEQUENCE: 9
ttatcaactt ttaattaagt agcgctgttt cggcgctttt                             40

<210> SEQ ID NO 10
<211> LENGTH: 40
<212> TYPE: DNA
<213> ORGANISM: Mycoplasma mobile

<400> SEQUENCE: 10
tatgccgtaa ctactactta ttttcaaaat aagtagtttt                             40
```

```
<210> SEQ ID NO 11
<211> LENGTH: 36
<212> TYPE: DNA
<213> ORGANISM: Campylobacter jejuni

<400> SEQUENCE: 11
gactctgcgg ggttacaatc ccctaaaacc gctttt                                 36

<210> SEQ ID NO 12
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
taatacgact cactataggg gatgcgcgca gttgtccgtt ttagagctag aaatagcaag        60
ttaaaataag gctagtccgt tatcaacttg aaaaagtggc accgagtcgg tgctttt         117

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
taatacgact cactata                                                      17

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggatgcgcgc agttgtcc                                                     18

<210> SEQ ID NO 15
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gttttagagc tagaaatagc aagttaaaat aaggctagtc cgttatcaac ttgaaaaagt        60
ggcaccgagt cggtgctttt                                                   80

<210> SEQ ID NO 16
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 16
gagctaatac gactcactat agggatgcg cgcagttgtc cgttttagag ctagaaatag    60
caagttaaaa taaggctagt ccgttatcaa cttgaaaaag tggcaccgag tcggtgcttt   120
t                                                                   121

<210> SEQ ID NO 17
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
cgagctaata cgactcacta tagggatgc gcgcagttgt ccgttttaga gctagaaata    60
gcaagttaaa ataaggctag tccgttatca acttgaaaaa gtggcaccga gtcggtgctt   120
tt                                                                  122

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
taatacgact cactatagg                                                 19

<210> SEQ ID NO 19
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aaaagcaccg actcggtgcc acttttcaa gttgataacg gactagcctt attttaactt    60
gctatttcta gctctaaaac                                                80

<210> SEQ ID NO 20
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
taatacgact cactataggg gatgcgcgca gttgtccgtt ttagagctag aaatagca      58

<210> SEQ ID NO 21
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 21
gaaattaata cgactcacta tagggatgc gcgcagttgt ccgttttaga gctagaaata    60
gcaag                                                                65

<210> SEQ ID NO 22
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gagctaatac gactcactat aggggatgcg cgcagttgtc cgttttagag ctagaaatag    60
caagtt                                                               66

<210> SEQ ID NO 23
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gagctaatac gactcactat aggggatgcg cgcagttgtc cgttttagag ctagaaatag    60
caagttaaaa taagg                                                     75

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aaaagcaccg actc                                                      14

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aaaagcaccg actcg                                                     15

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aaaagcaccg actcgg                                                    16

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aaaagcaccg actcggt                                                    17

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gaaattaata cgactcacta tagg                                            24

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gagctaatac gactcactat agg                                             23

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gcgagctaat acgactcact atagg                                           25

<210> SEQ ID NO 31
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
cgagctaata cgactcacta tagggcaca acgtggagga tggcagcgtg cagctggctg      60
atcactacca gcaaaacact ccaatcggtg atggtcctgt tgcaccgagt cggtgctttt    120

<210> SEQ ID NO 32
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cgagctaata cgactcacta tagggggcaca acgtggagga tggcagcgtg cagctggctg    60
atcactacca g                                                          71

<210> SEQ ID NO 33
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aaagcaccga ctcggtgcaa caggaccatc accgattgga gtgttttgct ggtagtgatc    60
agccagctg                                                             69

<210> SEQ ID NO 34
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (25)..(42)
<223> OTHER INFORMATION: a, c, t, g, unknown or other

<400> SEQUENCE: 34
cgagctaata cgactcacta taggnnnnnn nnnnnnnnnn nngttttaga gctatgctga    60
aaagcatagc aagttaaaat aaggctagtc cgttatcaac ttgaaaaagt ggcaccgagt   120
cggtgctttt                                                          130

<210> SEQ ID NO 35
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atgcgtaaag gcgaagagct gttcactggt gtcgtcccta ttctggtgga actggatggt    60
gatgtcaacg gtcataagtt ttccgtgcgt ggcgagggtg aaggtgacgc aactaatggt   120
aaactgacgc tgaagttcat ctgtactact ggtaaactgc cggtaccttg ccgactctg    180 gtaacgacgc tgacttatgg tgttcagtgc tttgctcgtt atccggacca tatgaagcag   240
catgacttct tcaagtccgc catgccggaa ggctatgtgc aggaacgcac gatttccttt   300
aaggatgacg gcacgtacaa aacgcgtgcg gaagtgaaat ttgaaggcga tacccctggta  360 aaccgcattg agctgaaagg cattgacttt aaagaagacg gcaatatcct gggccataag   420
ctggaataca ttttaacag ccacaatgtt tacatcaccg ccgataaaca aaaaaatggc    480
attaaagcga attttaaaat tcgccacaac gtggaggatg gcagcgtgca gctggctgat   540
cactaccagc aaaacactcc aatcggtgat ggtcctgttc tgctgccaga caatcactat   600
ctgagcacgc aaagcgttct gtctaaagat ccgaacgaga aacgcgatca tatggttctg   660
ctggagttcg taaccgcagc gggcatcacg catggtatgg atgaactgta caaatgataa   720

```
<210> SEQ ID NO 36
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cgagctaata cgactcacta taggaacgca cgatttcctt tagttttaga gctatgctga    60
aaagcatagc                                                           70

<210> SEQ ID NO 37
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cgagctaata cgactcacta taggcattga ctttaaagaa gagttttaga gctatgctga    60
aaagcatagc                                                           70

<210> SEQ ID NO 38
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cgagctaata cgactcacta taggaggatg gcagcgtgca gcgttttaga gctatgctga    60
aaagcatagc                                                           70

<210> SEQ ID NO 39
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
aaaagcaccg actcggtgcc acttttcaa gttgataacg gactagcctt attttaactt     60
gctatgcttt tcagcatagc tctaaaac                                       88

<210> SEQ ID NO 40
<211> LENGTH: 103
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 40
nnnnnnnnnn nnnnnnnnnn guuuuagagc uagaaauagc aaguuaaaau aaggcuaguc    60
cguuaucaac uugaaaaagu ggcaccgagu cggugcuuuu uuu                      103
```

```
<210> SEQ ID NO 41
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cgagctaata cgactcacta tagggatgc gcgcagttgt ccgttttaga gctagaaata    60
gcaagttaaa ataagg                                                   76

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
taaggctagt ccgttatcaa cttgaaaaag                                    30

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ctagtccgtt atcaacttga aaaagtg                                       27

<210> SEQ ID NO 44
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gaaattaata cgactcacta tagggatgc gcgcagttgt ccgttttaga gctagaaata    60
gcaagttaaa ataaggctag tccgttatca acttgaaaaa gtggcaccga gtcggtgctt   120
tt                                                                  122
```

DE NOVO SYNTHESIZED NUCLEIC ACID LIBRARIES

CROSS-REFERENCE

This application is a Divisional of U.S. patent application Ser. No. 15/682,100, filed Aug. 21, 2017, which claims the benefit of U.S. Provisional Application No. 62/419,881, filed on Nov. 9, 2016; U.S. Provisional Application No. 62/411,388, filed on Oct. 21, 2016; U.S. Provisional Application No. 62/393,948, filed on Sep. 13, 2016; U.S. Provisional Application No. 62/382,191, filed on Aug. 31, 2016; and U.S. Provisional Application No. 62/378,134, filed on Aug. 22, 2016, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 21, 2017, is named 44854-727_401_SL.txt and is 13,567 bytes in size.

BACKGROUND

The cornerstone of synthetic biology is the design, build, and test process—an iterative process that requires DNA to be made accessible for rapid and affordable generation and optimization of these custom pathways and organisms. In the design phase, the A, C, T, and G nucleotides that constitute DNA are formulated into the various sequences that would comprise a region of interest, with each sequence variant representing a specific hypothesis that will be tested. These variant sequences represent subsets of sequence space, a concept that originated in evolutionary biology and pertains to the totality of sequences that make up genes, genomes, transcriptome, and proteome. In the context of targeted genome editing, there exists a need for rapid generation of highly accurate and uniform nucleic acid libraries for specifically directing enzymatic editing of a gene, a gene cluster, a pathway, or an entire genome.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF SUMMARY

Provided herein are systems, methods, and compositions for the efficient de novo synthesis and screening of highly accurate nucleic acid libraries. Nucleic acid libraries as described herein comprise nucleic acids for specifically targeting and editing a gene, a gene cluster, a biological pathway, or an entire genome.

Provided herein are nucleic acid libraries, wherein the nucleic acid library comprises at least 500 non-identical DNA molecules, wherein each non-identical DNA molecule encodes for a different gRNA sequence, and wherein at least about 80% of the at least 500 non-identical DNA molecules are each present in the nucleic acid library in an amount within 2× of a mean frequency for each of the non-identical DNA molecules in the library. Provided herein are nucleic acid libraries, wherein each non-identical DNA molecule has a GC base content of about 20% to about 85%. Provided herein are nucleic acid libraries, wherein each non-identical DNA molecule has a GC base content of about 30% to about 70%. Provided herein are nucleic acid libraries, wherein at least about 90% of the at least 500 non-identical DNA molecules are each present in the nucleic acid library in an amount within 2× of the mean frequency for each of the non-identical DNA molecules in the library. Provided herein are nucleic acid libraries, wherein at least 99% of the at least 500 non-identical DNA molecules are each present in the nucleic acid library in an amount within 2× of the mean frequency for each of the non-identical DNA molecules in the library. Provided herein are nucleic acid libraries, wherein the at least 500 non-identical DNA molecules comprises at least 2000 non-identical DNA molecules. Provided herein are nucleic acid libraries, wherein the at least 500 non-identical DNA molecules comprises at least 3500 non-identical DNA molecules. Provided herein are nucleic acid libraries, wherein the at least 500 non-identical DNA molecules comprises at least 100,000 non-identical DNA molecules. Provided herein are nucleic acid libraries, wherein each non-identical DNA molecule comprises up to 200 bases in length. Provided herein are nucleic acid libraries, wherein each non-identical DNA molecule comprises about 100 to about 200 bases in length. Provided herein are nucleic acid libraries, wherein the at least 500 non-identical DNA molecules comprises non-identical DNA molecules encoding for gRNA sequences targeting genes in a biological pathway. Provided herein are nucleic acid libraries, wherein the at least 500 non-identical DNA molecules comprises non-identical DNA molecules encoding for gRNA sequences targeting genes in an entire genome. Provided herein are nucleic acid libraries, wherein the gRNA is a single gRNA or a dual gRNA.

Provided herein are nucleic acid libraries, wherein the nucleic acid library comprises at least 2000 non-identical nucleic acids, wherein each non-identical nucleic acid encodes for a different sgRNA sequence, wherein each sgRNA sequence comprises a targeting domain complementary to a eukaryotic gene, and wherein at least about 80% of the at least 2000 non-identical nucleic acids are present in the nucleic acid library in an amount within 2× of a mean frequency for each of the non-identical nucleic acids in the library. Provided herein are nucleic acid libraries, wherein each non-identical nucleic acid has a GC base content of about 20% to about 85%. Provided herein are nucleic acid libraries, wherein each non-identical nucleic acid has a GC base content of about 30% to about 70%. Provided herein are nucleic acid libraries, wherein at least about 90% of the at least 2000 non-identical nucleic acids are each present in the nucleic acid library in an amount within 2× of the mean frequency for each of the non-identical nucleic acids in the library. Provided herein are nucleic acid libraries, wherein at least 99% of the at least 2000 non-identical nucleic acids are each present in the nucleic acid library in an amount within 2× of the mean frequency for each of the non-identical nucleic acids in the library. Provided herein are nucleic acid libraries, wherein each non-identical nucleic acid comprises up to 200 bases in length. Provided herein are nucleic acid libraries, wherein each non-identical nucleic acid comprises about 100 to about 200 bases in length. Provided herein are nucleic acid libraries, wherein the at least 2000 non-identical nucleic acids comprise non-identical nucleic acids encoding for sgRNA sequences targeting genes in a biological pathway. Provided herein are nucleic acid libraries, wherein the at least 2000 non-identical nucleic acids comprise non-identical nucleic acids encoding for sgRNA sequences targeting genes in an entire genome. Provided herein are nucleic acid libraries, wherein each non-identical nucleic acid comprises DNA or RNA molecules.

Provided herein are amplicon libraries, wherein the amplicon library comprises a plurality of non-identical DNA molecules, wherein each non-identical DNA is present in a population of amplification products, wherein each non-identical DNA molecule encodes for a different gRNA sequence, and wherein at least about 80% of the plurality of non-identical DNA molecules are each present in the amplicon library in an amount within 2× of a mean frequency for each of the non-identical DNA molecules in the library. Provided herein are amplicon libraries, wherein each non-identical DNA molecule has a GC base content of about 30% to about 70%. Provided herein are amplicon libraries, wherein the gRNA is a single gRNA or a dual gRNA.

Provided herein are cell libraries, wherein the cell library comprises a plurality of cell populations, wherein each of the cell populations comprises a DNA molecule encoding for a different gRNA sequence, wherein each gRNA sequence comprises a targeting region for binding to a gene, and wherein at least 15% of the cell populations have at least 2-fold depletion in expression of the gene. Provided herein are cell libraries, wherein at least 45% of the cell populations have at least 2-fold depletion in expression of the gene. Provided herein are cell libraries, wherein the gRNA is a single gRNA or a dual gRNA. Provided herein are cell libraries, wherein the plurality of cell populations comprises DNA molecules encoding for at least 3 different gRNA sequences per a single gene. Provided herein are cell libraries, wherein the plurality of cell populations comprises DNA molecules encoding for at least 5 different gRNA sequences per a single gene. Provided herein are cell libraries, wherein the plurality of cell populations comprises at least 2000 cell populations. Provided herein are cell libraries, wherein the plurality of cell populations comprises DNA molecules encoding for gRNA sequences in a biological pathway. Provided herein are cell libraries, wherein the plurality of cell populations comprises DNA molecules encoding for gRNA sequences in an entire genome. Provided herein are cell libraries, wherein the genome is *Arabidopsis thaliana, Caenorhabditis elegans, Canis lupus familiaris, Chlamydomonas reinhardtii, Danio rerio, Dictyostelium discoideum, Drosophila melanogaster, Escherichia coli, Homo sapiens, Macaca mulatta, Mus musculus, Oryctolagus cuniculus, Rattus norvegicus, Saccharomyces cerevisiae,* or *Sus scrofa*. Provided herein are cell libraries, wherein each of the cell populations comprises prokaryotic cells. Provided herein are cell libraries, wherein each of the cell populations comprises eukaryotic cells. Provided herein are cell libraries, wherein each of the cell populations comprises mammalian cells. Provided herein are cell libraries, wherein each of the cell populations further comprises an exogenous nuclease enzyme. Provided herein are cell libraries, wherein the DNA molecule further comprises a vector sequence.

Provided herein are cell libraries, wherein the cell library comprises a plurality of cell populations, wherein each of the cell populations comprises a DNA molecule encoding for a different gRNA sequence, wherein each gRNA sequence comprises a targeting region for binding to a gene, and wherein at most 20% of the cell populations have a zero or negative depletion in expression of the gene. Provided herein are cell libraries, wherein the gRNA is a single gRNA or a dual gRNA. Provided herein are cell libraries, wherein the plurality of cell populations comprises DNA molecules encoding for at least 3 different gRNA sequences per a single gene. Provided herein are cell libraries, wherein the plurality of cell populations comprises DNA molecules encoding for at least 5 different gRNA sequences per a single gene. Provided herein are cell libraries, wherein the plurality of cell populations comprises at least 2000 cell populations. Provided herein are cell libraries, wherein the plurality of cell populations comprises at least 10000 cell populations.

Provided herein are methods for synthesis of a gRNA library, comprising: providing predetermined sequences for at least 500 non-identical DNA molecules, wherein each non-identical DNA molecule encodes for a gRNA; synthesizing the at least 500 non-identical DNA molecules; and transcribing the at least 500 non-identical DNA molecules to generate a library of gRNAs, wherein at least about 75% of the gRNAs in the library of gRNAs are error free compared to the predetermined sequences for the at least 500 non-identical DNA molecules. Provided herein are methods for synthesis of a gRNA library, further comprising transferring the at least 500 non-identical DNA molecules into cells prior to the transcribing step. Provided herein are methods for synthesis of a gRNA library, wherein at least 96% of the gRNAs encoded by the at least 500 non-identical DNA molecules are present in the library of gRNAs. Provided herein are methods for synthesis of a gRNA library, wherein at least 87% of the gRNAs in the library of gRNAs are error free compared to the predetermined sequences for the at least 500 non-identical DNA molecules. Provided herein are methods for synthesis of a gRNA library, further comprising inserting the at least 500 non-identical DNA molecules into vectors. Provided herein are methods for synthesis of a gRNA library, further comprising transferring the at least 500 non-identical DNA molecules to cells of an organism. Provided herein are methods for synthesis of a gRNA library, wherein the organism is *Arabidopsis thaliana, Caenorhabditis elegans, Canis lupus familiaris, Chlamydomonas reinhardtii, Danio rerio, Dictyostelium discoideum, Drosophila melanogaster, Escherichia coli, Homo sapiens, Macaca mulatta, Mus musculus, Oryctolagus cuniculus, Rattus norvegicus, Saccharomyces cerevisiae,* or *Sus scrofa*. Provided herein are methods for synthesis of a gRNA library, wherein each non-identical DNA molecule encodes for a single gRNA or a dual gRNA.

Provided herein are methods for synthesis of a gRNA library, comprising: providing predetermined sequences for a plurality of non-identical DNA molecules, wherein each non-identical DNA molecule encodes for a gRNA; providing a surface, wherein the surface comprises clusters of loci for nucleic acid extension reaction; synthesizing the plurality of non-identical DNA molecules, wherein each non-identical DNA molecule extends from the surface; and transferring the plurality of non-identical DNA molecules into cells. Provided herein are methods for synthesis of a gRNA library, wherein each cluster comprises about 50 to about 500 loci. Provided herein are methods for synthesis of a gRNA library, wherein each non-identical DNA molecule comprises up to about 200 bases in length. Provided herein are methods for synthesis of a gRNA library, wherein each non-identical DNA molecule encodes for a single gRNA or a dual gRNA. Provided herein are methods for synthesis of a gRNA library, wherein the cells are prokaryotic cells. Provided herein are methods for synthesis of a gRNA library, wherein the cells are eukaryotic cells. Provided herein are methods for synthesis of a gRNA library, wherein the eukaryotic are mammalian cells. Provided herein are methods for synthesis of a gRNA library, wherein each of the cells comprises an exogenous nuclease enzyme.

BRIEF DESCRIPTION OF THE DRAWINGS

FIG. 4A is diagram of a sgRNA sequence (SEQ ID NO: 40) having a base-pairing region, a dCas9 handle, and a *S. pyogenes* terminator region. FIG. 4B is a diagram of a sgRNA alone. FIG. 4C is a diagram of a dgRNA alone.

FIG. 12 depicts 4 sgRNA designs. FIG. 12 discloses SEQ ID NOS 20, 15, 21, 15, 22, 15, 41, 15, 42, and 43, respectively, in order of appearance.

FIG. 26B depicts a graph of percentage of sgRNAs with zero or negative depletion.

DETAILED DESCRIPTION

Figure 1A:
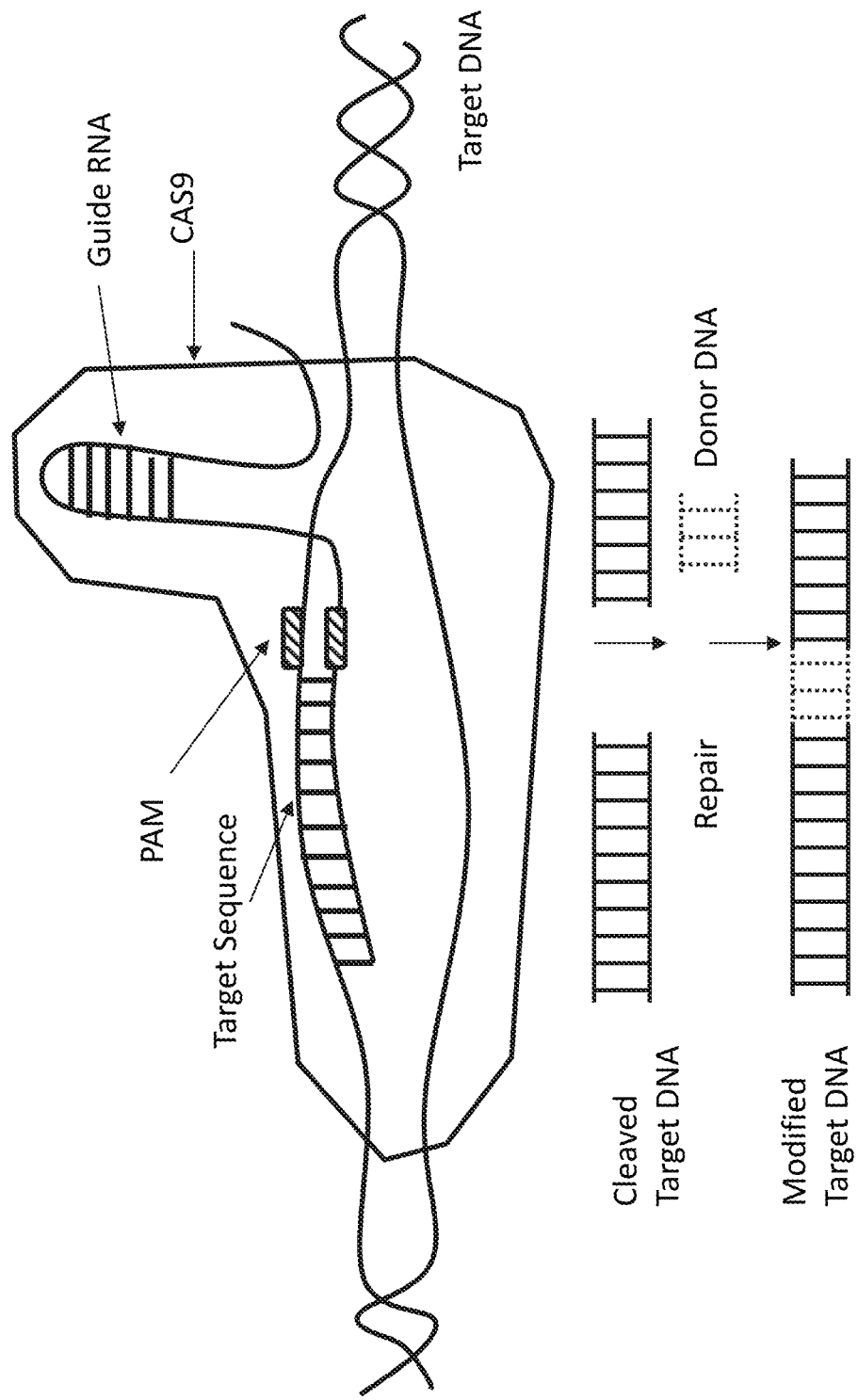
FIG. 1A illustrates a Clustered Regularly Interspaced Short Palindromic Repeats (CRISPR) complex which includes the following components: PAM, target sequence, CAS9 enzyme, Guide RNA (gRNA), and donor DNA.

Provided herein are systems, methods, and compositions for the efficient synthesis and screening of highly accurate guide RNA ("gRNA") libraries. De novo synthesis methods described herein provide for a rapid and highly accurate generation of large libraries of gRNA for incorporation into enzymatic systems for targeted gene editing.

Definitions

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The term "gRNA" as referred to herein refers to guide RNA sequence and encompasses both single and dual guide RNA sequence. Unless specifically stated or obvious from context, as used herein, the term "dgRNA" as referred to herein refers to dual guide RNA sequence: crRNA (spacer sequence comprising a seed region complementary to a target sequence) and a separate tracrRNA (trans-activating sequence), which are partially complementary RNAs. Unless specifically stated or obvious from context, as used herein, the term "sgRNA" as referred to herein refers to single guide RNA sequence, comprising both a fused crRNA and tracrRNA.

Unless specifically stated or obvious from context, as used herein, the terms "oligonucleotide," "polynucleotide," and "nucleic acid" encompass double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands). Nucleic acid sequences, when provided, are listed in the 5' to 3' direction, unless stated otherwise. Methods described herein provide for the generation of isolated nucleic acids. Methods described herein additionally provide for the generation of isolated and purified nucleic acids. An "oligonucleotide," "polynucleotide," and "nucleic acid" as referred to herein can comprise at least 5, 10, 20, 30, 40, 50, 60, 70, 80, 90, 100, 125, 150, 175, 200, 225, 250, 275, 300, 325, 350, 375, 400, 425, 450, 475, 500, 600, 700, 800, 900, 1000, 1100, 1200, 1300, 1400, 1500, 1600, 1700, 1800, 1900, 2000, or more bases in length.

Unless specifically stated or obvious from context, as used herein, the term "amplicon" as used herein refers to an amplification reaction product.

The present disclosure employs, unless otherwise indicated, conventional molecular biology techniques, which are within the skill of the art. Unless defined otherwise, all technical and scientific terms used herein have the same meaning as is commonly understood by one of ordinary skill in the art to which these inventions belong.

gRNA Library Screening

Provided herein are methods for designing, building, and screening a library of highly accurate gRNAs for incorporation in a Clustered Regularly Interspaced Short Palindromic Repeats (CRISPR)-enzyme complex. See, e.g., FIGS. 1A-AB. gRNA libraries generated using methods described herein include both sgRNA and dgRNA libraries. Provided herein are methods for highly uniform synthesis resulting in high representation of predetermined gRNAs in the resulting libraries. In the design phase, gRNAs are designed. See FIG. 2. Design strategies include, without limitation, design of gRNAs to span a gene. Depending on the desired workflow, the de novo synthesized nucleic acids are DNA or RNA bases.

Figure 2:
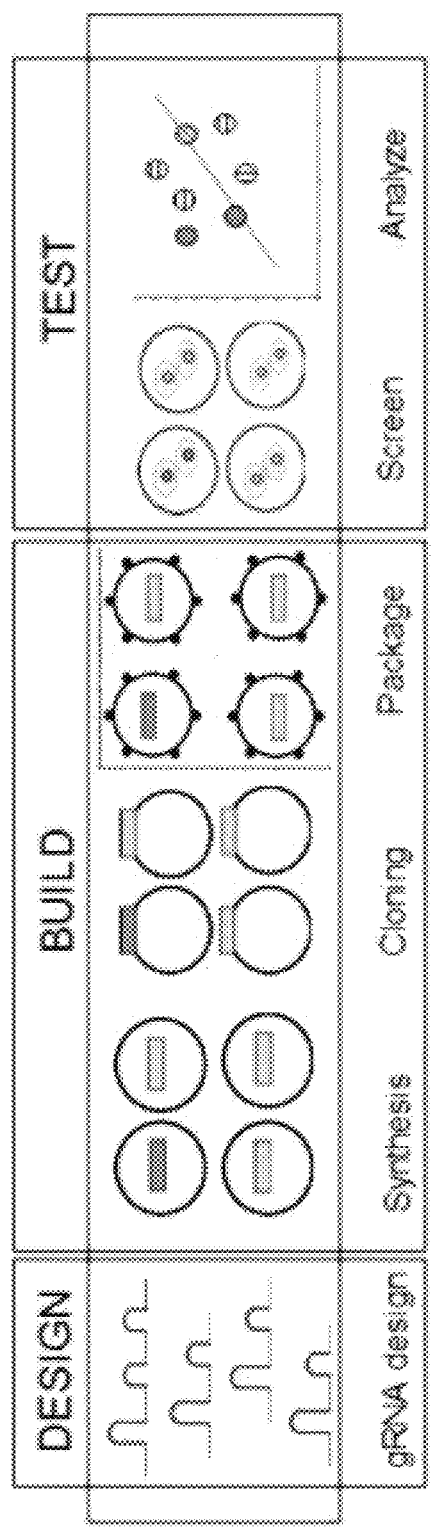
FIG. 2 illustrates a gRNA library screening workflow, including design, synthesis, cloning, packaging, screening and analysis of a gRNA library.

In the case of de novo synthesized DNA, a library comprising nucleic acids is synthesized, wherein each nucleic acid synthesized is a DNA sequence that encodes for a gRNA (e.g., sgRNA) sequence as a transcription product. In some instances, the synthesized nucleic acids are then inserted into expression vectors. In one exemplary workflow, the synthesized nucleic acids are inserted into viral vectors, and then packaged for transduction into cells, followed by screening and analysis. FIG. 2. Exemplary cells include without limitation, prokaryotic and eukaryotic cells. Exemplary eukaryotic cells include, without limitation, animal, plant, and fungal cells. Exemplary animal cells include, without limitation, insect, fish and mammalian cells. Exemplary mammalian cells include mouse, human, and primate cells. Exemplary cellular functions tested include, without limitation, changes in cellular proliferation, migration/adhesion, metabolic, and cell-signaling activity. In the case of de novo synthesized RNA, the gRNA itself is synthesized and available for downstream applications, such as transfection into cells.

Figure 3:
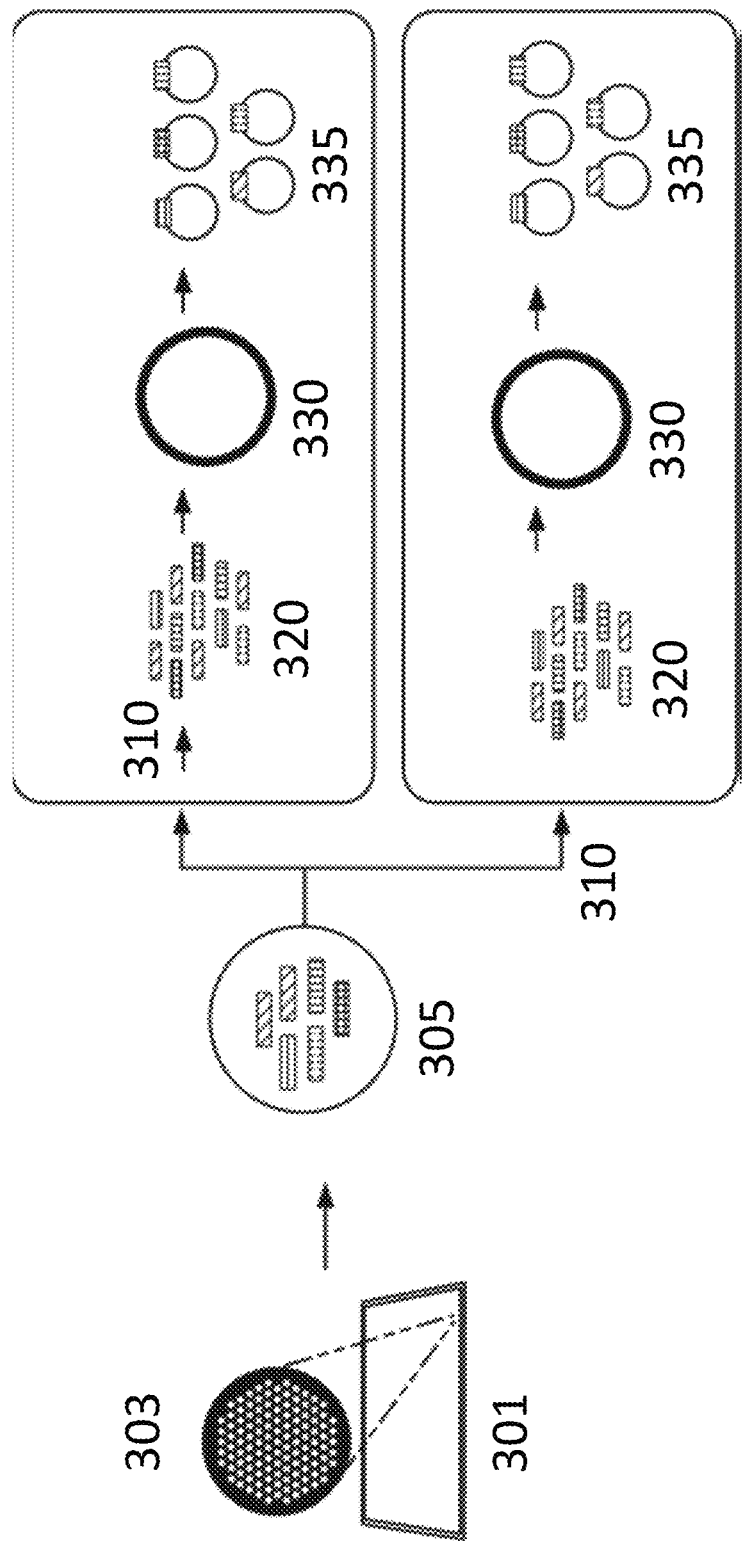
FIG. 3 illustrates gRNA library screening workflow for building a library, including: synthesizing an oligonucleotide library on an array, amplifying and transferring the oligonucleotides into vectors, and forming an expression library for gRNA expression.

Oligonucleotides may be synthesized within a cluster 303 of locations ("loci") for extension on an array 301. See FIG. 3. Such an arrangement may provide for improved oligonucleotide representation of products from amplification of the synthesized oligonucleotides—termed "amplicons"- when compared to amplification products of oligonucleotides synthesized across an entire plate without a clustered loci arrangement. In some instances, amplification 310 of oligonucleotides synthesized within a single cluster counters negative effects on representation due to repeated synthesis of large oligonucleotide populations having oligonucleotides with heavy GC content, commonly termed "drift," due to underrepresentation of GC low or GC high amplicons in the amplification reaction product. In some instances, the single cluster described herein, comprises about 50-1000, 75-900, 100-800, 125-700, 150-600, 200-500, or 300-400 discrete loci. In some instances, the single cluster comprises 50-500 discrete loci. In some instances, a locus is a spot, well, microwell, channel, or post. In some instances, each cluster has at least 1×, 2×, 3×, 4×, 5×, 6×, 7×, 8×, 9×, 10×, or more redundancy of separate features supporting extension of oligonucleotides having identical sequence.

Provided herein are gRNA libraries for insertion into expression vectors. Continuing the workflow in FIG. 3, an array 301 includes multiple clusters 303 of loci for oligonucleotide synthesis and extension. De novo DNA is synthesized and removed from the plate to form a population of oligonucleotides 305 (e.g., DNAs encoding for sgRNAs), which are subject to amplification 310 to form a library of amplified oligonucleotides 320 for insertion into a vector 330 to form a library of vectors including the synthesized DNAs 335. Once in the cells, the DNAs are transcribed into gRNAs (e.g., sgRNAs) and are available for binding with genomic editing regime (e.g., a Cas9-based system). The cells may have natural or ectopic expression of the editing enzyme (e.g., Cas9). The editing enzyme (e.g., Cas9) may have double DNA strand cleavage activity, or a modified activity, such as nicking, base swapping or sequence swapping activity. The synthesized DNA for insertion into a vector may comprise sgRNAs, dgRNAs, or fragments thereof.

Expression vectors for inserting nucleic acid libraries disclosed herein comprise eukaryotic or prokaryotic expression vectors. Exemplary expression vectors include, without limitation, mammalian expression vectors: pSF-CMV-NEO-NH2-PPT-3XFLAG, pSF-CMV-NEO-COOH-3XFLAG, pSF-CMV—PURO-NH2-GST-TEV, pSF-OXB20-COOH-TEV-FLAG(R)-6His, pCEP4 pDEST27, pSF-CMV-Ub-KrYFP, pSF-CMV-FMDV-daGFP, pEF1a-mCherry-N1 Vector, pEF1a-tdTomato Vector, pSF-CMV-FMDV-Hygro, pSF-CMV-PGK-Puro, pMCP-tag(m), and pSF-CMV—PURO-NH2-CMYC; bacterial expression vectors: pSF-OXB20-BetaGal, pSF-OXB20-Fluc, pSF-OXB20, and pSF-Tac; plant expression vectors: pRI 101-AN DNA and pCambia2301; and yeast expression vectors: pTYB21 and pKLAC2, and insect vectors: pAc5.1/V5-His A and pDEST8.

De novo oligonucleotide libraries synthesized by methods described herein may be expressed in cells. In some instances, the cells are associated with a disease state. For example, cells associated with a disease state include, but not limited to, cell lines, tissue samples, primary cells from a subject, cultured cells expanded from a subject, or cells in a model system. In some instances, the model system is a plant or animal system. In some instances, the de novo oligonucleotide libraries are expressed in cells to assess for a change in cellular activity. Exemplary cellular activities include, without limitation, proliferation, cycle progression, cell death, adhesion, migration, reproduction, cell signaling, energy production, oxygen utilization, metabolic activity, aging, response to free radical damage, or any combination thereof.

Provided herein are methods for synthesizing a gRNA library (or a DNA library that when transcribed results in a gRNA library), wherein the gRNA library comprises a plurality of non-identical gRNAs per a gene. The gRNA may encode a sgRNA or a dgRNA. In some instances, the gRNA library comprises at least 3, 4, 5, 6, 7, 8, 9, 10, or more than 10 non-identical gRNAs per the gene. In some instances, the gRNA library targets one or more genes. In some instances, the gRNA library targets about 1, 5, 10, 20, 30, 40, 50, 60, 70, 80, 90, 100, or more than 100 genes. In some instances, the gRNA library targets about 1-100, 2-95, 5-90, 10-85, 15-80, 20-75, 25-70, 30-65, 35-60, or 40-50 genes. In some instances, the gRNA library described herein targets genes in a pathway. Exemplary pathways include, without limitation a metabolic, cell death, cell cycle progression, immune cell activation, inflammatory response, angiogenesis, lymphogenesis, hypoxia and oxidative stress response, cell adhesion, and cell migration pathways.

Methods for synthesizing a gRNA library as described herein may provide for synthesis of non-identical gRNAs having a base-pairing region complementary to part of a genome, a genome target region. The genome target region may comprise exon, intron, coding, or non-coding sequence. In some instances, the gRNA library comprises non-identical gRNAs collectively having a base-pairing region complementary to at least or about 5% of the genes in an entire genome. In some instances, the gRNA library comprises non-identical gRNAs collectively having a base-pairing region complementary to at least or about 80% of the genes in an entire genome. In some instances, the gRNA library comprises non-identical gRNAs collectively having a base-pairing region complementary to at least or about 90% of the genes in an entire genome. In some instances, the gRNA library comprises non-identical gRNAs collectively having a base-pairing region complementary to at least or about 95% of the genes in an entire genome. In some instances, the gRNA library comprises non-identical gRNAs collectively having a base-pairing region complementary to at least or about 100% of the genes in an entire genome.

Provided herein are gRNA libraries synthesized by methods described herein that result in gRNAs with at least 2× depletion of a gene across different cells. In some instances, the gRNA libraries comprise at least or about 10%, 12%, 15%, 16%, 20%, 25%, 30%, 35%, 40%, 45%, 50%, 55%, 60%, 65% or more of gRNAs that provide for at least 2× depletion a gene when present in cells or in a plurality of cell populations. In some instances, the gene is an essential gene, i.e. a gene critical for cell survival. Exemplary essential genes include, without limitation, PCNA, PSMA7, RPP21, and SF3B3. In some instances, the gRNA libraries comprise gRNAs that provide for at least 2×, 3×, 4×, 5×, 6×, or more than 6× depletion of a gene when present in cells. In some instances, the gRNA libraries comprise at most 5%, 10%, 12%, 15%, or 20% of the gRNAs with zero or negative depletion of the gene when present in cells or in a plurality of cell populations. In some instances, the plurality of cell populations comprises at least or about 2000, 3000, 4000, 5000, 6000, 7000, 8000, 9000, 10000, 12000, 15000, 20000, 25000, 30000, or more than 30000 cell populations. In some instances, the gRNA libraries comprise gRNAs with at least 2×, 3×, 4×, 5×, 6×, or more than 6× depletion for the plurality of genes. In some instances, the gRNA libraries comprise an average of at least or about 40%, 45%, 50%, 60%, 65%, 70%, 75%, 80% or more than 90% of gRNAs providing at least 2× depletion for the plurality of genes. The gRNAs providing such gene deletion profiles can be sgRNAs or dgRNAs.

Provided herein are methods for synthesizing highly uniform libraries of oligonucleotides. In some cases, more than 90% of synthesized oligonucleotides (RNA or DNA) are represented within 4× of the mean for oligonucleotide representation for a nucleic acid library. In some cases, more than 90% of oligonucleotides are represented within 2× of the mean for oligonucleotide representation for the library. In some cases, more than 90% of oligonucleotides are represented within 1.5× of the mean for oligonucleotide representation for the library. In some cases, more than 80% of oligonucleotides are represented within 1.5× of the mean for oligonucleotide representation for the library.

Oligonucleotide libraries de novo synthesized by methods described herein comprise a high percentage of correct sequences compared to predetermined sequences. In some instances, de novo oligonucleotide libraries disclosed herein have greater than 70% correct sequence compared to predetermined sequences for oligonucleotides. In some instances, de novo oligonucleotide libraries disclosed herein have greater than 75% correct sequence compared to predetermined sequences for the oligonucleotides. In some instances, de novo oligonucleotide libraries disclosed herein have greater than 80% correct sequence compared to predetermined sequences for the oligonucleotides. In some instances, de novo oligonucleotide libraries disclosed herein have greater than 85% correct sequence compared to predetermined sequences for the oligonucleotides. In some instances, de novo oligonucleotide libraries disclosed herein have greater than 90% correct sequence compared to predetermined sequences for the oligonucleotides. In some instances, de novo oligonucleotide libraries disclosed herein have greater than 95% correct sequence compared to predetermined sequences for the oligonucleotides. In some instances, de novo oligonucleotide libraries disclosed herein have greater than 100% correct sequence compared to predetermined sequences for the oligonucleotides.

In some instances, de novo synthesized oligonucleotide libraries disclosed herein have greater than 70% correct sequence compared to predetermined sequences for the oligonucleotides following an amplification reaction. In some instances, de novo synthesized oligonucleotide libraries disclosed herein have greater than 75% correct sequence compared to predetermined sequences for the oligonucleotides following an amplification reaction. In some instances, de novo synthesized oligonucleotide libraries disclosed herein have greater than 80% correct sequence compared to predetermined sequences for the oligonucleotides following an amplification reaction. In some instances, de novo synthesized oligonucleotide libraries disclosed herein have greater than 85% correct sequence compared to predetermined sequences for the oligonucleotides following an amplification reaction. In some instances, de novo synthesized oligonucleotide libraries disclosed herein have greater than 90% correct sequence compared to predetermined sequences for the oligonucleotides following an amplification reaction. In some instances, de novo synthesized oligonucleotide libraries disclosed herein have greater than 95% correct sequence compared to predetermined sequences for the oligonucleotides following an amplification reaction. In some instances, de novo synthesized oligonucleotide libraries disclosed herein have 100% correct sequence compared to predetermined sequences for the oligonucleotides following an amplification reaction.

In some instances, de novo synthesized oligonucleotide libraries disclosed herein, when transferred into cells, results in greater than 80% correct sequence compared to predetermined sequences for the oligonucleotides. In some instances, de novo synthesized oligonucleotide libraries disclosed herein, when transferred into cells, results in greater than 85% correct sequence compared to predetermined sequences for the oligonucleotides. In some instances, de novo synthesized oligonucleotide libraries disclosed herein, when transferred into cells, results in greater than 90% correct sequence compared to predetermined sequences for the oligonucleotides. In some instances, de novo synthesized oligonucleotide libraries disclosed herein, when transferred into cells, results in greater than 95% correct sequence compared to predetermined sequences for the oligonucleotides. In some instances, de novo synthesized oligonucleotide libraries disclosed herein, when transferred into cells, results in 100% correct sequence compared to predetermined sequences for the oligonucleotides.

In some instances, de novo synthesized oligonucleotide libraries disclosed herein, when transferred into cells, result in greater than 80% sequence representation. In some instances, de novo synthesized oligonucleotide libraries disclosed herein, when transferred into cells, result in greater than 90% sequence representation. In some instances, de novo synthesized oligonucleotide libraries disclosed herein, when transferred into cells, result in greater than 95% sequence representation. In some instances, de novo synthesized oligonucleotide libraries disclosed herein, when transferred into cells, result in 100% sequence representation.

De novo oligonucleotide libraries described herein may be subject to amplification reactions with the addition of a polymerase enzyme and amplification reagents (e.g., buffers, phosphates, and dNTPs). In some instances, the de novo oligonucleotide libraries are amplified by PCR for at least or about 6, 8, 10, 15, 20, or more than 20 cycles. In some instances, the de novo oligonucleotide libraries are amplified by PCR in a range of about 6 to 20, 7 to 18, 8 to 17, 9 to 16, or 10 to 15 cycles. In some instances, the de novo oligonucleotide libraries are amplified by PCR for about 15 cycles.

In some instances, amplification of the de novo oligonucleotide libraries provides for an amplicon library of DNA molecules. In some instances, the amplicon library comprises non-identical nucleic acids that encode for a gRNA sequence. In some instances, the gRNA sequence is a sgRNA or a dgRNA.

In some instances, the de novo oligonucleotide libraries comprise non-identical nucleic acids, wherein each non-identical nucleic acid comprises DNA molecules. In some instances, the number of DNA molecules is about 500, 2000, 3500 or more molecules. In some instances, the number of DNA molecules is at least or about 250, 500, 1000, 1250, 2000, 2500, 3000, 3500, 4000, 4500, 5000, 5500, 6000, 6500, 7000, 7500, 8000, 8500, 9000, 9500, 10000, 15000, 20000, 50000, 100000, 250000, 500000, 750000, 1 million, or more than 1 million molecules. In some instances, the number of DNA molecules is at most 250, 500, 1000, 1250, 2000, 2500, 3000, 3500, 4000, 4500, 5000, 5500, 6000, 6500, 7000, 7500, 8000, 8500, 9000, 9500, 10000, 15000, 20000, 50000, 100000, 250000, 500000, 750000, 1 million, or more than 1 million molecules. In some instances, the DNA molecule encodes for a gRNA sequence. In some instances, the gRNA sequence is a sgRNA or a dgRNA.

In some instances, the de novo oligonucleotide libraries comprise non-identical nucleic acids, wherein each non-identical nucleic acid comprises RNA molecules. In some instances, the number of RNA molecules is about 2000 molecules. In some instances, the number of RNA molecules is at least or about 250, 500, 1000, 1250, 2000, 2500, 3000, 3500, 4000, 4500, 5000, 5500, 6000, 6500, 7000, 7500, 8000, 8500, 9000, 9500, 10000, 15000, 20000, 50000, 100000, 250000, 500000, 750000, 1 million, or more than 1 million molecules. In some instances, the number of RNA molecules is at most 250, 500, 1000, 1250, 2000, 2500, 3000, 3500, 4000, 4500, 5000, 5500, 6000, 6500, 7000, 7500, 8000, 8500, 9000, 9500, 10000, 15000, 20000, 50000, 100000, 250000, 500000, 750000, 1 million, or more than 1 million molecules. In some instances, the RNA molecule encodes for a gRNA sequence. In some instances, the gRNA sequence is a sgRNA or a dgRNA.

Provided herein are de novo oligonucleotide libraries having high uniformity following amplification. In some instances, more than 80% of oligonucleotides in a de novo oligonucleotide library described herein are represented within at least about 1.5× the mean representation for the entire library following amplification. In some instances, more than 90% of oligonucleotides in a de novo oligonucleotide library described herein are represented within at least about 1.5× the mean representation for the entire library following amplification. In some instances, more than 80% of oligonucleotides in a de novo oligonucleotide library described herein are represented within at least about 2× the mean representation for the entire library following amplification. In some instances, more than 80% of oligonucleotides in a de novo oligonucleotide library described herein are represented within at least about 2× the mean representation for the entire library following amplification.

An unamplified population of oligonucleotides de novo synthesized using methods described herein can vary in a number of non-identical oligonucleotide sequences. In some instances, the number of non-identical oligonucleotide sequences is in a range of about 2000-1 million, 3000 to 900000, 4000-800000, 5000-700000, 6000-600000, 7000-500000, 8000-400000, 9000-300000, 10000-200000, 11000-100000, 12000-75000, 14000-60000, and 20000-50000 sequences. In some cases, the number of non-identical oligonucleotide sequences is in the range of about 50-2000, 75-1800, 100-1700, 150-1600, 200-1500, 250-1400, 300-1300, 400-1200, 500-1100, 600-1000, 700-900 sequences. In some instances, the number of non-identical oligonucleotide sequences is 2000 sequences. In some instances, the number of non-identical oligonucleotide sequences is more than 1 million sequences. In some instances, the number of non-identical oligonucleotide sequences is at least 50, 100, 200, 400, 600, 800, 1000, 1200, 1400, 1600, 1800, 2000, 3000, 5000, 7000, 10000, 20000, 30000, 50000, 100000, 500000, 700000, 1000000, 10000000, 1000000000, or more sequences. In some instances, the number of non-identical oligonucleotide sequences is up to 50, 100, 200, 400, 600, 800, 1000, 1200, 1400, 1600, 1800, 2000, 3000, 5000, 7000, 10000, 20000, 30000, 50000, 100000, 500000, 700000, 1000000, or more sequences. In some instances, the number of non-identical oligonucleotide sequences is at most 50, 100, 200, 400, 600, 800, 1000, 1200, 1400, 1600, 1800, 2000, 3000, 5000, 7000, 10000, 20000, 30000, 50000, 100000, 500000, 700000, and 1000000 sequences.

An oligonucleotide of an unamplified population may be present in varying amounts. In some instances, an oligonucleotide of an unamplified population is present in an amount of at least or about 0.25 femtomole. In some instances, an oligonucleotide of an unamplified population is present in an amount of at least or about 1 femtomole. In some instances, an oligonucleotide of an unamplified population is present in an amount of at least 0.25, 1, 10, 20, 30, 40, 50, 100, 250, 500, 750, 1000, or more than 1000 femtomoles. In some instances, an oligonucleotide of an unamplified population is present in an amount of at most 0.25, 1, 10, 20, 30, 40, 50, 100, 250, 500, 750, and 1000 femtomoles.

Provided herein are methods for synthesizing libraries of non-identical oligonucleotides, wherein a sequence length or average sequence length of the non-identical oligonucleotides vary. In some cases, the sequence length or average sequence length of the non-identical oligonucleotides is up to 150 bases. In some cases, the sequence length or average sequence length of the non-identical oligonucleotides is in a range of about 100 to about 200 bases. In some instances, the sequence length or average sequence length of the non-identical oligonucleotides is at least 30, 50, 100, 125, 150, 200, 250, 300, 350, 400, 450, 500, or more than 500 bases. In some instances, the sequence length or average sequence length of the non-identical oligonucleotides is at most 150, 200, 250, 300, 350, 400, 450, or 500 bases. An exemplary sequence length of the non-identical oligonucleotide is in a range of about 25 to about 150 or about 50 to about 200 bases. In some cases, the sequence length or average sequence length of the non-identical oligonucleotides is in the range of about 125 to about 200 or about 150 to about 200 bases.

Guide RNA Sequences

Figure 4A:
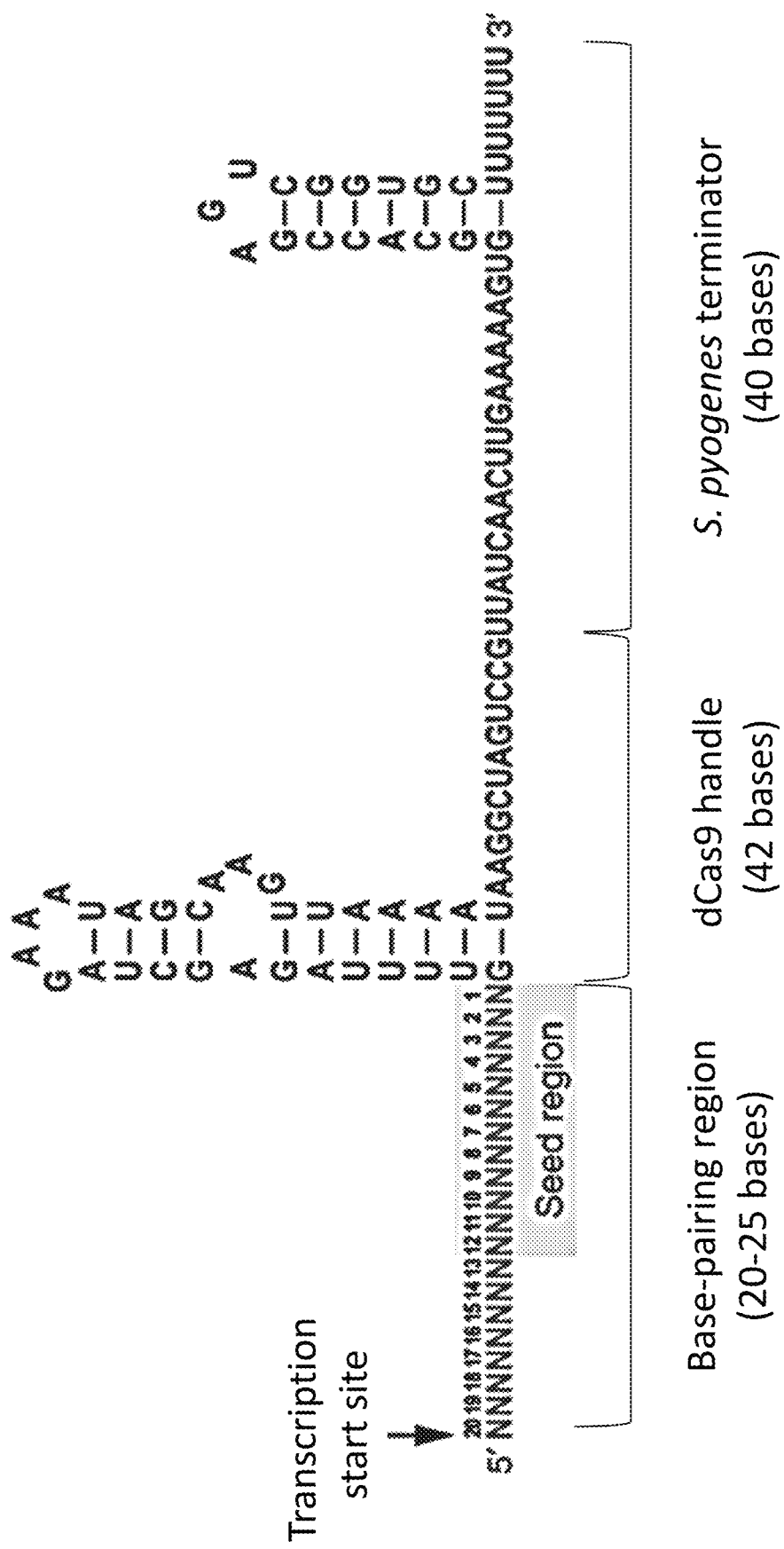
FIGS. 4A-4C are diagrams of various gRNAs.
Figure 4B:
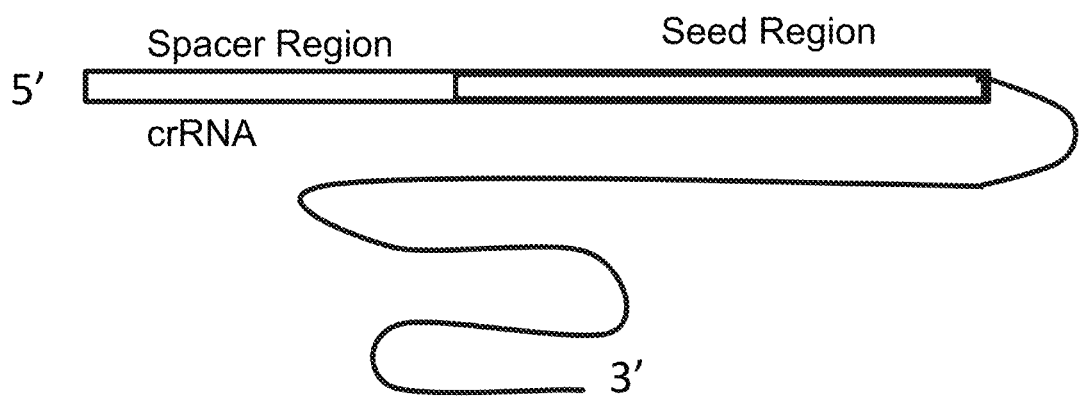
Figure 4C:
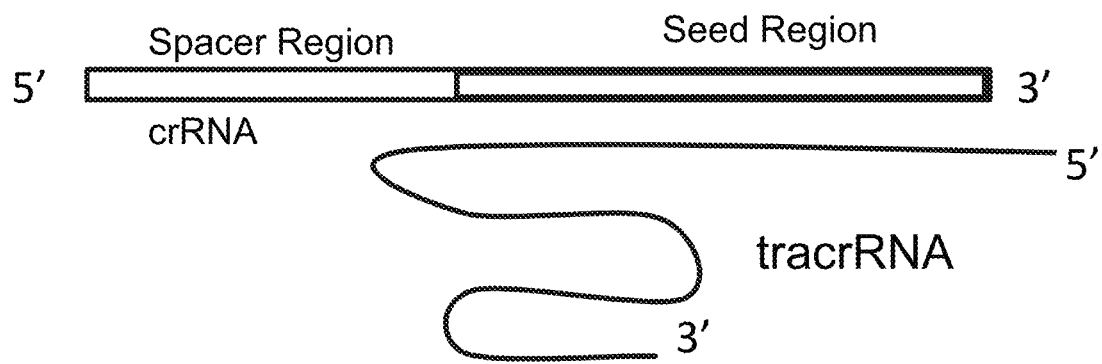

Provided herein are single guide RNA (sgRNA) sequences for directing a genomic sequence editing enzyme (e.g., Cas9) to a particular target nucleic acid sequence. An example sgRNA in complex with a Cas9 enzyme is illustrated in FIG. 4A, and an example alone in FIG. 4B. The gRNA may be a dual guide RNA, as illustrated in FIG. 4C. Guide sequences disclosed herein comprises a base-pairing region. The base-pairing region comprises a seed region for binding to a target sequence and, optionally, a spacer region. The base-pairing region may vary in length. For example, the base-pairing region may comprise about 1 to 10, 1 to 20, 20 to 25, or 1 to 30 bases in length. In some instance, the base-pairing region comprises at least 10, 15, 20, 25, 30 or more bases in length. In some instances, the base-pairing region comprises a seed region of at least 10 bases in length. The seed region may comprise about 8 to 20 bases in length. In some instances, the seed region is about 12 bases in length. In some instances, a base-pairing region described herein is designed to target a template strand during transcription, FIG. 5A. In some instances, a base-pairing region described herein is designed to target a non-template strand during transcription, FIG. 5B.

In some instances, 3' of the base-pairing region of a sgRNA is a Cas9 handle region for binding to Cas9. In some instances, the Cas9 handle region is a dCas9 handle region for binding to a dCas9 enzyme. The handle region may vary in length. For example, the handle region may comprise about 1 to 50, 20 to 45, or 15 to 60 bases in length. In some instance, the handle region comprises at least 35, 40, 45, 50 or more bases in length. The handle region may comprise about 42 bases in length.

In some instances, 3' of the handle region of the sgRNA is a terminator region. In some instances, the terminator region is a *S. pyogenes* terminator region. In some instances, the terminator region comprises at about 40 bases in length. In some instances, the terminator region comprises about 10 to 50, 20 to 60, or 30 to 55 bases in length.

Figure 6A:
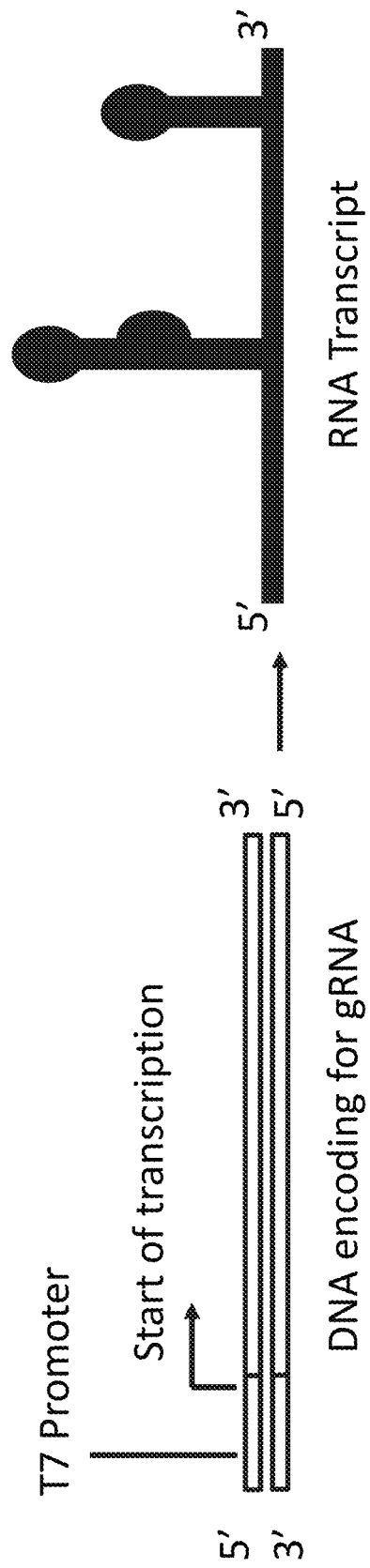
FIG. 6A is a diagram of a gRNA sequence with a T7 promoter that, when transcribed, results in gRNA sequence that forms hairpin secondary structure.
Figure 6B:
FIG. 6B is a diagram of a gRNA sequence with a T7 promoter that, when transcribed, results in gRNA sequence that does not form a hairpin secondary structure.

Design schemes for gRNA sequences described herein may comprise inclusion of a DNA dependent RNA polymerase promoter region 5' upstream of DNA encoding for the gRNA sequence. Exemplary DNA dependent RNA polymerase promoter regions include, without limitation a T3 and a T7 RNA polymerase promoter sequence. For example, FIG. 6A illustrates an arrangement where a T7 promoter region is 5' upstream of a gRNA and the resultant gRNA transcribed is produced wherein the gRNA includes hairpins. In some arrangements, a gRNA is designed to lack a sequence that forms a hairpin secondary structure, FIG. 6B. The hairpin secondary structure may be lacking in the Cas9 handle and/or the terminator region.

Provided herein are dgRNAs for directing a genomic sequence editing enzyme (e.g., Cas9) to a particular target nucleic acid sequence. In some instances, libraries comprise nucleic acid sequences that encode sequences for dgRNAs. In some instances, the libraries comprise nucleic acids, wherein each nucleic acid synthesized is a DNA sequence that encodes for a dgRNA sequence as a transcription product. In some instances, the libraries comprise nucleic acids, wherein each nucleic acid synthesized is a RNA sequence and the dgRNA itself is synthesized. In some instances, libraries of dgRNAs comprise nucleic acid sequences for crRNA and tracrRNA that are synthesized as separate nucleic acids. In some instances, the nucleic acids encode for crRNA and tracrRNA separately. In some instances, the nucleic acids encode for single sequence that when transcribed result in a separate crRNA sequence and a separate tracrRNA sequence. Exemplary sequences for crRNA and tracrRNA are seen in Table 1.

TABLE 1

| SEQ ID NO | Name | Sequence |
|---|---|---|
| 5 | crRNA-sp2 | 5'ATAACTCAATTTGTAAAAAAGTTTTAGAGCTAT GCTGTTTTG3' |

TABLE 1-continued

Figure 7:
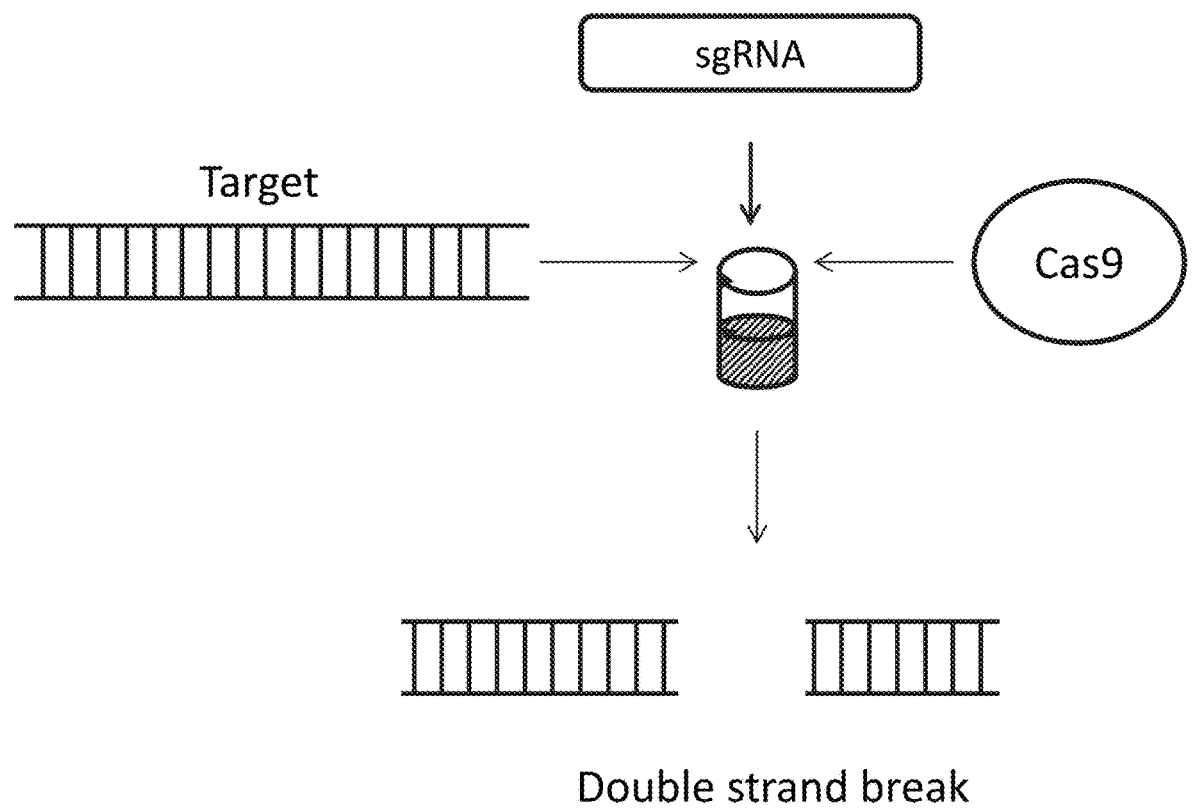
FIG. 7 depicts a workflow for in vitro Cas9 mediated cleavage of target DNA.

| SEQ ID NO | Name | Sequence |
|---|---|---|
| 6 | tracrRNA | 5'GGAACCATTCAAAACAGCATAGCAAGTTAAAA TAAGGCTAGTCCGTTATCAACTTGAAAAAGTGGC ACCGAGTCGGTGCTTTTTTT3' | gRNA libraries described herein may be used for in vitro screening and analysis. An illustration of such an arrangement is depicted in FIG. 7, where a target double-stranded DNA sequence is incubated with a gRNA sequence and Cas9 enzyme. The mixture results in a double strand DNA break. The DNA break may result in a measureable change in the function or expression of a genomic element. gRNAs described herein, or DNA encoding for gRNAs, may be added to cells via various methods known in the art, including, without limitation, transfection, transduction, or electroporation.

In some instances, gRNA libraries described herein are used for in vivo or ex vivo screening and analysis. Cells for screening include primary cells taken from living subjects or cell lines. Cells may be from prokaryotes (e.g., bacteria and fungi) or eukaryotes (e.g., animals and plants). Exemplary animal cells include, without limitation, those from a mouse, rabbit, primate, and insect. In some instances, gRNA libraries described herein may also be delivered to a multicellular organism. Exemplary multicellular organisms include, without limitation, a plant, a mouse, rabbit, primate, and insect.

Genome Engineering

Provided herein are libraries comprising nucleic acids for nuclease targeting of a particular target nucleic acid sequence. In some instances, libraries described herein comprise synthesized nucleic acids, wherein the nucleic acids is DNA, RNA, any analogs, or derivatives thereof. In some instances, the target nucleic acid sequence comprises DNA, RNA, any analogs, or derivatives thereof. In some instances, the nuclease cleaves the target nucleic acid sequence. In some instances, the nuclease binds the target nucleic acid but does not cleave it. Types of nucleases include, but are not limited to, Transcription Activator-Like Effector Nuclease (TALEN), zinc finger nuclease (ZFN), meganuclease, Argonaute, and Clustered Regularly Interspaced Short Palindromic Repeats (CRISPR)-associated (Cas) protein. In some instances, the nuclease is wild-type, genetically modified, or recombinant.

Figure 1B:
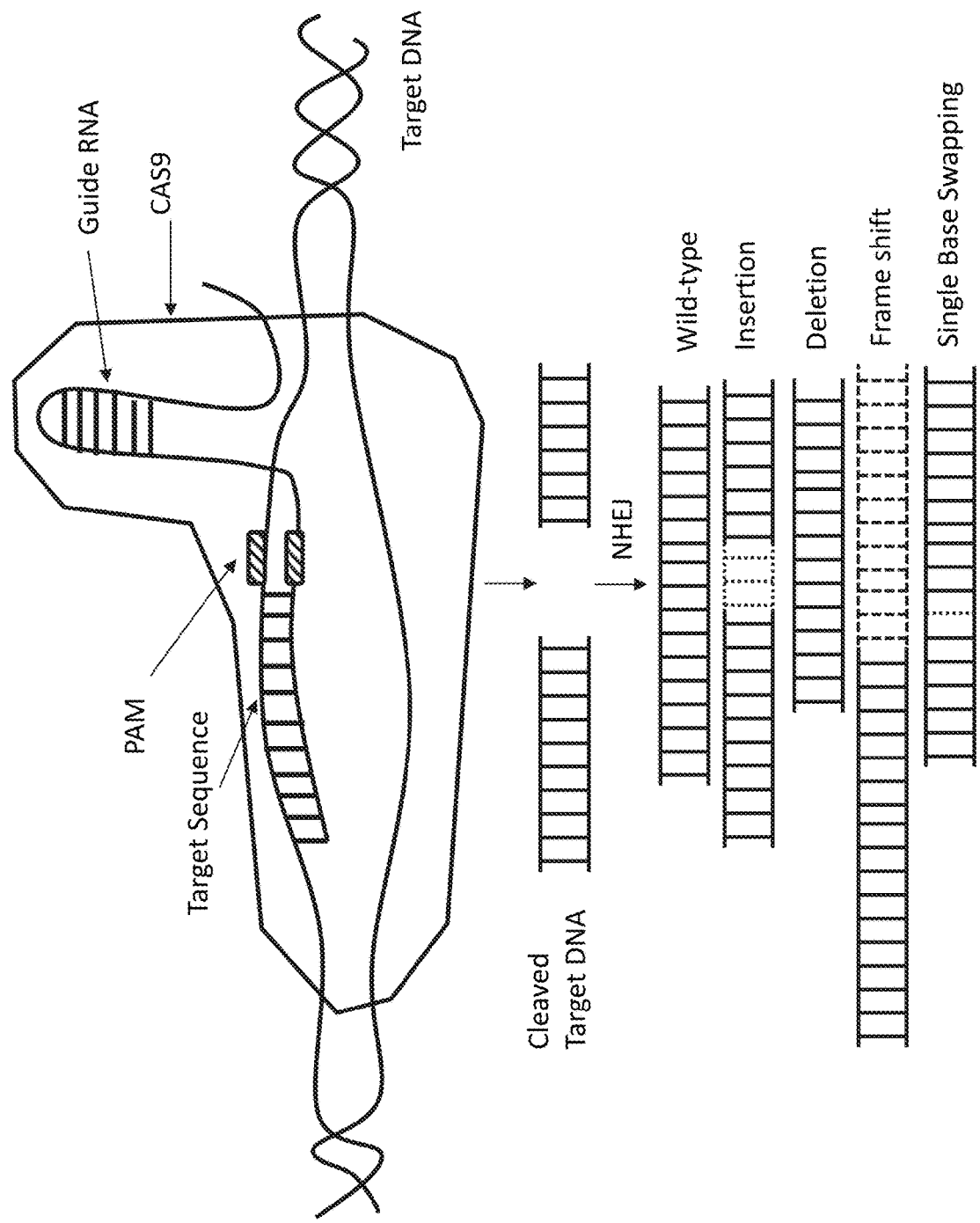
FIG. 1B illustrates a Clustered Regularly Interspaced Short Palindromic Repeats (CRISPR) complex which includes the following components: PAM, target sequence, CAS9 enzyme, Guide RNA (gRNA), and donor DNA for a non-homologous end joining repair (NHEJ) pathway.

A model system for targeted gene editing comprises a Cas9-based approach. When expressed or transferred into cells alongside a gRNA, Cas9 allows for the targeted introduction or deletion of genetic information via a complex with a Clustered Regularly Interspaced Short Palindromic Repeats (CRISPR) sequence of mRNA. A Cas9 complex, as illustrated in FIGS. 1A-1B, includes a Cas9 protein, engaged with a guide RNA ("gRNA") transcript. The illustrated gRNA contains a target sequence region, a PAM region, and a hairpin region. In a CRISPR/Cas9 process, a gRNA shepherds the Cas9 enzyme to a specific stretch of DNA. While the gRNA depicted is a sgRNA (single stranded guide RNA), the complex may be formed with a dgRNA (dual stranded guide RNA). Cas9 then cleaves the DNA to disable or repair a gene. A non-limiting list of exemplary modifications to this process is described here. In a CRISPR/dCas9 process, a disabled or "dead" Cas9 ("dCas9") no longer has a splicing function but, with the addition of another enzymatic activity, performs a different target molecule modifying function. For example, tethering a cytidine deaminase to dCas9 converts a C-G DNA base pair into T-A base pair. In an alternative dCas9 process, a different enzyme tethered to the dCas9 results in changing the base C into a T, or a G to an A in a target DNA. Alternatively, the dCas9 process can be modified by fusion of transcription factors to block or activate RNA polymerase activity, resulting in turning off (CRISPRi) or turning on (CRISPRa) gene transcription and therefore regulate gene expression. For example, the dCas9 process is modified by fusion with a transcriptional repressor. In some instances, the dCas9 process is modified by fusion with a transcriptional activator. In some instances, the dCas9 process is modified by fusion with a plurality of transcriptional repressors or transcriptional activators. In alternative arrangements, a gRNA has multiple sites for cleavage, resulting in a gRNA having multiple regions for gene editing. In the case of Cas9n, or "nicking Cas9," either the RuvC or HNH cleavage domain is modified to be inactive. This inactivation leaves Cas9 only able to produce only a stranded break in the DNA (a nick), not a double stranded break. In some arrangements, two Cas9n enzymes, one for each strand, are used to produce the double stranded break. As they can recognize both the upstream and downstream regions of the cut site, off target effects are ablated. In the case of hfCas9, instead of using dual Cas9n proteins to generate the off-target effect-free Cas9 cut, a modified Cas9 enzyme has relaxed binding target specificity stringency to allow for less than perfect matches prior to enzymatic activity. In some instances, the dCas9 process is modified by fusion with a label or tag for detecting a target nucleic acid. For example, the label is a fluorescent marker (e.g., GFP) for detecting the target nucleic acid. In some instances, the dCas9 is fused to an epitope tag and is used for purification of the target nucleic acid specified by a gRNA.

Provided herein are libraries comprising nucleic acids for directing a nuclease to a particular target nucleic acid sequence. In some instances, the target nucleic acid sequence comprises DNA. In some instances, the target nucleic acid sequence comprises RNA. For example, libraries comprising nucleic acids for directing C2c2 are generated for targeting a RNA sequence. In some instances, the DNA or RNA is single stranded or double stranded.

Provided herein are libraries comprising nucleic acids for nuclease targeting of a particular target nucleic acid sequence, wherein the nuclease is from a species of, but not limited to, *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Desulfurococcus, Opituaceae, Tuberibacillus, Bacillus, Brevibacilus, Methylobacterium, Natronobacterium, Flavobacterium, Saccharomyces, Chlamydomonas, Thermus, Pyrococcus, Mycoplasma,* or *Acidaminococcus*. Exemplary nucleases are listed in Table 2A. gRNAs described herein may bind to the terminator sequence of a nuclease from any of the species listed above, or nucleases from additional species where the enzyme allows for genome editing functions. Exemplary terminator sequences include, without limitation, those listed in Table 2B. Exemplary PAM sequences include, without limitation, those listed in Table 2C.

TABLE 2A

| Name | Accession Number | Species |
|---|---|---|
| Cas9 | Q99ZW2 | Streptococcus pyogenes |
| Cas9 | J7RUA5 | Staphylococcus aureus |
| Cas9 | G3ECR1 | Streptococcus thermophilus |
| C2c2 | P0DOC6 | Leptotrichia shahii |
| Cpf1 | U2UMQ6 | Acidaminococcus sp. |
| C2c1 | T0D7A2 | Alicyclobacillus acidoterrestris |
| FokI | P14870 | Flavobacterium okeanokoites |
| AciI | A0A0C5GQT3 | Lactobacillus acidophilus |
| I-SceI | P03882 | Saccharomyces cerevisiae |
| I-CreI | P05725 | Chlamydomonas reinhardtii |
| I-DmoI | 1B24_A | Desulfurococcus mobilis |
| TtAgo | Q746M7 | Thermus thermophilus |
| PfAgo | Q8U3D2 | Pyrococcus furiosus |
| NgAgo | A0A172MAH6 | Natronobacterium gregoryi |

TABLE 2B

| SEQ ID NO | Species | Sequence |
|---|---|---|
| 7 | Streptococcus thermophilus | 5' TACTCAACTTGAAAAGGTGG CACCGATTCGGTGTTTTT 3' |
| 8 | Streptococcus mutans | 5' TACACAACTTGAAAAAGTGC GCACCGATTCGGTGCTTTT 3' |
| 9 | Listeria innocua | 5' TTATCAACTTTTAATTAAGT AGCGCTGTTTCGGCGCTTTT 3' |
| 10 | Mycoplasma mobile | 5' TATGCCGTAACTACTACTTATTTT CAAAATAAGTAGTTTT 3' |
| 11 | Campylobacter jejuni | 5' GACTCTGCGGGGTTACAATCC CCTAAAACCGCTTTT 3' |

TABLE 2C

| Species/Variant of Cas9 | PAM Sequence |
|---|---|
| Streptococcus pyogenes/SpCas9 | NGG |
| Streptococcus pyogenes/SpCas9 D1135E variant | NGG |
| Streptococcus pyogenes/SpCas9 VRER variant | NGCG |
| Streptococcus pyogenes/SpCas9 EQR variant | NGAG |
| Streptococcus pyogenes/SpCas9 VQR variant | NGAN or NGNG |
| Staphylococcus aureus/SaCas9 | NNGRRT or NNGRR(N) |
| Neisseria meningitidis | NNNNGATT |
| Streptococcus thermophilus | NNAGAAW |
| Treponema denticola | NAAAAC |

Provided herein are libraries comprising nucleic acids for targeting one or more nuclease(s) to a particular nucleic acid sequence. In some instances, the nuclease is at least one of TALEN, ZFN, meganuclease, Argonaute, and Cas protein. For example, more than one nuclease can be multiplexed to generate large genomic deletions, modify multiple sequences at once, or be used in conjunction with other enzymes such as a nickase. In some instances, the number of nucleases is at least 2 nucleases for the target nucleic acid sequence. In some instances, the number of nucleases is in a range of about 2 to 3, 2 to 4, 2 to 5, 2 to 6, 2 to 7, 2 to 8, 2 to 9, or 2 to 10 nucleases for the target nucleic acid sequence.

Provided herein are libraries comprising synthesized nucleic acids for nickase targeting of a particular nucleic acid sequence. A nickase is an enzyme that generates a single stranded break in a nucleic acid sequence. In some instances, the synthesized nucleic acids are DNA, RNA, any analogs, or derivatives thereof. In some instances, the particular nucleic acid sequence comprises DNA, RNA, any analogs, or derivatives thereof. In some instances, the nickase cleaves the particular nucleic acid sequence. In some instances, the nickase binds the particular nucleic acid but does not cleave it. In some instances, the nickase is an altered nuclease, wherein the nuclease is TALEN, ZFN, meganuclease, Argonaute, or Cas protein. In some instances, the nickase is generated by altering a nuclease domain of TALEN, ZFN, meganuclease, Argonaute, or Cas protein. In some instances, the nickase is generated by altering the nuclease domain of Cas9.

In some instances, libraries comprise nucleic acids for one or more nickase(s) targeting of a particular nucleic acid sequence. In some instances, the number of nickases is at least 2 nickases for the particular nucleic acid sequence. In some instances, the number of nickases is in a range of about 2 to 3, 2 to 4, 2 to 5, 2 to 6, 2 to 7, 2 to 8, 2 to 9, or 2 to 10 nickases for the particular nucleic acid sequence. In some instances, libraries comprise nucleic acids for directing one or more nickase and one or more nuclease to the particular nucleic acid sequence.

Libraries comprising nucleic acids for targeting a nuclease to a particular nucleic acid sequence provided herein can result in cleavage of the particular nucleic acid sequence. In some instances, the nuclease is at least one of TALEN, ZFN, meganuclease, Argonaute, and Cas protein. In some instances, the nuclease is a chimeric nuclease that provides for a modification of the particular nucleic acid sequence other than cleavage. For example, the chimeric nuclease results in methylation, demethylation, polyadenylation, deadenylation, deamination, or polyuridinylation.

Transcription Activator-Like Effector Nuclease

Provided herein are methods for synthesizing nucleic acid libraries comprising nucleic acids for Transcription Activator-Like Effector Nuclease (TALEN) targeting of a particular nucleic acid sequence. TALENs are a class of engineered sequence-specific nucleases that can be used to induce double-strand breaks at specific target sequences. TALENs can be generated by fusing transcription activator-like (TAL) effector DNA-binding domain, or a functional part thereof, to the catalytic domain of a nuclease. The TAL effector DNA binding domain comprises a series of TAL repeats, which are generally highly conserved 33 or 34 amino acid sequence segments that each comprise a highly variable 12th and 13th amino acid known as the repeat variable diresidue (RVD). Each RVD can recognize and bind to a specific nucleotide. Thus, a TAL effector binding domain can be engineered to recognize a specific sequence of nucleotides by combining TAL repeats comprising the appropriate RVDs.

Provided herein are methods for synthesizing a nucleic acid library comprising non-identical nucleic acids that encode for a TAL effector DNA-binding domain. In some instances, the TAL effector DNA-binding domain is designed to recognize a particular target nucleic acid sequence and induce double-stranded breaks at a particular site. In some instances, the TAL effector DNA-binding domain comprises a number of TAL repeats that are designed to recognize and bind to a particular nucleic acid sequence. In some instances, the number of TAL repeats is at least or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or more TAL repeats.

In some instances, a nucleic acid library comprising non-identical nucleic acids encoding for TAL effector DNA-binding domain are synthesized. In some instances, the nucleic acid library as described herein that when translated encodes for a protein library. In some instances, the nucleic acid library is expressed in cells and a protein library is generated. In some instances, the synthesized nucleic acids libraries are inserted into expression vectors. In some instances, the synthesized nucleic acids libraries are inserted into expression vectors and expressed in cells.

Nucleic acid libraries comprising nucleic acids that encode for a TAL effector DNA-binding domain generated by methods described herein can be used for generating a TALEN. In some instances, this is accomplished by mixing the TAL effector binding domain library that is cloned and expressed in vectors with a nuclease. Exemplary nucleases include, but are not limited to, AciI, AcuI, AlwI, BbvI, BccI, BceAI, BciVI, BfuAI, BmgBI, BmrI, Bpml, BpuEI, BsaI, BsmAI, BsmFI, BseRI, BspCNI, BsrI, BsgI, BsmI, BspMI, BsrBI, BsrDI, BtgZI, BtsI, BtsCI, EarI, EciI, FokI, HgaI, HphI, HpyAV, MboII, MlyI, MmeI, MnlI, NmeAIII, PleI, SfaNI, BbvCI, Bpu10I, BspQI, SapI, BaeI, BsaXI, or CspCI. In some instances, mixing occurs by ligation. Exemplary ligases, included, but are not limited to, E. coli ligase, T4 ligase, mammalian ligases (e.g., DNA ligase I, DNA ligase II, DNA ligase III, DNA ligase IV), thermostable ligases, and fast ligases. TALENs generated by methods described herein can be inserted into expression vectors. In some instances, TALENs are inserted into expression vectors and expressed in cells.

Provided herein are methods for synthesizing a TAL effector DNA-binding domain library comprising non-identical nucleic acid sequences for a gene in a genome of a prokaryotic or eukaryotic organism. In some instances, the TAL effector DNA-binding domain library comprises at least 3, 4, 5, 6, 7, 8, 9, 10, or more than 10 non-identical nucleic acid sequences for a gene for at least 5% of the genome. In some instances, the TAL effector DNA-binding domain library comprise non-identical nucleic acid sequences for one or more genes for at least 5% of the genome. In some instances, the TAL effector DNA-binding domain library comprises non-identical nucleic acid sequence for about 1, 5, 10, 20, 30, 40, 50, 60, 70, 80, 90, 100, or more than 100 genes for at least 5% of the genome. In some instances, the TAL effector DNA-binding domain library comprises non-identical nucleic acid sequence for about 1-100, 2-95, 5-90, 10-85, 15-80, 20-75, 25-70, 30-65, 35-60, or 40-50 genes for at least 5% of the genome.

Zinc Finger Nucleases

Provided herein are methods for synthesizing nucleic acid libraries comprising nucleic acids for Zinc Finger Nuclease (ZFN) targeting of a particular nucleic acid sequence. ZFNs can be generated by fusion of a nuclease with a DNA binding zinc finger domain (ZFD). The ZFD can bind to a target nucleic acid sequence through one or more zinc fingers. In some instances, the ZFD comprises at least 2, 3, 4, 5, 6, 7, 8, 9, 10, or more zinc fingers. In some instances, the ZFD comprises at most 2, 3, 4, 5, 6, 7, 8, 9, 10, or more zinc fingers. In some instances, the ZFD is designed to recognize a particular target nucleic acid sequence and induce double-stranded breaks at a particular site.

Provided herein are methods for synthesizing a nucleic acid library comprising nucleic acids that when transcribed and translated encode for a ZFD. In some instances, when the nucleic acid library is translated encode for a protein library. In some instances, the nucleic acid library is expressed in cells and a protein library is generated. In some instances, the synthesized nucleic acids libraries are inserted into expression vectors. In some instances, the synthesized nucleic acids libraries are inserted into expression vectors and expressed in cells.

Nucleic acid libraries comprising nucleic acids that encode for a ZFD generated by methods described herein can be used for generating a ZFN. In some instances, this is accomplished by mixing the ZFD that is cloned and expressed in vectors with a nuclease. Exemplary nucleases include, but are not limited to, AciI, AcuI, AlwI, BbvI, BccI, BceAI, BciVI, BfuAI, BmgBI, BmrI, Bpml, BpuEI, BsaI, BsmAI, BsmFI, BseRI, BspCNI, BsrI, BsgI, BsmI, BspMI, BsrBI, BsrDI, BtgZI, BtsI, BtsCI, EarI, EciI, FokI, HgaI, HphI, HpyAV, MboII, MlyI, MmeI, MnlI, NmeAIII, PleI, SfaNI, BbvCI, Bpu10I, BspQI, SapI, BaeI, BsaXI, or CspCI. In some instances, mixing occurs by ligation. Exemplary ligases, included, but are not limited to, E. coli ligase, T4 ligase, mammalian ligases (e.g., DNA ligase I, DNA ligase II, DNA ligase III, DNA ligase IV), thermostable ligases, and fast ligases. ZFNs generated by methods described herein can be inserted into expression vectors. In some instances, ZFNs are inserted into expression vectors and expressed in cells.

Provided herein are methods for synthesizing a ZFD library comprising non-identical nucleic acid sequences for a gene in a genome of a prokaryotic or eukaryotic organism. In some instances, the ZFD library comprises at least 3, 4, 5, 6, 7, 8, 9, 10, or more than 10 non-identical nucleic acid sequences for a gene for at least 5% of the genome. In some instances, the ZFD library comprise non-identical nucleic acid sequences for one or more genes for at least 5% of the genome. In some instances, the ZFD library comprises non-identical nucleic acid sequence for about 1, 5, 10, 20, 30, 40, 50, 60, 70, 80, 90, 100, or more than 100 genes for at least 5% of the genome. In some instances, the ZFD library comprises non-identical nucleic acid sequence for about 1-100, 2-95, 5-90, 10-85, 15-80, 20-75, 25-70, 30-65, 35-60, or 40-50 genes for at least 5% of the genome.

Meganucleases

Provided herein are methods for synthesizing nucleic acid libraries comprising nucleic acids for meganuclease targeting of a particular nucleic acid sequence. Meganucleases are enzymes that can recognize and cleave long base pair (e.g., 12-40 base pairs) DNA targets. In some instances, meganucleases are engineered to comprise domains of other enzymes to confer specificity for a target nucleic acid sequence. For example, meganucleases are engineered to comprise a TAL effector DNA binding domain.

Provided herein are methods for synthesizing a nucleic acid library comprising nucleic acids that when transcribed and translated encode for a binding domain for use with a meganuclease. In some instances, when the nucleic acid library is translated encode for a protein library. In some instances, the nucleic acid library is expressed in cells and a protein library is generated. In some instances, the synthesized nucleic acids libraries are inserted into expression vectors. In some instances, the synthesized nucleic acids libraries are inserted into expression vectors and expressed in cells.

Nucleic acid libraries comprising nucleic acids that encode for a domain generated by methods described herein can be used for engineering a meganuclease for targeting a particular nucleic acid sequence. In some instances, this is accomplished by mixing a binding domain library such as a TAL effector binding domain library that is cloned and expressed in vectors with a meganuclease. Exemplary meganucleases for use with the methods provided herein include, but are not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, 1-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or fragments thereof. In some instances, mixing occurs by ligation. Exemplary ligases, included, but are not limited to, *E. coli* ligase, T4 ligase, mammalian ligases (e.g., DNA ligase I, DNA ligase II, DNA ligase III, DNA ligase IV), thermostable ligases, and fast ligases. Engineered meganucleases generated by methods described herein can be inserted into expression vectors. In some instances, the engineered meganucleases are inserted into expression vectors and expressed in cells.

Provided herein are methods for synthesizing a binding domain library for use with a meganuclease comprising non-identical nucleic acid sequences for a gene in a genome of a prokaryotic or eukaryotic organism. In some instances, the domain library comprises at least 3, 4, 5, 6, 7, 8, 9, 10, or more than 10 non-identical nucleic acid sequences for a gene for at least 5% of the genome. In some instances, the domain library comprise non-identical nucleic acid sequences for one or more genes for at least 5% of the genome. In some instances, the domain library comprises non-identical nucleic acid sequence for about 1, 5, 10, 20, 30, 40, 50, 60, 70, 80, 90, 100, or more than 100 genes for at least 5% of the genome. In some instances, the domain library comprises non-identical nucleic acid sequence for about 1-100, 2-95, 5-90, 10-85, 15-80, 20-75, 25-70, 30-65, 35-60, or 40-50 genes for at least 5% of the genome.

Argonautes

Provided herein are methods for synthesizing nucleic acid libraries comprising nucleic acids for Argonaute targeting of a particular nucleic acid sequence. Argonautes are a family of RNA or DNA guided nucleases. In some instances, Argonautes use a guide nucleic acid to identify a target nucleic acid. In some instances, the guide nucleic acid is a single guide RNA (sgRNA). In some instances, the guide nucleic acid is a guide DNA (gDNA). Exemplary Argonautes include, but are not limited to, TtAgo, PfAgo, and NgAgo. In some embodiments, the Argonaute is NgAgo.

Provided herein are methods for synthesizing a guide nucleic acid library comprising non-identical nucleic acid sequences for a gene in a genome of a prokaryotic or eukaryotic organism. In some instances, the guide nucleic acid library is a sgRNA library. In some instances, the guide nucleic acid library is a dgRNA library. In some instances, the guide nucleic acid library comprises at least 3, 4, 5, 6, 7, 8, 9, 10, or more than 10 non-identical nucleic acid sequences for a gene for at least 5% of the genome. In some instances, the guide nucleic acid library comprise non-identical nucleic acid sequences for one or more genes for at least 5% of the genome. In some instances, the guide nucleic acid library comprises non-identical nucleic acid sequence for about 1, 5, 10, 20, 30, 40, 50, 60, 70, 80, 90, 100, or more than 100 genes for at least 5% of the genome. In some instances, the guide nucleic acid library comprises non-identical nucleic acid sequence for about 1-100, 2-95, 5-90, 10-85, 15-80, 20-75, 25-70, 30-65, 35-60, or 40-50 genes for at least 5% of the genome.

CRISPR-Associated Proteins

Provided herein are methods for synthesizing nucleic acid libraries comprising nucleic acids encoding for gRNAs for CRISPR-associated (Cas) protein targeting of a particular nucleic acid sequence. In some instances, the Cas protein is at least one of Cpf1, C2c1, C2c2, Cas1, Cas1B, Cas2, Cas3, Cas4, Cas5, Cas6, Cas7, Cas8, Cas9 (Csn1 or Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, and modified versions thereof. In some instances, the Cas protein is Cas9.

Provided herein are methods for synthesizing a gRNA library comprising non-identical nucleic acid sequences for a gene in a genome of a prokaryotic or eukaryotic organism. In some instances, the gRNA library comprises at least 3, 4, 5, 6, 7, 8, 9, 10, or more than 10 non-identical nucleic acid sequences for a gene for at least 5% of the genome. In some instances, the gRNA library comprise non-identical nucleic acid sequences for one or more genes for at least 5% of the genome. In some instances, the gRNA library comprises non-identical nucleic acid sequence for about 1, 5, 10, 20, 30, 40, 50, 60, 70, 80, 90, 100, or more than 100 genes for at least 5% of the genome. In some instances, the gRNA library comprises non-identical nucleic acid sequence for about 1-100, 2-95, 5-90, 10-85, 15-80, 20-75, 25-70, 30-65, 35-60, or 40-50 genes for at least 5% of the genome. The gRNA library may encode for sgRNA or dgRNAs.

Variant Library Synthesis

Provided herein are methods for synthesis of a variant nucleic acid library generated by combination of nucleic acids encoding complete or partial gene sequence with gRNAs and a nuclease, e.g., Cas9 enzyme or Cas9 variant enzyme. The fragments may collectively space the entire region of a gene. In some cases, the library encodes DNA or RNA. In some cases, the library encodes for a single gene or for up to an entire genome. For example, a gRNA library encoding for 5 gRNAs per a gene for a genome comprising about 20,000 genes would result in about 100,000 gRNAs. Such a library can be used to selectively silence or modify a single gene, a pathway of genes, or all genes in a single genome. In some arrangement, gRNAs lack a homology sequence and random end joining occurs. Such a process results in non-homologous end joining ("NHEJ"). In some instances, following NHEJ, an insertion, a deletion, a frameshift, or single base swapping occurs. See FIG. 1B.

Synthesized libraries described herein may be used for application in CRISPR-Cas9 functions, wherein the gRNA sequence generated is used to disrupt expression of or alter the expression product sequence of a target DNA sequence in a cell or in a mixture comprising a target DNA and Cas9 enzyme. In some embodiments, each variant encodes for a codon resulting in a different amino acid during translation.

Table 3 provides a listing of each codon possible (and the representative amino acid) for a variant site.

TABLE 3

List of codons and amino acids

| Amino Acids | One letter code | Three letter code | Codons | | | | | |
|---|---|---|---|---|---|---|---|---|
| Alanine | A | Ala | GCA | GCC | GCG | | GCT | |
| Cysteine | C | Cys | TGC | | | TGT | | |
| Aspartic acid | D | Asp | GAC | | | GAT | | |
| Glutamic acid | E | Glu | GAA | | | GAG | | |
| Phenylalanine | F | Phe | TTC | | | TTT | | |
| Glycine | G | Gly | GGA | GGC | GGG | | GGT | |
| Histidine | H | His | CAC | | | CAT | | |
| Isoleucine | I | Iso | ATA | ATC | | ATT | | |
| Lysine | K | Lys | AAA | | | AAG | | |
| Leucine | L | Leu | TTA | TTG | CTA | CTC | CTG | CTT |
| Methionine | M | Met | | | ATG | | | |
| Asparagine | N | Asn | AAC | | | AAT | | |
| Proline | P | Pro | CCA | CCC | CCG | | CCT | |
| Glutamine | Q | Gln | CAA | | | CAG | | |
| Arginine | R | Arg | AGA | AGG | CGA | CGC | CGG | CGT |
| Serine | S | Ser | AGC | AGT | TCA | TCC | TCG | TCT |
| Threonine | T | Thr | ACA | ACC | ACG | | ACT | |
| Valine | V | Val | GTA | GTC | GTG | | GTT | |
| Tryptophan | W | Trp | | | TGG | | | |
| Tyrosine | Y | Tyr | TAC | | | TAT | | |

Provided herein are methods for synthesis of a variant nucleic acid library generated by combination of nucleic acids encoding complete or partial gene sequence with a nuclease, wherein the nuclease is TALEN, ZFN, or an engineered meganuclease. In some instances, methods for synthesis of a variant nucleic acid library generated by combination of nucleic acids encoding complete or partial gene sequence with guide nucleic acids such as sgRNAs with a nuclease, wherein the nuclease is Argonaute or a Cas protein. Synthesized libraries described herein may be used for application in nuclease functions, wherein the nucleic acid sequence generated is used to disrupt expression of or alter the expression product sequence of a target DNA sequence in a cell or in a mixture comprising a target DNA and a nuclease. In some embodiments, each variant encodes for a codon resulting in a different amino acid during translation.

Variant nucleic acid libraries as described herein may comprise sgRNAs or dgRNAs for varying a target nucleic acid sequence encoding in at least a single codon such that a plurality of different variants of a single residue in the subsequent protein encoded by the synthesized nucleic acid are generated by standard translation processes. In some instances, each variant encodes for a codon resulting in a different amino acid of a protein domain. For example, the protein domain is a conserved domain or catalytic domain. In some embodiments, the protein domain is, but not limited to, a kinase domain, an ATP-binding domain, a GTP-binding domain, a guanine nucleotide exchange factor (GEF) domain, a GTPase activating protein (GAP) domain, a hydrolase domain, an endonuclease domain, an exonuclease domain, a protease domain, a phosphatase domain, a phospholipase domain, a pleckstrin homology domain, a Src homology domain, and a ubiquitin-binding domain. In some instances, the variant nucleic acid libraries comprise sgRNAs or dgRNAs for targeting a nucleic acid sequence that encodes for variation in at least 1, 2, 3, 4, 5, 6, 7, 8, 9, 10, or more than 10 protein domains.

In some embodiments, the variants encode for amino acids for a protein with particular activity. For example, the variants encode for a protein that comprises methyltransferase activity, demethylase activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, remodelling activity, protease activity, oxidoreductase activity, transferase activity, hydrolase activity, lyase activity, isomerase activity, synthase activity, synthetase activity, or demyristoylation activity.

Variation Generated by Homology-Directed Repair (HDR)

In an exemplary process for variant nucleic acid library generation, Cas9 cleavage and homologous recombination are incorporated to generate variety in a target DNA library. First, a library of gRNA is synthesized (either by de novo synthesis of RNA or de novo synthesis of DNA followed by transcription (in vivo or in vitro) to generate gRNA), wherein the library comprises a plurality of gRNA molecules per a gene. For example, the gRNA library may comprise 1, 2, 3, 4, 5, 6, 7, 8, 9, 10 or more gRNAs per a gene. The gRNA library is mixed with a Cas9 enzyme and a target DNA library, where the target DNA library comprises nucleic acid sequence encoding for at least one gene fragment or at least one gene. For example, the target DNA library may comprise 1, 2, 3, 4, 5, 6, 7, 8, 9, 10 or more genes or gene fragments. In some instances, the target DNA library comprises sequence from multiple genes in a pathway or from all genes in an organism. Also added to the mixture are replacement sequences which comprise a homology sequence and a variant nucleic acid sequence such that variation is introduced into target DNA strands. The resultant target DNA library will comprise a plurality of variant DNA sequences. In some instances, variation introduces a deletion, frame shift, or insertion into target DNA sequence. In some instances, the variant DNA sequences result in variation for at least one codon per a gene or gene fragment. In some instances, a portion of a gene is inserted into the target DNA or, alternatively, a portion of a target DNA sequence (i.e. a fragment of a gene or an entire gene) is removed from the target DNA. In some instances, the variant DNA sequences result in variation for at least one transcription regulatory sequence, e.g., a promoter, UTR, or terminator sequence, associated with gene or gene fragment.

In some instances for variant nucleic acid library generation, nuclease cleavage and homologous recombination are incorporated to generate variety in a target DNA library, wherein the nuclease is a TALEN, a ZFN, a meganuclease, a Cas, or an Argonaute. In some instances, where the nuclease is TALEN, a library of TAL effector DNA-binding domains is synthesized (either by de novo synthesis of RNA or de novo synthesis of DNA followed by transcription and translation (in vivo or in vitro)), wherein the library comprises a plurality of TAL effector DNA-binding domain molecules per a gene. For example, the TAL effector DNA-binding domain library may comprise 1, 2, 3, 4, 5, 6, 7, 8, 9, 10 or more TAL effector DNA-binding domain molecules per a gene. The TAL effector DNA-binding domain library can then be mixed with a nuclease enzyme to generate a TALEN. In some instances, the TALEN is combined with a target DNA library, where the target DNA library comprises nucleic acid sequence encoding for at least one gene fragment or at least one gene. For example, the target DNA library may comprise 1, 2, 3, 4, 5, 6, 7, 8, 9, 10 or more genes or gene fragments. In some instances, the target DNA library comprises sequence from multiple genes in a pathway or from all genes in an organism. In some instances, also added to the mixture are replacement sequences which comprise a homology sequence and a variant nucleic acid sequence such that variation is introduced into target DNA strands. The resultant target DNA library will comprise a plurality of variant DNA sequences. In some instances, variation introduces a deletion, frame shift, or insertion into target DNA sequence. In some instances, the variant DNA sequences result in variation for at least one codon per a gene or gene fragment. In some instances, a portion of a gene is inserted into the target DNA or, alternatively, a portion of a target DNA sequence (i.e. a fragment of a gene or an entire gene) is removed from the target DNA. In some instances, the variant DNA sequences result in variation for at least one transcription regulatory sequence, e.g., a promoter, UTR, or terminator sequence, associated with gene or gene fragment.

Variation Generated by Modified Cas9 Enzymes

In a second exemplary process for variant nucleic acid library generation, modified Cas9 enzymes are incorporated to generate a variant target DNA library. First, a library of gRNA is synthesized (either by de novo synthesis of RNA or de novo synthesis of DNA followed by transcription to generate gRNA), wherein the library comprises a plurality of gRNA molecules per a gene. For example, the gRNA library may comprise 1, 2, 3, 4, 5, 6, 7, 8, 9, 10 or more gRNAs per a gene. The gRNA library is mixed with a modified Cas9 enzyme and a target DNA library, where the target DNA library comprises nucleic acid sequence encoding for at least one gene fragment or at least one gene. For example, the target DNA library may comprise 1, 2, 3, 4, 5, 6, 7, 8, 9, 10 or more genes or gene fragments. In some instances, the target DNA library comprises sequence from multiple genes in a pathway or from all genes in an organism. The modified Cas9 enzyme has tethered to it another enzyme with nucleic acid sequence modification capabilities. An exemplary modified Cas9 enzymes includes dCas9 process in which a disabled or "dead" Cas9 ("dCas9") no longer has a splicing function but, with the addition of another enzymatic activity, performs a different target molecule modifying function. For example, tethering a cytidine deaminase to dCas9 converts a C-G DNA base pair into T-A base pair. In an alternative dCas9 process, a different enzyme tethered to the dCas9 results in changing the base C into a T, or a G to an A in a target DNA. The resultant target DNA library comprises a plurality of variant target DNA sequences. In some instances, variation introduces a deletion, frame shift, or insertion into target DNA sequence. In some instances, the variant DNA sequences result in variation for at least one codon per a gene or gene fragment. In some instances, the variant DNA sequences result in variation for at least one transcription regulatory sequence, e.g., a promoter, UTR, or terminator sequence, associated with gene or gene fragment.

Variation Generated by Modified Nucleases

Provided herein are methods for variant nucleic acid library generation comprising a modified nuclease enzyme that is incorporated to generate a variant target DNA library. In some instances, the nuclease is TALEN. In some instances, a TAL effector DNA binding domain library is synthesized (either by de novo synthesis of RNA or de novo synthesis of DNA followed by transcription and translation to generate the TAL effector DNA binding domain library), wherein the library comprises a plurality of non-identical nucleic acid sequences per a gene. For example, the TAL effector DNA binding domain library may comprise 1, 2, 3, 4, 5, 6, 7, 8, 9, 10 or more non-identical nucleic acid sequences per a gene. The TAL effector DNA-binding domain library can then be mixed with a nuclease enzyme to generate a TALEN. In some instances, the TALEN is then mixed with a target DNA library, where the target DNA library comprises nucleic acid sequence encoding for at least one gene fragment or at least one gene. For example, the target DNA library may comprise 1, 2, 3, 4, 5, 6, 7, 8, 9, 10 or more genes or gene fragments. In some instances, the target DNA library comprises sequence from multiple genes in a pathway or from all genes in an organism.

In some instances, the nuclease is ZFN. In some instances, a ZFD library is synthesized (either by de novo synthesis of RNA or de novo synthesis of DNA followed by transcription and translation to generate the ZFD library), wherein the library comprises a plurality of non-identical nucleic acid sequences per a gene. For example, the ZFD library may comprise 1, 2, 3, 4, 5, 6, 7, 8, 9, 10 or more non-identical nucleic acid sequences per a gene. The ZFD library can then be mixed with a nuclease enzyme to generate a ZFN. In some instances, the ZFN is then mixed with a target DNA library, where the target DNA library comprises nucleic acid sequence encoding for at least one gene fragment or at least one gene. For example, the target DNA library may comprise 1, 2, 3, 4, 5, 6, 7, 8, 9, 10 or more genes or gene fragments. In some instances, the target DNA library comprises sequence from multiple genes in a pathway or from all genes in an organism.

In some instances, the nuclease is a meganuclease. In some instances, a binding domain library such as a TAL effector DNA binding domain library for targeting the meganuclease to a particular nucleic acid sequence is synthesized (either by de novo synthesis of RNA or de novo synthesis of DNA followed by transcription to generate the binding domain library), wherein the binding domain library comprises a plurality of non-identical nucleic acid sequences per a gene. For example, the binding domain library may comprise 1, 2, 3, 4, 5, 6, 7, 8, 9, 10 or more non-identical nucleic acid sequences per a gene. The binding domain library can then be mixed a meganuclease enzyme to generate an engineered meganuclease. In some instances, the engineered meganuclease is then mixed with a target DNA library, where the target DNA library comprises nucleic acid sequence encoding for at least one gene fragment or at least one gene. For example, the target DNA library may comprise 1, 2, 3, 4, 5, 6, 7, 8, 9, 10 or more genes or gene fragments. In some instances, the target DNA library comprises sequence from multiple genes in a pathway or from all genes in an organism.

In some instances, the nuclease is Argonaute. In some instances, a guide nucleic acid library (gRNA or gDNA) is synthesized (either by de novo synthesis of RNA or de novo synthesis of DNA followed by transcription to generate the guide nucleic acid library), wherein the guide nucleic acid library comprises a plurality of non-identical nucleic acid sequences per a gene. For example, the guide nucleic acid library may comprise 1, 2, 3, 4, 5, 6, 7, 8, 9, 10 or more non-identical nucleic acid sequences per a gene. The guide nucleic acid library is mixed with a modified Argonaute enzyme and a target DNA library, where the target DNA library comprises nucleic acid sequence encoding for at least one gene fragment or at least one gene. For example, the target DNA library may comprise 1, 2, 3, 4, 5, 6, 7, 8, 9, 10 or more genes or gene fragments. In some instances, the target DNA library comprises sequence from multiple genes in a pathway or from all genes in an organism.

In some instances, the modified nuclease enzyme has tethered to it another enzyme with nucleic acid sequence modification capabilities. Exemplary modification capabilities include, but are not limited to, methylation, demethylation, polyadenylation, deadenylation, deamination, and polyuridinylation. In some instances, a target DNA library comprising a plurality of variant target DNA sequences results in variation. In some instances, variation introduces a deletion, frame shift, or insertion into target DNA sequence. In some instances, the variant DNA sequences result in variation for at least one codon per a gene or gene fragment. In some instances, the variant DNA sequences result in variation for at least one transcription regulatory sequence, e.g., a promoter, UTR, or terminator sequence, associated with gene or gene fragment.

gRNA Library Synthesis for Targeting Genes of a Model System

Provided herein are methods for screening model systems with a nucleic acid library described herein. In some instances, the nucleic acid library is a gRNA library described herein. In some instances, the nucleic acid library is a DNA library described herein, that when transcribed results in transcription of gRNA sequences. A non-limiting exemplary list of model organisms is provided in Table 4.

TABLE 4

Organisms and Gene Number

| Model System | Protein Coding Genes* |
| --- | --- |
| Arabidopsis thaliana | 27000 |
| Caenorhabditis elegans | 20000 |
| Canis lupus familiaris | 19000 |
| Chlamydomonas reinhardtii | 14000 |
| Danio rerio | 26000 |
| Dictyostelium discoideum | 13000 |
| Drosophila melanogaster | 14000 |
| Escherichia coli | 4300 |
| Macaca mulatta | 22000 |
| Mus musculus | 20000 |
| Oryctolagus cuniculus | 27000 |
| Rattus norvegicus | 22000 |
| Saccharomyces cerevisiae | 6600 |
| Sus scrofa | 21000 |
| Homo sapiens | 21000 |

*Numbers here reflect the number of protein coding genes and excludes tRNA and non-coding RNA. Ron Milo & Rob Phillips, Cell Biology by the Numbers 286 (2015).

A library of gRNAs is synthesized (either by de novo synthesis of RNA or de novo synthesis of DNA followed by transcription to generate gRNAs), wherein the library comprises a plurality of gRNA molecules per a gene. For example, a library described herein may comprises 1, 2, 3, 4, 5, 6, 7, 8, 9, 10 or more gRNAs per a gene. In some instances, the nucleic acids within a de novo synthesized library encode sequences for at least or about 3 non-identical gRNAs per a single gene. In some instances, the nucleic acids encode sequences in a range of about 1 to about 10 non-identical gRNAs per a single gene. In some instances, the nucleic acids encode sequences for at least or about 1 non-identical gRNAs per a single gene. In some instances, the nucleic acids encode sequences for at most 10 non-identical gRNAs per a single gene. In some instances, the nucleic acids encode sequences for 1 to 2, 1 to 3, 1 to 4, 1 to 5, 1 to 6, 1 to 7, 1 to 8, 1 to 9, or 1 to 10 non-identical gRNAs per a single gene. In some instances, the gRNAs are sgRNAs. In some instances, the gRNAs are dgRNAs.

In some instances, a gRNA library described herein comprises one or more non-identical gRNAs per a gene of an organism. In some instances, the gRNA library comprises 1, 2, 3, 4, 5, 6, 7, 8, 9, 10 or more non-identical gRNAs per a gene for the organism. Exemplary organisms include, without limitation, Arabidopsis thaliana, Caenorhabditis elegans, Canis lupus familiaris, Chlamydomonas reinhardtii, Danio rerio, Dictyostelium discoideum, Drosophila melanogaster, Escherichia coli, Macaca mulatta, Mus musculus, Oryctolagus cuniculus, Rattus norvegicus, Saccharomyces cerevisiae, Sus scrofa, and Homo sapiens. In some instances, the gRNAs are sgRNAs. In some instances, the gRNAs are dgRNAs. In some cases, the gRNA library comprises non-identical gRNAs for at least or about 5% of the entire genome of the organism. In some cases, the gRNA library comprises non-identical gRNAs for about 5% to about 100% of the entire genome of the organism. In some instances, the gRNA library comprises non-identical gRNAs for at least or about 80% of the entire genome of the organism. In some instances, the sgRNA library comprises non-identical gRNAs for at least or about 90% of the entire genome of the organism. In some instances, the gRNA library comprises non-identical gRNAs for at least or about 95% of the entire genome of the organism. In some cases, the gRNA library comprises non-identical gRNAs for at least or about 100% of the entire genome of the organism. In some cases, the gRNA library comprises non-identical gRNAs for about 5% to 10%, 5% to 20%, 5% to 30%, 5% to 40%, 5% to 50%, 5% to 60%, 5% to 70%, 5% to 80%, 5% to 90%, 5% to 95%, 5% to 100%, 10% to 20%, 10% to 30%, 10% to 40%, 10% to 50%, 10% to 60%, 10% to 70%, 10% to 80%, 10% to 90%, 10% to 95%, 10% to 100%, 20% to 30%, 20% to 40%, 20% to 50%, 20% to 60%, 20% to 70%, 20% to 80%, 20% to 90%, 20% to 95%, 20% to 100%, 30% to 40%, 30% to 50%, 30% to 60%, 30% to 70%, 30% to 80%, 30% to 90%, 30% to 95%, 30% to 100%, 40% to 50%, 40% to 60%, 40% to 70%, 40% to 80%, 40% to 90%, 40% to 95%, 40% to 100%, 50% to 60%, 50% to 70%, 50% to 80%, 50% to 90%, 50% to 95%, 50% to 100%, 60% to 70%, 60% to 80%, 60% to 90%, 60% to 95%, 60% to 100%, 70% to 80%, 70% to 90%, 70% to 95%, 70% to 100%, 80% to 90%, 80% to 95%, 80% to 100%, 90% to 95%, 90% to 100%, or 95% to 100% of the entire genome of the organism. In some instances, the gRNA library comprises sequences from multiple genes in a pathway or from all genes in an organism. The number of gRNAs may comprise at least 2×, 3×, 5×, or 10× per a gene in an organism listed in Table 4. In some instances, the gRNA library targets at least one of a gene, a group of genes (e.g., 3-10 genes), a pathway (e.g., 10-100 genes), or a chassis (e.g., 100-1000 genes).

Highly Parallel De Novo Nucleic Acid Synthesis

Described herein is a platform approach utilizing miniaturization, parallelization, and vertical integration of the end-to-end process from oligonucleotide synthesis to gene assembly within nanowells on silicon to create a revolutionary synthesis platform. Devices described herein provide, with the same footprint as a 96-well plate, a silicon synthesis platform is capable of increasing throughput by a factor of 100 to 1,000 compared to traditional synthesis methods, with production of up to approximately 1,000,000 oligonucleotides in a single highly-parallelized run. In some instances, a single silicon plate described herein provides for synthesis of about 6100 non-identical oligonucleotides. In some instances, each of the non-identical oligonucleotides is located within a cluster. A cluster may comprise 50 to 500 non-identical oligonucleotides.

In some instances, DNA libraries encoding for gRNA libraries described herein have an error rate of less than 1:500 when compared to predetermined sequences for the DNAs. In some instances, de novo oligonucleotide libraries disclosed herein have an aggregated error rate of less than 1:500, 1:1000, 1:1500, 1:2000, 1:3000, 1:5000 or less when compared to predetermined sequences for the DNAs. In some instances, the aggregate error rate is less than 1:1000 when compared to predetermined sequences for the DNAs. The error rate may be an aggregate error rate or an average error rate.

In some instances, RNA libraries encoding for gRNA libraries described herein have an error rate of less than 1:500 when compared to predetermined sequences for the RNAs. In some instances, de novo oligonucleotide libraries disclosed herein have an aggregated error rate of less than 1:500, 1:1000, 1:1500, 1:2000, 1:3000, 1:5000, 1:10,000 or less when compared to predetermined sequences for the RNAs. In some instances, the aggregate error rate is less than 1:1000 when compared to predetermined sequences for the RNAs.

Substrates

In some cases, described herein are substrates comprising a plurality of clusters, wherein each cluster comprises a plurality of loci that support the attachment and synthesis of oligonucleotides. The term "locus" as used herein refers to a discrete region on a structure which provides support for oligonucleotides encoding for a single predetermined sequence to extend from the surface. In some embodiments, a locus is on a two dimensional surface, e.g., a substantially planar surface. In some embodiments, a locus is on a three-dimensional surface, e.g., a well, microwell, channel, or post. In some embodiments, a surface of a locus comprises a material that is actively functionalized to attach to at least one nucleotide for oligonucleotide synthesis, or preferably, a population of identical nucleotides for synthesis of a population of oligonucleotides. In some embodiments, oligonucleotide refers to a population of oligonucleotides encoding for the same nucleic acid sequence. In some cases, a surface of a substrate is inclusive of one or a plurality of surfaces of a substrate. The average error rates for oligonucleotides synthesized within a library using the systems and methods provided are often less than 1 in 1000, less than about 1 in 2000, less than about 1 in 3000 or less often.

In some embodiments, a substrate comprises a surface that supports the synthesis of a plurality of oligonucleotides having different predetermined sequences at addressable locations on a common support. In some embodiments, a substrate provides support for the synthesis of more than 50, 100, 200, 400, 600, 800, 1000, 1200, 1400, 1600, 1800, 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more non-identical oligonucleotides. In some cases, the substrate provides support for the synthesis of more than 50, 100, 200, 400, 600, 800, 1000, 1200, 1400, 1600, 1800, 2,000; 5,000; 10,000; 20,000; 50,000; 100,000; 200,000; 300,000; 400, 000; 500,000; 600,000; 700,000; 800,000; 900,000; 1,000, 000; 1,200,000; 1,400,000; 1,600,000; 1,800,000; 2,000, 000; 2,500,000; 3,000,000; 3,500,000; 4,000,000; 4,500, 000; 5,000,000; 10,000,000 or more oligonucleotides encoding for distinct sequences. In some embodiments, at least a portion of the oligonucleotides have an identical sequence or are configured to be synthesized with an identical sequence. In some embodiments, the substrate provides a surface environment for the growth of oligonucleotides having at least 80, 90, 100, 120, 150, 175, 200, 225, 250, 275, 300, 325, 350, 375, 400, 425, 450, 475, 500 bases or more.

In some embodiments, oligonucleotides are synthesized on distinct loci of a substrate, wherein each locus supports the synthesis of a population of oligonucleotides. In some cases, each locus supports the synthesis of a population of oligonucleotides having a different sequence than a population of oligonucleotides grown on another locus. In some embodiments, the loci of a substrate are located within a plurality of clusters. In some instances, a substrate comprises at least 10, 500, 1000, 2000, 3000, 4000, 5000, 6000, 7000, 8000, 9000, 10000, 11000, 12000, 13000, 14000, 15000, 20000, 30000, 40000, 50000 or more clusters. In some embodiments, a substrate comprises more than 2,000; 5,000; 10,000; 100,000; 200,000; 300,000; 400,000; 500, 000; 600,000; 700,000; 800,000; 900,000; 1,000,000; 1,100, 000; 1,200,000; 1,300,000; 1,400,000; 1,500,000; 1,600, 000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; or 10,000,000 or more distinct loci. In some embodiments, a substrate comprises about 10,000 distinct loci. The amount of loci within a single cluster is varied in different embodiments. In some cases, each cluster includes 1, 2, 3, 4, 5, 6, 7, 8, 9, 10, 20, 30, 40, 50, 60, 70, 80, 90, 100, 120, 130, 150, 200, 300, 400, 500 or more loci. In some embodiments, each cluster includes about 50-500 loci. In some embodiments, each cluster includes about 100-200 loci. In some embodiments, each cluster includes about 100-150 loci. In some embodiments, each cluster includes about 109, 121, 130 or 137 loci. In some embodiments, each cluster includes about 19, 20, 61, 64 or more loci.

Provided herein are methods for synthesizing non-identical oligonucleotides on a silicon plate. In some instances, the silicon plate includes about 1-10, 1-50, or 50-500 clusters. In some instances, the silicon plate includes more than about 50, 100, 250, 500, 2500, 5000, 6000, 6150, 10000 or more clusters. In some instances, each cluster includes 121 loci. In some instances, each cluster includes about 50-500, 50-200, 100-150 loci. In some instances, each cluster includes at least about 50, 100, 150, 200, 500, 1000 or more loci. In some instances, a single plate includes 100, 500, 10000, 20000, 30000, 50000, 100000, 500000, 700000, 1000000 or more loci.

In some embodiments, the number of distinct oligonucleotides synthesized on a substrate is dependent on the number of distinct loci available in the substrate. In some embodiments, the density of loci within a cluster of a substrate is at least or about 1 locus per $mm^2$, 10 loci per $mm^2$, 25 loci per $mm^2$, 50 loci per $mm^2$, 65 loci per $mm^2$, 75 loci per $mm^2$, 100 loci per $mm^2$, 130 loci per $mm^2$, 150 loci per $mm^2$, 175 loci per $mm^2$, 200 loci per $mm^2$, 300 loci per $mm^2$, 400 loci per $mm^2$, 500 loci per $mm^2$, 1,000 loci per $mm^2$ or more. In some cases, a substrate comprises from about 10 loci per $mm^2$ to about 500 $mm^2$, from about 25 loci per $mm^2$ to about 400 $mm^2$, from about 50 loci per $mm^2$ to about 500 $mm^2$, from about 100 loci per $mm^2$ to about 500 $mm^2$, from about 150 loci per $mm^2$ to about 500 $mm^2$, from about 10 loci per $mm^2$ to about 250 $mm^2$, from about 50 loci per $mm^2$ to about 250 $mm^2$, from about 10 loci per $mm^2$ to about 200 $mm^2$, or from about 50 loci per $mm^2$ to about 200 $mm^2$. In some embodiments, the distance between the centers of two adjacent loci within a cluster is from about 10 um to about 500 um, from about 10 um to about 200 um, or from about 10 um to about 100 um. In some cases, the distance between two centers of adjacent loci is greater than about 10 um, 20 um, 30 um, 40 um, 50 um, 60 um, 70 um, 80 um, 90 um or 100 um. In some cases, the distance between the centers of two adjacent loci is less than about 200 um, 150 um, 100 um, 80 um, 70 um, 60 um, 50 um, 40 um, 30 um, 20 um or 10 um. In some instances, each loci has a width of about 0.5 um, 1 um, 2 um, 3 um, 4 um, 5 um, 6 um, 7 um, 8 um, 9 um, 10 um, 20 um, 30 um, 40 um, 50 um, 60 um, 70 um, 80 um, 90 um or 100 um. In some cases, the each loci is has a width of about 0.5 um to 100 um, about 0.5 um to 50 um, about 10 um to 75 um, or about 0.5 um to 50 um.

In some embodiments, the density of clusters within a substrate is at least or about 1 cluster per 100 $mm^2$, 1 cluster per 10 $mm^2$, 1 cluster per 5 $m^2$, 1 cluster per 4 $mm^2$, 1 cluster per 3 cluster per 100 $mm^2$, 1 cluster per 10 mm, 1 cluster per 5 mm, 1 cluster per 4 $mm^2$, 1 cluster per 3 $mm^2$, 1 cluster per 2 $mm^2$, 1 cluster per 1 $mm^2$, 2 clusters per 1 $mm^2$, 3 clusters per 1 $mm^2$, 4 clusters per 1 $mm^2$, 5 clusters per 1 $mm^2$, 10 clusters per 1 $mm^2$, 50 clusters per 1 $mm^2$ or more. In some embodiments, a substrate comprises from about 1 cluster per 10 $mm^2$ to about 10 clusters per 1 $mm^2$. In some embodiments, the distance between the centers of two adjacent clusters is less than about 50 um, 100 um, 200 um, 500 um, 1000 um, or 2000 um or 5000 um. In some cases, the distance between the centers of two adjacent clusters is between about 50 um and about 100 um, between about 50 um and about 200 um, between about 50 um and about 300 um, between about 50 um and about 500 um, and between about 100 um to about 2000 um. In some cases, the distance between the centers of two adjacent clusters is between about 0.05 mm to about 50 mm, between about 0.05 mm to about 10 mm, between about 0.05 mm and about 5 mm, between about 0.05 mm and about 4 mm, between about 0.05 mm and about 3 mm, between about 0.05 mm and about 2 mm, between about 0.1 mm and 10 mm, between about 0.2 mm and 10 mm, between about 0.3 mm and about 10 mm, between about 0.4 mm and about 10 mm, between about 0.5 mm and 10 mm, between about 0.5 mm and about 5 mm, or between about 0.5 mm and about 2 mm. In some cases, each cluster has a cross section of about 0.5 to 2 mm, about 0.5 to 1 mm, or about 1 to 2 mm. In some cases, each cluster has a cross section of about 0.5, 0.6, 0.7, 0.8, 0.9, 1, 1.1, 1.2, 1.3, 1.4, 1.5, 1.6, 1.7, 1.8, 1.9 or 2 mm. In some cases, each cluster has an interior cross section of about 0.5, 0.6, 0.7, 0.8, 0.9, 1, 1.1, 1.15, 1.2, 1.3, 1.4, 1.5, 1.6, 1.7, 1.8, 1.9 or 2 mm.

In some embodiments, a substrate is about the size of a standard 96 well plate, for example between about 100 and 200 mm by between about 50 and 150 mm. In some embodiments, a substrate has a diameter less than or equal to about 1000 mm, 500 mm, 450 mm, 400 mm, 300 mm, 250 nm, 200 mm, 150 mm, 100 mm or 50 mm. In some embodiments, the diameter of a substrate is between about 25 mm and 1000 mm, between about 25 mm and about 800 mm, between about 25 mm and about 600 mm, between about 25 mm and about 500 mm, between about 25 mm and about 400 mm, between about 25 mm and about 300 mm, or between about 25 mm and about 200. Non-limiting examples of substrate size include about 300 mm, 200 mm, 150 mm, 130 mm, 100 mm, 76 mm, 51 mm and 25 mm. In some embodiments, a substrate has a planar surface area of at least about 100 $mm^2$; 200 $mm^2$; 500 $mm^2$; 1,000 $mm^2$; 2,000 $mm^2$; 5,000 $mm^2$; 10,000 $mm^2$; 12,000 $mm^2$; 15,000 $mm^2$; 20,000 $mm^2$; 30,000 $mm^2$; 40,000 $mm^2$; 50,000 $mm^2$ or more. In some embodiments, the thickness of a substrate is between about 50 mm and about 2000 mm, between about 50 mm and about 1000 mm, between about 100 mm and about 1000 mm, between about 200 mm and about 1000 mm, or between about 250 mm and about 1000 mm. Non-limiting examples of substrate thickness include 275 mm, 375 mm, 525 mm, 625 mm, 675 mm, 725 mm, 775 mm and 925 mm. In some cases, the thickness of a substrate varies with diameter and depends on the composition of the substrate. For example, a substrate comprising materials other than silicon has a different thickness than a silicon substrate of the same diameter. Substrate thickness may be determined by the mechanical strength of the material used and the substrate must be thick enough to support its own weight without cracking during handling.

Surface Materials

Substrates, devices and reactors provided herein are fabricated from any variety of materials suitable for the methods and compositions described herein. In certain embodiments, substrate materials are fabricated to exhibit a low level of nucleotide binding. In some cases, substrate materials are modified to generate distinct surfaces that exhibit a high level of nucleotide binding. In some embodiments, substrate materials are transparent to visible and/or UV light. In some embodiments, substrate materials are sufficiently conductive, e.g., are able to form uniform electric fields across all or a portion of a substrate. In some embodiments, conductive materials are connected to an electric ground. In some cases, the substrate is heat conductive or insulated. In some cases, the materials are chemical resistant and heat resistant to support chemical or biochemical reactions, for example oligonucleotide synthesis reaction processes. In some embodiments, a substrate comprises flexible materials. Flexible materials include, without limitation, modified nylon, unmodified nylon, nitrocellulose, polypropylene, and the like. In some embodiments, a substrate comprises rigid materials. Rigid materials include, without limitation, glass, fuse silica, silicon, silicon dioxide, silicon nitride, plastics (for example, polytetraflouroethylene, polypropylene, polystyrene, polycarbonate, and blends thereof, and the like), and metals (for example, gold, platinum, and the like). In some embodiments, a substrate is fabricated from a material comprising silicon, polystyrene, agarose, dextran, cellulosic polymers, polyacrylamides, polydimethylsiloxane (PDMS), glass, or any combination thereof. In some cases, a substrate is manufactured with a combination of materials listed herein or any other suitable material known in the art.

Surface Architecture

In various embodiments, a substrate comprises raised and/or lowered features. One benefit of having such features is an increase in surface area to support oligonucleotide synthesis. In some embodiments, a substrate having raised and/or lowered features is referred to as a three-dimensional substrate. In some cases, a three-dimensional substrate comprises one or more channels. In some cases, one or more loci comprise a channel. In some cases, the channels are accessible to reagent deposition via a deposition device such as an oligonucleotide synthesizer. In some cases, reagents and/or fluids collect in a larger well in fluid communication one or more channels. For example, a substrate comprises a plurality of channels corresponding to a plurality of loci with a cluster, and the plurality of channels are in fluid communication with one well of the cluster. In some methods, a library of oligonucleotides is synthesized in a plurality of loci of a cluster.

In some embodiments, the structure is configured to allow for controlled flow and mass transfer paths for oligonucleotide synthesis on a surface. In some embodiments, the configuration of a substrate allows for the controlled and even distribution of mass transfer paths, chemical exposure times, and/or wash efficacy during oligonucleotide synthesis. In some embodiments, the configuration of a substrate allows for increased sweep efficiency, for example by providing sufficient volume for a growing an oligonucleotide such that the excluded volume by the growing oligonucleotide does not take up more than 50, 45, 40, 35, 30, 25, 20, 15, 14, 13, 12, 11, 10, 9, 8, 7, 6, 5, 4, 3, 2, 1%, or less of the initially available volume that is available or suitable for growing the oligonucleotide. In some embodiments, a three-dimensional structure allows for managed flow of fluid to allow for the rapid exchange of chemical exposure.

In some embodiments, segregation is achieved by physical structure. In some embodiments, segregation is achieved by differential functionalization of the surface generating active and passive regions for oligonucleotide synthesis. Differential functionalization is also be achieved by alternating the hydrophobicity across the substrate surface, thereby creating water contact angle effects that cause beading or wetting of the deposited reagents. Employing larger structures can decrease splashing and cross-contamination of distinct oligonucleotide synthesis locations with reagents of the neighboring spots. In some cases, a device, such as an oligonucleotide synthesizer, is used to deposit reagents to distinct oligonucleotide synthesis locations. Substrates having three-dimensional features are configured in a manner that allows for the synthesis of a large number of oligonucleotides (e.g., more than about 10,000) with a low error rate (e.g., less than about 1:500, 1:1000, 1:1500, 1:2,000; 1:3,000; 1:5,000; or 1:10,000). In some cases, a substrate comprises features with a density of about or greater than about 1, 5, 10, 20, 30, 40, 50, 60, 70, 80, 100, 110, 120, 130, 140, 150, 160, 170, 180, 190, 200, 300, 400 or 500 features per mm$^2$.

A well of a substrate may have the same or different width, height, and/or volume as another well of the substrate. A channel of a substrate may have the same or different width, height, and/or volume as another channel of the substrate. In some embodiments, the diameter of a cluster or the diameter of a well comprising a cluster, or both, is between about 0.05 mm to about 50 mm, between about 0.05 mm to about 10 mm, between about 0.05 mm and about 5 mm, between about 0.05 mm and about 4 mm, between about 0.05 mm and about 3 mm, between about 0.05 mm and about 2 mm, between about 0.05 mm and about 1 mm, between about 0.05 mm and about 0.5 mm, between about 0.05 mm and about 0.1 mm, between about 0.1 mm and 10 mm, between about 0.2 mm and 10 mm, between about 0.3 mm and about 10 mm, between about 0.4 mm and about 10 mm, between about 0.5 mm and 10 mm, between about 0.5 mm and about 5 mm, or between about 0.5 mm and about 2 mm. In some embodiments, the diameter of a cluster or well or both is less than or about 5 mm, 4 mm, 3 mm, 2 mm, 1 mm, 0.5 mm, 0.1 mm, 0.09 mm, 0.08 mm, 0.07 mm, 0.06 mm or 0.05 mm. In some embodiments, the diameter of a cluster or well or both is between about 1.0 and 1.3 mm. In some embodiments, the diameter of a cluster or well, or both is about 1.150 mm. In some embodiments, the diameter of a cluster or well, or both is about 0.08 mm. The diameter of a cluster refers to clusters within a two-dimensional or three-dimensional substrate.

In some embodiments, the height of a well is from about 20 um to about 1000 um, from about 50 um to about 1000 um, from about 100 um to about 1000 um, from about 200 um to about 1000 um, from about 300 um to about 1000 um, from about 400 um to about 1000 um, or from about 500 um to about 1000 um. In some cases, the height of a well is less than about 1000 um, less than about 900 um, less than about 800 um, less than about 700 um, or less than about 600 um.

In some embodiments, a substrate comprises a plurality of channels corresponding to a plurality of loci within a cluster, wherein the height or depth of a channel is from about 5 um to about 500 um, from about 5 um to about 400 um, from about 5 um to about 300 um, from about 5 um to about 200 um, from about 5 um to about 100 um, from about 5 um to about 50 um, or from about 10 um to about 50 um. In some cases, the height of a channel is less than 100 um, less than 80 um, less than 60 um, less than 40 um or less than 20 um.

In some embodiments, the diameter of a channel, locus (e.g., in a substantially planar substrate) or both channel and locus (e.g., in a three-dimensional substrate wherein a locus corresponds to a channel) is from about 1 um to about 1000 um, from about 1 um to about 500 um, from about 1 um to about 200 um, from about 1 um to about 100 um, from about 5 um to about 100 urn, or from about 10 um to about 100 um, for example, about 90 um, 80 um, 70 um, 60 um, 50 um, 40 um, 30 um, 20 um or 10 um. In some embodiments, the diameter of a channel, locus, or both channel and locus is less than about 100 um, 90 um, 80 um, 70 um, 60 um, 50 um, 40 um, 30 um, 20 um or 10 um. In some embodiments, the distance between the center of two adjacent channels, loci, or channels and loci is from about 1 um to about 500 um, from about 1 um to about 200 um, from about 1 um to about 100 um, from about 5 um to about 200 um, from about 5 um to about 100 urn, from about 5 um to about 50 um, or from about 5 um to about 30 um, for example, about 20 um.

Surface Modifications

In various embodiments, surface modifications are employed for the chemical and/or physical alteration of a surface by an additive or subtractive process to change one or more chemical and/or physical properties of a substrate surface or a selected site or region of a substrate surface. For example, surface modifications include, without limitation, (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

In some cases, the addition of a chemical layer on top of a surface (referred to as adhesion promoter) facilitates structured patterning of loci on a surface of a substrate. Exemplary surfaces for application of adhesion promotion include, without limitation, glass, silicon, silicon dioxide and silicon nitride. In some cases, the adhesion promoter is a chemical with a high surface energy. In some embodiments, a second chemical layer is deposited on a surface of a substrate. In some cases, the second chemical layer has a low surface energy. In some cases, surface energy of a chemical layer coated on a surface supports localization of droplets on the surface. Depending on the patterning arrangement selected, the proximity of loci and/or area of fluid contact at the loci are alterable.

In some embodiments, a substrate surface, or resolved loci, onto which nucleic acids or other moieties are deposited, e.g., for oligonucleotide synthesis, are smooth or substantially planar (e.g., two-dimensional) or have irregularities, such as raised or lowered features (e.g., three-dimensional features). In some embodiments, a substrate surface is modified with one or more different layers of compounds. Such modification layers of interest include, without limitation, inorganic and organic layers such as metals, metal oxides, polymers, small organic molecules and the like. Non-limiting polymeric layers include peptides, proteins, nucleic acids or mimetics thereof (e.g., peptide nucleic acids and the like), polysaccharides, phospholipids, polyurethanes, polyesters, polycarbonates, polyureas, polyamides, polyetheyleneamines, polyarylene sulfides, polysiloxanes, polyimides, polyacetates, and any other suitable compounds described herein or otherwise known in the art. In some cases, polymers are heteropolymeric. In some cases, polymers are homopolymeric. In some cases, polymers comprise functional moieties or are conjugated.

In some embodiments, resolved loci of a substrate are functionalized with one or more moieties that increase and/or decrease surface energy. In some cases, a moiety is chemically inert. In some cases, a moiety is configured to support a desired chemical reaction, for example, one or more processes in an oligonucleotide synthesis reaction. The surface energy, or hydrophobicity, of a surface is a factor for determining the affinity of a nucleotide to attach onto the surface. In some embodiments, a method for substrate functionalization comprises: (a) providing a substrate having a surface that comprises silicon dioxide; and (b) silanizing the surface using, a suitable silanizing agent described herein or otherwise known in the art, for example, an organofunctional alkoxysilane molecule. In some cases, the organofunctional alkoxysilane molecule comprises dimethylchloro-octodecyl-silane, methyldichloro-octodecyl-silane, trichloro-octodecyl-silane, trimethyl-octodecyl-silane, triethyl-octodecyl-silane, or any combination thereof. In some embodiments, a substrate surface comprises functionalized with polyethylene/polypropylene (functionalized by gamma irradiation or chromic acid oxidation, and reduction to hydroxyalkyl surface), highly crosslinked polystyrene-divinylbenzene (derivatized by chloromethylation, and aminated to benzylamine functional surface), nylon (the terminal aminohexyl groups are directly reactive), or etched with reduced polytetrafluoroethylene. Other methods and functionalizing agents are described in U.S. Pat. No. 5,474,796, which is herein incorporated by reference in its entirety.

In some embodiments, a substrate surface is functionalized by contact with a derivatizing composition that contains a mixture of silanes, under reaction conditions effective to couple the silanes to the substrate surface, typically via reactive hydrophilic moieties present on the substrate surface. Silanization generally covers a surface through self-assembly with organofunctional alkoxysilane molecules. A variety of siloxane functionalizing reagents can further be used as currently known in the art, e.g., for lowering or increasing surface energy. The organofunctional alkoxysilanes are classified according to their organic functions. Non-limiting examples of siloxane functionalizing reagents include hydroxyalkyl siloxanes (silylate surface, functionalizing with diborane and oxidizing the alcohol by hydrogen peroxide), diol (dihydroxyalkyl) siloxanes (silylate surface, and hydrolyzing to diol), aminoalkyl siloxanes (amines require no intermediate functionalizing step), glycidoxysilanes (3-glycidoxypropyl-dimethyl-ethoxysilane, glycidoxy-trimethoxysilane), mercaptosilanes (3-mercaptopropyl-trimethoxysilane, 3-4 epoxycyclohexyl-ethyltrimethoxysilane or 3-mercaptopropyl-methyl-dimethoxysilane), bicycloheptenyl-trichlorosilane, butyl-aldehydr-trimethoxysilane, or dimeric secondary aminoalkyl siloxanes. Exemplary hydroxyalkyl siloxanes include allyl trichlorochlorosilane turning into 3-hydroxypropyl, or 7-oct-1-enyl trichlorochlorosilane turning into 8-hydroxyoctyl. The diol (dihydroxyalkyl) siloxanes include glycidyl trimethoxysilane-derived (2,3-dihydroxypropyloxy)propyl (GOPS). The aminoalkyl siloxanes include 3-aminopropyl trimethoxysilane turning into 3-aminopropyl (3-aminopropyl-triethoxysilane, 3-aminopropyl-diethoxymethylsilane, 3-aminopropyl-dimethyl-ethoxysilane, or 3-aminopropyl-trimethoxysilane). Exemplary dimeric secondary aminoalkyl siloxanes include bis (3-trimethoxysilylpropyl) amine turning into bis(silyloxylpropyl)amine. In some embodiments, the functionalizing agent comprises 11-acetoxyundecyltriethoxysilane, n-decyltriethoxysilane, (3-aminopropyl)trimethoxysilane, (3-aminopropyl)triethoxysilane, glycidyloxypropyl/trimethoxysilane and N-(3-triethoxysilylpropyl)-4-hydroxybutyramide.

Oligonucleotide Synthesis

Methods for oligonucleotide synthesis, in various embodiments, include processes involving phosphoramidite chemistry. In some embodiments, oligonucleotide synthesis comprises coupling a base with phosphoramidite. In some embodiments, oligonucleotide synthesis comprises coupling a base by deposition of phosphoramidite under coupling conditions, wherein the same base is optionally deposited with phosphoramidite more than once, i.e., double coupling. In some embodiments, oligonucleotide synthesis comprises capping of unreacted sites. In some cases, capping is optional. In some embodiments, oligonucleotide synthesis comprises oxidation. In some embodiments, oligonucleotide synthesis comprises deblocking or detritylation. In some embodiments, oligonucleotide synthesis comprises sulfurization. In some cases, oligonucleotide synthesis comprises either oxidation or sulfurization. In some embodiments, between one or each step during an oligonucleotide synthesis reaction, the substrate is washed, for example, using tetrazole or acetonitrile. Time frames for any one step in a phosphoramidite synthesis method include less than about 2 min, 1 min, 50 sec, 40 sec, 30 sec, 20 sec and 10 sec.

Oligonucleotide synthesis using a phosphoramidite method comprises the subsequent addition of a phosphoramidite building block (e.g., nucleoside phosphoramidite) to a growing oligonucleotide chain for the formation of a phosphite triester linkage. Phosphoramidite oligonucleotide synthesis proceeds in the 3' to 5' direction. Phosphoramidite oligonucleotide synthesis allows for the controlled addition of one nucleotide to a growing nucleic acid chain per synthesis cycle. In some embodiments, each synthesis cycle comprises a coupling step. Phosphoramidite coupling involves the formation of a phosphite triester linkage between an activated nucleoside phosphoramidite and a nucleoside bound to the substrate, for example, via a linker. In some embodiments, the nucleoside phosphoramidite is provided to the substrate activated. In some embodiments, the nucleoside phosphoramidite is provided to the substrate with an activator. In some embodiments, nucleoside phosphoramidites are provided to the substrate in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some embodiments, the addition of nucleoside phosphoramidite is performed in an anhydrous environment, for example, in anhydrous acetonitrile. Following addition of a nucleoside phosphoramidite, the substrate is optionally washed. In some embodiments, the coupling step is repeated one or more additional times, optionally with a wash step between nucleoside phosphoramidite additions to the substrate. In some embodiments, an oligonucleotide synthesis method used herein comprises 1, 2, 3 or more sequential coupling steps. Prior to coupling, in many cases, the nucleoside bound to the substrate is deprotected by removal of a protecting group, where the protecting group functions to prevent polymerization. A common protecting group is 4,4'-dimethoxytrityl (DMT).

Following coupling, phosphoramidite oligonucleotide synthesis methods optionally comprise a capping step. In a capping step, the growing oligonucleotide is treated with a capping agent. A capping step is useful to block unreacted substrate-bound 5'-OH groups after coupling from further chain elongation, preventing the formation of oligonucleotides with internal base deletions. Further, phosphoramidites activated with 1H-tetrazole may react, to a small extent, with the O6 position of guanosine. Without being bound by theory, upon oxidation with $I_2$/water, this side product, possibly via O6-N7 migration, may undergo depurination. The apurinic sites may end up being cleaved in the course of the final deprotection of the oligonucleotide thus reducing the yield of the full-length product. The O6 modifications may be removed by treatment with the capping reagent prior to oxidation with $I_2$/water. In some embodiments, inclusion of a capping step during oligonucleotide synthesis decreases the error rate as compared to synthesis without capping. As an example, the capping step comprises treating the substrate-bound oligonucleotide with a mixture of acetic anhydride and 1-methylimidazole. Following a capping step, the substrate is optionally washed.

In some embodiments, following addition of a nucleoside phosphoramidite, and optionally after capping and one or more wash steps, the substrate bound growing nucleic acid is oxidized. The oxidation step comprises the phosphite triester is oxidized into a tetracoordinated phosphate triester, a protected precursor of the naturally occurring phosphate diester internucleoside linkage. In some cases, oxidation of the growing oligonucleotide is achieved by treatment with iodine and water, optionally in the presence of a weak base (e.g., pyridine, lutidine, collidine). Oxidation may be carried out under anhydrous conditions using, e.g. tert-Butyl hydroperoxide or (1S)-(+)-(10-camphorsulfonyl)-oxaziridine (CSO). In some methods, a capping step is performed following oxidation. A second capping step allows for substrate drying, as residual water from oxidation that may persist can inhibit subsequent coupling. Following oxidation, the substrate and growing oligonucleotide is optionally washed. In some embodiments, the step of oxidation is substituted with a sulfurization step to obtain oligonucleotide phosphorothioates, wherein any capping steps can be performed after the sulfurization. Many reagents are capable of the efficient sulfur transfer, including but not limited to 3-(Dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

In order for a subsequent cycle of nucleoside incorporation to occur through coupling, the protected 5' end of the substrate bound growing oligonucleotide is removed so that the primary hydroxyl group is reactive with a next nucleoside phosphoramidite. In some embodiments, the protecting group is DMT and deblocking occurs with trichloroacetic acid in dichloromethane. Conducting detritylation for an extended time or with stronger than recommended solutions of acids may lead to increased depurination of solid support-bound oligonucleotide and thus reduces the yield of the desired full-length product. Methods and compositions of the invention described herein provide for controlled deblocking conditions limiting undesired depurination reactions. In some cases, the substrate bound oligonucleotide is washed after deblocking. In some cases, efficient washing after deblocking contributes to synthesized oligonucleotides having a low error rate.

Methods for the synthesis of oligonucleotides typically involve an iterating sequence of the following steps: application of a protected monomer to an actively functionalized surface (e.g., locus) to link with either the activated surface, a linker or with a previously deprotected monomer; deprotection of the applied monomer so that it is reactive with a subsequently applied protected monomer; and application of another protected monomer for linking. One or more intermediate steps include oxidation or sulfurization. In some cases, one or more wash steps precede or follow one or all of the steps.

Methods for phosphoramidite based oligonucleotide synthesis comprise a series of chemical steps. In some embodiments, one or more steps of a synthesis method involve reagent cycling, where one or more steps of the method comprise application to the substrate of a reagent useful for the step. For example, reagents are cycled by a series of liquid deposition and vacuum drying steps. For substrates comprising three-dimensional features such as wells, microwells, channels and the like, reagents are optionally passed through one or more regions of the substrate via the wells and/or channels.

Oligonucleotides synthesized using the methods and/or substrates described herein comprise, in various embodiments, at least about 20, 30, 40, 50, 60, 70, 75, 80, 90, 100, 120, 150 or more bases. In some embodiments, at least about 1 pmol, 10 pmol, 20 pmol, 30 pmol, 40 pmol, 50 pmol, 60 pmol, 70 pmol, 80 pmol, 90 pmol, 100 pmol, 150 pmol, 200 pmol, 300 pmol, 400 pmol, 500 pmol, 600 pmol, 700 pmol, 800 pmol, 900 pmol, 1 nmol, 5 nmol, 10 nmol, 100 nmol or more of an oligonucleotide is synthesized within a locus. Methods for oligonucleotide synthesis on a surface provided herein allow for synthesis at a fast rate. As an example, at least 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 100, 125, 150, 175, 200 nucleotides per hour, or more are synthesized. Nucleotides include adenine, guanine, thymine, cytosine, uridine building blocks, or analogs/modified versions thereof. In some embodiments, libraries of oligonucleotides are synthesized in parallel on substrate. For example, a substrate comprising about or at least about 100; 1,000; 10,000; 100,000; 1,000,000; 2,000,000; 3,000,000; 4,000,000; or 5,000,000 resolved loci is able to support the synthesis of at least the same number of distinct oligonucleotides, wherein oligonucleotide encoding a distinct sequence is synthesized on a resolved locus. In some embodiments, a library of oligonucleotides are synthesized on a substrate with low error rates described herein in less than about three months, two months, one month, three weeks, 15, 14, 13, 12, 11, 10, 9, 8, 7, 6, 5, 4, 3, 2 days, 24 hours or less. In some embodiments, larger nucleic acids assembled from an oligonucleotide library synthesized with low error rate using the substrates and methods described herein are prepared in less than about three months, two months, one month, three weeks, 15, 14, 13, 12, 11, 10, 9, 8, 7, 6, 5, 4, 3, 2 days, 24 hours or less.

Once large oligonucleotides for generation are selected, a predetermined library of oligonucleotides is designed for de novo synthesis. Various suitable methods are known for generating high density oligonucleotide arrays. In the workflow example, a substrate surface layer is provided. In the example, chemistry of the surface is altered in order to improve the oligonucleotide synthesis process. Areas of low surface energy are generated to repel liquid while areas of high surface energy are generated to attract liquids. The surface itself may be in the form of a planar surface or contain variations in shape, such as protrusions or microwells which increase surface area. In the workflow example, high surface energy molecules selected serve a dual function of supporting DNA chemistry, as disclosed in International Patent Application Publication WO/2015/021080, which is herein incorporated by reference in its entirety.

In situ preparation of oligonucleotide arrays is generated on a solid support and utilizes single nucleotide extension process to extend multiple oligomers in parallel. A deposition device, such as an oligonucleotide synthesizer, is designed to release reagents in a step wise fashion such that multiple oligonucleotides extend, in parallel, one residue at a time to generate oligomers with a predetermined nucleic acid sequence. In some cases, oligonucleotides are cleaved from the surface at this stage. Cleavage includes gas cleavage, e.g., with ammonia or methylamine.

Computer Systems

Any of the systems described herein, may be operably linked to a computer and may be automated through a computer either locally or remotely. In various embodiments, the methods and systems of the invention may further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the invention. The computer systems may be programmed to interface between the user specified base sequence and the position of a material deposition device to deliver the correct reagents to specified regions of the substrate.

Figure 8:
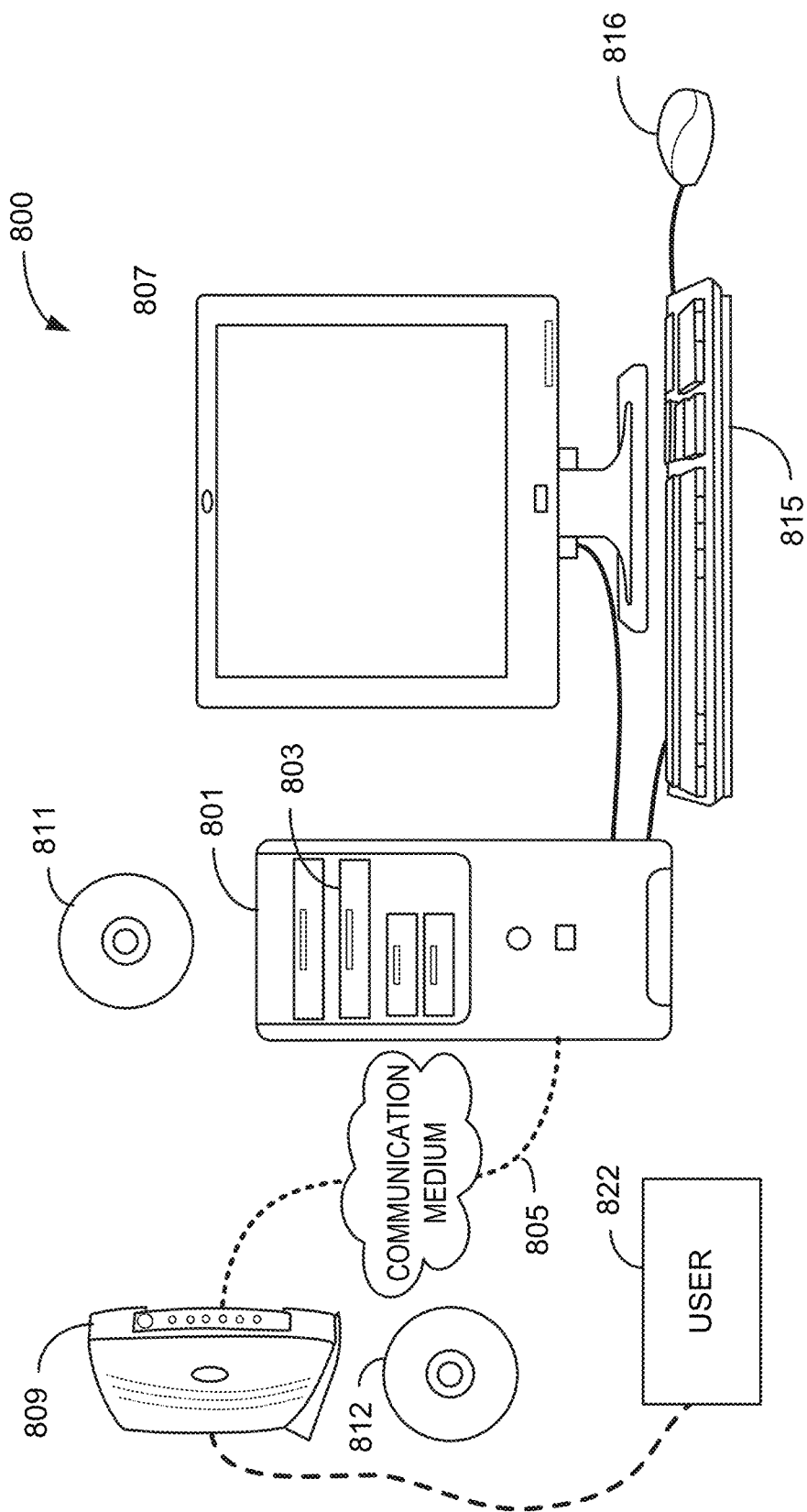
FIG. 8 illustrates an example of a computer system.

The computer system 800 illustrated in FIG. 8 may be understood as a logical apparatus that can read instructions from media 811 and/or a network port 805, which can optionally be connected to server 809 having fixed media 812. The system, such as shown in FIG. 8 can include a CPU 801, disk drives 803, optional input devices such as keyboard 815 and/or mouse 816 and optional monitor 807. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 822 as illustrated in FIG. 8.

Figure 9:
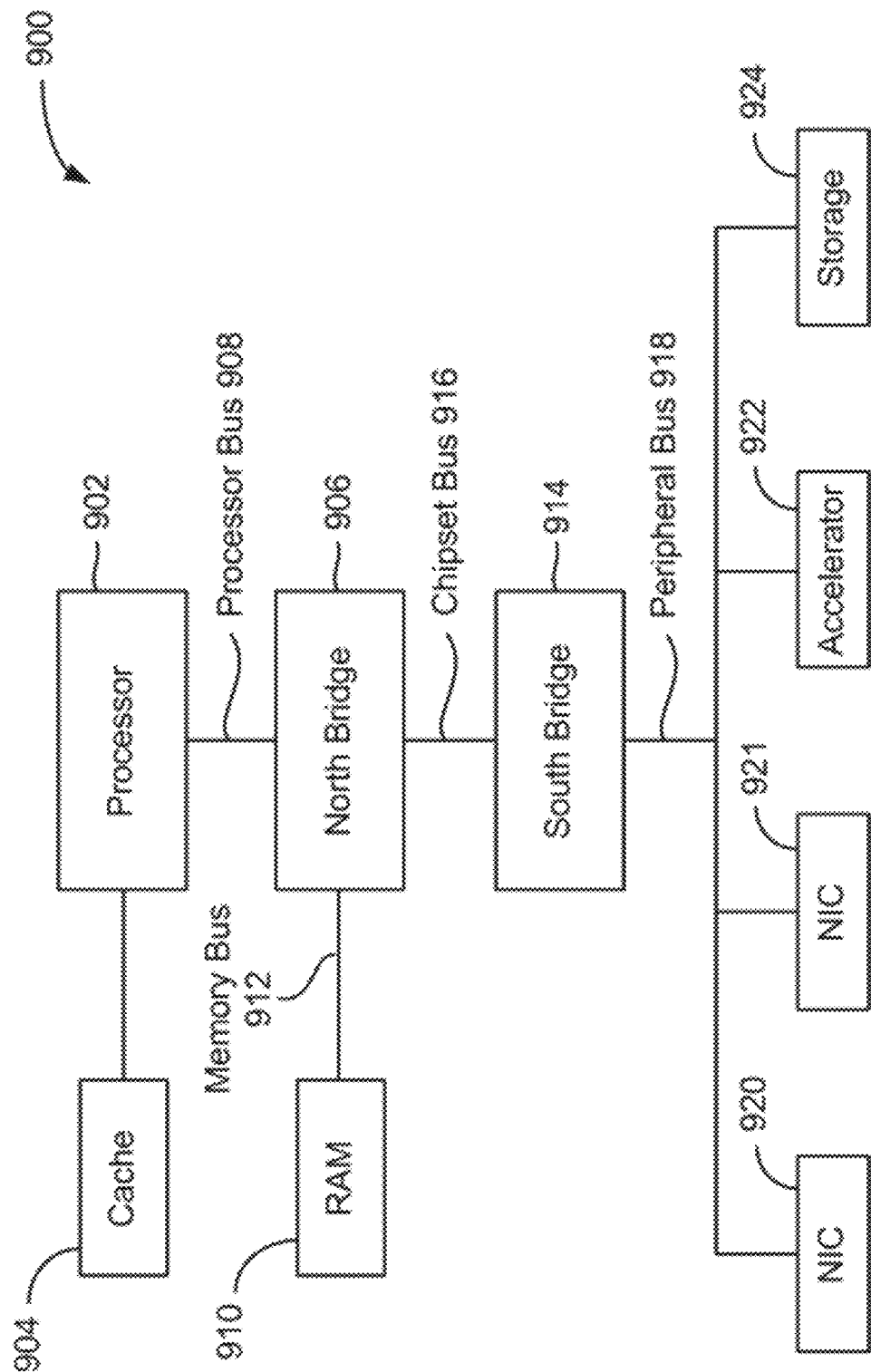
FIG. 9 is a block diagram illustrating an example architecture of a computer system.

FIG. 9 is a block diagram illustrating a first example architecture of a computer system 900 that can be used in connection with example embodiments of the present invention. As depicted in FIG. 9, the example computer system can include a processor 902 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices.

As illustrated in FIG. 9, a high speed cache 904 can be connected to, or incorporated in, the processor 902 to provide a high speed memory for instructions or data that have been recently, or are frequently, used by processor 902. The processor 902 is connected to a north bridge 906 by a processor bus 908. The north bridge 906 is connected to random access memory (RAM) 910 by a memory bus 912 and manages access to the RAM 910 by the processor 902. The north bridge 906 is also connected to a south bridge 914 by a chipset bus 916. The south bridge 914 is, in turn, connected to a peripheral bus 918. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 918. In some alternative architectures, the functionality of the north bridge can be incorporated into the processor instead of using a separate north bridge chip. In some embodiments, system 900 can include an accelerator card 922 attached to the peripheral bus 918. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 924 and can be loaded into RAM 910 and/or cache 904 for use by the processor. The system 900 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention. In this example, system 900 also includes network interface cards (NICs) 920 and 921 connected to the peripheral bus for providing network interfaces to external storage, such as Network Attached Storage (NAS) and other computer systems that can be used for distributed parallel processing.

Figure 10:
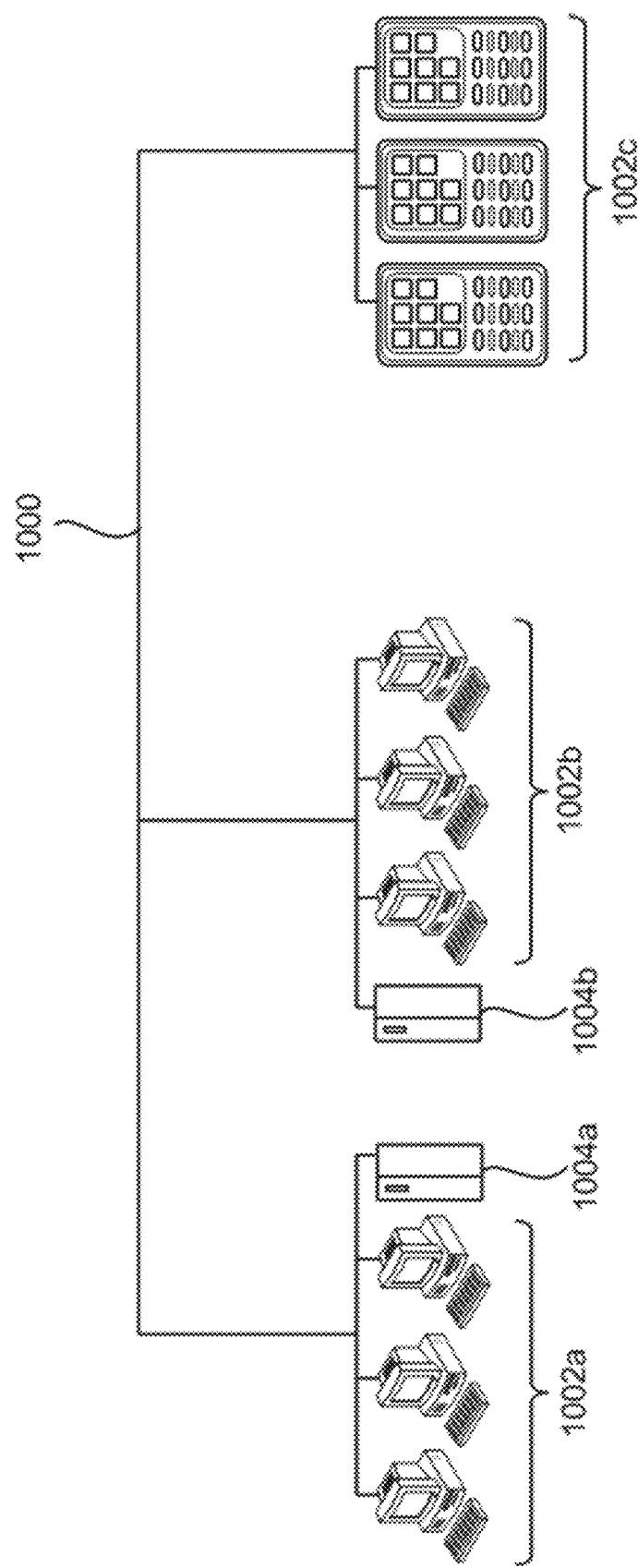
FIG. 10 is a diagram demonstrating a network configured to incorporate a plurality of computer systems, a plurality of cell phones and personal data assistants, and Network Attached Storage (NAS).

FIG. 10 is a diagram showing a network 1000 with a plurality of computer systems 1002a, and 1002b, a plurality of cell phones and personal data assistants 1002c, and Network Attached Storage (NAS) 1004a, and 1004b. In example embodiments, systems 1002a, 1002b, and 1002c can manage data storage and optimize data access for data stored in Network Attached Storage (NAS) 1004a and 1004b. A mathematical model can be used for the data and be evaluated using distributed parallel processing across computer systems 1002a, and 1002b, and cell phone and personal data assistant systems 1002c. Computer systems 1002a, and 1002b, and cell phone and personal data assistant systems 1002c can also provide parallel processing for adaptive data restructuring of the data stored in Network Attached Storage (NAS) 1004a and 1004b. FIG. 10 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface. In some example embodiments, processors can maintain separate memory spaces and transmit data through network interfaces, back plane or other connectors for parallel processing by other processors. In other embodiments, some or all of the processors can use a shared virtual address memory space.

Figure 11:
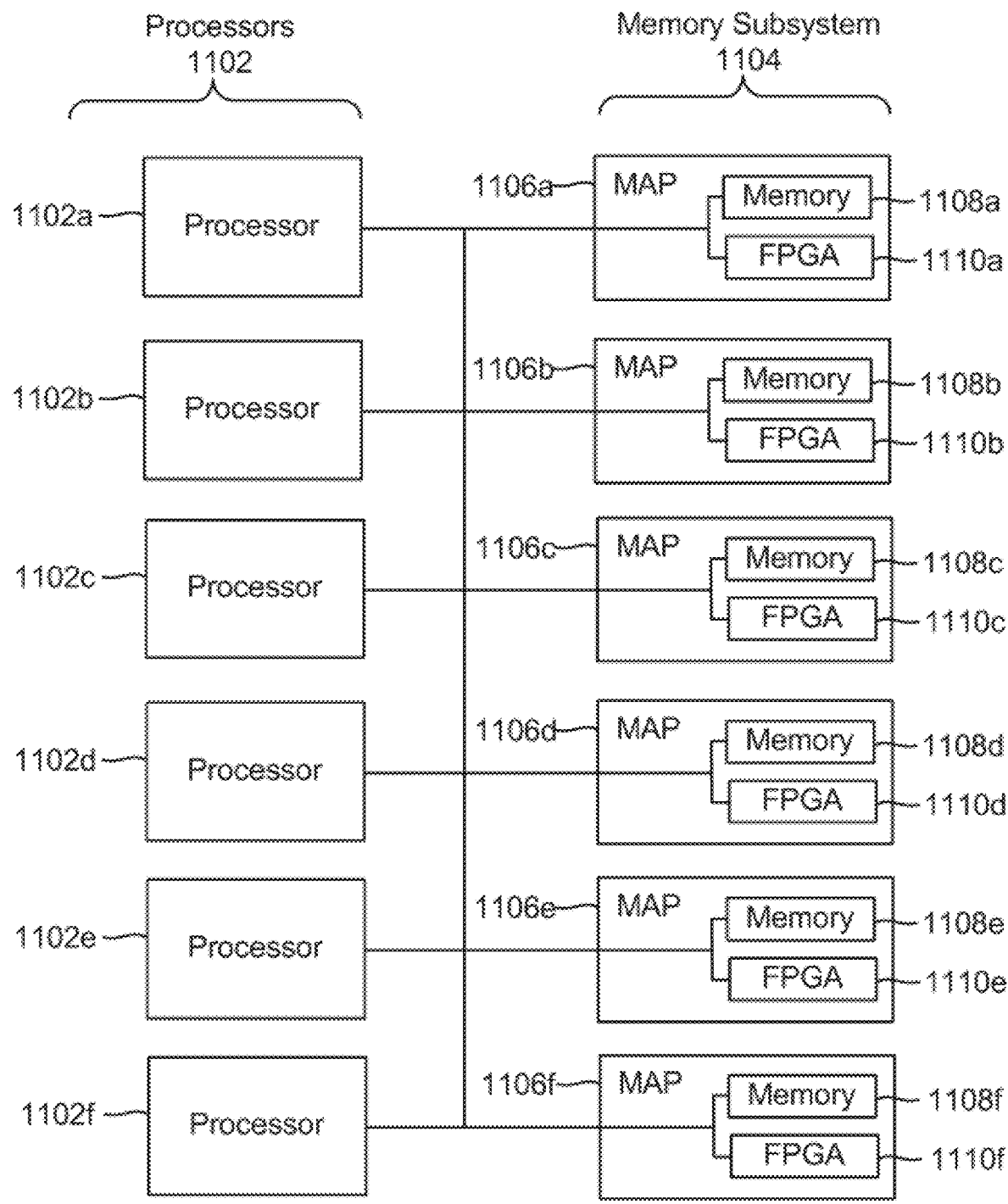
FIG. 11 is a block diagram of a multiprocessor computer system using a shared virtual address memory space.

FIG. 11 is a block diagram of a multiprocessor computer system using a shared virtual address memory space in accordance with an example embodiment. The system includes a plurality of processors 1102a-f that can access a shared memory subsystem 1104. The system incorporates a plurality of programmable hardware memory algorithm processors (MAPs) 1106a-f in the memory subsystem 1104. Each MAP 1106a-f can comprise a memory 1108a-f and one or more field programmable gate arrays (FPGAs) 1110a-f. The MAP provides a configurable functional unit and particular algorithms or portions of algorithms can be provided to the FPGAs 1110a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 1108a-f, allowing it to execute tasks independently of, and asynchronously from, the respective microprocessor 1102a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 11, system on chips (SOCs), application specific integrated circuits (ASICs), or other processing and logic elements. For example, the Set Processor and Optimizer can be implemented with hardware acceleration through the use of a hardware accelerator card, such as accelerator card 922 illustrated in FIG. 9.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Functionalization of a Substrate Surface

A substrate was functionalized to support the attachment and synthesis of a library of oligonucleotides. The substrate surface was first wet cleaned using a piranha solution comprising 90% $H_2SO_4$ and 10% $H_2O_2$ for 20 minutes. The substrate was rinsed in several beakers with DI water, held under a DI water gooseneck faucet for 5 min, and dried with $N_2$. The substrate was subsequently soaked in $NH_4OH$ (1:100; 3 mL:300 mL) for 5 min, rinsed with DI water using a handgun, soaked in three successive beakers with DI water for 1 min each, and then rinsed again with DI water using the handgun. The substrate was then plasma cleaned by exposing the substrate surface to $O_2$. A SAMCO PC-300 instrument was used to plasma etch $O_2$ at 250 watts for 1 min in downstream mode.

The cleaned substrate surface was actively functionalized with a solution comprising N-(3-triethoxysilylpropyl)-4-hydroxybutyramide using a YES-1224P vapor deposition oven system with the following parameters: 0.5 to 1 torr, 60 min, 70° C., 135° C. vaporizer. The substrate surface was resist coated using a Brewer Science 200× spin coater. SPR™ 3612 photoresist was spin coated on the substrate at 2500 rpm for 40 sec. The substrate was pre-baked for 30 min at 90° C. on a Brewer hot plate. The substrate was subjected to photolithography using a Karl Suss MA6 mask aligner instrument. The substrate was exposed for 2.2 sec and developed for 1 min in MSF 26A. Remaining developer was rinsed with the handgun and the substrate soaked in water for 5 min. The substrate was baked for 30 min at 100° C. in the oven, followed by visual inspection for lithography defects using a Nikon L200. A cleaning process was used to remove residual resist using the SAMCO PC-300 instrument to $O_2$ plasma etch at 250 watts for 1 min.

The substrate surface was passively functionalized with a 100 µL solution of perfluorooctyltrichlorosilane mixed with 10 µL light mineral oil. The substrate was placed in a chamber, pumped for 10 min, and then the valve was closed to the pump and left to stand for 10 min. The chamber was vented to air. The substrate was resist stripped by performing two soaks for 5 min in 500 mL NMP at 70° C. with ultrasonication at maximum power (9 on Crest system). The substrate was then soaked for 5 min in 500 mL isopropanol at room temperature with ultrasonication at maximum power. The substrate was dipped in 300 mL of 200 proof ethanol and blown dry with $N_2$. The functionalized surface was activated to serve as a support for oligonucleotide synthesis.

Example 2: Synthesis of a 50-Mer Sequence on an Oligonucleotide Synthesis Device A two dimensional oligonucleotide synthesis device was assembled into a flowcell, which was connected to a flowcell (Applied Biosystems "ABI394 DNA Synthesizer"). The two-dimensional oligonucleotide synthesis device was uniformly functionalized with N-(3-TRIETHOXYSILYLPROPYL)-4-HYDROXYBUTYRAMIDE (Gelest) was used to synthesize an exemplary oligonucleotide of 50 bp ("50-mer oligonucleotide") using oligonucleotide synthesis methods described herein.

The sequence of the 50-mer was as described in SEQ ID NO.: 1. 5'AGACAATCAACCATTTGGGGTGGACAGCC-TTGACCTCTAGACTTCGGCAT##TTTTTTTTTT3' (SEQ ID NO.: 1), where # denotes Thymidine-succinyl hexamide CED phosphoramidite (CLP-2244 from Chem-Genes), which is a cleavable linker enabling the release of oligonucleotides from the surface during deprotection.

The synthesis was done using standard DNA synthesis chemistry (coupling, capping, oxidation, and deblocking) according to the protocol in Table 5 and an ABI synthesizer.

TABLE 5

| General DNA Synthesis | Table 5 | |
|---|---|---|
| Process Name | Process Step | Time (sec) |
| WASH (Acetonitrile Wash Flow) | Acetonitrile System Flush | 4 |
| | Acetonitrile to Flowcell | 23 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 6 |
| | Activator + Phosphoramidite to Flowcell | 6 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 5 |
| | Activator + Phosphoramidite to Flowcell | 18 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| CAPPING (CapA + B, 1:1, Flow) | CapA + B to Flowcell | 15 |
| WASH (Acetonitrile Wash Flow) | Acetonitrile System Flush | 4 |
| | Acetonitrile to Flowcell | 15 |
| | Acetonitrile System Flush | 4 |
| OXIDATION (Oxidizer Flow) | Oxidizer to Flowcell | 18 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 15 |
| | Acetonitrile System Flush | 4 |
| | Acetonitrile to Flowcell | 15 |
| | N2 System Flush | 4 |
| | Acetonitrile System Flush | 4 |
| | Acetonitrile to Flowcell | 23 |
| | N2 System Flush | 4 |
| | Acetonitrile System Flush | 4 |
| DEBLOCKING (Deblock Flow) | Deblock to Flowcell | 36 |
| WASH (Acetonitrile Wash Flow) | Acetonitrile System Flush | 4 |
| | N2 System Flush | 4 |

TABLE 5-continued

| General DNA Synthesis | Table 5 | |
|---|---|---|
| Process Name | Process Step | Time (sec) |
| | Acetonitrile System Flush | 4 |
| | Acetonitrile to Flowcell | 18 |
| | N2 System Flush | 4.13 |
| | Acetonitrile System Flush | 4.13 |
| | Acetonitrile to Flowcell | 15 |

The phosphoramidite/activator combination was delivered similar to the delivery of bulk reagents through the flowcell. No drying steps were performed as the environment stays "wet" with reagent the entire time.

The flow restrictor was removed from the ABI 394 synthesizer to enable faster flow. Without flow restrictor, flow rates for amidites (0.1 M in ACN), Activator, (0.25 M Benzoylthiotetrazole ("BTT"; 30-3070-xx from GlenResearch) in ACN), and Ox (0.02 M 12 in 20% pyridine, 10% water, and 70% THF) were roughly ~100 uL/sec, for acetonitrile ("ACN") and capping reagents (1:1 mix of CapA and CapB, wherein CapA is acetic anhydride in THF/Pyridine and CapB is 16% 1-methylimidizole in THF), roughly ~200 uL/sec, and for Deblock (3% dichloroacetic acid in toluene), roughly 300 uL/sec (compared to ~50 uL/sec for all reagents with flow restrictor). The time to completely push out Oxidizer was observed, the timing for chemical flow times was adjusted accordingly and an extra ACN wash was introduced between different chemicals. After oligonucleotide synthesis, the chip was deprotected in gaseous ammonia overnight at 75 psi. Five drops of water were applied to the surface to recover oligonucleotides. The recovered oligonucleotides were then analyzed on a Bio-Analyzer small RNA chip (data not shown).

Example 3: Synthesis of a 100-Mer Sequence on an Oligonucleotide Synthesis Device The same process as described in Example 2 for the synthesis of the 50-mer sequence was used for the synthesis of a 100-mer oligonucleotide ("100-mer oligonucleotide"; 5' CGGGATCCTTATCGTCATCGTCGTACAGATCCCGA-CCCATTTGCTGTCCACCAGTCATGCTAGCCATACC-ATGATGATGATGATGATGAGAACCCCGCAT##TTTT-TTTTTT3', where # denotes Thymidine-succinyl hexamide CED phosphoramidite (CLP-2244 from ChemGenes); SEQ ID NO.: 2) on two different silicon chips, the first one uniformly functionalized with N-(3-TRIETHOXYSILYL-PROPYL)-4-HYDROXYBUTYRAMIDE and the second one functionalized with 5/95 mix of 11-acetoxyundecyltriethoxysilane and n-decyltriethoxysilane, and the oligonucleotides extracted from the surface were analyzed on a Bio-Analyzer instrument (data not shown).

All ten samples from the two chips were further PCR amplified using a forward (5'ATGCGGGGTTCTCAT-CATC3'; SEQ ID NO.: 3) and a reverse (5'CGGGATCCT-TATCGTCATCG3'; SEQ ID NO.: 4) primer in a 50 uL PCR mix (25 uL NEB Q5 mastermix, 2.5 uL 10 uM Forward primer, 2.5 uL 10 uM Reverse primer, 1 uL oligonucleotide extracted from the surface, and water up to 50 uL) using the following thermalcycling program:

98° C., 30 sec

98° C., 10 sec; 63° C., 10 sec; 72° C., 10 sec; repeat 12 cycles

72° C., 2 min

The PCR products were also run on a BioAnalyzer (data not shown), demonstrating sharp peaks at the 100-mer position. Next, the PCR amplified samples were cloned, and Sanger sequenced. Table 6 summarizes the results from the Sanger sequencing for samples taken from spots 1-5 from chip 1 and for samples taken from spots 6-10 from chip 2.

TABLE 6

| Spot | Error rate | Cycle efficiency |
|---|---|---|
| 1 | 1/763 bp | 99.87% |
| 2 | 1/824 bp | 99.88% |
| 3 | 1/780 bp | 99.87% |
| 4 | 1/429 bp | 99.77% |
| 5 | 1/1525 bp | 99.93% |
| 6 | 1/1615 bp | 99.94% |

TABLE 6-continued

| Spot | Error rate | Cycle efficiency |
|---|---|---|
| 7 | 1/531 bp | 99.81% |
| 8 | 1/1769 bp | 99.94% |
| 9 | 1/854 bp | 99.88% |
| 10 | 1/1451 bp | 99.93% |

Thus, the high quality and uniformity of the synthesized oligonucleotides were repeated on two chips with different surface chemistries. Overall, 89%, corresponding to 233 out of 262 of the 100-mers that were sequenced were perfect sequences with no errors.

Finally, Table 7 summarizes key error characteristics for the sequences obtained from the oligonucleotide samples from spots 1-10.

TABLE 7

| | Sample ID/Spot no. | | | | |
|---|---|---|---|---|---|
| | OSA_0046/1 | OSA_0047/2 | OSA_0048/3 | OSA_0049/4 | OSA_0050/5 |
| Total Sequences | 32 | 32 | 32 | 32 | 32 |
| Sequencing Quality | 25 of 28 | 27 of 27 | 26 of 30 | 21 of 23 | 25 of 26 |
| Oligo Quality | 23 of 25 | 25 of 27 | 22 of 26 | 18 of 21 | 24 of 25 |
| ROI Match Count | 2500 | 2698 | 2561 | 2122 | 2499 |
| ROI Mutation | 2 | 2 | 1 | 3 | 1 |
| ROI Multi Base Deletion | 0 | 0 | 0 | 0 | 0 |
| ROI Small Insertion | 1 | 0 | 0 | 0 | 0 |
| ROI Single Base Deletion | 0 | 0 | 0 | 0 | 0 |
| Large Deletion Count | 0 | 0 | 1 | 0 | 0 |
| Mutation: G > A | 2 | 2 | 1 | 2 | 1 |
| Mutation: T > C | 0 | 0 | 0 | 1 | 0 |
| ROI Error Count | 3 | 2 | 2 | 3 | 1 |
| ROI Error Rate | Err: ~1 in 834 | Err: ~1 in 1350 | Err: ~1 in 1282 | Err: ~1 in 708 | Err: ~1 in 2500 |
| ROI Minus Primer Error Rate | MP Err: ~1 in 763 | MP Err: ~1 in 824 | MP Err: ~1 in 780 | MP Err: ~1 in 429 | MP Err: ~1 in 1525 |

| | Sample ID/Spot no. | | | | |
|---|---|---|---|---|---|
| | OSA_0051/6 | OSA_0052/7 | OSA_0053/8 | OSA_0054/9 | OSA_0055/10 |
| Total Sequences | 32 | 32 | 32 | 32 | 32 |
| Sequencing Quality | 29 of 30 | 27 of 31 | 29 of 31 | 28 of 29 | 25 of 28 |
| Oligo Quality | 25 of 29 | 22 of 27 | 28 of 29 | 26 of 28 | 20 of 25 |
| ROI Match Count | 2666 | 2625 | 2899 | 2798 | 2348 |
| ROI Mutation | 0 | 2 | 1 | 2 | 1 |
| ROI Multi Base Deletion | 0 | 0 | 0 | 0 | 0 |
| ROI Small Insertion | 0 | 0 | 0 | 0 | 0 |
| ROI Single Base Deletion | 0 | 0 | 0 | 0 | 0 |
| Large Deletion Count | 1 | 1 | 0 | 0 | 0 |
| Mutation: G > A | 0 | 2 | 1 | 2 | 1 |
| Mutation: T > C | 0 | 0 | 0 | 0 | 0 |
| ROI Error Count | 1 | 3 | 1 | 2 | 1 |
| ROI Error Rate | Err: ~1 in 2667 | Err: ~1 in 876 | Err: ~1 in 2900 | Err: ~1 in 1400 | Err: ~1 in 2349 |
| ROI Minus Primer Error Rate | MP Err: ~1 in 1615 | MP Err: ~1 in 531 | MP Err: ~1 in 1769 | MP Err: ~1 in 854 | MP Err: ~1 in 1451 |

Example 4: sgRNA Design

Figure 5A:
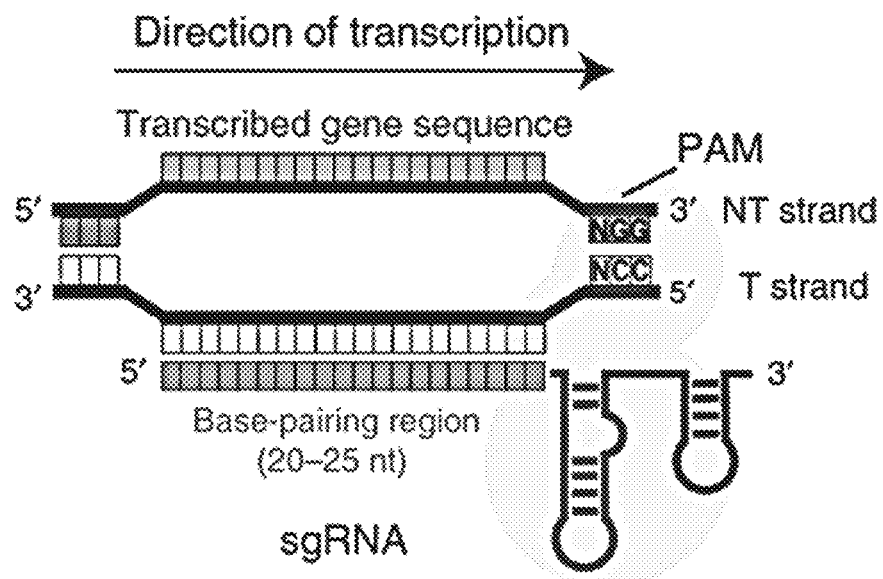
FIG. 5A is a diagram of a sgRNA sequence in a template strand targeting arrangement.
Figure 5B:
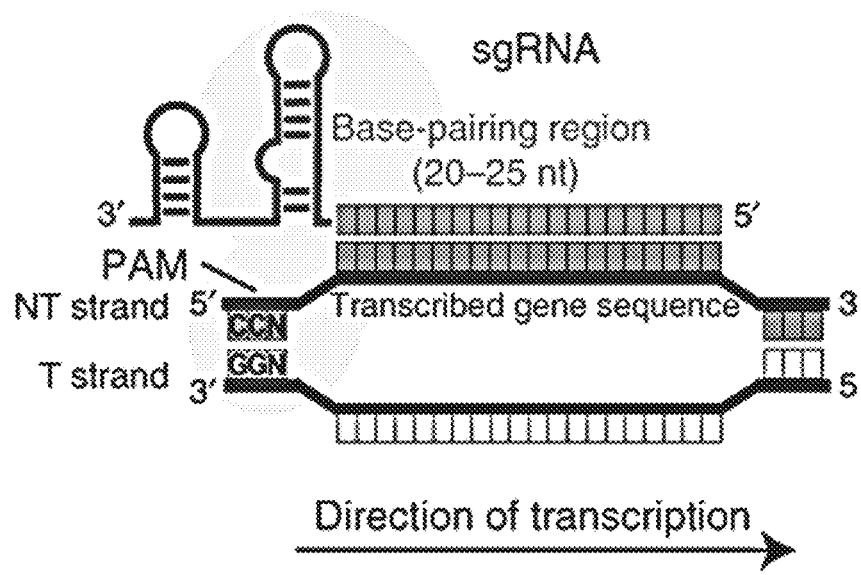
FIG. 5B is a diagram of a sgRNA sequence in a non-template strand targeting arrangement.

A chimera sgRNA sequence with a variable region at the 5' end was designed for direct sequence specific cleavage by the Cas9 protein. See FIG. 4A. The sgRNA sequence had a base-pairing region of 20 bases for specific DNA binding, which included a seed region of 12 bases. The 5' end of the base-pairing region was designed to be the transcription start site. 3' proximal to the base-pairing region was the dCas9 handled region for Cas9 binding, which was 42 bases in length. 3' proximal to the dCas9 handled region was the *S. pyogenes* terminator region which was 40 bases in length. The dCas9 handled region and the terminator region each were designed to include sequence that would result in a hairpin structure.

sgRNAs were also designed to target the template (T) or nontemplate (NT) DNA strands, FIGS. 5A-5B. sgRNAs designed for targeting the template DNA strand included a base-pairing region of the sgRNA having the same sequence identity as the transcribed sequence. sgRNAs designed for targeting the nontemplate DNA strand included the base-pairing region of the sgRNA that was a reverse-complement of the transcribed sequence.

In an additional arrangement, a T7 promoter was designed immediately upstream of variable base-pairing region. See FIGS. 6A-6B. The T7 promoter region was added to enable in vitro production of the sgRNA with T7 polymerase.

Example 5: Synthesis of DNA Encoding for sgRNA—Design and Polymerase Analysis DNA nucleic acids were designed as fragments that, when joined, encode for an sgRNA sequence. FIG. 12. The sgRNAs were designed for inclusion of a T7 promoter immediately upstream of a variable sequence region 1233. Following de novo synthesis of the DNA nucleic acids, an amplification reaction was performed to join and extend overlapping fragments.

Transcription of the DNA nucleic acids at 1201 resulted in in vitro production of the sgRNA with T7 polymerase from a DNA template.

A sequence for Design 1 1220, Design 2 1222, Design 3 1224, and Design 4 1226 was designed as indicated in Table 8. The sequence for each Design 1, Design 2, Design 3, and Design 4 comprises a T7 promoter, a variable sequence portion, and a constant sequence region (the handle and terminator) (Table 8). Specifically, the constant sequence region as seen in FIG. 12 comprises a Cas9 handle hairpin comprising base pairing regions 1211, 1213, 1215, 1217, 1223, and 1225, and a terminator hairpin comprising base pairing regions 1219 and 1221.

TABLE 8

| SEQ ID NO | Name | Sequence |
|---|---|---|
| 12 | Design 1 | TAATACGACTCACTATAGGGGATGCGCGCAGTTGTCCGTTTTAGAGCTAGAAATAGCAAGTTAAAATAAGGCTAGTCCGTTATCAACTTGAAAAAGTGGCACCGAGTCGGTGCTTTT |
| 13 | T7 Promoter of Design 1 | TAATACGACTCACTATA |
| 14 | Variable Sequence of Design 1 | GGATGCGCGCAGTTGTCC |
| 15 | Handle and Terminator of Design 1 | GTTTTAGAGCTAGAAATAGCAAGTTAAAATAAGGCTAGTCCGTTATCAACTTGAAAAAGTGGCACCGAGTCGGTGCTTTT |
| 44 | Design 2 | GAAATTAATACGACTCACTATAGGGGATGCGCGCAGTTGTCCGTTTTAGAGCTAGAAATAGCAAGTTAAAATAAGGCTAGTCCGTTATCAACTTGAAAAAGTGGCACCGAGTCGGTGCTTTT |
| 13 | T7 Promoter of Design 2 | TAATACGACTCACTATA |
| 14 | Variable Sequence of Design 2 | GGATGCGCGCAGTTGTCC |
| 15 | Handle and Terminator of Design 2 | GTTTTAGAGCTAGAAATAGCAAGTTAAAATAAGGCTAGTCCGTTATCAACTTGAAAAAGTGGCACCGAGTCGGTGCTTTT |
| 16 | Design 3 | GAGCTAATACGACTCACTATAGGGGATGCGCGCAGTTGTCCGTTTTAGAGCTAGAAATAGCAAGTTAAAATAAGGCTAGTCCGTTATCAACTTGAAAAAGTGGCACCGAGTCGGTGCTTTT |
| 13 | T7 Promoter of Design 3 | TAATACGACTCACTATA |
| 14 | Variable Sequence of Design 3 | GGATGCGCGCAGTTGTCC |
| 15 | Handle and Terminator of Design 3 | GTTTTAGAGCTAGAAATAGCAAGTTAAAATAAGGCTAGTCCGTTATCAACTTGAAAAAGTGGCACCGAGTCGGTGCTTTT |

TABLE 8-continued

| SEQ ID NO | Name | Sequence |
|---|---|---|
| 17 | Design 4 | CGAGCTAATACGACTCACTATAGGGGATGCGCGCA GTTGTCCGTTTTAGAGCTAGAAATAGCAAGTTAAAA TAAGGCTAGTCCGTTATCAACTTGAAAAAGTGGCA CCGAGTCGGTGCTTTT |
| 13 | T7 Promoter of Design 4 | TAATACGACTCACTATA |
| 14 | Variable Sequence of Design 4 | GGATGCGCGCAGTTGTCC |
| 15 | Handle and Terminator of Design 4 | GTTTTAGAGCTAGAAATAGCAAGTTAAAATAAGGC TAGTCCGTTATCAACTTGAAAAAGTGGCACCGAGTC GGTGCTTTT |

For in vitro analysis, it is noted that the T7 RNA polymerase promoter region should be double stranded for recognition by T7 RNA polymerase. An antisense nucleic acid was used for hybridization: 5'-TAATACGACTCAC-TATAGG-3' (SEQ ID NO: 18). In addition, Table 9 provides a list of primers that were used for analysis of 4 different sets of template and amplification nucleic acids. See FIG. 12.

Polymerase-1 PCR concentration of 600 nMol. Using the gradient on the Eppendorf Mastercycler, 3 annealing temps (50° C., 55° C., 60° C.) were evaluated in a 25 cycle PCR using two high fidelity DNA polymerases (polymerase 1 and 3) and standard DNA polymerase (polymerase 2). Table 10 provides a summary of reaction conditions and Table 11 provides the amplification protocol.

TABLE 9

| SEQ ID NO | Name (# bases-melting temp.) | Sequence |
|---|---|---|
| 19 | SgR1-R1 (80 bp) | AAAAGCACCGACTCGGTGCCACTTTTTCAAGTTG ATAACGGACTAGCCTTATTTTAACTTGCTATTTCT AGCTCTAAAAC |
| 20 | SgR1-F1 (58 bp-51° C./54° C.) | TAATACGACTCACTATAGGGGATGCGCGCAGTTG TCCGTTTTAGAGCTAGAAATAGCA |
| 21 | SgR1-F2 (65 bp-56° C./56° C.) | GAAATTAATACGACTCACTATAGGGGATGCGCGC AGTTGTCCGTTTTAGAGCTAGAAATAGCAAG |
| 22 | SgR1-F3 (66 bp-59° C./58° C.) | GAGCTAATACGACTCACTATAGGGGATGCGCGCA GTTGTCCGTTTTAGAGCTAGAAATAGCAAGTT |
| 23 | SgR1-F4 (78 bp-62° C./62° C.) | GAGCTAATACGACTCACTATAGGGGATGCGCGCA GTTGTCCGTTTTAGAGCTAGAAATAGCAAGTTAA AATAAGG |
| 24 | SgR1-AR1 (14 bp-52° C.) | AAAAGCACCGACTC |
| 25 | SgR1-AR2 (15 bp-56° C.) | AAAAGCACCGACTCG |
| 26 | SgR1-AR3 (16 bp-60° C.) | AAAAGCACCGACTCGG |
| 27 | SgR1-AR4 (17 bp-62° C.) | AAAAGCACCGACTCGGT |
| 18 | sgR1-AF1 (19 bp-51° C.) | TAATACGACTCACTATAGG |
| 28 | SgR1-AF2 (24 bp-56° C.) | GAAATTAATACGACTCACTATAGG |
| 29 | SgR1-AF3 (25 bp-59° C.) | GAGCTAATACGACTCACTATAGG |
| 30 | SgR1-AF4 (25 bp-62° C.) | GCGAGCTAATACGACTCACTATAGG |

The 4 different sets of template and amplification nucleic acids were analyzed under a variety of condition to optimize purity and yield of the full length template. 10 ul PCR reactions were performed with the template nucleic acids (SgR1-R1 & SgR1-F1, SgR1-F2, SgR1-F3, SgR1-F4) at 100 fMol and the respective sets of amplification primers at

TABLE 10

| | Pol. 1 | | Pol. 2 | | Pol. 3 | |
|---|---|---|---|---|---|---|
| Reagents (10 ul rxns) | 1x | 15x | 1x | 15x | 1x | 15x |
| Pol | 0.1 | 1.5 | 0.1 | 1.5 | 0.1 | 1.5 |
| Buffer | 2 | 30 | 1 | 15 | 2 | 30 |

TABLE 10-continued

|  | Pol. 1 | | Pol. 2 | | Pol. 3 | |
| --- | --- | --- | --- | --- | --- | --- |
| Reagents (10 ul rxns) | 1x | 15x | 1x | 15x | 1x | 15x |
| dNTP's | 0.2 | 3 | 0.2 | 3 | 0.2 | 3 |
| Amp Primers (10 uM) | 0.6 | | 0.6 | | 0.6 | |
| Template Oligos (100 nM) | 1 | | 1 | | 1 | |
| H2O | 6.1 | 91.5 | 7.1 | 106.5 | 6.1 | 91.5 |
| Total | 10 | 150 | 10 | 150 | 10 | 150 |

TABLE 11

| Polymerase 1, 2 | | | Polymerase 3 | | |
| --- | --- | --- | --- | --- | --- |
| 98 | 30 sec | | 95 | 3 min | |
| 98 | 10 sec | 25x | 98 | 10 sec | 25x |
| 50/55/60 | 15 sec | | 50/55/60 | 15 sec | |
| 72 | 10 sec | | 72 | 10 sec | |
| 72 | 30 sec | | 72 | 30 sec | |
| 4 | hold | | 4 | hold | |

Results from Polymerase-1 PCR reactions were run on a BioAnalyzer (data not shown) to estimate the yield, and are summarized in Table 12. DNA yield is presented in ng/ul (Table 12). Nucleic acid designs 3 and 4 each resulted in higher DNA yield than nucleic acid designs 1 and 2. Higher annealing temperatures resulted in increased yield as well, with 60° C. having higher yields.

TABLE 12

| Polymerase 1 | 50° C. | 55° C. | 60° C. |
| --- | --- | --- | --- |
| Nucleic acid design 1 | 0 | 0 | 0 |
| Nucleic acid design 2 | 2.9 | 4.5 | 3.7 |
| Nucleic acid design 3 | 6.8 | 9.2 | 10 |
| Nucleic acid design 4 | 9.9 | 13 | 15.3 |

Yields listed in ng/ul.

Results from the Polymerase 2 PCR reactions were run on a BioAnalyzer (data not shown) to estimate the yield, and are summarized in Table 13. DNA yield is presented in ng/ul (Table 13). Again, nucleic acid designs 3 and 4 each resulted in higher DNA yield than nucleic acid designs 1 and 2. Higher annealing temperatures resulted in increased yield as well, with 60° C. having higher yields.

TABLE 13

| Polymerase 2 | 50° C. | 55° C. | 60° C. |
| --- | --- | --- | --- |
| Nucleic acid design 1 | 0 | 0 | 0 |
| Nucleic acid design 2 | 7.6 | 5.9 | 6.9 |
| Nucleic acid design 3 | 6.1 | 8.5 | 10.5 |
| Nucleic acid design 4 | 7.4 | 11.1 | 19.4 |

Yields listed in ng/ul.

Results from the Polymerase 3 PCR reactions were run on a BioAnalyzer (data not shown) to estimate the yield, and are summarized in Table 14. DNA yield is presented in ng/ul (Table 14). Nucleic acid designs 3 and 4 each resulted in higher DNA yield than nucleic acid designs 1 and 2. Higher annealing temperatures resulted in increased yield as well, with 60° C. having higher yields.

TABLE 14

| Polymerase 3 | 50° C. | 55° C. | 60° C. |
| --- | --- | --- | --- |
| Nucleic acid design 1 | 10 | 13 | 12.1 |
| Nucleic acid design 2 | 12.4 | 14.3 | 15.9 |
| Nucleic acid design 3 | 13.2 | 26.1 | 28.8 |
| Nucleic acid design 4 | 16.1 | 13.2 | 18.5 |

Yields listed in ng/ul.

In sum, nucleic acid designs 3 and 4 resulted in increased DNA yield with all three polymerases. In addition, the higher annealing temperature of 60° C. resulted in increased DNA yield.

Example 6: CRISPR sgRNA Synthesis—Temperature Analysis

Using nucleic acid primers from Example 5, the impact of increase annealing temperature conditions was analyzed after running a PCR reaction as described in Example 5. Amplification product was run on a BioAnalyzer (data not shown) to estimate the yield, and is summarized in Table 15. DNA yield is presented in ng/ul (Table 15). In sum, Polymerase 3 provides increased DNA yield and 60° C. annealing temperature resulted in an increased DNA yield.

TABLE 15

| | Nucleic Acid design 3 | | | | Nucleic Acid design 4 | | | |
| --- | --- | --- | --- | --- | --- | --- | --- | --- |
| | Polymerase 3 | | Polymerase 1 | | Polymerase 3 | | Polymerase 1 | |
| | 60° C. | 65° C. | 60° C. | 65° C. | 60° C. | 65° C. | 60° C. | 65° C. |
| 25 cycles | 27.3 | 15.2 | 11.6 | 3.9 | 28.4 | 29.5 | 13.8 | 10.2 |

Yields listed in ng/ul.

Example 7: sgRNA Generation—Structure Free RNA

Two assembly nucleic acids were designed to generate a modified sgRNA template (120 bp) with T7 promoter sequence and terminator, but without the tracrRNA hairpin containing sequence. See Table 16.

TABLE 16

| SEQ ID NO | Name | Sequence |
|---|---|---|
| 31 | sgR2-Template | CGAGCTAATACGACTCACTATAGGGGCACAACGTGG AGGATGGCAGCGTGCAGCTGGCTGATCACTACCAGC AAAACACTCCAATCGGTGATGGTCCTGTTGCACCGA GTCGGTGCTTTT |
| 32 | sgR2-F | CGAGCTAATACGACTCACTATAGGGGCACAACGTGG AGGATGGCAGCGTGCAGCTGGCTGATCACTACCAG |
| 33 | sgR2-R | AAAGCACCGACTCGGTGCAACAGGACCATCACCGAT TGGAGTGTTTTGCTGGTAGTGATCAGCCAGCTG |

The assembly nucleic acids were amplified with same primer nucleic acids used to amplify the sgRNA in Example 5. The reaction conditions used are summarized in Table 17.

TABLE 17

| Ingredients | 1x | PCR Condition | Time | Cycles |
|---|---|---|---|---|
| Pol 1 | 0.1 | 95° C. | 3 min | |
| Buffer | 2 | 98° C. | 10 sec | 25 x |
| dNTP's | 0.2 | 65° C. | 15 sec | |
| Amp Primers (10 um) | 0.6 | 72° C. | 10 sec | |
| Template Oligos (100 nm) | 1 | 72° C. | 30 sec | |
| H2O | 6.1 | 4° C. | hold | |
| Total | 10 | | | |

Figure 13A:
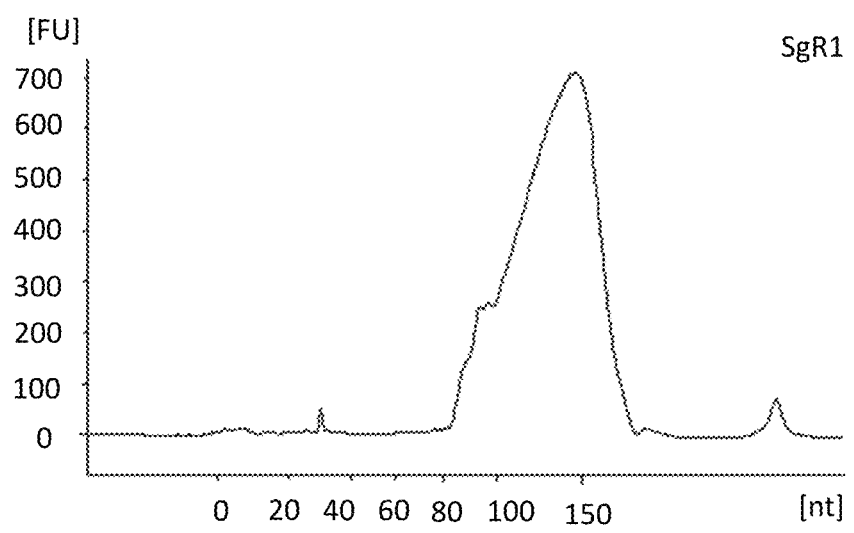
FIGS. 13A-13B are plots from a BioAnalyzer reading, with nucleotide bases on the X axis and fluorescent units on the Y axis.
Figure 13B:
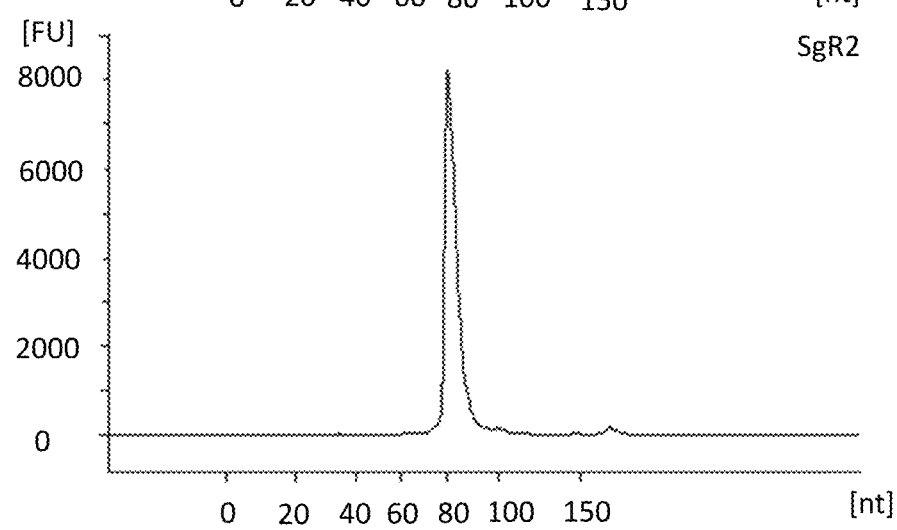

Transcription with T7 RNA polymerase was expected to yield an RNA product of 80 bp, devoid of secondary structure. Transcription of the amplification product was carried out with an in vitro transcription kit (NEB HiScribe). The reaction mixture was analyzed on a BioAnalyzer. See FIGS. 13A-13B. The modified sgRNA product was cleaner with the structure free design (FIG. 13B) than the sgRNA having the tracrRNA hairpin containing sequence (FIG. 13A).

Example 8: sgRNA Directed Cas9 Cleavage

Three sgRNA sequences were designed with a T7 promoter region and each with a different recognition sequence for regions of a 720 bp GFP encoding sequence. Each of the sgRNA sequences was assembled from PCR of two nucleic acids. The sgRNA backbone and primers are provided in Table 18.

TABLE 18

| SEQ ID NO | Name | Sequence |
|---|---|---|
| 34 | sgRNA backbone | CGAGCTAATACGACTCACTATAGgNNNNNNNNNNNN NNNNNNGTTTTAGAGCTATGCTGAAAAGCATAGCAA GTTAAAATAAGGCTAGTCCGTTATCAACTTGAAAAAG TGGCACCGAGTCGGTGCTTTT |
| 35 | GFP | ATGcgtAAAggcGAAgagCTGttcACTggtGTCgtcCCTattCTG gtgGAActgGATggtGATgtcAACggtCATaagTTTtccGTGcgtG GCgagGGTgaaGGTgacGCAactAATggtAAActgACGctgAAG ttcATCtgtACTactGGTaaaCTGccgGTAcctTGGccgACTctgGT AacgACGctgACTttatGGTgttCAGtgcTTTgctCGTtatCCGgacC ATatgAAGcagCATgacTTCttcAAGtccGCCatgCCGgaaGGCta tGTGcagGAAcgcACGattTCCtttAAGgatGACggcACGtacAA AacgCGTgcgGAAgtgAAAtttGAAggcGATaccCTGgtaAACcg cATTgagCTGaaaGGCattGACtttAAAgaaGACggcAATatcCT GggcCATaagCTGgaaTACaatTTTaacAGCcacAATgttTACatc ACCgccGATaaaCAAaaaAATggcATTaaaGCGaatTTTaaaAT TcgcCACaacGTGgagGATggcAGCgtgCAGctgGCTgatCACta cCAGcaaAACactCCAatcGGTgatGGTcctGTTctgCTGccaGA CaatCACtatCTGagcACGcaaAGCgttCTGtctAAAgatCCGaac GAGaaaCGCgatCATatgGTTctgCTGgagTTCgtaACCgcaGCG ggcATCacgCATggtATGgatGAActgTACaaaTGAtaa |
| 36 | sgR35-F | CGAGCTAATACGACTCACTATAGGGAAcgcACGattTCCttt AGTTTTAGAGCTATGCTGAAAAGCATAGC |
| 37 | sgR36-F | CGAGCTAATACGACTCACTATAGGCattGACtttAAAgaaG AGTTTTAGAGCTATGCTGAAAAGCATAGC |
| 38 | sgR37-F | CGAGCTAATACGACTCACTATAGGagGATggcAGCgtgC AGcGTTTTAGAGCTATGCTGAAAAGCATAGC |
| 39 | sgR3-R | AAAAGCACCGACTCGGTGCCACTTTTTCAAGTTGATA ACGGACTAGCCTTATTTTAACTTGCTATGCTTTTCAGC ATAGCTCTAAAAC |
| 30 | SgR1-AF4 | GCGAGCTAATACGACTCACTATAGG |
| 27 | SgR1-AR4 | AAAAGCACCGACTCGGT |

The assembly nucleic acids were amplified under reaction conditions summarized in Table 19.

TABLE 19

| Ingredients | 1x | PCR Condition | Time | Cycles |
| --- | --- | --- | --- | --- |
| Polymerase 3 | 0.1 | 95° C. | 3 min | |
| Buffer | 2 | 98° C. | 10 sec | 25 x |
| dNTP's | 0.2 | 95° C. | 15 sec | |
| Amp Primers (10 um) | 0.6 | 60° C. | 15 sec | |
| Template Oligos (100 nm) | 1 | 72° C. | 10 sec | |
| H2O | 6.1 | 72° C. | 30 sec | |
| Total | 10 | 4° C. | hold | |

Figure 14A:
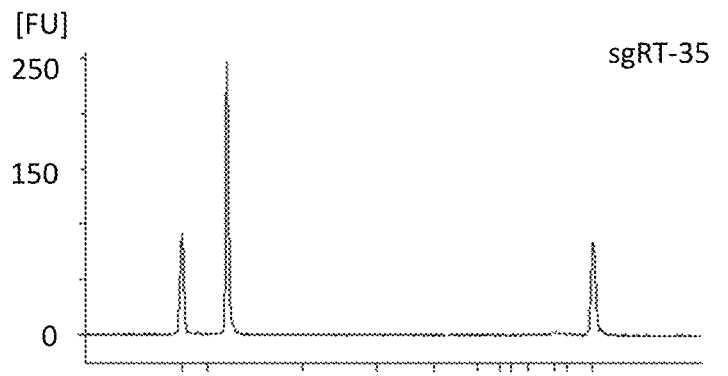
FIGS. 14A-14J are plots from a BioAnalyzer reading, with nucleotide bases on the X axis and fluorescent units on the Y axis.
Figure 14B:
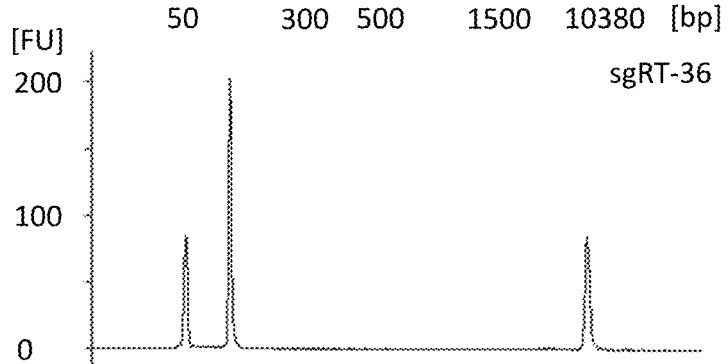
Figure 14C:
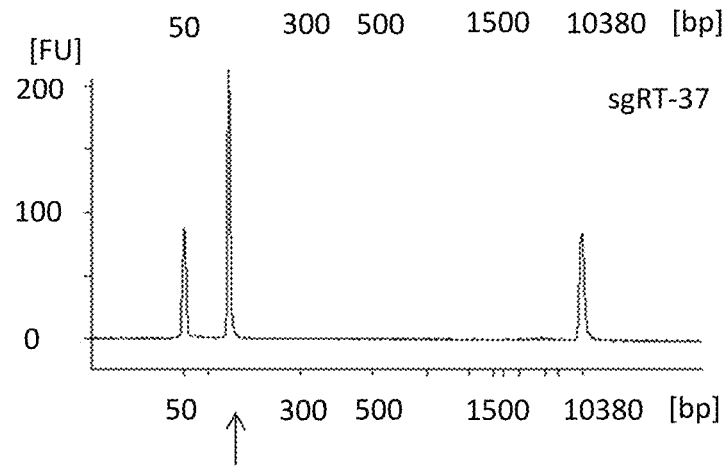
Figure 14D:
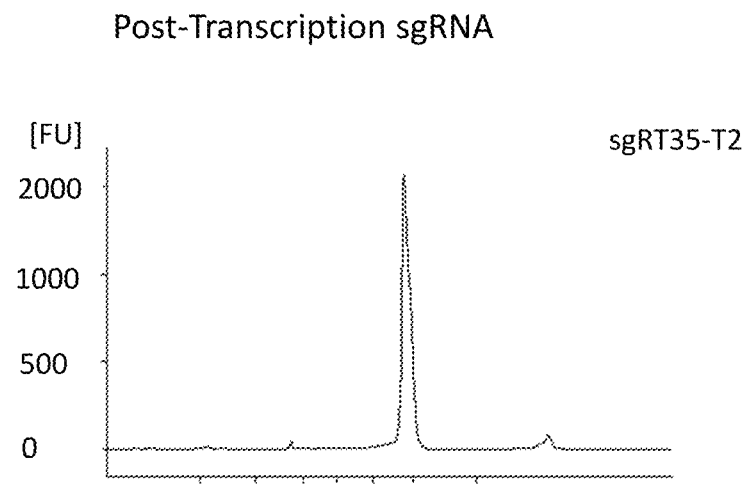
Figure 14E:
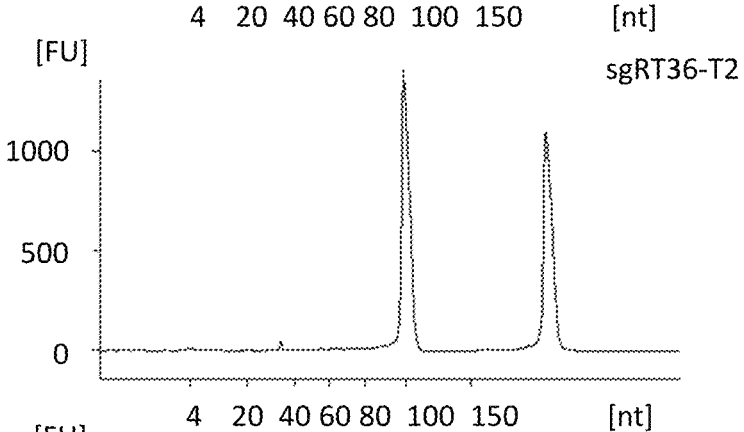
Figure 14F:
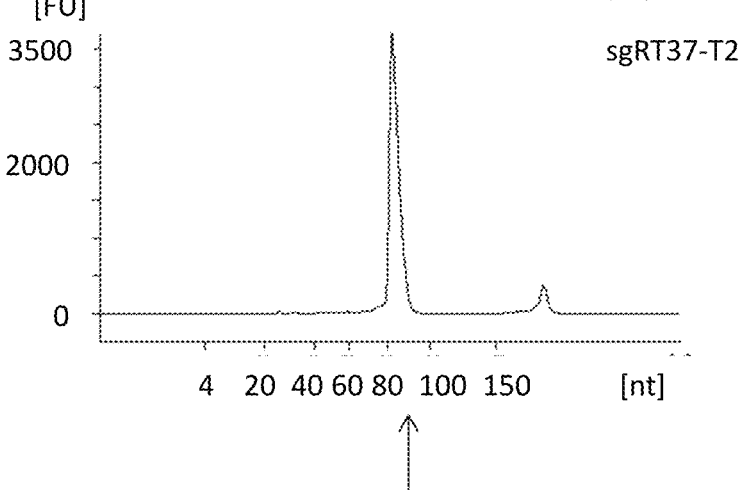
Figure 14G:
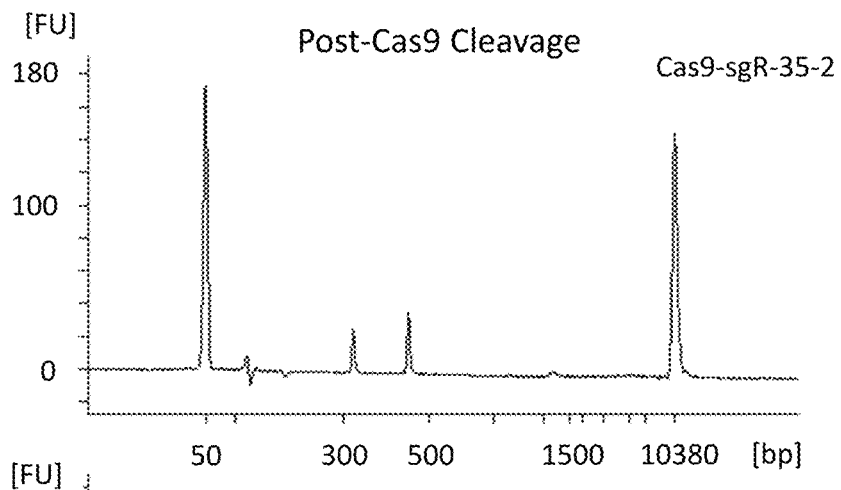
Figure 14H:
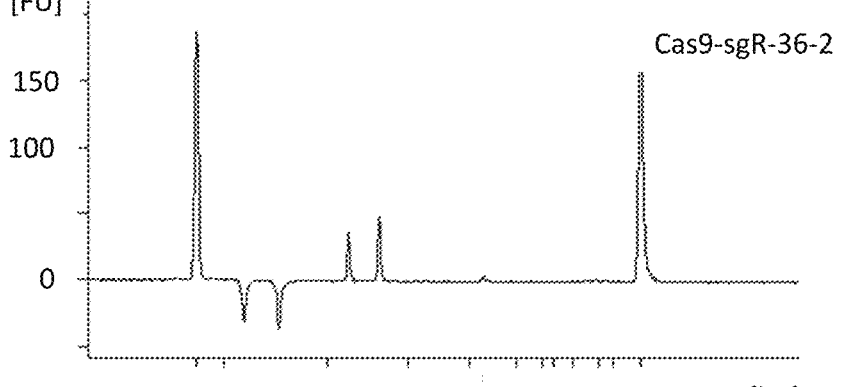
Figure 14I:
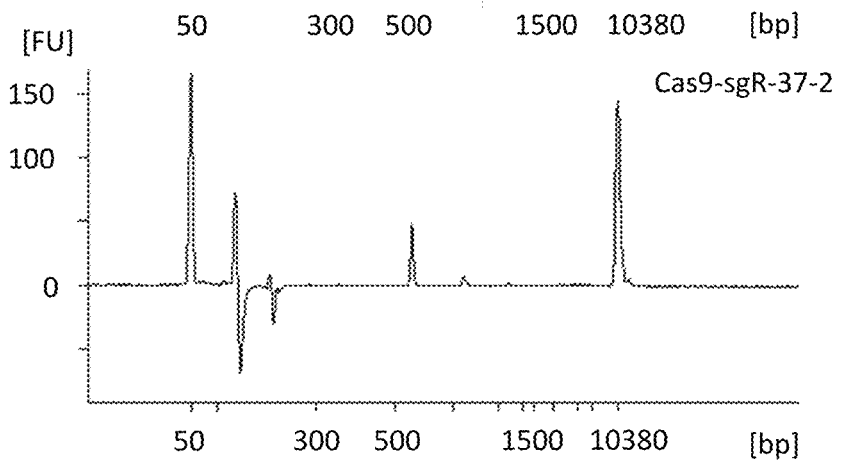
Figure 14J:
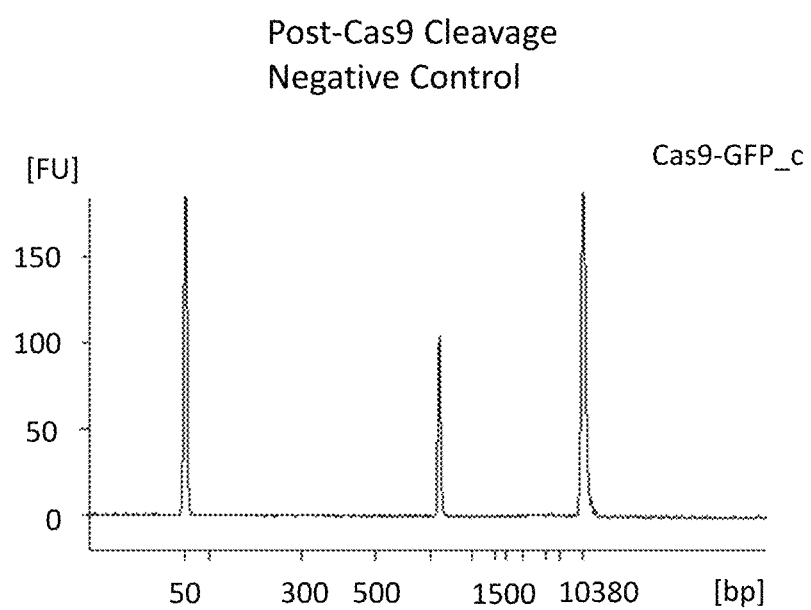

Samples from each sgRNA assembly reaction were analyzed on a BioAnalyzer (FIGS. 14A-14C). Transcription reactions using T7 RNA polymerase PCR amplification product were conducted. Samples from each reaction were analyzed on a BioAnalyzer (FIGS. 14D-14F).

Cas9 digests were prepared using GFP amplification product, Cas9 and the transcribed sgRNA. 2 peaks were observed for all three digests, compared to a single peak for the control. (FIGS. 14G-14J). Expected and resultant fragments from Cas9 cleavage using the 3 synthesized sgRNAs are listed Table 20.

TABLE 20

| sgRNA | Predicted Fragment 1 | Resultant Fragment 1 | Predicted Fragment 2 | Resultant Fragment 2 |
| --- | --- | --- | --- | --- |
| sgR35 | 321 | 324 | 439 | 451 |
| sgR36 | 342 | 350 | 418 | 430 |
| sgR37 | 208 | 137 | 552 | 560 |

Cas9 digestion samples were purified and analyzed again on a BioAnalyzer (data not shown). Results from purified samples are summarized in Table 21.

TABLE 21

| sgRNA | Predicted Fragment 1 | Resultant Fragment 1 | Predicted Fragment 2 | Resultant Fragment 2 |
| --- | --- | --- | --- | --- |
| sgR35 | 321 | 323 | 439 | 451 |
| sgR36 | 342 | 353 | 418 | 427 |
| sgR37 | 208 | 220 | 552 | 560 |

Example 9: Parallel Assembly of 29,040 Unique Oligonucleotides

Figure 15:
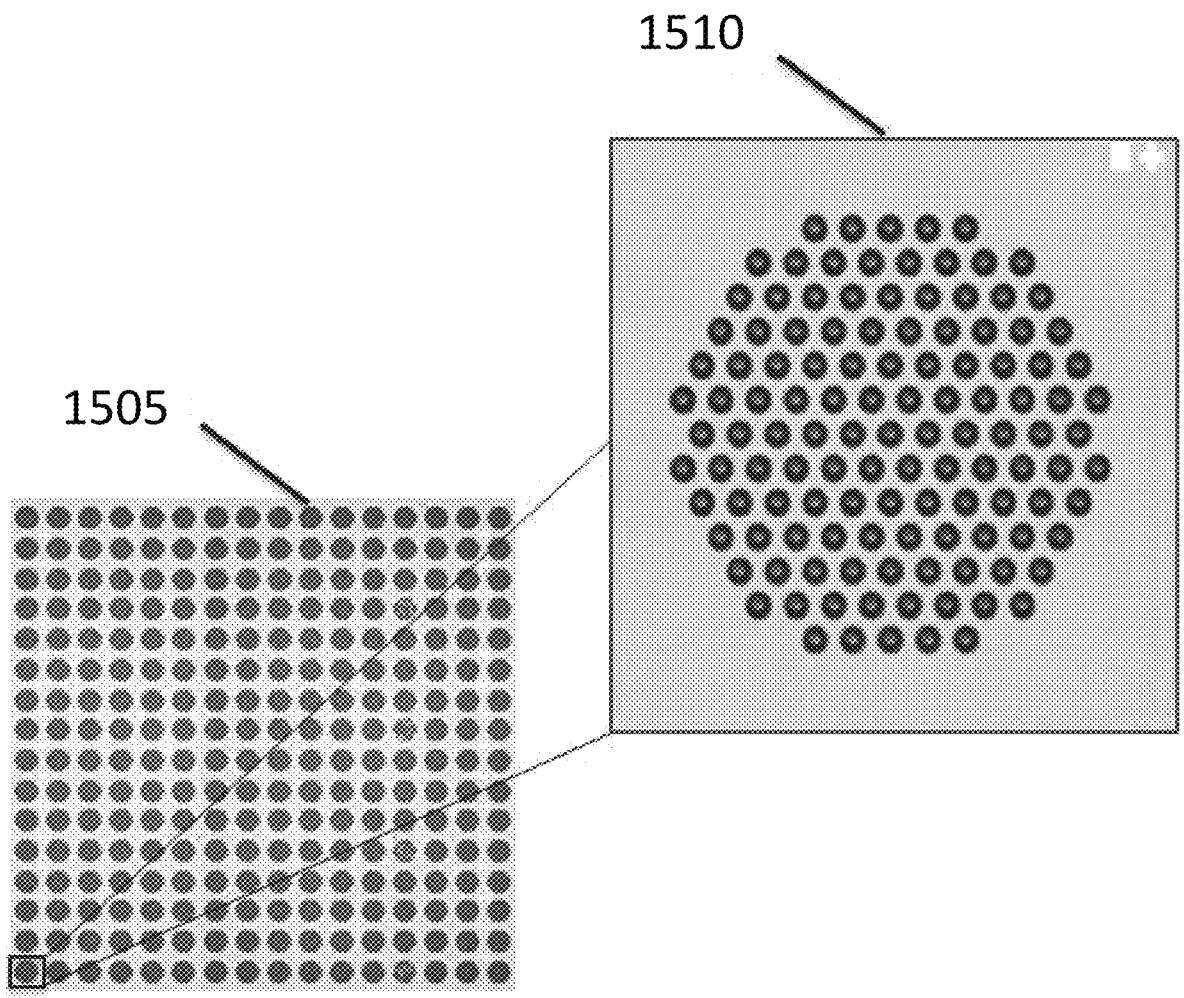
FIG. 15 is an image of a 256 clusters, each cluster having 121 loci with oligonucleotides extending therefrom.
Figure 16A:
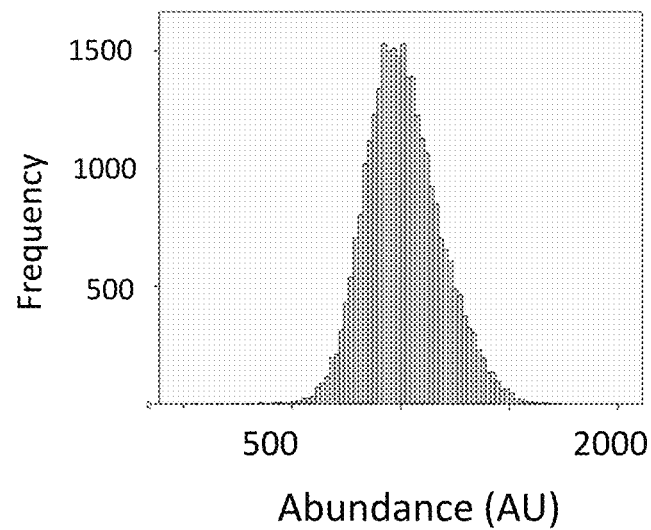
FIG. 16A is a plot of oligonucleotide representation (oligonucleotide frequency v. absorbance) across a plate from synthesis of 29,040 unique oligonucleotides from 240 clusters, each cluster having 121 oligonucleotides.
Figure 16B:
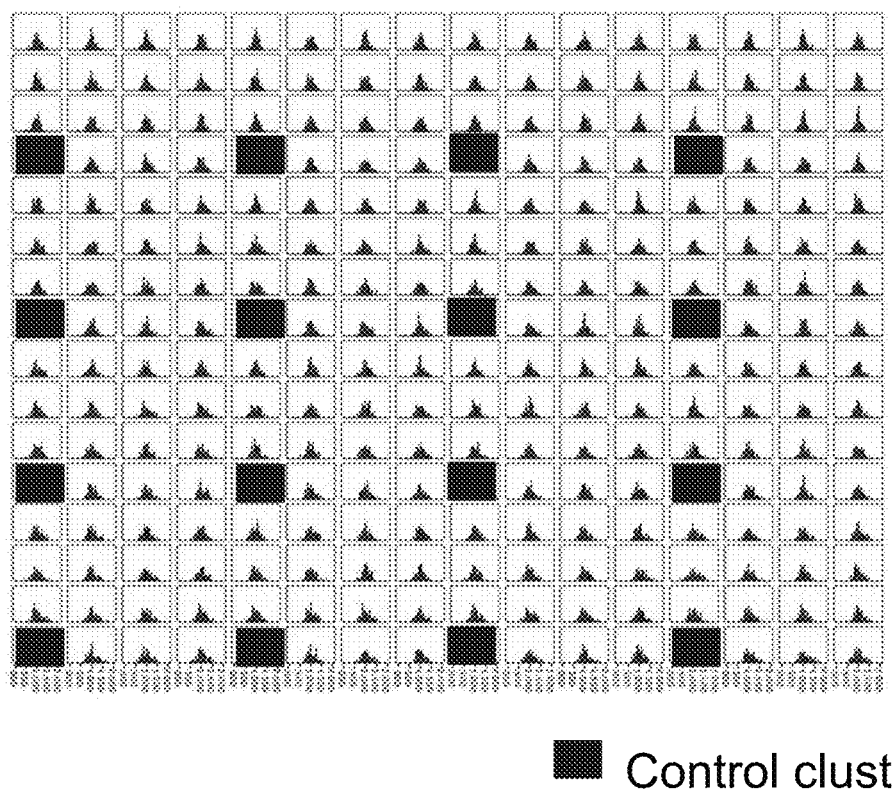
FIG. 16B is a plot of measurement of oligonucleotide frequency v. absorbance across each individual cluster, with control clusters identified by a box.
Figure 17:
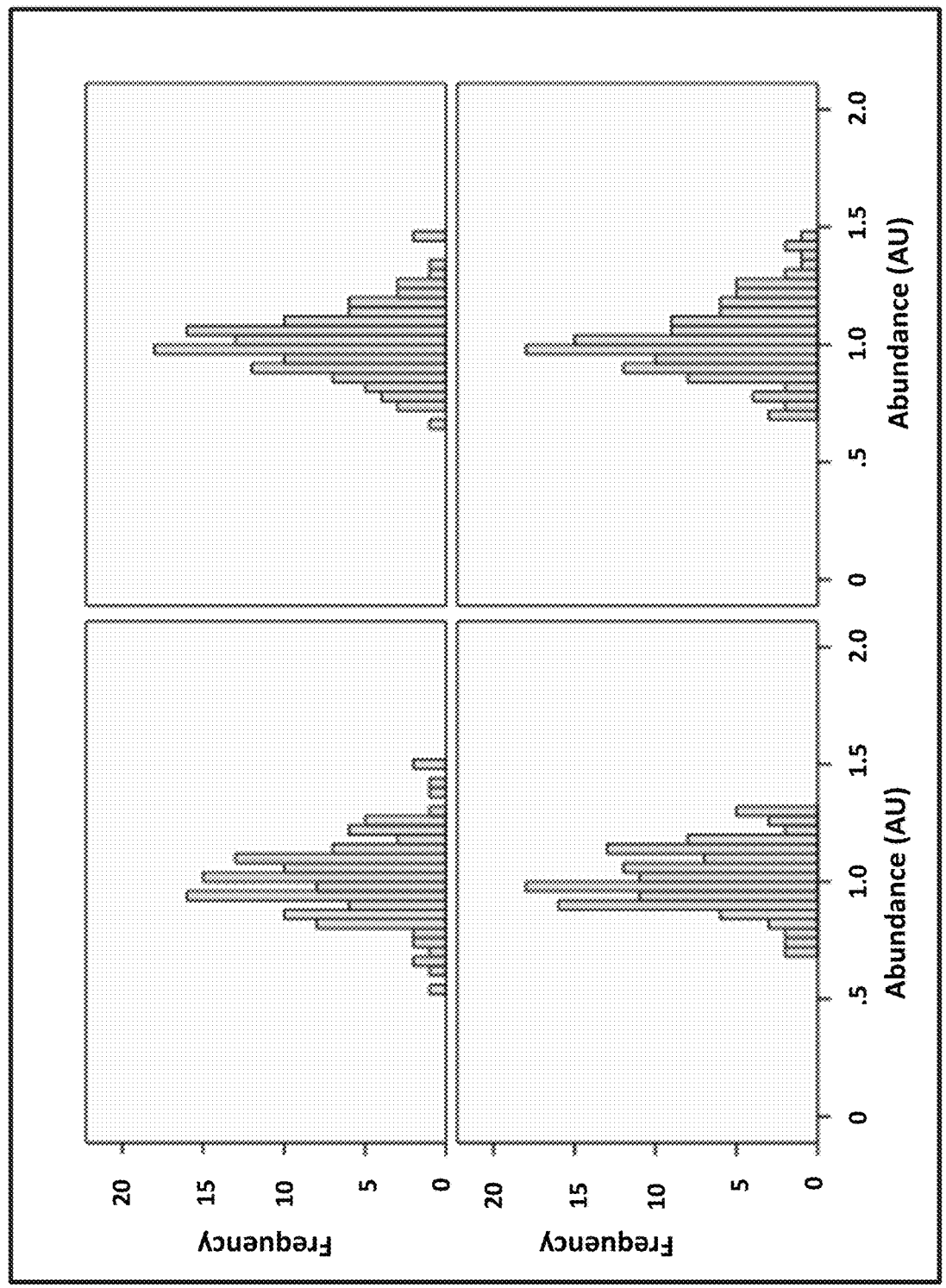
FIG. 17 is a plot of measurements of oligonucleotide frequency v. absorbance across four individual clusters.

A structure comprising 256 clusters 1505 each comprising 121 loci on a flat silicon plate was manufactured as shown in FIG. 15. An expanded view of a cluster is shown in 1510 with 121 loci. Loci from 240 of the 256 clusters provided an attachment and support for the synthesis of oligonucleotides having distinct sequences. Oligonucleotide synthesis was performed by phosphoramidite chemistry using general methods from Example 3. Loci from 16 of the 256 clusters were control clusters. The global distribution of the 29,040 unique oligonucleotides synthesized (240 non-control clusters×121 oligonucleotide populations per cluster) is shown in FIG. 16A. NGS sequencing confirmed 100% representation of designed oligonucleotides selected for synthesis. Distribution was measured for each cluster, as shown in FIG. 16B. The distribution of unique oligonucleotides synthesized in 4 representative clusters is shown in FIG. 17. On a global level, all oligonucleotides the designed for synthesis were present and 99% of the oligonucleotides had abundance that was within 2× of the mean, indicating high synthesis uniformity. This same observation was consistent on a per-cluster level.

Figure 18A:
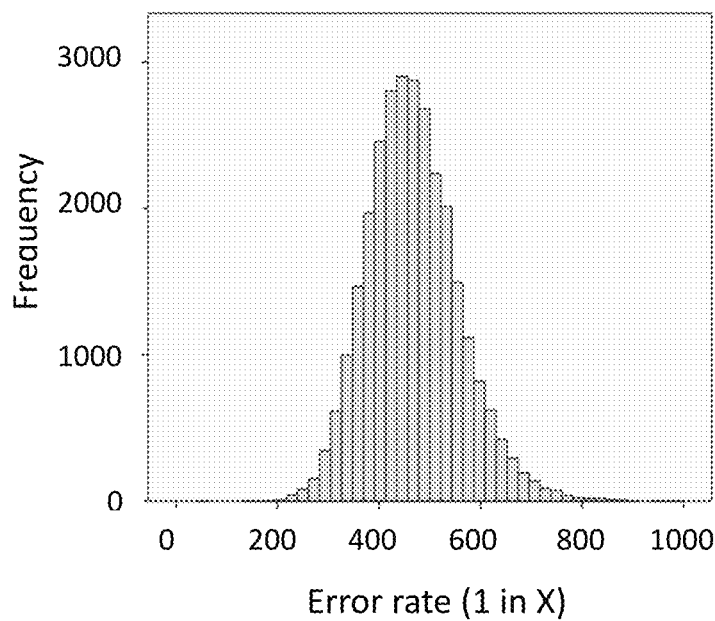
FIG. 18A is a plot of on error rate v. frequency across a plate from synthesis of 29,040 unique oligonucleotides from 240 clusters, each cluster having 121 oligonucleotides.
Figure 18B:
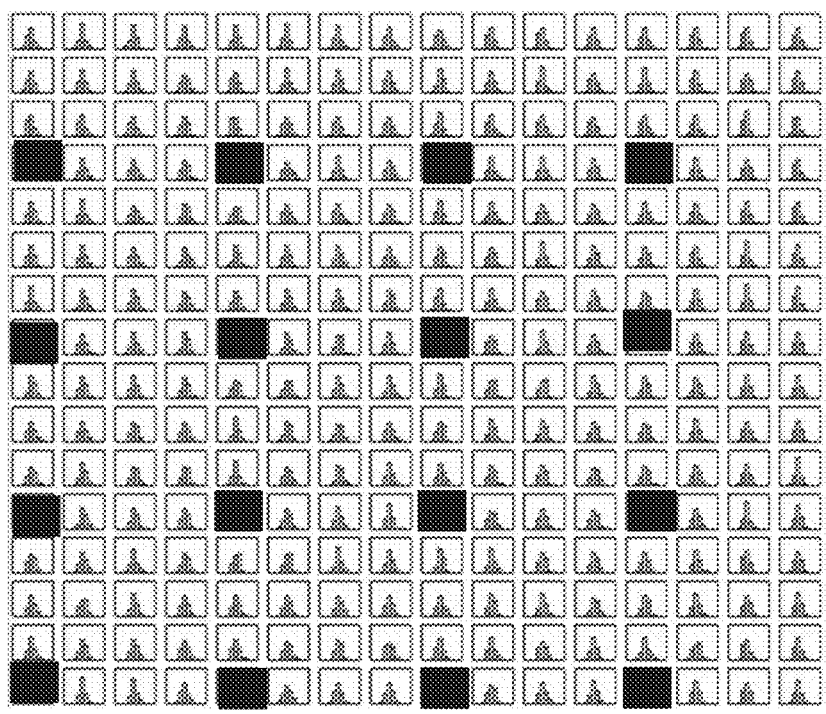
FIG. 18B is a plot of measurement of oligonucleotide error rate v. frequency across each individual cluster, with control clusters identified by a box.
Figure 19:
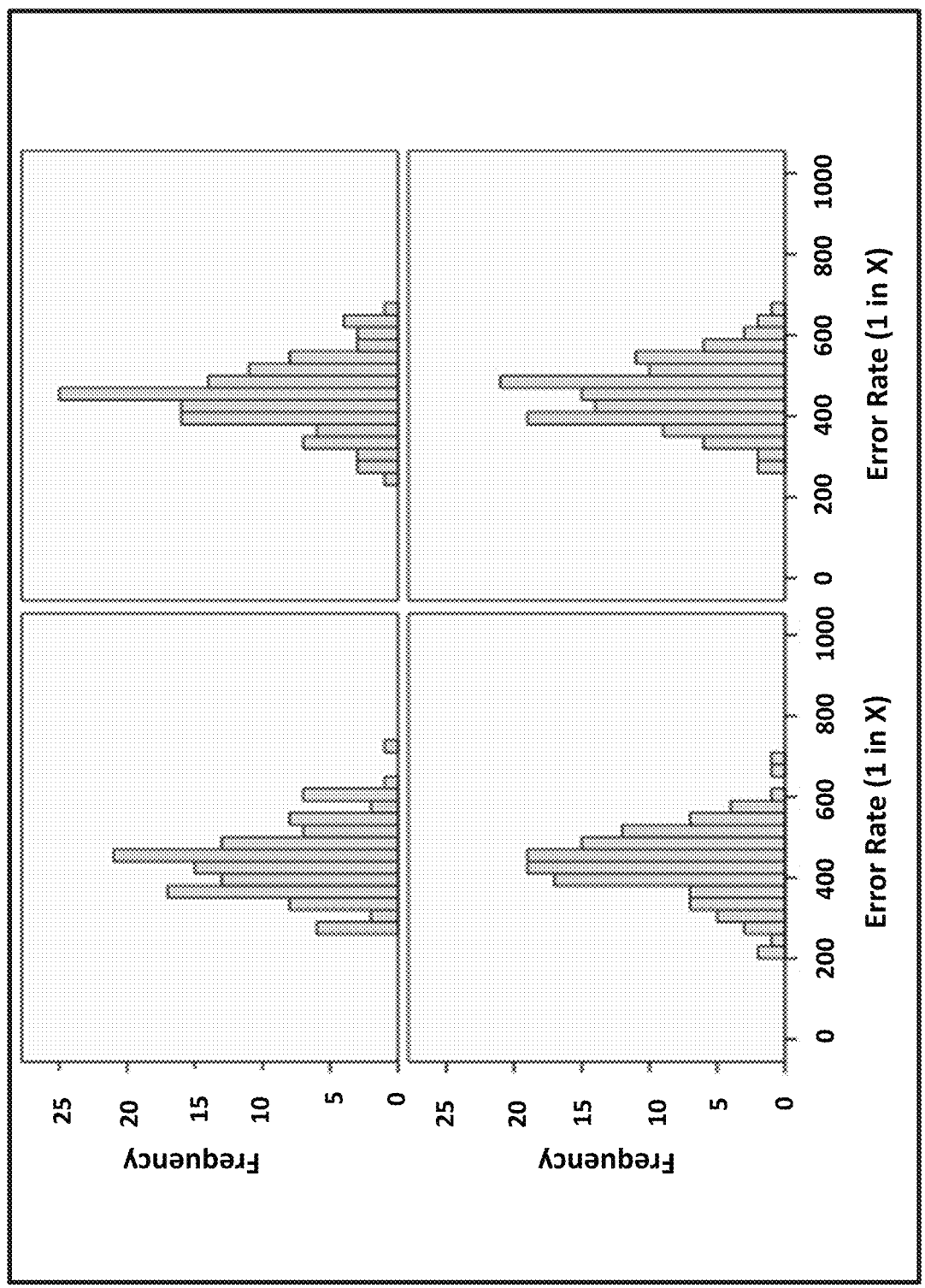
FIG. 19 is a plot of measurements of oligonucleotide error rate v. frequency across four clusters.
Figure 20:
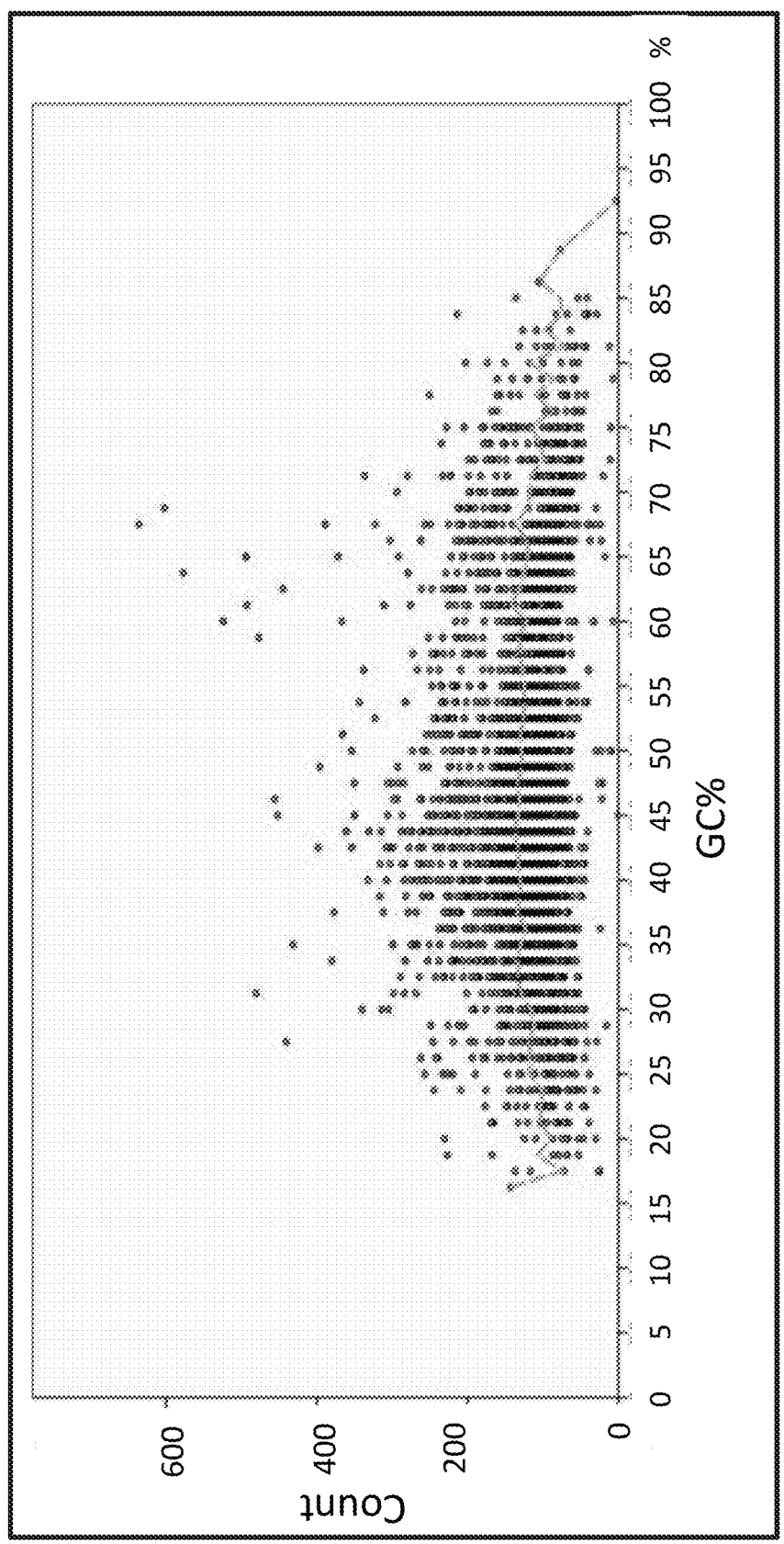
FIG. 20 is a plot of GC content as a measure of percent per oligonucleotide v. the number of oligonucleotides.

The error rate for each oligonucleotide was determined using an Illumina MiSeq gene sequencer. The error rate distribution for the 29,040 unique oligonucleotides is shown in FIG. 18A and averages around 1 in 500 bases, with some error rates as low as 1 in 800 bases. Distribution was measured for each cluster, as shown in FIG. 18B. The error rate distribution for unique oligonucleotides in four representative clusters is shown in FIG. 19. The library of 29,040 unique oligonucleotides was synthesized in less than 20 hours. Analysis of GC percentage v. oligonucleotide representation across all of the 29,040 unique oligonucleotides showed thatsynthesis was uniform despite GC content (roughly 20% to 85% GC per oligonucleotide), FIG. 20.

Figure 21:
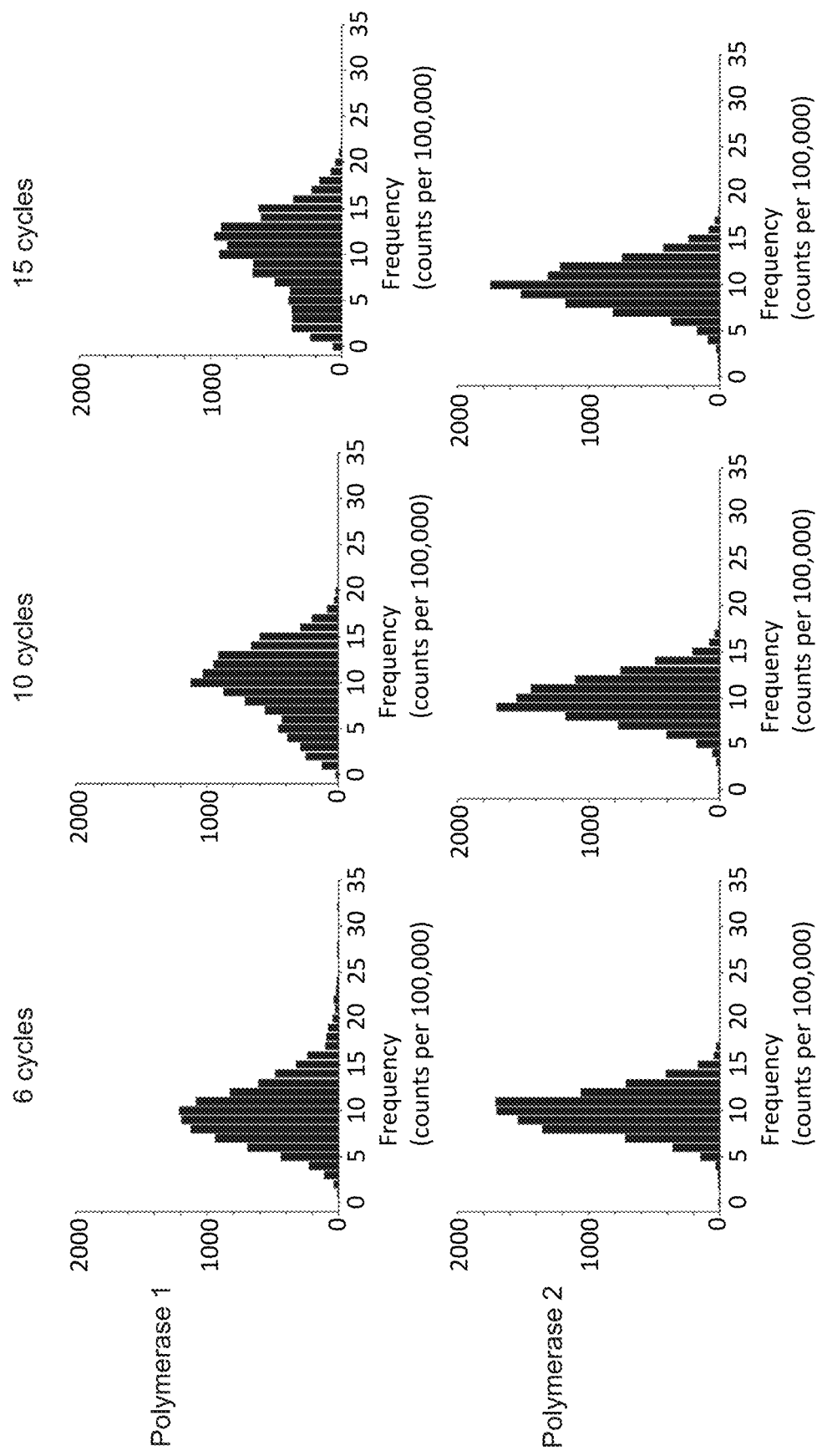
FIG. 21 provides plots with results from PCR with two different polymerases. Each chart depicts "observed frequency" ("0 to 35" measured in counts per 100,000) v. number of oligonucleotides (0 to 2000).

Example 10: PCR Amplification Analysis of De Novo Synthesized DNA Library Encoding for sgRNAs 9,996 oligonucleotides 100 bases in length of randomized sequences with varying GC content, from 20-80% GC were designed and synthesized on a structure with a similar arrangement is described in Example 9. To determine the effect of PCR amplification on GC representation, the oligonucleotide population was amplified for either 6 or 20 cycles with a high fidelity DNA polymerase (DNA polymerase 1). Alternatively, the oligonucleotide population was amplified using two other high-fidelity PCR enzymes for 6, 8, 10, or 15 cycles, to determine whether polymerase selection had an effect on overall sequence representation post-amplification. Following PCR amplification, samples were prepped for next generation sequencing and sequenced on the Illumina MiSeq platform. 150 base pair SE reads were generated to an approximate read coverage of 100×. Raw FASTQ files were analyzed. Oligonucleotide representation with either polymerase for 6, 10 or 15 cycles is depicted in FIG. 21. Oligonucleotide uniformity measured by frequency of representation in sequencing reads was assessed for the various conditions and is summarized in Table 22.

TABLE 22

| | Cycles | % within 1.5x | % within 2x |
| --- | --- | --- | --- |
| Polymerase 1 | 6 | 72.1% | 92.6% |
| | 8 | 76.1% | 90.3% |
| | 10 | 70.9% | 86.6% |
| | 15 | 64.1% | 82.7% |
| Polymerase 2 | 6 | 91.9% | 98.9% |
| | 8 | 89.9% | 98.1% |
| | 10 | 90.1% | 98.4% |
| | 15 | 89.2% | 97.9% |

Figure 22:
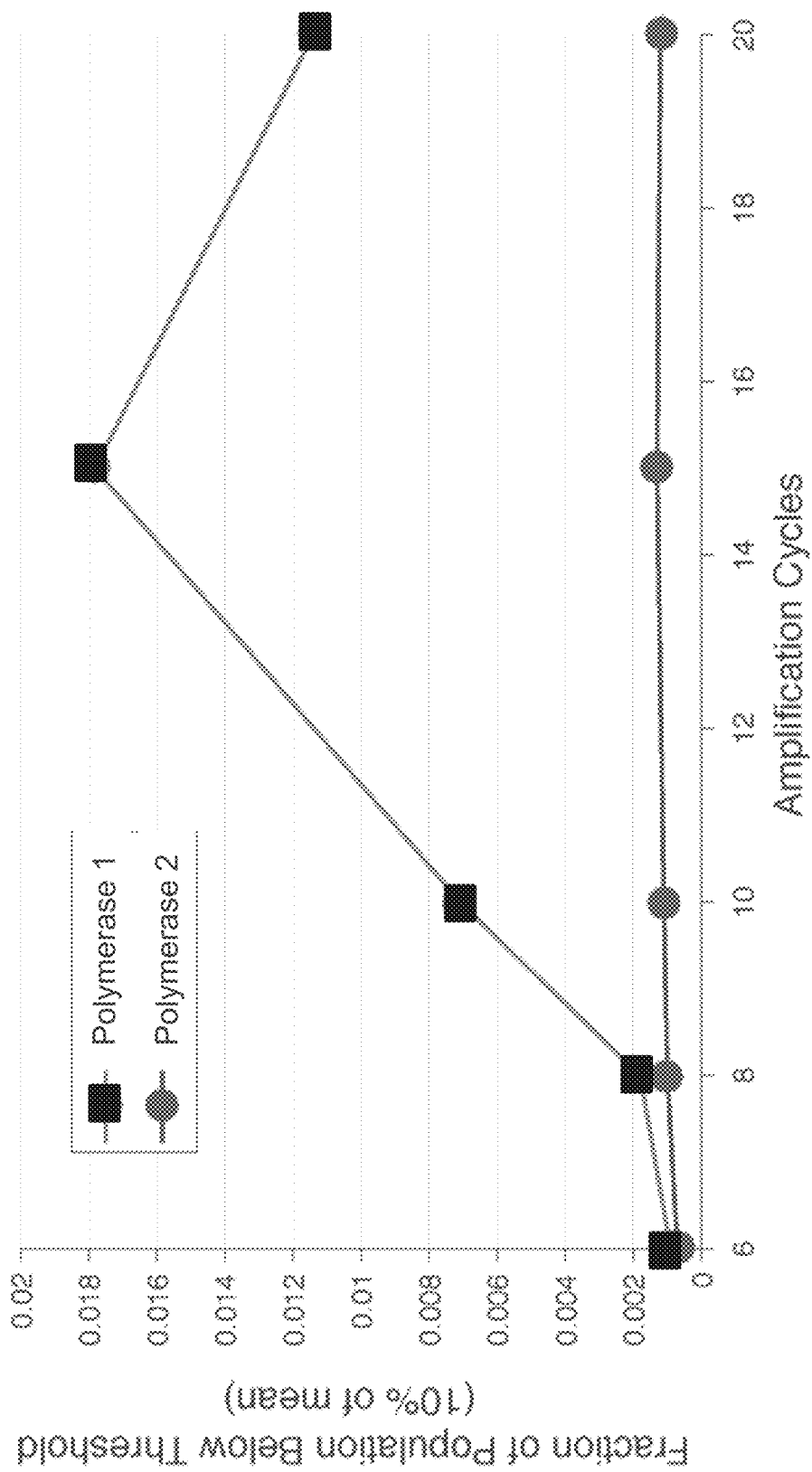
FIG. 22 provides a chart with quantification of oligonucleotide population uniformity post amplification that was recorded.

The number of dropouts for each amplified oligonucleotide population was quantified as shown in FIG. 22, amplification cycles v. fraction of population below a 10% of mean threshold. Polymerase 1 dropouts grew quickly whereas Polymerase 2 dropouts stayed relatively constant.

Figure 23:
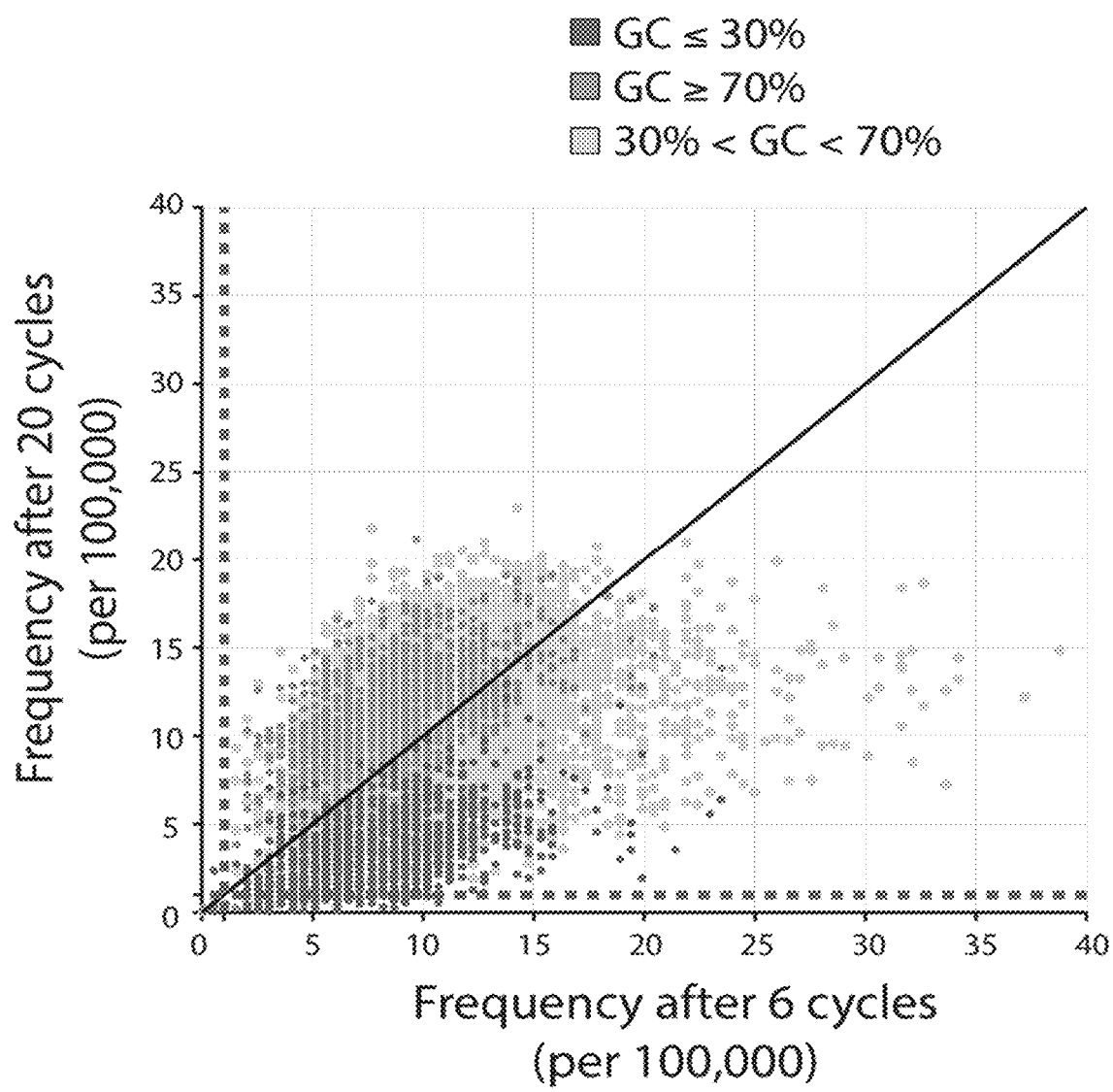
FIG. 23 depicts a plot of impact of over amplification on sequence dropouts.

The impact of over amplification on GC distribution was assessed, FIG. 23. Generally, oligonucleotides with a GC content 30% to 70% followed the trend line, Y=X, and increased in frequency with more cycles. Oligonucleotides with a GC content greater than 70% were, generally, slightly more frequent after 20 cycles, while oligonucleotides with a GC content lower than 30% were, generally, slightly more frequent after 6 cycles.

Example 11: Human Epigenetic CRISPR Screen

A sgRNA screen was performed to introduce mutations into exons that encode functional domains using CRISPR-Cas9. About 10,000 DNA oligonucleotides were de novo synthesized using methods similar to those described in Example 3 on a silicon chip as described in Example 1 on a structure with a similar arrangement is described in Example 9. Collectively, the oligonucleotides had an aggregated error rate of about 1:500 or lower. Each oligonucleotide was up to 200 bases in length, and at least 1 fmole per an oligonucleotide species was generated. The oligonucleotides were PCR amplified, cloned into vectors, and electroporated into cultured cells for sgRNA transcription. Nucleic acids were isolated from the cells and sequenced, using next generation sequencing.

Figures 24A, 24B:
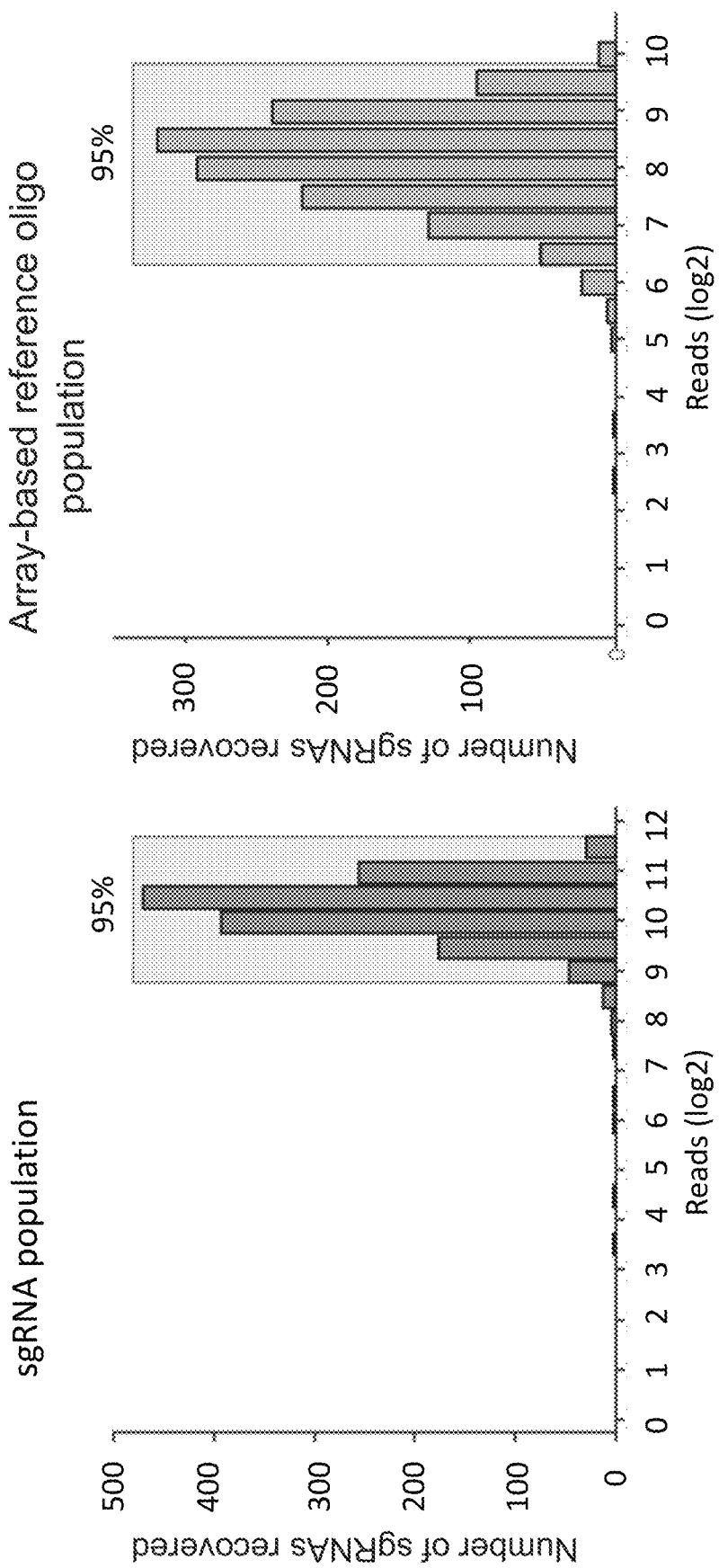
FIGS. 24A-24B depict results from sequencing recovered oligonucleotides from a 10,000 sgRNA nucleic acid CRISPR library.

Sequencing results showed highly accurate and uniform library synthesis with minimal bias and high fidelity production of sgRNAs. More reads per guide sequence with minimal sequencing 30% higher recovery of sgRNA with correct sequence for downstream screening compared to a commercially available pool. See Table 23. Pooled sequencing results showed more reads per guide sequence and a much tighter distribution of reads (4 logs) compared to 6 logs with the array based commercially available pool. See FIGS. 24A-24B. Sequencing validation of clones showed 100% sgRNA recovery (FIG. 24A) and higher sequence accuracy compared to a commercially available array-based pool (FIG. 24B). Of the clones that were sequenced, significantly more were recovered with the correct sgRNA sequence. See Table 23. 100% of the predetermined sequences were represented in the oligonucleotide population. NGS-based validation of sgRNA clones showed 100% sgRNA recovery and 13% higher accuracy of synthesis per clone compared to the commercially available population (data not shown).

TABLE 23

|  | Synthesized oligo population | Commercially available oligo population |
| --- | --- | --- |
| sgRNA oligos recovered | 100% | >95.5% |
| Correct sequence rate (MiSeq) | about 87% | about 74% |
| Correct sequence (Sanger 10 clones) | about 100% | about 70% |
| Ave reads per sgRNA in cloned oligo population (100x normalized) | about 256 | about 1024 |

Example 12: Whole Genome sgRNA Library

A DNA library was designed to include DNAs encoding for sgRNAs for generating clones for 101,000 different oligonucleotides (5 sgRNAs per 20200 gene targets). 101,000 oligonucleotides were de novo synthesized using methods similar to those described in Example 3 on a silicon chip as described in Example 1 on a structure with a similar arrangement is described in Example 9. The synthesized oligonucleotides were PCR amplified, digested and cloned into lentiviral vectors, and transformed into cells. Nucleic acids were isolated from the cells and sequenced, using next generation sequencing. Alternatively, the synthesized oligonucleotides were PCR amplified to form an amplicon-based library and sequenced.

Figure 25:
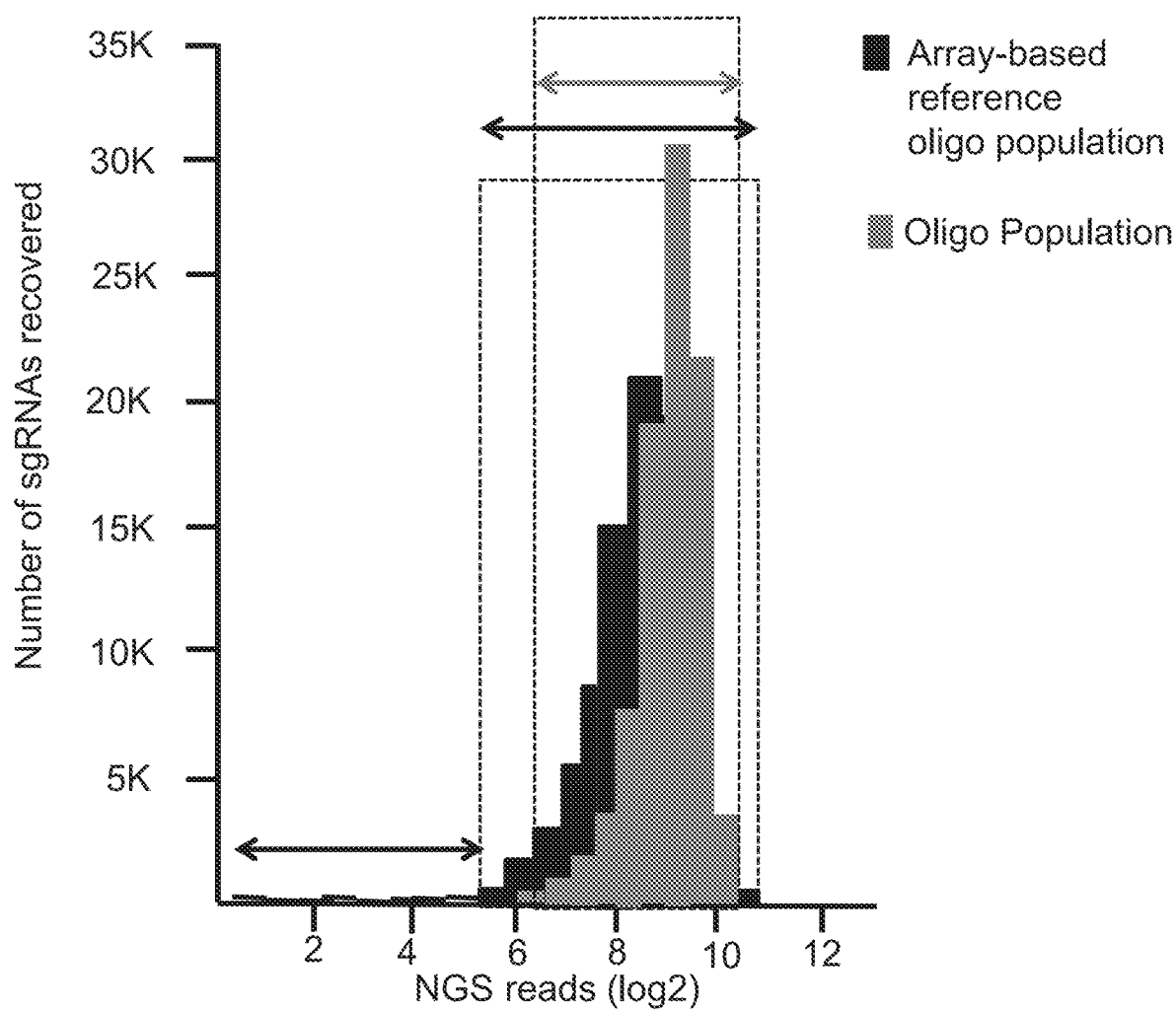
FIG. 25 depicts results from sequencing recovered oligonucleotides from a 101,000 sgRNA nucleic acid CRISPR library.

A plot of next generation sequencing reads v. number of sgRNAs recovered shows that as the oligonucleotide pool size increases, the oligonucleotide population maintained a more uniform tighter distribution of reads across the entire library, with a minimal tail compared to a commercially available array-based reference oligonucleotide population. FIG. 25.

Example 13. Design of sgRNA Libraries with Improved Targeting and Activity sgRNA libraries were designed and de novo synthesized using methods similar to those described in Example 3 on a silicon chip as described in Example 1 on a structure with a similar arrangement is described in Example 9. The synthesized oligonucleotides were PCR amplified, digested and cloned into vectors, and transferred into cells for use for downstream applications including screening and analysis.

Figure 26A:
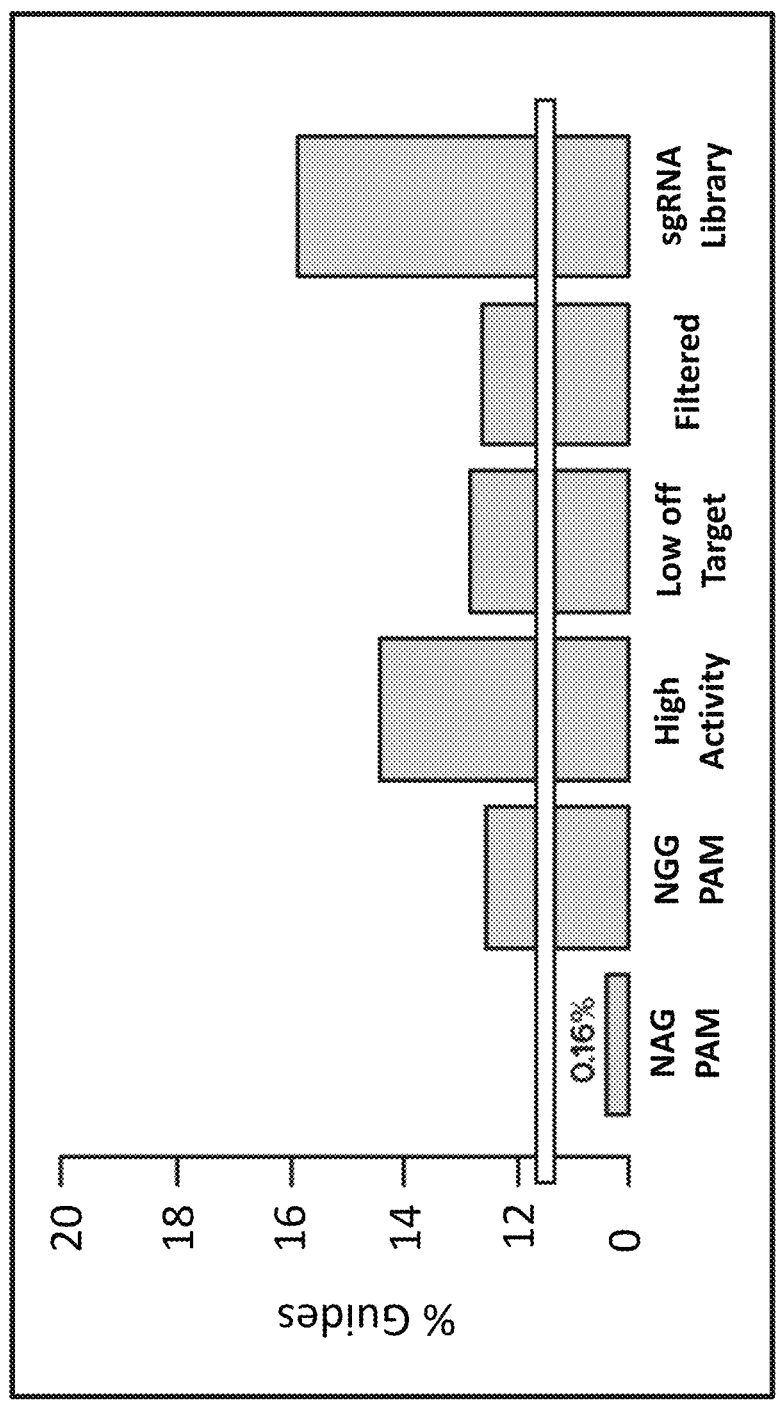
FIG. 26A depicts a graph of percentage of sgRNAs with at least 2-fold depletion.

Different sgRNA design parameters were compared including libraries characterized by a NAG PAM, a NGG PAM, high activity, low off-target, and filtered. The sgRNA library designed by methods described herein provided for a higher percentage of sgRNAs resulting in at least 2-fold depletion of gene expression, around 16% of sgRNAs, compared to other commercially available gRNA systems. FIG. 26A. The sgRNA libraries also provided for a lower percentage of sgRNAs resulting in zero or negative depletion of gene expression, around 17%, compared to other commercially available gRNA systems. FIG. 26B.

sgRNA-mediated depletion was assessed for essential gene expression levels as well, where the following genes were targeted by sgRNAs: PCNA, PSMA7, RPP21, and SF3B3. Analyzing the number of sgRNAs that exhibited at least 2-fold depletion, the sgRNA library had a higher percentage sgRNAs depleting essential genes as compared to Comparator 1, Comparator 2, and Comparator 3. See Table 24.

TABLE 24

| Gene Name | Comparator 1 | Comparator 2 | Comparator 3 | CRISPR Library |
| --- | --- | --- | --- | --- |
| PCNA | 1/5 | 2/6 | 5/9 | 5/5 |
| PSMA7 | 1/5 | 0/6 | 2/9 | 3/5 |
| RPP21 | 3/5 | 1/6 | 4/9 | 2/5 |
| SF3B3 | 0/5 | 0/6 | 4/9 | 3/5 |
| Average (%) | 25% | 12.5% | 42% | 65% |

Example 14. sgRNA Library for MS2

A DNA library comprising non-identical DNA sequences encoding for sgRNAs was designed for sequence specific cleavage by the C2c2 protein. The library comprised all possible spacer sequences for C2c2 targeting of bacteriophage MS2 genome. Because mature crRNAs of C2c2 from *Leptotrichia shahii* comprises a maximum spacer length of 28 nucleotides, tiling all possible 28 nucleotide target sites in the bacteriophage genome resulted in a library of about 3500 spacer sequences.

About 3500 non-identical oligonucleotides were de novo synthesized using methods similar to those described in Example 3 on a silicon chip as described in Example 1 on a structure with a similar arrangement is described in Example 9. The library of about 3500 sequences were inserted into vectors and transformed into E. coli. E. coli cells were infected with MS2 bacteriophage using three dilutions of MS2. The library was then screened for sequences that conferred E. coli resistance to MS2 infection.

A number of spacer sequences were found to confer resistance. Comparing spacer representation (crRNA frequencies), many spacer sequences exhibited more than 1.25 log$_2$-fold enrichment in the three dilutions of MS2 infection whereas no non-targeting spacer sequences were found to be enriched.

Example 15: sgRNA Library for Zebrafish

A DNA library is designed with sequences encoding for about 130,000 sgRNAs. On average, about 5 sgRNAs templates are designed for each zebrafish gene. The oligonucleotides are de novo synthesized using methods similar to those described in Example 3 on a silicon chip as described in Example 1 on a structure with a similar arrangement as described in Example 9. De novo synthesis produces the 130,000 oligonucleotides, each extending from a different locus on the surface of a silicon plate. The oligonucleotides are removed from the plate, amplified by PCR, and cloned into expression vectors. Each template is subject to sequencing. The sgRNA library is injected into zebrafish embryos. Zebrafish are raised to adulthood. Sperm are then cryopreserved and screened by sequencing to identify the sequence of germline transmitted insertions and deletions. Following the germline screen, sperm are genotyped by competitive allele-specific PCR.

Example 16: gRNA Library for Mouse

A DNA library is designed with sequences encoding for about 100,000 sgRNAs. On average, about 5 sgRNAs templates are designed per mouse gene. The oligonucleotides are de novo synthesized using methods similar to those described in Example 3 on a silicon chip as described in Example 1 on a structure with a similar arrangement as described in Example 9. A sgRNA library encoding for the sgRNA sequences is de novo synthesized to generate 100,000 oligonucleotides. De novo synthesis produces the 100,000 oligonucleotides, each extending from a different locus on the surface of a silicon plate. The oligonucleotides are removed from the plate, amplified by PCR, and cloned into vectors. Each template is subject to sequencing. sgRNA on-target efficiency is verified by surveyor nuclease assay or sequencing. sgRNAs are then microinjected in mouse zygotes with a desired genetic background. Alternately, following verification of sgRNA efficiency, sgRNAs are packaged into viral vectors such as adeno-associated viruses (AAVs). sgRNAs are then stereotactically delivered into mice at a desired location. Expression levels for the preselected target genes are observed in tissue collected from mice.

Example 17: gRNA Library for a Receptor Tyrosine Kinases

A DNA nucleic acid library is designed with sequences encoding for 5 sgRNAs targeting genes for 58 human receptor tyrosine kinases listed in Table 25, totaling 290 different DNA nucleic acids. The nucleic acids are de novo synthesized using methods similar to those described in Example 3 on a silicon chip as described in Example 1 on a structure with a similar arrangement as described in Example 9. The oligonucleotides are removed from the plate, amplified by PCR, cloned into vectors, and transferred into preselected populations of cells. Expression levels for the preselected genes listed in Table 25 are compared in each preselected populations of cells against a control population of cells exposed to a control vector without the kinase-specific sgRNA.

TABLE 25

| Gene | Hs NT ACC # | Hs PROT ACC# |
|---|---|---|
| ALK | NM_004304 | NP_004295 |
| LTK | NM_002344 | NP_002335 |
| AXL | NM_001699 | NP_001690 |
| MER | NM_006343 | NP_006334 |
| TYRO3 | NM_006293 | NP_006284 |
| DDR1 | NM_013993 | NP_001945 |
| DDR2 | NM_006182 | NP_006173 |
| EGFR | NM_005228 | NP_005219 |
| ERBB2 | NM_004448 | NP_004439 |
| ERBB3 | NM_001982 | NP_001973 |
| ERBB4 | NM_005235 | NP_005226 |
| EPHA1 | NM_005232 | NP_005223 |
| EPHA2 | NM_004431 | NP_004422 |
| EPHA3 | NM_005233 | NP_005224 |
| EPHA4 | NM_004438 | NP_004429 |
| EPHA5 | L36644 | P54756 |
| EPHA6 | AL133666 | |
| EPHA7 | NM_004440 | NP_004431 |
| EPHA8 | AB040892 | CAB81612 |
| EPHB1 | NM_004441 | NP_004432 |
| EPHB2 | AF025304 | AAB94602 |
| EPHB3 | NM_004443 | NP_004434 |
| EPHB4 | NM_004444 | NP_004435 |
| EPHB6 | NM_004445 | NP_004436 |
| EPHX | | |
| FGFR1 | M34641 | AAA35835 |
| FGFR2 | NM_000141 | NP_000132 |
| FGFR3 | NM_000142 | NP_000133 |
| FGFR4 | NM_002011 | NP_002002 |
| IGF1R | NM_000875 | NP_000866 |
| INSR | NM_000208 | NP_000199 |
| INSRR | J05046 | AAC31759 |
| MET | NM_000245 | NP_000236 |
| RON | NM_002447 | NP_002438 |
| MUSK | NM_005592 | NP_005583 |
| CSF1R | NM_005211 | NP_005202 |
| FLT3 | NM_004119 | NP_0041110 |
| KIT | NM_000222 | NP_000213 |
| PDGFRA | NM_006206 | NP_006197 |
| PDGFRB | NM_002609 | NP_002600 |
| PTK7 | NM_002821 | NP_002812 |
| RET | X12949 | P07949 |
| ROR1 | NM_005012 | NP_005003 |
| ROR2 | NM_004560 | NP_004551 |
| ROS1 | NM_002944 | NP_002935 |
| RYK | S59184 | AAB26341 |
| TEK | NM_000459 | NP_000450 |
| TIE | NM_005424 | NP_005415 |
| NTRK1 | NM_002529 | NP_002520 |
| NTRK2 | NM_006180 | NP_006171 |
| NTRK3 | NM_002530 | NP_002521 |
| VEGFR1 | NM_002019 | NP_002010 |
| VEGFR2 | | AAB88005 |
| VEGFR3 | NM_002020 | NP_002011 |
| AATYK | NM_004920 | NP_004911 |
| AATYK2 | NM_014916 | NP_055731 |
| AATYK3 | | |
| DKFZp761P1010 | NM_018423 | NP_060893 |

Example 18: gRNA Library for Human Kinome

A DNA nucleic acid library is designed with sequences encoding for 5 sgRNAs targeting genes for 518 human kinases, totaling 2,590 different DNA nucleic acids. The oligonucleotides are removed from the plate, amplified by PCR, cloned into vectors, and transferred into preselected populations of cells. Expression levels for the preselected 518 genes are compared in each preselected populations of cells against a control population of cells exposed to a control vector without the kinase-specific sgRNA.

Example 19: gRNA Library for Human Phosphatome

A DNA nucleic acid library is designed with sequences encoding for 5 sgRNAs targeting genes for 200 human phosphatases, totaling 1000 different DNA nucleic acids. The nucleic acids are removed from the plate, amplified by PCR, cloned into vectors, and transferred into preselected populations of cells. Expression levels for the 200 preselected genes are compared in each preselected populations of cells against a control population of cells exposed to a control vector without the kinase-specific sgRNA.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for synthesis of a gRNA library, comprising:
    (a) providing predetermined sequences for at least 500 non-identical DNA molecules, wherein each non-identical DNA molecule encodes for a different gRNA;
    (b) providing a surface, wherein the surface comprises clusters of loci for nucleic acid extension reaction;
    (c) synthesizing a nucleic acid library comprising the at least 500 non-identical DNA molecules, wherein each non-identical DNA molecule extends from the surface, and wherein at least about 80% of the at least 500 non-identical DNA molecules are each present in the nucleic acid library in an amount within 2× of a mean frequency for each of the non-identical DNA molecules in the library; and
    (d) transferring the at least 500 non-identical DNA molecules into cells capable of generating the gRNA library transcribed from the at least 500 non-identical DNA molecules.

2. The method of claim 1, wherein each of the clusters comprises about 50 to about 500 loci.

3. The method of claim 1, wherein each non-identical DNA molecule comprises up to about 200 bases in length.

4. The method of claim 1, wherein each non-identical DNA molecule encodes for a single gRNA or a dual gRNA.

5. The method of claim 1, wherein the cells are prokaryotic cells.

6. The method of claim 1, wherein the cells are eukaryotic cells.

7. The method of claim 1, wherein the cells are mammalian cells.

8. The method of claim 1, wherein each of the cells comprises an exogenous nuclease enzyme.

9. The method of claim 1, wherein each non-identical DNA molecule further comprises a vector sequence.

10. The method of claim 1, wherein each non-identical DNA molecule has a GC base content of 20% to 85%.

11. The method of claim 1, wherein each non-identical DNA molecule has a GC base content of 30% to 70%.

12. The method of claim 1, wherein at least 96% of the gRNAs encoded by the at least 500 non-identical DNA molecules are present in the gRNA library.

13. The method of claim 1, wherein the at least 500 non-identical DNA molecules comprises at least 2000 non-identical DNA molecules.

14. The method of claim 1, wherein the at least 500 non-identical DNA molecules comprises at least 100,000 non-identical DNA molecules.

15. The method of claim 1, wherein the gRNA targets genes in a biological pathway.

16. The method of claim 1, wherein the gRNA targets genes in an entire genome.

* * * * *